(12) United States Patent
Fieldhouse et al.

(10) Patent No.: US 9,493,432 B2
(45) Date of Patent: Nov. 15, 2016

(54) CYCLOPENTYLBENZAMIDE DERIVATIVES AND THEIR USE FOR THE TREATMENT OF PSYCHOTIC AND COGNITIVE DISORDERS

(71) Applicant: Takeda Pharmaceutical Company Limited, Osaka (JP)

(72) Inventors: Charlotte Fieldhouse, Cambridge (GB); Angela Glen, Cambridge (GB); John Stephen Robinson, Cambridge (GB); Tatsuhiko Fujimoto, Fujisawa (JP)

(73) Assignee: Takeda Pharmaceuticals Company Limited, Osaka (JP)

( * ) Notice: Subject to any disclaimer, the term of this patent is extended or adjusted under 35 U.S.C. 154(b) by 0 days.

(21) Appl. No.: 15/029,356

(22) PCT Filed: Oct. 14, 2014

(86) PCT No.: PCT/GB2014/053079
§ 371 (c)(1),
(2) Date: Apr. 14, 2016

(87) PCT Pub. No.: WO2015/055994
PCT Pub. Date: Apr. 23, 2015

(65) Prior Publication Data
US 2016/0222030 A1  Aug. 4, 2016

(30) Foreign Application Priority Data
Oct. 15, 2013 (GB) .................................. 1318222.5

(51) Int. Cl.
| | | |
|---|---|---|
| *C07D 277/82* | (2006.01) | |
| *C07D 241/44* | (2006.01) | |
| *C07D 401/12* | (2006.01) | |
| *C07D 263/58* | (2006.01) | |
| *C07D 413/12* | (2006.01) | |
| *C07D 417/14* | (2006.01) | |
| *C07D 417/12* | (2006.01) | |
| *C07D 277/64* | (2006.01) | |
| *C07D 403/12* | (2006.01) | |
| *C07D 215/12* | (2006.01) | |
| *C07D 513/04* | (2006.01) | |

(52) U.S. Cl.
CPC ........... *C07D 277/82* (2013.01); *C07D 215/12* (2013.01); *C07D 241/44* (2013.01); *C07D 263/58* (2013.01); *C07D 277/64* (2013.01); *C07D 401/12* (2013.01); *C07D 403/12* (2013.01); *C07D 413/12* (2013.01); *C07D 417/14* (2013.01); *C07D 417/12* (2013.01); *C07D 513/04* (2013.01)

(58) Field of Classification Search
CPC  C07D 277/82; C07D 241/44; C07D 401/12; C07D 263/58; C07D 413/12; C07D 417/14; C07D 417/12; C07D 277/64; C07D 403/12; C07D 215/12; C07D 513/04
See application file for complete search history.

(56) References Cited

U.S. PATENT DOCUMENTS

| | | | |
|---|---|---|---|
| 6,548,539 B1 | 4/2003 | Pikul et al. | |
| 2010/0222366 A1* | 9/2010 | Santella ............... | C07D 211/52 514/255.05 |

FOREIGN PATENT DOCUMENTS

| | | |
|---|---|---|
| EP | 2653469 A1 | 10/2013 |
| WO | 9606098 A1 | 2/1996 |
| WO | 97/23466 A1 | 7/1997 |
| WO | 97/30998 A1 | 8/1997 |
| WO | 98/51671 A | 11/1998 |
| WO | 99/03859 A1 | 1/1999 |
| WO | 99/05134 A1 | 2/1999 |
| WO | 99/27783 A | 6/1999 |
| WO | 00/42044 A1 | 7/2000 |
| WO | 01/29034 A1 | 4/2001 |
| WO | 01/36417 A1 | 5/2001 |
| WO | 01/60821 A1 | 8/2001 |
| WO | 02/08212 A1 | 2/2002 |
| WO | 02/094794 A1 | 11/2002 |
| WO | 02/096912 A1 | 12/2002 |
| WO | 03/087102 A1 | 10/2003 |
| WO | 03/087103 A1 | 10/2003 |

(Continued)

OTHER PUBLICATIONS

International Preliminary Report on Patentability, issued in connection with International Application No. PCT/GB2014/053079 on Apr. 19, 2016, 7 pages.

(Continued)

*Primary Examiner* — Matthew Coughlin
(74) *Attorney, Agent, or Firm* — Barnes & Thornburg LLP; Scott D. Rothenberger

(57) ABSTRACT

The present invention provides compounds of formula (I) and pharmaceutically acceptable salts thereof, wherein n, L, X, $R^a$, $R^b$, $R^1$, $R^2$ and $R^3$ their preparation, pharmaceutical compositions containing them and their use in therapy.

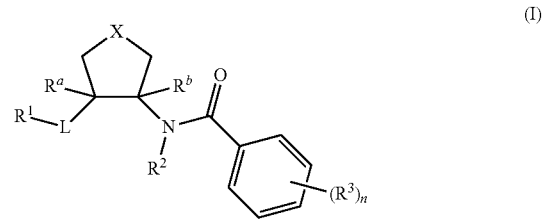

(I)

15 Claims, No Drawings

(56) References Cited

FOREIGN PATENT DOCUMENTS

| WO | 03/087104 A1 | 10/2003 |
|---|---|---|
| WO | 03099276 A1 | 12/2003 |
| WO | 2004/016616 A1 | 2/2004 |
| WO | 2004/016617 A1 | 2/2004 |
| WO | 2004/019947 A1 | 3/2004 |
| WO | 2008008517 A2 | 1/2008 |
| WO | 2009003993 A1 | 1/2009 |
| WO | 2009080533 A1 | 7/2009 |
| WO | 2012081692 A1 | 6/2012 |
| WO | 2015055994 A1 | 4/2015 |

OTHER PUBLICATIONS

Search Report issued by the United Kingdom Intellectual Property Office for Application No. GB1318222.5, Apr. 14, 2014, 4 pages.
International Search Report and Written Opinion, International Application No. PCT/GB2014/053079, mailed Nov. 19, 2014, 10 pages.
Coleman et al., "Orexin receptor antagonists: a review of promising compounds patented since 2006", Expert Opinion on Therapeutic Patents, Informa Healthcare, GB, vol. 20, No. 3, Mar. 1, 2010, 18 pages.
Hess, H. M.; Brown, H. C., Synthesis of 3-cyclopenten-1-one and 3-cyclopenten-1-ol, J. Org Chem., 1967, 32, 4138-4139.
Brookes, P.; Milne, D. J.; Murphy, P. J.; Spolaore, B., Epoxide rearrangements using dilithiated amino alcohols as chiral bases, Tetrahedron 2002, 58, 4675-4680.
Guan, Y.; Grenn, M. A.; Bergstrom, D. E., Stereocontrolled Synthesis of (1R,3R,4S)- and (1S,3R,4S)-3,4-diaminocyclopentanols, Synlett 1999, 4, 426-428.
Sakurai et al., "Orexins and Orexin Receptors: A Family of Hypothalamic Neuropeptides and G Protein-Coupled Receptors that Regulate Feeding Behavior", Cell, 1998, 92, 573.
De Lecea et al., "The hypocretins: Hypothalamus-specific peptides with neuroexcitatory activity", Proc. Nat. Acad. Sci., 1998, 95, 322.
Chemelli et al., "Narcolepsy in orexin Knockout Mice: Molecular Genetics of Sleep Regulation", Cell, 1999, 98, 437.
Harris et al., "Arousal and reward: a dichotomy in orexin function", Trends Neurosci., 2006, 29, 571.

* cited by examiner

CYCLOPENTYLBENZAMIDE DERIVATIVES AND THEIR USE FOR THE TREATMENT OF PSYCHOTIC AND COGNITIVE DISORDERS

CROSS-REFERENCE TO RELATED APPLICATIONS

This application is a 35 U.S.C. §371(b) National Stage Application of International Application No. PCT/GB2014/053079, filed Oct. 14, 2014, and published as WO2015055994 on Apr. 23, 2015, which claims priority from GB 1318222.5, filed Oct. 15, 2013, the contents of which are hereby incorporated in their entirety by reference.

The present invention relates to amide derivatives, processes for their preparation, pharmaceutical compositions containing them and their use in therapy, particularly in the treatment or prevention of conditions having an association with the orexin sub-type 1 receptor.

The orexin peptides (orexin A and orexin B, OxA and OxB), also known as hypocretins, were discovered in 1998 by two groups (Sakurai et al., Cell, 1998, 92, 573 and De Lecea et al., Proc. Nat. Acad. Sci., 1998, 95, 322). These neuropeptides are both derived from the common precursor pre-pro-orexin and are produced in the lateral hypothalamus. OxA is a 33 amino acid residue which has similar potency at both the Ox1R (orexin 1 receptors) and Ox2R (orexin 2 receptors) whereas OxB is made up of 28 amino acids and binds selectively to the Ox2R.

Orexin receptors are believed to be implicated in both feeding behavior (Sakurai et al., Cell, 1998, 92, 573) and also in regulating sleep architecture (Chemelli et al., Cell, 1999, 98, 437). More recently, it has been shown that orexin receptors are implicated in arousal, reward, learning and memory (Harris et al., Trends Neurosci., 2006, 29, 571).

WO 2003/099276 describes a broad class of compounds, including certain amides, which are useful as factor Xa inhibitors for treating thromboembolic disorders. In addition, U.S. Pat. No. 6,548,539 describes certain amide derivatives for use in treating cancer.

We have now discovered a class of compounds that are orexin receptor antagonists which, in general, show selectivity for the orexin 1 receptor over the orexin 2 receptor.

In accordance with the present invention, there is therefore provided a compound of formula (I)

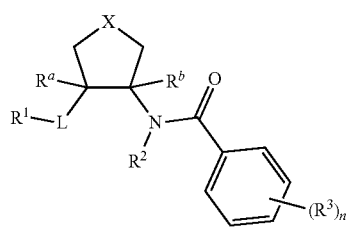

(I)

wherein
$R^1$ represents an 8- to 10-membered fused bicyclic heteroaromatic group optionally substituted by at least one substituent selected from halogen, cyano, hydroxyl, $C_3$-$C_6$ cycloalkyl, $C_1$-$C_3$ alkyl, $C_1$-$C_3$ alkoxy, $C_1$-$C_3$ alkoxycarbonyl, $C_1$-$C_3$ alkoxycarbonylamino, $C_1$-$C_3$ haloalkoxy, —$NR^4R^5$, $C_3$-$C_6$ cycloalkylamino, $C_1$-$C_3$ alkylcarbonyloxy, $C_1$-$C_3$ alkylcarbonylamino, sulphonamido (—$SO_2NH_2$), $C_1$-$C_3$ alkylsulphonyl, $C_1$-$C_3$ alkylsulphonylamino and —$C(O)NR^6R^7$;

L represents $CH_2$, O, NH or $N(CH_3)$;
$R^a$ represents a hydrogen atom or a $C_1$-$C_3$ alkyl or $C_1$-$C_3$ haloalkyl group;
$R^b$ represents a hydrogen atom or a $C_1$-$C_3$ alkyl or $C_1$-$C_3$ haloalkyl group;
X represents $CF_2$, $CHR^8$, O or $NC(O)R^9$;
$R^2$ represents a hydrogen atom or a $C_1$-$C_6$ alkyl group;
n is 0 or an integer 1, 2, 3, 4 or 5;
each $R^3$ independently represents halogen, hydroxyl, cyano, $C_1$-$C_3$ alkyl, $C_1$-$C_3$ haloalkyl, $C_1$-$C_3$ hydroxyalkyl, $C_1$-$C_3$ alkoxy, $C_1$-$C_3$ haloalkoxy, $C_2$-$C_4$ alkenyl, $C_1$-$C_3$ alkylcarbonyloxy, $C_1$-$C_3$ alkoxycarbonyl, —$NR^{10}R^{11}$, —$CONR^{12}R^{13}$, $C_3$-$C_6$ cycloalkyl, $C_3$-$C_6$ cycloalkyloxy, $C_3$-$C_6$ cycloalkylmethyl or a 5- to 6-membered heteroaryl group, the heteroaryl group being optionally substituted by at least one substituent selected from $C_1$-$C_6$ alkyl, $C_1$-$C_6$ alkoxy and $C_1$-$C_6$ haloalkoxy;
$R^4$ and $R^5$ each independently represent a hydrogen atom or a $C_1$-$C_3$ alkyl or $C_3$-$C_6$ cycloalkyl group, or $R^4$ and $R^5$ may together with the nitrogen atom to which they are attached form a 4- to 7-membered saturated heterocyclic ring optionally substituted by at least one substituent selected from halogen and hydroxyl;
$R^6$ and $R^7$ each independently represent a hydrogen atom or a $C_1$-$C_3$ alkyl or $C_3$-$C_6$ cycloalkyl group, or $R^6$ and $R^7$ may together with the nitrogen atom to which they are attached form a 4- to 7-membered saturated heterocyclic ring optionally substituted by at least one substituent selected from halogen and hydroxyl;
$R^8$ represents a hydrogen or halogen atom or a hydroxyl group;
$R^9$ represents a $C_1$-$C_6$ alkyl, $C_1$-$C_6$ alkoxy, benzyloxy, $C_6$-$C_{10}$ aryl, or heteroaryl group;
$R^{10}$ and $R^{11}$ each independently represent a hydrogen atom or a $C_1$-$C_3$ alkyl or $C_3$-$C_6$ cycloalkyl group, or $R^{10}$ and $R^{11}$ may together with the nitrogen atom to which they are attached form a 4- to 7-membered saturated heterocyclic ring optionally substituted by at least one substituent selected from halogen and hydroxyl; and
$R^{12}$ and $R^{13}$ each independently represent a hydrogen atom or a $C_1$-$C_3$ alkyl or $C_3$-$C_6$ cycloalkyl group, or $R^{12}$ and $R^{13}$ may together with the nitrogen atom to which they are attached form a 4- to 7-membered saturated heterocyclic ring optionally substituted by at least one substituent selected from halogen and hydroxyl;
or a pharmaceutically acceptable salt thereof.

In one aspect, the invention provides a compound of formula (I) wherein
$R^1$ represents an 8- to 10-membered fused bicyclic heteroaromatic group optionally substituted by at least one substituent selected from halogen, cyano, hydroxyl, $C_3$-$C_6$ cycloalkyl, $C_1$-$C_3$ alkyl, $C_1$-$C_3$ alkoxy, $C_1$-$C_3$ alkoxycarbonyl, $C_1$-$C_3$ alkoxycarbonylamino, $C_1$-$C_3$ haloalkoxy, —$NR^4R^5$, $C_3$-$C_6$ cycloalkylamino, $C_1$-$C_3$ alkylcarbonyloxy, $C_1$-$C_3$ alkylcarbonylamino, sulphonamido (—$SO_2NH_2$), $C_1$-$C_3$ alkylsulphonyl, $C_1$-$C_3$ alkylsulphonylamino and —$C(O)NR^6R^7$;
L represents $CH_2$, O, NH or $N(CH_3)$;
$R^a$ represents a hydrogen atom;
$R^b$ represents a hydrogen atom;
X represents $CHR^8$, O or $NC(O)R^9$;
$R^2$ represents a hydrogen atom or a $C_1$-$C_6$ alkyl group;
n is 0 or an integer 1, 2, 3, 4 or 5;
each $R^3$ independently represents halogen, hydroxyl, cyano, $C_1$-$C_3$ alkyl, $C_1$-$C_3$ haloalkyl, $C_1$-$C_3$ hydroxyalkyl, $C_1$-$C_3$ alkoxy, $C_1$-$C_3$ haloalkoxy, $C_2$-$C_4$ alkenyl, $C_1$-$C_3$ alkylcarbonyloxy, $C_1$-$C_3$ alkoxycarbonyl, —$NR^{10}R^{11}$, —$CONR^{12}R^{13}$, $C_3$-$C_6$ cycloalkyl, $C_3$-$C_6$ cycloalkyloxy, $C_3$-$C_6$ cycloalkylmethyl or a 5- to 6-membered heteroaryl group, the heteroaryl group being optionally substituted by at least one substituent selected from $C_1$-$C_6$ alkyl, $C_1$-$C_6$ alkoxy and $C_1$-$C_6$ haloalkoxy;

$R^4$ and $R^5$ each independently represent a hydrogen atom or a $C_1$-$C_3$ alkyl or $C_3$-$C_6$ cycloalkyl group, or $R^4$ and $R^5$ may together with the nitrogen atom to which they are attached form a 4- to 7-membered saturated heterocyclic ring optionally substituted by at least one substituent selected from halogen and hydroxyl;

$R^6$ and $R^7$ each independently represent a hydrogen atom or a $C_1$-$C_3$ alkyl or $C_3$-$C_6$ cycloalkyl group, or $R^6$ and $R^7$ may together with the nitrogen atom to which they are attached form a 4- to 7-membered saturated heterocyclic ring optionally substituted by at least one substituent selected from halogen and hydroxyl;

$R^8$ represents a hydrogen or halogen atom or a hydroxyl group;

$R^9$ represents a $C_1$-$C_6$ alkyl, $C_1$-$C_6$ alkoxy, benzyloxy, $C_6$-$C_{10}$ aryl, or heteroaryl group;

$R^{10}$ and $R^{11}$ each independently represent a hydrogen atom or a $C_1$-$C_3$ alkyl or $C_3$-$C_6$ cycloalkyl group, or $R^{10}$ and $R^{11}$ may together with the nitrogen atom to which they are attached form a 4- to 7-membered saturated heterocyclic ring optionally substituted by at least one substituent selected from halogen and hydroxyl; and $R^{12}$ and $R^{13}$ each independently represent a hydrogen atom or a $C_1$-$C_3$ alkyl or $C_3$-$C_6$ cycloalkyl group, or $R^{12}$ and $R^{13}$ may together with the nitrogen atom to which they are attached form a 4- to 7-membered saturated heterocyclic ring optionally substituted by at least one substituent selected from halogen and hydroxyl;

or a pharmaceutically acceptable salt thereof.

In the context of the present specification, unless otherwise stated, an "alkyl" substituent group or an alkyl moiety in a substituent group may be linear or branched. Examples of $C_1$-$C_8$ alkyl groups/moieties include methyl, ethyl, propyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, n-butyl, isobutyl, tert-butyl, n-pentyl, isopentyl, neopentyl, n-hexyl, n-heptyl and n-octyl.

An "alkenyl" substituent or an alkenyl moiety in a substituent group refers to an unsaturated alkyl group having one or more double bonds. Examples of $C_2$-$C_6$ alkenyl groups/moieties include ethenyl, propenyl, 1-butenyl, 2-butenyl, 1-pentenyl, 1-hexenyl, 1,3-butadienyl, 1,3-pentadienyl, 1,4-pentadienyl and 1,4-hexadienyl.

A "cycloalkyl" substituent group/moiety is a saturated hydrocarbyl ring containing, for example, from 3 to 8 carbon atoms, examples of which include cyclopropyl, cyclobutyl, cyclopentyl and cyclohexyl.

A "haloalkyl" or "haloalkoxy" substituent group/moiety will comprise at least one halogen atom, e.g. one, two, three, four or five halogen atoms. Examples of $C_1$-$C_6$ haloalkyl and $C_1$-$C_6$ haloalkoxy groups/moieties include fluoromethyl, difluoromethyl, trifluoromethyl, 2,2,2-trifluoroethyl, pentafluoroethyl, fluoromethoxy, difluoromethoxy and trifluoromethoxy.

It will be understood that if $R^4$ and $R^5$ together with the nitrogen atom to which they are attached form a 4- to 7-membered saturated heterocyclic ring, the heterocyclic ring may contain one or more (e.g. one or two) further ring heteroatoms (e.g. nitrogen, oxygen or sulphur atoms) in addition to the nitrogen atom to which $R^4$ and $R^5$ are attached. However, it will be appeciated that the invention does not encompass any unstable ring structures or any O—O, O—S or S—S bonds. If a substituent is present on the ring, it may be attached to any suitable ring atom. Examples of such heterocyclic rings include azetidinyl, pyrrolidinyl, piperidinyl, morpholinyl, thiomorpholinyl, piperazinyl, 1,4-azathianyl, azepanyl and 1,4-oxaazepanyl moieties. Similar comments apply with respect to $R^6$ and $R^7$, $R^{10}$ and $R^{11}$ and $R^{12}$ and $R^{13}$ when they form a 4- to 7-membered saturated heterocyclic ring.

A "$C_6$-$C_{10}$ aryl" group refers to a group derived from an aromatic hydrocarbon containing from five to ten carbon atoms. The aryl group may be monocyclic or polycyclic (e.g. bicyclic) in which the two or more rings are fused, examples of which include phenyl, 1-naphthyl and 2-naphthyl. Also included within the scope of the term "aryl", as it is used herein, is a group in which an aromatic ring is fused to one or more non-aromatic rings as exemplified by indanyl and tetrahydronaphthyl. An aryl group may be bonded at any suitable ring atom.

A "heteroaryl" group is a 5- to 10-membered aryl group in which from 1 to 4 ring carbon atoms are replaced by heteroatoms independently selected from nitrogen, oxygen and sulphur. The heteroaryl group can be bonded at any suitable ring atom (i.e. at any carbon or heteroatom of the heteroaryl ring system). Examples of heteroaryl groups include the following:

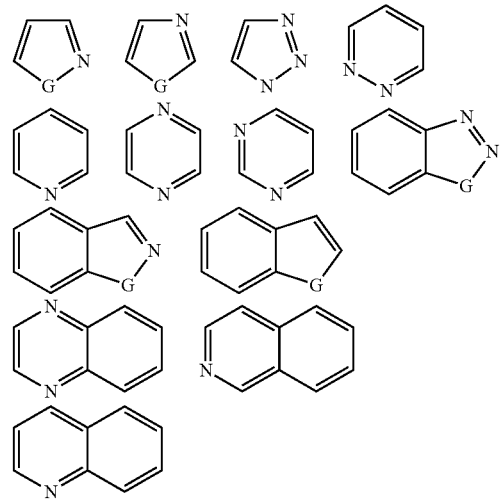

When any chemical moiety or group in formula (I) is described as being optionally substituted, it will be appreciated that the moiety or group may be either unsubstituted or substituted by one or more of the specified substituents. It will be appreciated that the number and nature of substituents will be selected so as to avoid sterically undesirable combinations.

$R^1$ represents an 8-, 9- or 10-membered fused bicyclic heteroaromatic group optionally substituted by at least one substituent, e.g. one, two, three or four substituents, independently selected from halogen (e.g. fluorine, chlorine, bromine or iodine), cyano, hydroxyl, $C_3$-$C_6$ cycloalkyl (cyclopropyl, cyclobutyl, cyclopentyl or cyclohexyl), $C_1$, $C_2$ or $C_3$ alkyl, $C_1$, $C_2$ or $C_3$ alkoxy, $C_1$, $C_2$ or $C_3$ alkoxycarbonyl, $C_1$, $C_2$ or $C_3$ alkoxycarbonylamino, $C_1$, $C_2$ or $C_3$ haloalkoxy, —NR$^4$R$^5$, $C_3$-$C_6$ cycloalkylamino (cyclopropylamino, cyclobutylamino, cyclopentylamino or cyclohexylamino), $C_1$, $C_2$ or $C_3$ alkylcarbonyloxy, $C_1$, $C_2$ or $C_3$ alkylcarbonylamino, sulphonamido, $C_1$, $C_2$ or $C_3$ alkylsulphonyl, $C_1$, $C_2$ or $C_3$ alkylsulphonylamino and —C(O)NR$^6$R$^7$.

The fused bicyclic heteroaromatic group in R$^1$ comprises one or more, e.g. one, two, three or four, ring heteroatoms independently selected from nitrogen, oxygen and sulphur. Examples of such heteroaromatic groups include quinoxalinyl, benzothiazolyl, benzoxazolyl, quinolinyl, quinazolinyl, indolyl, 7-azaindolyl, indolizinyl, indazolyl, imidazo[1,2-a]pyridinyl, 1,3-thiazolo[5,4-b]pyridinyl, 1,3-thiazolo[5,4-c]pyridinyl and 7H-pyrrolo[2,3-d]pyrimidinyl.

In an embodiment of the invention, R$^1$ represents a 9- or 10-membered fused bicyclic heteroaromatic group containing one, two or three ring heteroatoms independently selected from nitrogen, oxygen and sulphur (such as quinoxalinyl, benzothiazolyl, benzoxazolyl, quinolinyl, 1,3-thiazolo[5,4-b]pyridinyl, 1,3-thiazolo[5,4-c]pyridinyl and quinazolinyl), the heteroaromatic group being optionally substituted by at least one substituent, e.g. one, two, three or four substituents, independently selected from halogen (e.g. fluorine, chlorine, bromine or iodine), cyano, hydroxyl, $C_3$-$C_6$ cycloalkyl (cyclopropyl, cyclobutyl, cyclopentyl or cyclohexyl), $C_1$, $C_2$ or $C_3$ alkyl, $C_1$, $C_2$ or $C_3$ alkoxy, $C_1$, $C_2$ or $C_3$ alkoxycarbonyl, $C_1$, $C_2$ or $C_3$ alkoxycarbonylamino, $C_1$, $C_2$ or $C_3$ haloalkoxy, —NR$^4$R$^5$, $C_3$-$C_6$ cycloalkylamino (cyclopropylamino, cyclobutylamino, cyclopentylamino or cyclohexylamino), $C_1$, $C_2$ or $C_3$ alkylcarbonyloxy, $C_1$, $C_2$ or $C_3$ alkylcarbonylamino, sulphonamido, $C_1$, $C_2$ or $C_3$ alkylsulphonyl, $C_1$, $C_2$ or $C_3$ alkylsulphonylamino and —C(O)NR$^6$R$^7$.

In another embodiment, R$^1$ represents a 9- or 10-membered fused bicyclic heteroaromatic group containing one, two or three ring heteroatoms independently selected from nitrogen, oxygen and sulphur (such as quinoxalinyl, benzothiazolyl, benzoxazolyl, quinolinyl, 1,3-thiazolo[5,4-b]pyridinyl, 1,3-thiazolo[5,4-c]pyridinyl and quinazolinyl), the heteroaromatic group being optionally substituted by one, two, three or four substituents independently selected from halogen (e.g. fluorine, chlorine, bromine or iodine), cyano, hydroxyl, $C_5$-$C_6$ cycloalkyl, $C_1$, $C_2$ or $C_3$ alkyl, $C_1$, $C_2$ or $C_3$ alkoxy, $C_1$, $C_2$ or $C_3$ alkoxycarbonyl, $C_1$, $C_2$ or $C_3$ alkoxycarbonylamino, $C_1$, $C_2$ or $C_3$ haloalkoxy, —NR$^4$R$^5$, $C_5$-$C_6$ cycloalkylamino, $C_1$, $C_2$ or $C_3$ alkylcarbonyloxy, $C_1$, $C_2$ or $C_3$ alkylcarbonylamino, sulphonamido, $C_1$, $C_2$ or $C_3$ alkylsulphonyl, $C_1$, $C_2$ or $C_3$ alkylsulphonylamino and —C(O)NR$^6$R$^7$.

In a further embodiment, R$^1$ represents a 9- or 10-membered fused bicyclic heteroaromatic group containing one, two or three ring heteroatoms independently selected from nitrogen, oxygen and sulphur (such as quinoxalinyl, benzothiazolyl, benzoxazolyl, quinolinyl, 1,3-thiazolo[5,4-b]pyridinyl, 1,3-thiazolo[5,4-c]pyridinyl and quinazolinyl), the heteroaromatic group being optionally substituted by one or more (e.g. one or two) halogen, particularly fluorine or chlorine, atoms.

In a still further embodiment, R$^1$ represents any one of the following moieties or is selected from a group containing two or more of such moieties in any combination:
(i) quinoxalin-2-yl,
(ii) 6-fluoro-1,3-benzothiazol-2-yl,
(iii) 5-fluoro-1,3-benzothiazol-2-yl,
(iv) 1,3-benzothiazol-2-yl,
(v) 5-chloro-1,3-benzothiazol-2-yl,
(vi) 1,3-benzoxazol-2-yl,
(vii) 6-chloro-1,3-benzothiazol-2-yl,
(viii) quinolin-2-yl,
(ix) quinazolin-2-yl,
(x) 6-fluoro-1,3-benzoxazol-2-yl,
(xi) 5-fluoro-1,3-benzoxazol-2-yl,
(xii) 4,6-difluoro-1,3-benzothiazol-2-yl,
(xiii) 4-fluoro-1,3-benzothiazol-2-yl,
(xiv) 1,3-thiazolo[5,4-b]pyridin-2-yl,
(xv) 1,3-thiazolo[5,4-c]pyridin-2-yl, and
(xvi) 7-chloro-1,3-thiazolo[5,4-b]pyridin-2-yl.

In an embodiment of the invention, L represents CH$_2$ or NH.

In a further embodiment, L represents NH.

R$^a$ and R$^b$ each independently represent a hydrogen atom or a $C_1$, $C_2$ or $C_3$ alkyl or $C_1$, $C_2$ or $C_3$ haloalkyl group.

In one embodiment, R$^a$ and R$^b$ each represent a hydrogen atom.

In another embodiment, one of R$^a$ and R$^b$ represents a hydrogen atom and the other of R$^a$ and R$^b$ represents a $C_1$ alkyl (i.e. methyl) or haloalkyl (e.g. trifluoromethyl) group.

In an embodiment of the invention, X represents CHR$^8$.

R$^8$ represents a hydrogen or halogen (e.g. fluorine, chlorine, bromine or iodine) atom or a hydroxyl group.

In one embodiment, R$^8$ represents a hydrogen or fluorine atom or a hydroxyl group.

In another embodiment, R$^8$ represents a hydrogen atom.

R$^2$ represents a hydrogen atom or a $C_1$-$C_6$, or $C_1$-$C_4$, or $C_1$-$C_2$ alkyl group.

In one embodiment, R$^2$ represents a hydrogen atom or a methyl group.

In an embodiment of the invention, n represents an integer 1 or 2.

The substituent(s) R$^3$ is/are preferably attached to the phenyl ring in the 2-, 3-, 5- and/or 6-positions relative to the point of attachment of the amide moiety, —NR$^2$C(O)— as illustrated in the diagram below in which the above-mentioned points of attachment are marked with an asterisk (*):

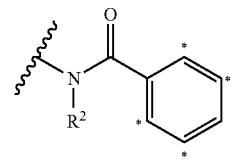

If n is 1, the R$^3$ substituent is preferably attached at the 2-position of the phenyl ring. If n is 2, the R$^3$ substituents are preferably attached to different ring carbon atoms, for example, in the 2- and 5-positions or the 2- and 6-positions of the phenyl ring.

If present, each R$^3$ independently represents halogen (e.g. fluorine, chlorine, bromine or iodine), hydroxyl, cyano, $C_1$, $C_2$ or $C_3$ alkyl, $C_1$, $C_2$ or $C_3$ haloalkyl, $C_1$, $C_2$ or $C_3$ hydroxyalkyl, $C_1$, $C_2$ or $C_3$ alkoxy, $C_1$, $C_2$ or $C_3$ haloalkoxy, $C_2$-$C_4$ alkenyl, $C_1$, $C_2$ or $C_3$ alkylcarbonyloxy, $C_1$, $C_2$ or $C_3$ alkoxycarbonyl, —NR$^{10}$R$^{11}$, —CONR$^{12}$R$^{13}$, $C_3$-$C_6$ cycloalkyl (cyclopropyl, cyclobutyl, cyclopentyl or cyclohexyl), $C_3$-$C_6$ cycloalkyloxy (cyclopropyloxy, cyclobutyloxy, cyclopentyloxy or cyclohexyloxy), $C_3$-$C_6$ cycloalkylmethyl (cyclopropylmethyl, cyclobutylmethyl, cyclopentylmethyl or cyclohexylmethyl) or a 5- to 6-membered heteroaryl group, the heteroaryl group being optionally substituted by at least one substituent, e.g. one, two, three or four substituents, independently selected from $C_1$-$C_6$, or $C_1$-$C_4$, or $C_1$-$C_2$ alkyl, $C_1$-$C_6$, or $C_1$-$C_4$, or $C_1$-$C_2$ alkoxy and $C_1$-$C_6$, or $C_1$-$C_4$, or $C_1$-$C_2$ haloalkoxy.

The term "heteroaryl", as used in $R^3$, refers to an aromatic monocyclic heterocyclic group having a total of from 5 to 6 ring atoms, of which one, two, three or four ring atoms are heteroatoms independently selected from nitrogen, oxygen and sulphur atoms. Examples of such heteroaryl groups include pyrrolyl, imidazolyl, pyrazolyl, triazolyl, tetrazolyl, pyridinyl, pyrazinyl, pyrimidinyl, pyridazinyl, triazinyl, thienyl, furyl, furazanyl, oxazolyl, thiazolyl, oxadiazolyl, isothiazolyl, isoxazolyl, thiadiazolyl, pyranyl and tetrazinyl.

In an embodiment of the invention, each $R^3$ independently represents fluorine, chlorine, hydroxyl, cyano, $C_1$, $C_2$ or $C_3$ alkyl, $C_1$, $C_2$ or $C_3$ haloalkyl, $C_1$, $C_2$ or $C_3$ hydroxyalkyl, $C_1$, $C_2$ or $C_3$ alkoxy, $C_1$, $C_2$ or $C_3$ haloalkoxy, $C_2$-$C_4$ alkenyl, $C_1$, $C_2$ or $C_3$ alkylcarbonyloxy, $C_1$, $C_2$ or $C_3$ alkoxycarbonyl, —$NR^{10}R^{11}$, —$CONR^{12}R^{13}$, $C_3$-$C_5$ cycloalkyl, $C_3$-$C_5$ cycloalkyloxy, $C_3$-$C_5$ cycloalkylmethyl or a 5- to 6-membered heteroaryl group (such as triazolyl, pyrazolyl, oxadiazolyl, pyrimidinyl and imidazolyl), the heteroaryl group being optionally substituted by at least one substituent, e.g. one, two, three or four substituents, independently selected from $C_1$-$C_6$, or $C_1$-$C_4$, or $C_1$-$C_2$ alkyl, $C_1$-$C_6$, or $C_1$-$C_4$, or $C_1$-$C_2$ alkoxy and $C_1$-$C_6$, or $C_1$-$C_4$, or $C_1$-$C_2$ haloalkoxy.

In another embodiment, each $R^3$ independently represents fluorine, chlorine, $C_1$, $C_2$ or $C_3$ alkyl, $C_1$, $C_2$ or $C_3$ haloalkyl, $C_1$, $C_2$ or $C_3$ alkoxy, $C_1$, $C_2$ or $C_3$ haloalkoxy, cyclopropyl or a 5- to 6-membered heteroaryl group (such as triazolyl, pyrazolyl, oxadiazolyl, pyrimidinyl and imidazolyl), the heteroaryl group being optionally substituted by at least one substituent, e.g. one, two, three or four substituents, independently selected from $C_1$-$C_2$ alkyl, $C_1$-$C_2$ alkoxy and $C_1$-$C_2$ haloalkoxy.

In yet another embodiment, each $R^3$ independently represents fluorine, chlorine, $C_1$-$C_2$ alkyl, $C_1$-$C_2$ alkoxy, $C_1$-$C_2$ haloalkoxy, cyclopropyl or a 5- to 6-membered heteroaryl group (such as triazolyl, pyrazolyl, oxadiazolyl, pyrimidinyl and imidazolyl), the heteroaryl group being optionally substituted by one or two substituents independently selected from $C_1$-$C_2$ alkyl, $C_1$-$C_2$ alkoxy and $C_1$-$C_2$ haloalkoxy.

In a still further embodiment, each $R^3$ independently represents any one of the following moieties or is independently selected from a group containing two or more of such moieties in any combination:
(i) methyl,
(ii) methoxy,
(iii) ethoxy,
(iv) triazolyl (e.g. 1,2,3-triazol-2-yl, 1,2,3-triazol-1-yl or 1,2,4-triazol-1-yl),
(v) pyrazolyl (e.g. pyrazol-1-yl),
(vi) fluorine,
(vii) chlorine,
(viii) oxadiazolyl (e.g. 1,2,4-oxadiazol-2-yl or 1,3,4-oxadiazol-2-yl),
(ix) 3-methyl-1,2,4-oxadiazol-5-yl,
(x) 5-methyl-1,3,4-oxadiazol-2-yl,
(xi) pyrimidinyl (e.g. pyrimidin-2-yl),
(xii) imidazolyl (e.g. imidazol-1-yl),
(xiii) difluoromethoxy, and
(xiv) cyclopropyl.

$R^4$ and $R^5$ each independently represent a hydrogen atom or a $C_1$, $C_2$ or $C_3$ alkyl or $C_3$-$C_6$ cycloalkyl (cyclopropyl, cyclobutyl, cyclopentyl or cyclohexyl) group, or $R^4$ and $R^5$ may together with the nitrogen atom to which they are attached form a 4-, 5-, 6- or 7-membered saturated heterocyclic ring optionally substituted by at least one substituent, e.g. one or two substituents, independently selected from halogen (e.g. fluorine, chlorine, bromine or iodine) and hydroxyl.

In one aspect, the saturated heterocyclic ring may contain a single ring heteroatom (being the nitrogen atom to which $R^4$ and $R^5$ are attached).

In an alternative aspect, the saturated heterocyclic ring may contain a second ring heteroatom selected from a nitrogen or oxygen atom.

In one embodiment, $R^4$ and $R^5$ each independently represent a hydrogen atom or a $C_1$, $C_2$ or $C_3$ alkyl or $C_3$-$C_6$ or $C_3$-$C_5$ or $C_5$-$C_6$, particularly cyclopropyl, group, or $R^4$ and $R^5$ may together with the nitrogen atom to which they are attached form a 4- or 5-membered saturated heterocyclic ring optionally substituted by one or two substituents independently selected from fluorine, chlorine, bromine and hydroxyl.

In a second embodiment, $R^4$ and $R^5$ each represent a hydrogen atom.

In a third embodiment, $R^4$ and $R^5$ each represent a $C_1$-$C_3$ alkyl group.

In a fourth embodiment, one of $R^4$ and $R^5$ represents a hydrogen atom and the other of $R^4$ and $R^5$ represents a $C_1$-$C_3$ alkyl group.

In a fifth embodiment, one of $R^4$ and $R^5$ represents a cyclopropyl group and the other of $R^4$ and $R^5$ represents a $C_1$-$C_3$ alkyl group.

In a sixth embodiment, $R^4$ and $R^5$ together with the nitrogen atom to which they are attached form an azetidinyl or pyrrolidinyl ring optionally substituted by one or two substituents independently selected from fluorine and hydroxyl.

$R^6$ and $R^7$ are defined as for $R^4$ and $R^5$ above.

$R^9$ represents a $C_1$-$C_6$, or $C_1$-$C_4$, or $C_1$-$C_2$ alkyl, $C_1$-$C_6$, or $C_1$-$C_4$, or $C_1$-$C_2$ alkoxy, benzyloxy, $C_6$-$C_{10}$ aryl, or heteroaryl group.

In one embodiment, $R^9$ represents a $C_1$-$C_2$ alkyl, $C_1$-$C_2$ alkoxy or benzyloxy group.

In another embodiment, $R^9$ represents a $C_1$-$C_2$ alkoxy or benzyloxy group.

$R^{10}$ and $R^{11}$ are defined as for $R^4$ and $R^5$ above.
$R^{12}$ and $R^{13}$ are defined as for $R^4$ and $R^5$ above.

In a preferred embodiment of the invention,
$R^1$ represents a 9- to 10-membered fused bicyclic heteroaromatic group optionally substituted by at least one halogen atom;
L represents $CH_2$, NH or $N(CH_3)$;
X represents $CHR^8$, O or $NC(O)R^9$;
$R^2$ represents hydrogen or methyl;
n is 1 or 2;
each $R^3$ independently represents fluorine, chlorine, $C_1$-$C_2$ alkyl, $C_1$-$C_2$ alkoxy, $C_1$-$C_2$ haloalkoxy, cyclopropyl or a 5- to 6-membered heteroaryl group, the heteroaryl group being optionally substituted by at least one $C_1$-$C_2$ alkyl group;
$R^8$ represents a hydrogen or halogen atom or a hydroxyl group; and
$R^9$ represents a $C_1$-$C_2$ alkoxy or benzyloxy group.

In another preferred embodiment of the invention:
$R^1$ represents a benzothiazolyl group optionally substituted by at least one halogen atom (e.g. 6-fluoro-1,3-benzothiazol-2-yl or 6-chloro-1,3-benzothiazol-2-yl);
L represents NH;
X represents $CHR^8$;
$R^2$ represents a hydrogen atom;
n is 1 or 2;

each R³ independently represents fluorine, chlorine, C₁-C₂ alkyl, C₁-C₂ alkoxy, C₁-C₂ haloalkoxy, cyclopropyl or a 5- to 6-membered heteroaryl group, the heteroaryl group being optionally substituted by at least one C₁-C₂ alkyl group; and R⁸ represents a hydrogen atom.

In still another preferred embodiment:

R¹ represents a benzothiazolyl group optionally substituted by at least one halogen atom (e.g. 6-fluoro-1,3-benzothiazol-2-yl or 6-chloro-1,3-benzothiazol-2-yl);

L represents NH;

X represents CHR⁸;

R² represents a hydrogen atom;

n is 1 or 2;

each R³ independently represents C₁-C₂ alkoxy or a 5- to 6-membered heteroaryl group (e.g. triazolyl such as 1,2,3-triazol-2-yl), the heteroaryl group being optionally substituted by at least one C₁-C₂ alkyl group; and R⁸ represents a hydrogen atom.

Examples of compounds of the invention include:

2,6-Dimethoxy-N-[(1S,2R)-2-[(quinoxalin-2-yl)amino]cyclopentyl]-benzamide,
2,6-Dimethoxy-N-((1S,2S)-2-(quinoxalin-2-ylamino)cyclopentyl)benzamide,
2,6-Dimethoxy-N-((1R,2S)-2-(quinoxalin-2-ylamino)cyclopentyl)benzamide,
2,6-Dimethoxy-N-((1R,2R)-2-(quinoxalin-2-ylamino)cyclopentyl)benzamide,
N-[(1S,2S)-2-[(6-Fluoro-1,3-benzothiazol-2-yl)amino]cyclopentyl]-2,6-dimethoxybenzamide,
N-[(1R,2S)-2-[(6-Fluoro-1,3-benzothiazol-2-yl)amino]cyclopentyl]-2,6-dimethoxybenzamide,
N-[(1R,2R)-2-[(6-Fluoro-1,3-benzothiazol-2-yl)amino]cyclopentyl]-2,6-dimethoxybenzamide,
N-[(1S,2R)-2-[(6-Fluoro-1,3-benzothiazol-2-yl)amino]cyclopentyl]-2,6-dimethoxybenzamide,
N-[(1S,2S)-2-[(1,3-Benzothiazol-2-yl)amino]cyclopentyl]-2,6-dimethoxybenzamide,
N-[(1S,2R)-2-[(1,3-Benzothiazol-2-yl)amino]cyclopentyl]-2,6-dimethoxybenzamide,
N-[(1R,2S)-2-[(1,3-Benzothiazol-2-yl)amino]cyclopentyl]-2,6-dimethoxybenzamide,
N-[(1R,2R)-2-[(1,3-Benzothiazol-2-yl)amino]cyclopentyl]-2,6-dimethoxybenzamide,
N-[(1S,2S)-2-[(5-Chloro-1,3-benzothiazol-2-yl)amino]cyclopentyl]-2,6-dimethoxybenzamide,
N-[(1S,2R)-2-[(5-Chloro-1,3-benzothiazol-2-yl)amino]cyclopentyl]-2,6-dimethoxybenzamide,
N-[(1R,2S)-2-[(5-Chloro-1,3-benzothiazol-2-yl)amino]cyclopentyl]-2,6-dimethoxybenzamide,
N-[(1R,2R)-2-[(5-Chloro-1,3-benzothiazol-2-yl)amino]cyclopentyl]-2,6-dimethoxybenzamide,
N-[(1S,2R)-2-[(1,3-Benzoxazol-2-yl)amino]cyclopentyl]-2,6-dimethoxybenzamide,
N-[(1S,2S)-2-[(1,3-Benzoxazol-2-yl)amino]cyclopentyl]-2,6-dimethoxybenzamide,
N-[(1R,2R)-2-[(1,3-Benzoxazol-2-yl)amino]cyclopentyl]-2,6-dimethoxy-benzamide,
N-[(1R,2S)-2-[(1,3-Benzoxazol-2-yl)amino]cyclopentyl]-2,6-dimethoxy-benzamide,
N-[(1S,2S)-2-[(6-Fluoro-1,3-benzothiazol-2-yl)(methyl)amino]cyclopentyl]-2,6-dimethoxybenzamide,
N-[(1S,2R)-2-[(6-Fluoro-1,3-benzothiazol-2-yl)(methyl)amino]cyclopentyl]-2,6-dimethoxybenzamide,
N-[(1R,2S)-2-[(6-Fluoro-1,3-benzothiazol-2-yl)(methyl)amino]cyclopentyl]-2,6-dimethoxybenzamide,
N-[(1R,2R)-2-[(6-Fluoro-1,3-benzothiazol-2-yl)(methyl)amino]cyclopentyl]-2,6-dimethoxybenzamide,
N-[(1S,2S)-2-[(6-Chloro-1,3-benzothiazol-2-yl)amino]cyclopentyl]-2,6-dimethoxy-benzamide,
N-[(1R,2S)-2-[(6-Chloro-1,3-benzothiazol-2-yl)amino]cyclopentyl]-2,6-dimethoxybenzamide,
N-[(1R,2R)-2-[(6-Chloro-1,3-benzothiazol-2-yl)amino]cyclopentyl]-2,6-dimethoxybenzamide,
N-[(1S,2R)-2-[(6-Chloro-1,3-benzothiazol-2-yl)amino]cyclopentyl]-2,6-dimethoxybenzamide,
N-[(1S,2S)-2-[(6-Fluoro-1,3-benzothiazol-2-yl)amino]cyclopentyl]-5-methyl-2-(2H-1,2,3-triazol-2-yl)benzamide,
N-[(1S,2R)-2-[(6-Fluoro-1,3-benzothiazol-2-yl)amino]cyclopentyl]-5-methyl-2-(2H-1,2,3-triazol-2-yl)benzamide,
N-[(1R,2S)-2-[(6-Fluoro-1,3-benzothiazol-2-yl)amino]cyclopentyl]-5-methyl-2-(2H-1,2,3-triazol-2-yl)benzamide,
N-[(1R,2R)-2-[(6-Fluoro-1,3-benzothiazol-2-yl)amino]cyclopentyl]-5-methyl-2-(2H-1,2,3-triazol-2-yl)benzamide,
N-[(1R,2S)-2-[(1,3-Benzoxazol-2-yl)amino]cyclopentyl]-2,6-diethoxy-benzamide,
N-[(1S,2R)-2-[(1,3-Benzoxazol-2-yl)amino]cyclopentyl]-2,6-diethoxy-benzamide,
N-[(1S,2S)-2-[(1,3-Benzoxazol-2-yl)amino]cyclopentyl]-2,6-diethoxy-benzamide,
N-[(1R,2R)-2-[(1,3-Benzoxazol-2-yl)amino]cyclopentyl]-2,6-diethoxy-benzamide,
N-[(1S,2S)-2-[(1,3-Benzothiazol-2-yl)amino]cyclopentyl]-5-methyl-2-(2H-1,2,3-triazol-2-yl)benzamide,
N-[(1S,2R)-2-[(1,3-Benzothiazol-2-yl)amino]cyclopentyl]-5-methyl-2-(2H-1,2,3-triazol-2-yl)benzamide,
N-[(1R,2S)-2-[(1,3-Benzothiazol-2-yl)amino]cyclopentyl]-5-methyl-2-(2H-1,2,3-triazol-2-yl)benzamide,
N-[(1R,2R)-2-[(1,3-Benzothiazol-2-yl)amino]cyclopentyl]-5-methyl-2-(2H-1,2,3-triazol-2-yl)benzamide,
5-Methyl-N-[(1S,2S)-2-[(quinolin-2-yl)amino]cyclopentyl]-2-(2H-1,2,3-triazol-2-yl)benzamide,
5-Methyl-N-[(1S,2R)-2-[(quinolin-2-yl)amino]cyclopentyl]-2-(2H-1,2,3-triazol-2-yl)benzamide,
5-Methyl-N-[(1R,2S)-2-[(quinolin-2-yl)amino]cyclopentyl]-2-(2H-1,2,3-triazol-2-yl)benzamide,
5-Methyl-N-[(1R,2R)-2-[(quinolin-2-yl)amino]cyclopentyl]-2-(2H-1,2,3-triazol-2-yl)benzamide,
5-Methyl-N-((1S, 2S)-2-(quinoxalin-2-ylamino)cyclopentyl)-2-(2H-1,2,3-triazol-2-yl)benzamide,
5-Methyl-N-((1S, 2R)-2-(quinoxalin-2-ylamino)cyclopentyl)-2-(2H-1,2,3-triazol-2-yl)benzamide,
5-Methyl-N-((1R,2S)-2-(quinoxalin-2-ylamino)cyclopentyl)-2-(2H-1,2,3-triazol-2-yl)benzamide,
5-Methyl-N-((1R,2R)-2-(quinoxalin-2-ylamino)cyclopentyl)-2-(2H-1,2,3-triazol-2-yl)benzamide,
Benzyl cis-3-[(6-chloro-1,3-benzothiazol-2-yl)amino]-4-[(2,6-dimethoxybenzene)amido]pyrrolidine-1-carboxylate,
Ethyl cis-3-[(6-Chloro-1,3-benzothiazol-2-yl)amino]-4-[(2,6-dimethoxy-benzene)amido]pyrrolidine-1-carboxylate,
N-{cis-4-[(6-Chloro-1,3-benzothiazol-2-yl)amino]oxolan-3-yl}-2,6-dimethoxybenzamide,
N-[(1S,2R,4R)-2-[(6-Chloro-1,3-benzothiazol-2-yl)amino]-4-hydroxycyclopentyl]-2,6-dimethoxybenzamide,
N-[(1S,2R)-2-[(6-Chloro-1,3-benzothiazol-2-yl)amino]-4-fluorocyclopentyl]-2,6-dimethoxybenzamide,
N-[(1R,2S)-2-[(6-Chloro-1,3-benzothiazol-2-yl)amino]-4-fluorocyclopentyl]-2,6-dimethoxybenzamide,
N-[(1R,2R)-2-[(6-Chloro-1,3-benzothiazol-2-yl)amino]-4-fluorocyclopentyl]-2,6-dimethoxybenzamide,
N-[(1S,2S)-2-[(6-Chloro-1,3-benzothiazol-2-yl)amino]-4-fluorocyclopentyl]-2,6-dimethoxybenzamide, 5-Methyl-N-[2-(quinolin-2-ylmethyl)cyclopentyl]-2-(2H-1,2,3-triazol-2-yl)benzamide,
5-Methyl-N-[2-(quinolin-2-ylmethyl)cyclopentyl]-2-(2H-1,2,3-triazol-2-yl)benzamide (an isomer substantially as described herein and with reference to Example 61),
5-Methyl-N-[2-(quinolin-2-ylmethyl)cyclopentyl]-2-(2H-1,2,3-triazol-2-yl)benzamide (an isomer substantially as described herein and with reference to Example 62),
2-Ethoxy-5-methyl-N-[2-(quinolin-2-ylmethyl)cyclopentyl]-benzamide,
2,6-Dimethoxy-N-[2-(quinolin-2-ylmethyl)cyclopentyl]benzamide,
2,6-Diethoxy-N-(2-(quinolin-2-ylmethyl)cyclopentyl)benzamide,
N-{2-[(6-Chloro-1,3-benzothiazol-2-yl)methyl]cyclopentyl}-2,6-dimethoxybenzamide,
N-{2-[(6-Chloro-1,3-benzothiazol-2-yl)methyl]cyclopentyl}-5-methyl-2-(2H-1,2,3-triazol-2-yl)benzamide,
N-[(1S,2S)-2-[(6-Fluoro-1,3-benzothiazol-2-yl)amino]cyclopentyl]-2,6-dimethoxy-N-methylbenzamide,
N-[(1S,2R)-2-[(6-Fluoro-1,3-benzothiazol-2-yl)amino]cyclopentyl]-2,6-dimethoxy-N-methylbenzamide,
N-[(1R,2S)-2-[(6-Fluoro-1,3-benzothiazol-2-yl)amino]cyclopentyl]-2,6-dimethoxy-N-methylbenzamide,
N-[(1R,2R)-2-[(6-Fluoro-1,3-benzothiazol-2-yl)amino]cyclopentyl]-2,6-dimethoxy-N-methylbenzamide,
N-[(1S,2S)-2-[(6-Fluoro-1,3-benzothiazol-2-yl)amino]cyclopentyl]-2-(1H-pyrazol-1-yl)benzamide,
N-[(1S,2R)-2-[(6-Fluoro-1,3-benzothiazol-2-yl)amino]cyclopentyl]-2-(1H-pyrazol-1-yl)benzamide,
N-[(1R,2S)-2-[(6-Fluoro-1,3-benzothiazol-2-yl)amino]cyclopentyl]-2-(1H-pyrazol-1-yl)benzamide,
N-[(1R,2R)-2-[(6-Fluoro-1,3-benzothiazol-2-yl)amino]cyclopentyl]-2-(1H-pyrazol-1-yl)benzamide,
5-Fluoro-N-[(1S,2S)-2-[(6-fluoro-1,3-benzothiazol-2-yl)amino]cyclopentyl]-2-(2H-1,2,3-triazol-2-yl)benzamide,
5-Fluoro-N-[(1S,2R)-2-[(6-fluoro-1,3-benzothiazol-2-yl)amino]cyclopentyl]-2-(2H-1,2,3-triazol-2-yl)benzamide,
5-Fluoro-N-[(1R,2S)-2-[(6-fluoro-1,3-benzothiazol-2-yl)amino]cyclopentyl]-2-(2H-1,2,3-triazol-2-yl)benzamide,
5-Fluoro-N-[(1R,2R)-2-[(6-fluoro-1,3-benzothiazol-2-yl)amino]cyclopentyl]-2-(2H-1,2,3-triazol-2-yl)benzamide,
2-Chloro-N-[(1S,2S)-2-[(6-fluoro-1,3-benzothiazol-2-yl)amino]cyclopentyl]benzamide,
2-Chloro-N-[(1S,2R)-2-[(6-fluoro-1,3-benzothiazol-2-yl)amino]cyclopentyl]benzamide,
2-Chloro-N-[(1R,2S)-2-[(6-fluoro-1,3-benzothiazol-2-yl)amino]cyclopentyl]benzamide,
2-Chloro-N-[(1R,2R)-2-[(6-fluoro-1,3-benzothiazol-2-yl)amino]cyclopentyl]benzamide,
N-[(1S,2S)-2-[(6-Fluoro-1,3-benzothiazol-2-yl)amino]cyclopentyl]-5-methyl-2-(1H-1,2,3-triazol-1-yl)benzamide,
N-[(1S,2R)-2-[(6-Fluoro-1,3-benzothiazol-2-yl)amino]cyclopentyl]-5-methyl-2-(1H-1,2,3-triazol-1-yl)benzamide,
N-[(1R,2S)-2-[(6-Fluoro-1,3-benzothiazol-2-yl)amino]cyclopentyl]-5-methyl-2-(1H-1,2,3-triazol-1-yl)benzamide,
N-[(1R,2R)-2-[(6-Fluoro-1,3-benzothiazol-2-yl)amino]cyclopentyl]-5-methyl-2-(1H-1,2,3-triazol-1-yl)benzamide,
N-[(1S,2S)-2-[(6-Fluoro-1,3-benzothiazol-2-yl)amino]cyclopentyl]-2-(3-methyl-1,2,4-oxadiazol-5-yl)benzamide,
N-[(1S,2R)-2-[(6-Fluoro-1,3-benzothiazol-2-yl)amino]cyclopentyl]-2-(3-methyl-1,2,4-oxadiazol-5-yl)benzamide,
N-[(1R,2S)-2-[(6-Fluoro-1,3-benzothiazol-2-yl)amino]cyclopentyl]-2-(3-methyl-1,2,4-oxadiazol-5-yl)benzamide,
N-[(1R,2R)-2-[(6-Fluoro-1,3-benzothiazol-2-yl)amino]cyclopentyl]-2-(3-methyl-1,2,4-oxadiazol-5-yl)benzamide,
N-[(1S,2S)-2-[(6-Fluoro-1,3-benzothiazol-2-yl)amino]cyclopentyl]-2-(pyrimidin-2-yl)benzamide,
N-[(1S,2R)-2-[(6-Fluoro-1,3-benzothiazol-2-yl)amino]cyclopentyl]-2-(pyrimidin-2-yl)benzamide,
N-[(1R,2S)-2-[(6-Fluoro-1,3-benzothiazol-2-yl)amino]cyclopentyl]-2-(pyrimidin-2-yl)benzamide,
N-[(1R,2R)-2-[(6-Fluoro-1,3-benzothiazol-2-yl)amino]cyclopentyl]-2-(pyrimidin-2-yl)benzamide,
N-[(1S,2S)-2-[(6-Fluoro-1,3-benzothiazol-2-yl)amino]cyclopentyl]-2,5-dimethoxybenzamide,
N-[(1S,2R)-2-[(6-Fluoro-1,3-benzothiazol-2-yl)amino]cyclopentyl]-2,5-dimethoxybenzamide,
N-[(1R,2S)-2-[(6-Fluoro-1,3-benzothiazol-2-yl)amino]cyclopentyl]-2,5-dimethoxybenzamide,
N-[(1R,2R)-2-[(6-Fluoro-1,3-benzothiazol-2-yl)amino]cyclopentyl]-2,5-dimethoxybenzamide,
5-Fluoro-N-[(1S,2S)-2-[(6-fluoro-1,3-benzothiazol-2-yl)amino]cyclopentyl]-2-(pyrimidin-2-yl)benzamide,
5-Fluoro-N-[(1S,2R)-2-[(6-fluoro-1,3-benzothiazol-2-yl)amino]cyclopentyl]-2-(pyrimidin-2-yl)benzamide,
5-Fluoro-N-[(1R,2S)-2-[(6-fluoro-1,3-benzothiazol-2-yl)amino]cyclopentyl]-2-(pyrimidin-2-yl)benzamide,
5-Fluoro-N-[(1R,2R)-2-[(6-fluoro-1,3-benzothiazol-2-yl)amino]cyclopentyl]-2-(pyrimidin-2-yl)benzamide,
N-[(1S,2S)-2-[(6-Fluoro-1,3-benzothiazol-2-yl)amino]cyclopentyl]-2-(1H-imidazol-1-yl)benzamide,
N-[(1S,2R)-2-[(6-Fluoro-1,3-benzothiazol-2-yl)amino]cyclopentyl]-2-(1H-imidazol-1-yl)benzamide,
N-[(1R,2S)-2-[(6-Fluoro-1,3-benzothiazol-2-yl)amino]cyclopentyl]-2-(1H-imidazol-1-yl)benzamide,
N-[(1R,2R)-2-[(6-Fluoro-1,3-benzothiazol-2-yl)amino]cyclopentyl]-2-(1H-imidazol-1-yl)benzamide,
N-[(1S,2S)-2-[(6-Fluoro-1,3-benzothiazol-2-yl)amino]cyclopentyl]-2-(1H-1,2,4-triazol-1-yl)benzamide,
N-[(1S,2R)-2-[(6-Fluoro-1,3-benzothiazol-2-yl)amino]cyclopentyl]-2-(1H-1,2,4-triazol-1-yl)benzamide,
N-[(1R,2S)-2-[(6-Fluoro-1,3-benzothiazol-2-yl)amino]cyclopentyl]-2-(1H-1,2,4-triazol-1-yl)benzamide,
N-[(1R,2R)-2-[(6-Fluoro-1,3-benzothiazol-2-yl)amino]cyclopentyl]-2-(1H-1,2,4-triazol-1-yl)benzamide,
5-Fluoro-N-[(1S,2S)-2-[(6-fluoro-1,3-benzothiazol-2-yl)amino]cyclopentyl]-2-(1H-1,2,3-triazol-1-yl)benzamide,
5-Fluoro-N-[(1S,2R)-2-[(6-fluoro-1,3-benzothiazol-2-yl)amino]cyclopentyl]-2-(1H-1,2,3-triazol-1-yl)benzamide,
5-Fluoro-N-[(1R,2S)-2-[(6-fluoro-1,3-benzothiazol-2-yl)amino]cyclopentyl]-2-(1H-1,2,3-triazol-1-yl)benzamide,
5-Fluoro-N-[(1R,2R)-2-[(6-fluoro-1,3-benzothiazol-2-yl)amino]cyclopentyl]-2-(1H-1,2,3-triazol-1-yl)benzamide,
2-Fluoro-N-[(1S,2S)-2-[(6-fluoro-1,3-benzothiazol-2-yl)amino]cyclopentyl]-6-methoxybenzamide,
2-Fluoro-N-[(1S,2R)-2-[(6-fluoro-1,3-benzothiazol-2-yl)amino]cyclopentyl]-6-methoxybenzamide,
2-Fluoro-N-[(1R,2S)-2-[(6-fluoro-1,3-benzothiazol-2-yl)amino]cyclopentyl]-6-methoxybenzamide,
2-Fluoro-N-[(1R,2R)-2-[(6-fluoro-1,3-benzothiazol-2-yl)amino]cyclopentyl]-6-methoxybenzamide,
2,6-Difluoro-N-[(1S,2S)-2-[(6-fluoro-1,3-benzothiazol-2-yl)amino]-cyclopentyl]benzamide,
2,6-Difluoro-N-[(1S,2R)-2-[(6-fluoro-1,3-benzothiazol-2-yl)amino]-cyclopentyl]benzamide,
2,6-Difluoro-N-[(1R,2S)-2-[(6-fluoro-1,3-benzothiazol-2-yl)amino]-cyclopentyl]benzamide,
2,6-Difluoro-N-[(1R,2R)-2-[(6-fluoro-1,3-benzothiazol-2-yl)amino]-cyclopentyl]benzamide,
2-Fluoro-N-[(1S,2S)-2-[(6-fluoro-1,3-benzothiazol-2-yl)amino]cyclopentyl]-benzamide, 2-Fluoro-N-[(1S,2R)-2-[(6-fluoro-1,3-benzothiazol-2-yl)amino]cyclopentyl]-benzamide,
2-Fluoro-N-[(1R,2S)-2-[(6-fluoro-1,3-benzothiazol-2-yl)amino]cyclopentyl]-benzamide,
2-Fluoro-N-[(1R,2R)-2-[(6-fluoro-1,3-benzothiazol-2-yl)amino]cyclopentyl]-benzamide,
2-Ethoxy-N-[(1S,2S)-2-[(6-fluoro-1,3-benzothiazol-2-yl)amino]cyclopentyl]-benzamide,
2-Ethoxy-N-[(1S,2R)-2-[(6-fluoro-1,3-benzothiazol-2-yl)amino]cyclopentyl]-benzamide,
2-Ethoxy-N-[(1R,2S)-2-[(6-fluoro-1,3-benzothiazol-2-yl)amino]cyclopentyl]-benzamide,
2-Ethoxy-N-[(1R,2R)-2-[(6-fluoro-1,3-benzothiazol-2-yl)amino]cyclopentyl]-benzamide,
N-[(1S,2S)-2-[(6-Fluoro-1,3-benzothiazol-2-yl)amino]cyclopentyl]-2-methoxybenzamide,
N-[(1S,2R)-2-[(6-Fluoro-1,3-benzothiazol-2-yl)amino]cyclopentyl]-2-methoxybenzamide,
N-[(1R,2S)-2-[(6-Fluoro-1,3-benzothiazol-2-yl)amino]cyclopentyl]-2-methoxybenzamide,
N-[(1R,2R)-2-[(6-Fluoro-1,3-benzothiazol-2-yl)amino]cyclopentyl]-2-methoxybenzamide,
N-[(1 S,2S)-2-[(6-Fluoro-1,3-benzothiazol-2-yl)amino]cyclopentyl]-2-methylbenzamide,
N-[(1S,2R)-2-[(6-Fluoro-1,3-benzothiazol-2-yl)amino]cyclopentyl]-2-methylbenzamide,
N-[(1R,2S)-2-[(6-Fluoro-1,3-benzothiazol-2-yl)amino]cyclopentyl]-2-methylbenzamide,
N-[(1R,2R)-2-[(6-Fluoro-1,3-benzothiazol-2-yl)amino]cyclopentyl]-2-methylbenzamide,
2,6-Dichloro-N-[(1S,2S)-2-[(6-fluoro-1,3-benzothiazol-2-yl)amino]-cyclopentyl]benzamide,
2,6-Dichloro-N-[(1S,2R)-2-[(6-fluoro-1,3-benzothiazol-2-yl)amino]-cyclopentyl]benzamide,
2,6-Dichloro-N-[(1R,2S)-2-[(6-fluoro-1,3-benzothiazol-2-yl)amino]-cyclopentyl]benzamide,
2,6-Dichloro-N-[(1R,2R)-2-[(6-fluoro-1,3-benzothiazol-2-yl)amino]-cyclopentyl]benzamide,
5-Fluoro-N-[(1S,2S)-2-[(6-fluoro-1,3-benzothiazol-2-yl)amino]cyclopentyl]-2-methoxybenzamide,
5-Fluoro-N-[(1S,2R)-2-[(6-fluoro-1,3-benzothiazol-2-yl)amino]cyclopentyl]-2-methoxybenzamide,
5-Fluoro-N-[(1R,2S)-2-[(6-fluoro-1,3-benzothiazol-2-yl)amino]cyclopentyl]-2-methoxybenzamide,
5-Fluoro-N-[(1R,2R)-2-[(6-fluoro-1,3-benzothiazol-2-yl)amino]cyclopentyl]-2-methoxybenzamide,
3-Fluoro-N-[(1S,2S)-2-[(6-fluoro-1,3-benzothiazol-2-yl)amino]cyclopentyl]-2-methoxybenzamide,
3-Fluoro-N-[(1S,2R)-2-[(6-fluoro-1,3-benzothiazol-2-yl)amino]cyclopentyl]-2-methoxybenzamide,
3-Fluoro-N-[(1R,2S)-2-[(6-fluoro-1,3-benzothiazol-2-yl)amino]cyclopentyl]-2-methoxybenzamide,
3-Fluoro-N-[(1R,2R)-2-[(6-fluoro-1,3-benzothiazol-2-yl)amino]cyclopentyl]-2-methoxybenzamide,
2-(Difluoromethoxy)-N-[(1S,2S)-2-[(6-fluoro-1,3-benzothiazol-2-yl)amino]-cyclopentyl]benzamide,
2-(Difluoromethoxy)-N-[(1S,2R)-2-[(6-fluoro-1,3-benzothiazol-2-yl)amino]-cyclopentyl]benzamide,
2-(Difluoromethoxy)-N-[(1R,2S)-2-[(6-fluoro-1,3-benzothiazol-2-yl)amino]-cyclopentyl]benzamide,
2-(Difluoromethoxy)-N-[(1R,2R)-2-[(6-fluoro-1,3-benzothiazol-2-yl)amino]-cyclopentyl]benzamide,
N-[(1S,2S)-2-[(6-Fluoro-1,3-benzothiazol-2-yl)amino]cyclopentyl]-3-methoxybenzamide,
N-[(1S,2R)-2-[(6-Fluoro-1,3-benzothiazol-2-yl)amino]cyclopentyl]-3-methoxybenzamide,
N-[(1R,2S)-2-[(6-Fluoro-1,3-benzothiazol-2-yl)amino]cyclopentyl]-3-methoxybenzamide,
N-[(1R,2R)-2-[(6-Fluoro-1,3-benzothiazol-2-yl)amino]cyclopentyl]-3-methoxybenzamide,
N-[(1S,2S)-2-[(6-Fluoro-1,3-benzothiazol-2-yl)amino]cyclopentyl]-3-methylbenzamide,
N-[(1S,2R)-2-[(6-Fluoro-1,3-benzothiazol-2-yl)amino]cyclopentyl]-3-methylbenzamide,
N-[(1R,2S)-2-[(6-Fluoro-1,3-benzothiazol-2-yl)amino]cyclopentyl]-3-methylbenzamide,
N-[(1R,2R)-2-[(6-Fluoro-1,3-benzothiazol-2-yl)amino]cyclopentyl]-3-methylbenzamide,
2-Cyclopropyl-N-[(1S,2S)-2-[(6-fluoro-1,3-benzothiazol-2-yl)amino-cyclopentyl]benzamide,
2-Cyclopropyl-N-[(1S,2R)-2-[(6-fluoro-1,3-benzothiazol-2-yl)amino-cyclopentyl]benzamide,
2-Cyclopropyl-N-[(1R,2S)-2-[(6-fluoro-1,3-benzothiazol-2-yl)amino-cyclopentyl]benzamide,
2-Cyclopropyl-N-[(1R,2R)-2-[(6-fluoro-1,3-benzothiazol-2-yl)amino-cyclopentyl]benzamide,
N-[(1S,2S)-2-[(6-Fluoro-1,3-benzothiazol-2-yl)amino]cyclopentyl]-2-(2H-1,2,3-triazol-2-yl)benzamide,
N-[(1S,2R)-2-[(6-Fluoro-1,3-benzothiazol-2-yl)amino]cyclopentyl]-2-(2H-1,2,3-triazol-2-yl)benzamide,
N-[(1R,2S)-2-[(6-Fluoro-1,3-benzothiazol-2-yl)amino]cyclopentyl]-2-(2H-1,2,3-triazol-2-yl)benzamide,
N-[(1R,2R)-2-[(6-Fluoro-1,3-benzothiazol-2-yl)amino]cyclopentyl]-2-(2H-1,2,3-triazol-2-yl)benzamide,
5-Methyl-N-[(1S,2S)-2-[(quinazolin-2-yl)amino]cyclopentyl]-2-(2H-1,2,3-triazol-2-yl)benzamide,
5-Methyl-N-[(1S,2R)-2-[(quinazolin-2-yl)amino]cyclopentyl]-2-(2H-1,2,3-triazol-2-yl)benzamide,
5-Methyl-N-[(1R,2S)-2-[(quinazolin-2-yl)amino]cyclopentyl]-2-(2H-1,2,3-triazol-2-yl)benzamide,
5-Methyl-N-[(1R,2R)-2-[(quinazolin-2-yl)amino]cyclopentyl]-2-(2H-1,2,3-triazol-2-yl)benzamide,
5-Methyl-N-[2-(quinoxalin-2-ylmethyl)cyclopentyl]-2-(2H-1,2,3-triazol-2-yl)benzamide,
trans-N-{4-[(6-Fluoro-1,3-benzothiazol-2-yl)amino]oxolan-3-yl}-2,6-dimethoxybenzamide,
N-[(1S,2S)-2-[(6-Fluoro-1,3-benzoxazol-2-yl)amino]cyclopentyl]-2,6-dimethoxybenzamide,
N-[(1S,2R)-2-[(6-Fluoro-1,3-benzoxazol-2-yl)amino]cyclopentyl]-2,6-dimethoxybenzamide,
N-[(1R,2S)-2-[(6-Fluoro-1,3-benzoxazol-2-yl)amino]cyclopentyl]-2,6-dimethoxybenzamide,
N-[(1R,2R)-2-[(6-Fluoro-1,3-benzoxazol-2-yl)amino]cyclopentyl]-2,6-dimethoxybenzamide,
N-[(1S,2S)-2-[(6-Fluoro-1,3-benzothiazol-2-yl)amino]cyclopentyl]-2-methoxy-5-methylbenzamide,
N-[(1S,2R)-2-[(6-Fluoro-1,3-benzothiazol-2-yl)amino]cyclopentyl]-2-methoxy-5-methylbenzamide,
N-[(1R,2S)-2-[(6-Fluoro-1,3-benzothiazol-2-yl)amino]cyclopentyl]-2-methoxy-5-methylbenzamide,
N-[(1R,2R)-2-[(6-Fluoro-1,3-benzothiazol-2-yl)amino]cyclopentyl]-2-methoxy-5-methylbenzamide,
N-[(1S,2S)-2-[(6-Fluoro-1,3-benzothiazol-2-yl)amino]cyclopentyl]-2,6-dimethylbenzamide,
N-[(1S,2R)-2-[(6-Fluoro-1,3-benzothiazol-2-yl)amino]cyclopentyl]-2,6-dimethylbenzamide,
N-[(1R,2S)-2-[(6-Fluoro-1,3-benzothiazol-2-yl)amino]cyclopentyl]-2,6-dimethylbenzamide,
N-[(1R,2R)-2-[(6-Fluoro-1,3-benzothiazol-2-yl)amino]cyclopentyl]-2,6-dimethylbenzamide,
2-Fluoro-N-[(1S,2S)-2-[(6-fluoro-1,3-benzothiazol-2-yl)amino]cyclopentyl]-6-(2H-1,2,3-triazol-2-yl)benzamide, 2-Fluoro-N-[(1S,2R)-2-[(6-fluoro-1,3-benzothiazol-2-yl)amino]cyclopentyl]-6-(2H-1,2,3-triazol-2-yl)benzamide,
2-Fluoro-N-[(1R,2S)-2-[(6-fluoro-1,3-benzothiazol-2-yl)amino]cyclopentyl]-6-(2H-1,2,3-triazol-2-yl)benzamide,
2-Fluoro-N-[(1R,2R)-2-[(6-fluoro-1,3-benzothiazol-2-yl)amino]cyclopentyl]-6-(2H-1,2,3-triazol-2-yl)benzamide,
2-Chloro-6-fluoro-N-[(1S,2S)-2-[(6-fluoro-1,3-benzothiazol-2-yl)amino]cyclopentyl]benzamide,
2-Chloro-6-fluoro-N-[(1S,2R)-2-[(6-fluoro-1,3-benzothiazol-2-yl)amino]cyclopentyl]benzamide,
2-Chloro-6-fluoro-N-[(1R,2S)-2-[(6-fluoro-1,3-benzothiazol-2-yl)amino]cyclopentyl]benzamide,
2-Chloro-6-fluoro-N-[(1R,2R)-2-[(6-fluoro-1,3-benzothiazol-2-yl)amino]cyclopentyl]benzamide,
2-Chloro-N-[(1S,2S)-2-[(6-fluoro-1,3-benzothiazol-2-yl)amino]cyclopentyl]-6-(2H-1,2,3-triazol-2-yl)benzamide,
2-Chloro-N-[(1S,2R)-2-[(6-fluoro-1,3-benzothiazol-2-yl)amino]cyclopentyl]-6-(2H-1,2,3-triazol-2-yl)benzamide,
2-Chloro-N-[(1R,2S)-2-[(6-fluoro-1,3-benzothiazol-2-yl)amino]cyclopentyl]-6-(2H-1,2,3-triazol-2-yl)benzamide,
2-Chloro-N-[(1R,2R)-2-[(6-fluoro-1,3-benzothiazol-2-yl)amino]cyclopentyl]-6-(2H-1,2,3-triazol-2-yl)benzamide,
N-[(1S,2S)-2-[(6-Fluoro-1,3-benzothiazol-2-yl)amino]cyclopentyl]-2-(5-methyl-1,3,4-oxadiazol-2-yl)benzamide,
N-[(1S,2R)-2-[(6-Fluoro-1,3-benzothiazol-2-yl)amino]cyclopentyl]-2-(5-methyl-1,3,4-oxadiazol-2-yl)benzamide,
N-[(1R,2S)-2-[(6-Fluoro-1,3-benzothiazol-2-yl)amino]cyclopentyl]-2-(5-methyl-1,3,4-oxadiazol-2-yl)benzamide,
N-[(1R,2R)-2-[(6-Fluoro-1,3-benzothiazol-2-yl)amino]cyclopentyl]-2-(5-methyl-1,3,4-oxadiazol-2-yl)benzamide,
N-[(1S,2S)-2-[(6-Fluoro-1,3-benzothiazol-2-yl)amino]cyclopentyl]-2-(1H-1,2,3-triazol-1-yl)benzamide,
N-[(1S,2R)-2-[(6-Fluoro-1,3-benzothiazol-2-yl)amino]cyclopentyl]-2-(1H-1,2,3-triazol-1-yl)benzamide,
N-[(1R,2S)-2-[(6-Fluoro-1,3-benzothiazol-2-yl)amino]cyclopentyl]-2-(1H-1,2,3-triazol-1-yl)benzamide,
N-[(1R,2R)-2-[(6-Fluoro-1,3-benzothiazol-2-yl)amino]cyclopentyl]-2-(1H-1,2,3-triazol-1-yl)benzamide,
5-Chloro-N-[(1S,2S)-2-[(6-fluoro-1,3-benzothiazol-2-yl)amino]cyclopentyl]-2-(1H-pyrazol-1-yl)benzamide,
5-Chloro-N-[(1S,2R)-2-[(6-fluoro-1,3-benzothiazol-2-yl)amino]cyclopentyl]-2-(1H-pyrazol-1-yl)benzamide,
5-Chloro-N-[(1R,2S)-2-[(6-fluoro-1,3-benzothiazol-2-yl)amino]cyclopentyl]-2-(1H-pyrazol-1-yl)benzamide,
5-Chloro-N-[(1R,2R)-2-[(6-fluoro-1,3-benzothiazol-2-yl)amino]cyclopentyl]-2-(1H-pyrazol-1-yl)benzamide,
2,6-Difluoro-N-[(1S,2S)-2-[(6-fluoro-1,3-benzothiazol-2-yl)amino]cyclopentyl]-N-methylbenzamide,
2,6-Difluoro-N-[(1S,2R)-2-[(6-fluoro-1,3-benzothiazol-2-yl)amino]cyclopentyl]-N-methylbenzamide,
2,6-Difluoro-N-[(1R,2S)-2-[(6-fluoro-1,3-benzothiazol-2-yl)amino]cyclopentyl]-N-methylbenzamide,
2,6-Difluoro-N-[(1R,2R)-2-[(6-fluoro-1,3-benzothiazol-2-yl)amino]cyclopentyl]-N-methylbenzamide,
N-[(1S,2S)-2-[(6-Fluoro-1,3-benzothiazol-2-yl)amino]cyclopentyl]-2-methoxy-N-methylbenzamide,
N-[(1S,2R)-2-[(6-Fluoro-1,3-benzothiazol-2-yl)amino]cyclopentyl]-2-methoxy-N-methylbenzamide,
N-[(1R,2S)-2-[(6-Fluoro-1,3-benzothiazol-2-yl)amino]cyclopentyl]-2-methoxy-N-methylbenzamide,
N-[(1R,2R)-2-[(6-Fluoro-1,3-benzothiazol-2-yl)amino]cyclopentyl]-2-methoxy-N-methylbenzamide,
2-Chloro-N-[(1S,2S)-2-[(6-fluoro-1,3-benzothiazol-2-yl)amino]cyclopentyl]-N-methylbenzamide,
2-Chloro-N-[(1S,2R)-2-[(6-fluoro-1,3-benzothiazol-2-yl)amino]cyclopentyl]-N-methylbenzamide,
2-Chloro-N-[(1R,2S)-2-[(6-fluoro-1,3-benzothiazol-2-yl)amino]cyclopentyl]-N-methylbenzamide,
2-Chloro-N-[(1R,2R)-2-[(6-fluoro-1,3-benzothiazol-2-yl)amino]cyclopentyl]-N-methylbenzamide,
N-[(1S,2S)-2-[(6-Fluoro-1,3-benzothiazol-2-yl)amino]cyclopentyl]-N-methyl-2-(1H-pyrazol-1-yl)benzamide,
N-[(1S,2R)-2-[(6-Fluoro-1,3-benzothiazol-2-yl)amino]cyclopentyl]-N-methyl-2-(1H-pyrazol-1-yl)benzamide,
N-[(1R,2S)-2-[(6-Fluoro-1,3-benzothiazol-2-yl)amino]cyclopentyl]-N-methyl-2-(1H-pyrazol-1-yl)benzamide,
N-[(1R,2R)-2-[(6-Fluoro-1,3-benzothiazol-2-yl)amino]cyclopentyl]-N-methyl-2-(1H-pyrazol-1-yl)benzamide,
N-[(1S,2S)-2-[(6-Fluoro-1,3-benzothiazol-2-yl)amino]cyclopentyl]-N-methyl-2-(2H-1,2,3-triazol-2-yl)benzamide,
N-[(1S,2R)-2-[(6-Fluoro-1,3-benzothiazol-2-yl)amino]cyclopentyl]-N-methyl-2-(2H-1,2,3-triazol-2-yl)benzamide,
N-[(1R,2S)-2-[(6-Fluoro-1,3-benzothiazol-2-yl)amino]cyclopentyl]-N-methyl-2-(2H-1,2,3-triazol-2-yl)benzamide,
N-[(1R,2R)-2-[(6-Fluoro-1,3-benzothiazol-2-yl)amino]cyclopentyl]-N-methyl-2-(2H-1,2,3-triazol-2-yl)benzamide,
5-Fluoro-N-[(1S,2S)-2-[(6-fluoro-1,3-benzothiazol-2-yl)amino]cyclopentyl]-N-methyl-2-(2H-1,2,3-triazol-2-yl)benzamide,
5-Fluoro-N-[(1S,2R)-2-[(6-fluoro-1,3-benzothiazol-2-yl)amino]cyclopentyl]-N-methyl-2-(2H-1,2,3-triazol-2-yl)benzamide,
5-Fluoro-N-[(1R,2S)-2-[(6-fluoro-1,3-benzothiazol-2-yl)amino]cyclopentyl]-N-methyl-2-(2H-1,2,3-triazol-2-yl)benzamide,
5-Fluoro-N-[(1R,2R)-2-[(6-fluoro-1,3-benzothiazol-2-yl)amino]cyclopentyl]-N-methyl-2-(2H-1,2,3-triazol-2-yl)benzamide,
N-[(1S,2S)-2-[(6-Fluoro-1,3-benzothiazol-2-yl)amino]cyclopentyl]-N-methyl-2-(pyrimidin-2-yl)benzamide,
N-[(1S,2R)-2-[(6-Fluoro-1,3-benzothiazol-2-yl)amino]cyclopentyl]-N-methyl-2-(pyrimidin-2-yl)benzamide,
N-[(1R,2S)-2-[(6-Fluoro-1,3-benzothiazol-2-yl)amino]cyclopentyl]-N-methyl-2-(pyrimidin-2-yl)benzamide,
N-[(1R,2R)-2-[(6-Fluoro-1,3-benzothiazol-2-yl)amino]cyclopentyl]-N-methyl-2-(pyrimidin-2-yl)benzamide,
N-[(1S,2S)-2-[(6-Fluoro-1,3-benzothiazol-2-yl)amino]cyclopentyl]-N-methyl-2-(3-methyl-1,2,4-oxadiazol-5-yl)benzamide,
N-[(1S,2R)-2-[(6-Fluoro-1,3-benzothiazol-2-yl)amino]cyclopentyl]-N-methyl-2-(3-methyl-1,2,4-oxadiazol-5-yl)benzamide,
N-[(1R,2S)-2-[(6-Fluoro-1,3-benzothiazol-2-yl)amino]cyclopentyl]-N-methyl-2-(3-methyl-1,2,4-oxadiazol-5-yl)benzamide,
N-[(1R,2R)-2-[(6-Fluoro-1,3-benzothiazol-2-yl)amino]cyclopentyl]-N-methyl-2-(3-methyl-1,2,4-oxadiazol-5-yl)benzamide,
N-[(1S,2S)-2-[(5-Fluoro-1,3-benzothiazol-2-yl)amino]cyclopentyl]-2,6-dimethoxybenzamide,
N-[(1S,2R)-2-[(5-Fluoro-1,3-benzothiazol-2-yl)amino]cyclopentyl]-2,6-dimethoxybenzamide,
N-[(1R,2S)-2-[(5-Fluoro-1,3-benzothiazol-2-yl)amino]cyclopentyl]-2,6-dimethoxybenzamide,
N-[(1R,2R)-2-[(5-Fluoro-1,3-benzothiazol-2-yl)amino]cyclopentyl]-2,6-dimethoxybenzamide,
N-[(1S,2S)-2-[(5-Fluoro-1,3-benzoxazol-2-yl)amino]cyclopentyl]-2,6-dimethoxybenzamide, N-[(1S,2R)-2-[(5-Fluoro-1,3-benzoxazol-2-yl)amino]cyclopentyl]-2,6-dimethoxybenzamide,
N-[(1R,2S)-2-[(5-Fluoro-1,3-benzoxazol-2-yl)amino]cyclopentyl]-2,6-dimethoxybenzamide,
N-[(1R,2R)-2-[(5-Fluoro-1,3-benzoxazol-2-yl)amino]cyclopentyl]-2,6-dimethoxybenzamide,
N-[(1S,2S)-2-[(1,3-Benzoxazol-2-yl)amino]cyclopentyl]-2-(2H-1,2,3-triazol-2-yl)benzamide,
N-[(1S,2R)-2-[(1,3-Benzoxazol-2-yl)amino]cyclopentyl]-2-(2H-1,2,3-triazol-2-yl)benzamide,
N-[(1R,2S)-2-[(1,3-Benzoxazol-2-yl)amino]cyclopentyl]-2-(2H-1,2,3-triazol-2-yl)benzamide,
N-[(1R,2R)-2-[(1,3-Benzoxazol-2-yl)amino]cyclopentyl]-2-(2H-1,2,3-triazol-2-yl)benzamide,
N-[(1S,2S)-2-[(6-Fluoro-1,3-benzoxazol-2-yl)amino]cyclopentyl]-2-(2H-1,2,3-triazol-2-yl)benzamide,
N-[(1S,2R)-2-[(6-Fluoro-1,3-benzoxazol-2-yl)amino]cyclopentyl]-2-(2H-1,2,3-triazol-2-yl)benzamide,
N-[(1R,2S)-2-[(6-Fluoro-1,3-benzoxazol-2-yl)amino]cyclopentyl]-2-(2H-1,2,3-triazol-2-yl)benzamide,
N-[(1R,2R)-2-[(6-Fluoro-1,3-benzoxazol-2-yl)amino]cyclopentyl]-2-(2H-1,2,3-triazol-2-yl)benzamide,
N-[(1S,2S)-2-[(5-Fluoro-1,3-benzoxazol-2-yl)amino]cyclopentyl]-2-(2H-1,2,3-triazol-2-yl)benzamide,
N-[(1S,2R)-2-[(5-Fluoro-1,3-benzoxazol-2-yl)amino]cyclopentyl]-2-(2H-1,2,3-triazol-2-yl)benzamide,
N-[(1R,2S)-2-[(5-Fluoro-1,3-benzoxazol-2-yl)amino]cyclopentyl]-2-(2H-1,2,3-triazol-2-yl)benzamide,
N-[(1R,2R)-2-[(5-Fluoro-1,3-benzoxazol-2-yl)amino]cyclopentyl]-2-(2H-1,2,3-triazol-2-yl)benzamide,
N-[(1S,2S)-2-[(5-Chloro-1,3-benzothiazol-2-yl)amino]cyclopentyl]-2-(2H-1,2,3-triazol-2-yl)benzamide,
N-[(1S,2R)-2-[(5-Chloro-1,3-benzothiazol-2-yl)amino]cyclopentyl]-2-(2H-1,2,3-triazol-2-yl)benzamide,
N-[(1R,2S)-2-[(5-Chloro-1,3-benzothiazol-2-yl)amino]cyclopentyl]-2-(2H-1,2,3-triazol-2-yl)benzamide,
N-[(1R,2R)-2-[(5-Chloro-1,3-benzothiazol-2-yl)amino]cyclopentyl]-2-(2H-1,2,3-triazol-2-yl)benzamide,
N-[(1S,2S)-2-[(1,3-Benzothiazol-2-yl)amino]cyclopentyl]-2-(2H-1,2,3-triazol-2-yl)benzamide,
N-[(1S,2R)-2-[(1,3-Benzothiazol-2-yl)amino]cyclopentyl]-2-(2H-1,2,3-triazol-2-yl)benzamide,
N-[(1R,2S)-2-[(1,3-Benzothiazol-2-yl)amino]cyclopentyl]-2-(2H-1,2,3-triazol-2-yl)benzamide,
N-[(1R,2R)-2-[(1,3-Benzothiazol-2-yl)amino]cyclopentyl]-2-(2H-1,2,3-triazol-2-yl)benzamide,
N-[(1S,2S)-2-[(6-Chloro-1,3-benzothiazol-2-yl)amino]cyclopentyl]-2-(2H-1,2,3-triazol-2-yl)benzamide,
N-[(1S,2R)-2-[(6-Chloro-1,3-benzothiazol-2-yl)amino]cyclopentyl]-2-(2H-1,2,3-triazol-2-yl)benzamide,
N-[(1R,2S)-2-[(6-Chloro-1,3-benzothiazol-2-yl)amino]cyclopentyl]-2-(2H-1,2,3-triazol-2-yl)benzamide,
N-[(1R,2R)-2-[(6-Chloro-1,3-benzothiazol-2-yl)amino]cyclopentyl]-2-(2H-1,2,3-triazol-2-yl)benzamide,
N-[(1S,2S)-2-[(5-Fluoro-1,3-benzothiazol-2-yl)amino]cyclopentyl]-2-(2H-1,2,3-triazol-2-yl)benzamide,
N-[(1S,2R)-2-[(5-Fluoro-1,3-benzothiazol-2-yl)amino]cyclopentyl]-2-(2H-1,2,3-triazol-2-yl)benzamide,
N-[(1R,2S)-2-[(5-Fluoro-1,3-benzothiazol-2-yl)amino]cyclopentyl]-2-(2H-1,2,3-triazol-2-yl)benzamide,
N-[(1R,2R)-2-[(5-Fluoro-1,3-benzothiazol-2-yl)amino]cyclopentyl]-2-(2H-1,2,3-triazol-2-yl)benzamide,
N-[(1S,2S)-2-[(4,6-Difluoro-1,3-benzothiazol-2-yl)amino]cyclopentyl]-2-(2H-1,2,3-triazol-2-yl)benzamide,
N-[(1S,2R)-2-[(4,6-Difluoro-1,3-benzothiazol-2-yl)amino]cyclopentyl]-2-(2H-1,2,3-triazol-2-yl)benzamide,
N-[(1R,2S)-2-[(4,6-Difluoro-1,3-benzothiazol-2-yl)amino]cyclopentyl]-2-(2H-1,2,3-triazol-2-yl)benzamide,
N-[(1R,2R)-2-[(4,6-Difluoro-1,3-benzothiazol-2-yl)amino]cyclopentyl]-2-(2H-1,2,3-triazol-2-yl)benzamide,
N-[(1S,2S)-2-[(4-Fluoro-1,3-benzothiazol-2-yl)amino]cyclopentyl]-2-(2H-1,2,3-triazol-2-yl)benzamide,
N-[(1S,2R)-2-[(4-Fluoro-1,3-benzothiazol-2-yl)amino]cyclopentyl]-2-(2H-1,2,3-triazol-2-yl)benzamide,
N-[(1R,2S)-2-[(4-Fluoro-1,3-benzothiazol-2-yl)amino]cyclopentyl]-2-(2H-1,2,3-triazol-2-yl)benzamide,
N-[(1R,2R)-2-[(4-Fluoro-1,3-benzothiazol-2-yl)amino]cyclopentyl]-2-(2H-1,2,3-triazol-2-yl)benzamide,
N-[(1S,2S)-2-({[1,3]Thiazolo[5,4-b]pyridin-2-yl}amino)cyclopentyl]-2-(2H-1,2,3-triazol-2-yl)benzamide,
N-[(1S,2R)-2-({[1,3]Thiazolo[5,4-b]pyridin-2-yl}amino)cyclopentyl]-2-(2H-1,2,3-triazol-2-yl)benzamide,
N-[(1R,2S)-2-({[1,3]Thiazolo[5,4-b]pyridin-2-yl}amino)cyclopentyl]-2-(2H-1,2,3-triazol-2-yl)benzamide,
N-[(1R,2R)-2-({[1,3]Thiazolo[5,4-b]pyridin-2-yl}amino)cyclopentyl]-2-(2H-1,2,3-triazol-2-yl)benzamide,
N-[(1S,2S)-2-({7-Chloro-[1,3]thiazolo[5,4-c]pyridin-2-yl}amino)cyclopentyl]-2-(2H-1,2,3-triazol-2-yl)benzamide,
N-[(1S,2R)-2-({7-Chloro-[1,3]thiazolo[5,4-c]pyridin-2-yl}amino)cyclopentyl]-2-(2H-1,2,3-triazol-2-yl)benzamide,
N-[(1R,2S)-2-({7-Chloro-[1,3]thiazolo[5,4-c]pyridin-2-yl}amino)cyclopentyl]-2-(2H-1,2,3-triazol-2-yl)benzamide,
N-[(1R,2R)-2-({7-Chloro-[1,3]thiazolo[5,4-c]pyridin-2-yl}amino)cyclopentyl]-2-(2H-1,2,3-triazol-2-yl)benzamide,
N-[(1S,2S)-2-({[1,3]Thiazolo[5,4-c]pyridin-2-yl}amino)cyclopentyl]-2-(2H-1,2,3-triazol-2-yl)benzamide,
N-[(1S,2R)-2-({[1,3]Thiazolo[5,4-c]pyridin-2-yl}amino)cyclopentyl]-2-(2H-1,2,3-triazol-2-yl)benzamide,
N-[(1R,2S)-2-({[1,3]Thiazolo[5,4-c]pyridin-2-yl}amino)cyclopentyl]-2-(2H-1,2,3-triazol-2-yl)benzamide,
N-[(1R,2R)-2-({[1,3]Thiazolo[5,4-c]pyridin-2-yl}amino)cyclopentyl]-2-(2H-1,2,3-triazol-2-yl)benzamide,
N-[(1S,2S)-2-[(6-Fluoro-1,3-benzoxazol-2-yl)amino]cyclopentyl]-2-(3-methyl-1,2,4-oxadiazol-5-yl)benzamide,
N-[(1S,2R)-2-[(6-Fluoro-1,3-benzoxazol-2-yl)amino]cyclopentyl]-2-(3-methyl-1,2,4-oxadiazol-5-yl)benzamide,
N-[(1R,2S)-2-[(6-Fluoro-1,3-benzoxazol-2-yl)amino]cyclopentyl]-2-(3-methyl-1,2,4-oxadiazol-5-yl)benzamide,
N-[(1R,2R)-2-[(6-Fluoro-1,3-benzoxazol-2-yl)amino]cyclopentyl]-2-(3-methyl-1,2,4-oxadiazol-5-yl)benzamide,
trans-N-{4-[(6-Fluoro-1,3-benzothiazol-2-yl)amino]oxolan-3-yl}-2-(2H-1,2,3-triazol-2-yl)benzamide,
cis-N-[4-(1,3-Benzothiazol-2-ylmethyl)oxolan-3-yl]-5-methyl-2-(2H-1,2,3-triazol-2-yl)benzamide,
N-{4,4-Difluoro-2-[(6-fluoro-1,3-benzothiazol-2-yl)amino]cyclopentyl}-2-(2H-1,2,3-triazol-2-yl)benzamide (Enantiomer 1 substantially as described herein and with reference to Example 103),
N-{4,4-Difluoro-2-[(6-fluoro-1,3-benzothiazol-2-yl)amino]cyclopentyl}-2-(2H-1,2,3-triazol-2-yl)benzamide (Enantiomer 2 substantially as described herein and with reference to Example 104),
N-{2-[(6-Chloro-1,3-benzothiazol-2-yl)amino]-4,4-difluorocyclopentyl}-2-(2H-1,2,3-triazol-2-yl)benzamide (Enantiomer 1 substantially as described herein and with reference to Example 105), N-{2-[(6-Chloro-1,3-benzothiazol-2-yl)amino]-4,4-difluorocyclopentyl}-2-(2H-1,2,3-triazol-2-yl)benzamide (Enantiomer 2 substantially as described herein and with reference to Example 106), N-{2-[(6-Fluoro-1,3-benzothiazol-2-yl)amino]-2-methylcyclopentyl}-2-(2H-1,2,3-triazol-2-yl)benzamide, N-{2-[(6-Chloro-1,3-benzothiazol-2-yl)amino]-2-methylcyclopentyl}-2-(2H-1,2,3-triazol-2-yl)benzamide and pharmaceutically acceptable salts of any one thereof.

It should be noted that each of the chemical compounds listed above represents a particular and independent aspect of the invention.

The present invention further provides a process for the preparation of a compound of formula (I) or a pharmaceutically acceptable salt thereof as defined above which comprises (i) reacting a compound of formula

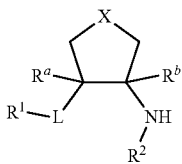

(II)

wherein L, X, $R^a$, $R^b$, $R^1$ and $R^2$ are as defined in formula (I), with a compound of formula

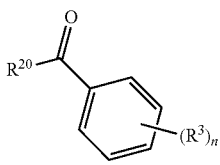

(III)

wherein $R^{20}$ represents a halogen atom (e.g. chlorine atom) or a hydroxyl group and n and $R^3$ are as defined in formula (I), or a salt (e.g. hydrochloride salt) thereof; or (ii) when L represents NH or N(CH$_3$), reacting a compound of formula

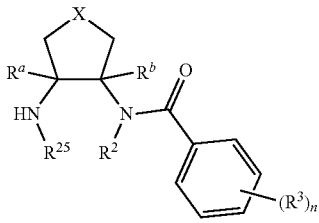

(IV)

wherein $R^{25}$ represents a hydrogen atom or methyl group and n, X, $R^a$, $R^b$, $R^2$ and $R^3$ are as defined in formula (I), with a compound of formula (V), $R^1$-$LG^1$, wherein $LG^1$ represents a leaving group (e.g. a halogen atom) and $R^1$ is as defined in formula (I);

and optionally thereafter carrying out one or more of the following procedures:
converting a compound of formula (I) into another compound of formula (I)
removing any protecting groups
forming a pharmaceutically acceptable salt.

Process (i) may conveniently be carried out by combining the amine of formula (II) with an acid chloride of formula (III) in the presence of a base such as triethyl amine or DIPEA (N,N-diisopropylethylamine) in a solvent such as dichloromethane. Alternatively the reaction can be carried out from the amine of formula (II) and a carboxylic acid of formula (III) using any of the known coupling reagents such as EDC (1-ethyl-3-(3-dimethylaminopropyl)carbodiimide) with HOAt (7-aza-1-hydroxybenzotriazole), DIPEA with HOAt and EDC, or DIPEA with TBTU (O-(benzotriazol-1-yl)-N,N,N',N'-tetramethyluronium tetrafluoroborate). Another method is to activate the carboxylic acid to the corresponding acid chloride in situ for example with oxalyl chloride in the presence of a catalytic amount of DMF.

Process (ii) may conveniently be carried out by mixing the compound of formula (IV) with the compound of formula (V) in a solvent such as DMSO, acetonitrile or toluene and optionally in the presence of a base such as DIPEA, and heating conventionally or using microwave irradiation.

Compounds of formula (II) in which $R^a$ and $R^b$ represent hydrogen and L represents CH$_2$ may be prepared according to the scheme below. The heterocyclic bromomethylene compound is likely to be commercially available or prepared by bromination of the corresponding heterocyclic methyl compound using, for example, N-bromosuccinimide and benzoyl peroxide in carbon tetrachloride and at elevated temperature. Reaction of the heterocyclic bromomethylene compound with triphenylphoshpine in toluene at raised temperature will afford the corresponding phosphonium bromide which on treatment with a base such as n-butyl lithium in the presence of the Boc-protected cyclic ketone will afford the corresponding alkene. The alkene can be reduced by hydrogenation using hydrogen gas in the presence of a catalyst such as palladium on carbon. Finally, the Boc protecting group can be removed using methods known to those skilled in the art, e.g. acid hydrolysis.

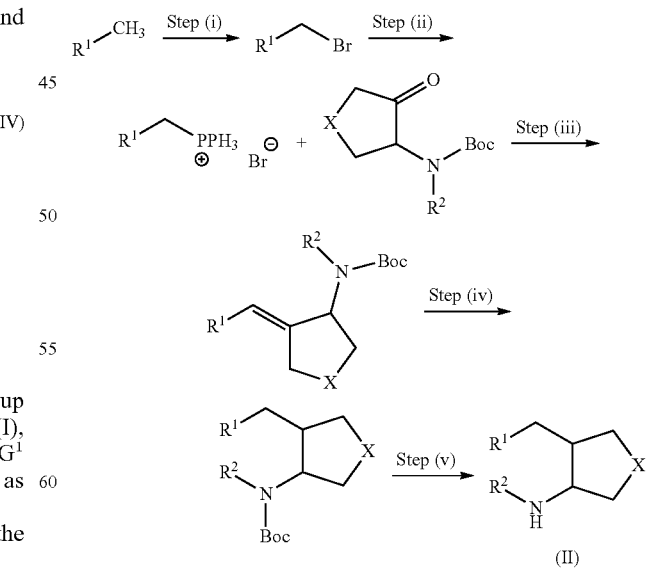

Boc = tert-butyloxycarbonyl

Compounds of formula (II) in which L represents an oxygen atom may be prepared by reacting a compound of formula

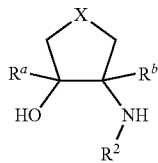

(VI)

wherein X, $R^a$, $R^b$ and $R^2$ are as defined in formula (II), with a compound of formula (V) as defined above, in the presence of a base such as sodium hydride.

Compounds of formula (II) in which L represents NH or $N(CH_3)$ may be prepared by reacting a compound of formula

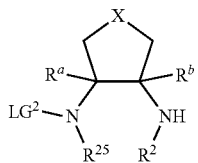

(X)

in which $LG^2$ represents a leaving group such as a tert-butyloxycarbonyl group, and X, $R^a$, $R^b$, $R^2$ and $R^{25}$ are as defined in formula (IV) above, with a compound of formula (V) as defined above.

Compounds of formula (II) in which X represents NC(O)$R^9$ may be prepared by acylating a compound of formula

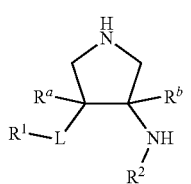

(XI)

in which L, $R^a$, $R^b$, $R^1$ and $R^2$ are as defined in formula (II), with an acylating agent of formula (XII), $R^9C(O)$-$LG^3$, in which $LG^3$ represents a leaving group (e.g. a halogen atom) and $R^9$ is as defined in formula (I).

Compounds of formula (IV) may be prepared by reacting a compound of formula (X) with a compound of formula (III) followed by removal of the leaving group, $LG^2$, by acid treatment using, for example, an acid such as hydrochloric acid.

Compounds of formula (IV) in which X represents NC(O)$R^9$ may be prepared by acylating a compound of formula

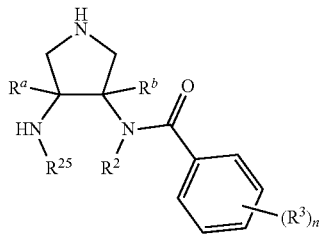

(XIII)

in which n, R, $R^b$, $R^2$, $R^3$ and $R^{25}$ are as defined in formula (IV), with an acylating agent of formula (XII) as defined above.

Compounds of formula (IV) in which X represents $CF_2$ may be prepared by fluorinating a compound of formula

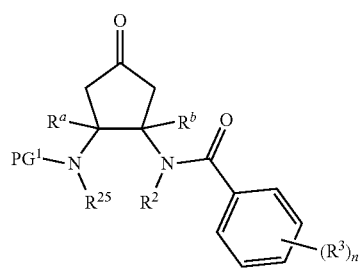

(XIV)

in which $PG^1$ represents an amine-protecting group such as tert-butyloxycarbonyl and n, $R^a$, $R^b$, $R^2$, $R^3$ and $R^{25}$ are as defined in formula (IV) using a fluorinating agent such as diethylaminosulfur trifluoride, followed by removal of the protecting group, $PG^1$, e.g. by acid hydrolysis using an acid such as hydrochloric acid.

Compounds of formulae (III), (V), (VI), (X), (XI), (XII), (XIII) and (XIV) are either commercially available, are well known in the literature or may be prepared using known techniques.

It will be appreciated by those skilled in the art that in the processes of the present invention certain functional groups such as phenol, hydroxyl or amino groups in the reagents may need to be protected by protecting groups. Thus, the preparation of the compounds of formula (I) may involve, at an appropriate stage, the introduction and/or removal of one or more protecting groups.

The protection and deprotection of functional groups is described in 'Protective Groups in Organic Chemistry', edited by J. W. F. McOmie, Plenum Press (1973) and 'Protective Groups in Organic Synthesis', 3$^{rd}$ edition, T. W. Greene and P. G. M. Wuts, Wiley-Interscience (1999).

The compounds of formula (I) above may be converted to a pharmaceutically acceptable salt thereof, preferably an acid addition salt such as a formate, hemi-formate, hydrochloride, hydrobromide, benzenesulphonate (besylate), saccharin (e.g. monosaccharin), trifluoroacetate, sulphate, nitrate, phosphate, acetate, fumarate, maleate, tartrate, lactate, citrate, pyruvate, succinate, valerate, propanoate, butanoate, malonate, oxalate, 1-hydroxy-2-napthoate (xinafoate), methanesulphonate or p-toluenesulphonate salt.

In one aspect of the invention, compounds of formula (I) may bear one or more radiolabels. Such radiolabels may be introduced by using radiolabel-containing reagents in the synthesis of the compounds of formula (I), or may be introduced by coupling the compounds of formula (I) to chelating moieties capable of binding to a radioactive metal atom. Such radiolabeled versions of the compounds may be used, for example, in diagnostic imaging studies.

Unless stated otherwise, any atom specified herein may also be an isotope of said atom. For example, the term "hydrogen" encompasses $^1H$, $^2H$ and $^3H$. Similarly carbon atoms are to be understood to include $^{12}C$, $^{13}C$ and $^{14}C$, nitrogen atoms are to be understood to include $^{14}N$ and $^{15}N$, and oxygen atoms are to be understood to include $^{16}O$, $^{17}O$ and $^{18}O$.

In a further aspect of the invention, compounds of formula (I) may be isotopically labelled. As used herein, an "isotopically labelled" compound is one in which the abundance of a particular nuclide at a particular atomic position within the molecule is increased above the level at which it occurs in nature.

Compounds of formula (I) and their salts may be in the form of hydrates or solvates which form an aspect of the present invention. Such solvates may be formed with common organic solvents, including but not limited to, alcoholic solvents e.g. methanol, ethanol or isopropanol.

Where compounds of formula (I) are capable of existing in stereoisomeric forms, it will be understood that the invention encompasses the use of all geometric and optical isomers (including atropisomers) of the compounds of formula (I) and mixtures thereof including racemates. The use of tautomers and mixtures thereof also form an aspect of the present invention. Enantiomerically pure forms are particularly desired.

Compounds of formula (I) and their salts may be amorphous or in a polymorphic form or a mixture of any of these, each of which forms an aspect of the present invention.

The compounds of formula (I) and their pharmaceutically acceptable salts have activity as pharmaceuticals, in particular as orexin receptor antagonists, and thus may be used in the treatment of schizophrenia and other psychotic disorders (e.g., psychotic disorder, psychosis or schizoaffective disorder); dementia and other cognitive disorders; anxiety disorders (e.g., generalized anxiety disorder, post-traumatic stress disorder, panic disorders, acute stress disorder, social anxiety disorder, phobias including agoraphobia, obsessive compulsive disorder, trichlofillomania or body dismorphic disorder); mood disorders (e.g., depressive disorders, major depressive disorders, bipolar disorders including bipolar I and II, bipolar mania, bipolar depression); addiction including substance dependence (e.g. cocaine, opiates, cannabis or prescription drug dependence), alcohol dependence, nicotine dependence or gambling disorder; eating disorders (e.g. binge eating, bulimia nervosa, anorexia nervosa or obesity); sleep disorders (e.g. rapid eye movement sleep disorder); disorders usually first diagnosed in infancy, childhood, or adolescence (e.g., attention-deficit disorder, autistic spectrum disorders, Rett syndrome, Fragile X syndrome, Asperger syndrome and disruptive behaviour disorders); restless leg syndrome; pain (e.g. neuropathic pain including chemotherapy induced pain or migraine); and neurodegenerative disorders (e.g. Parkinson's or Alzheimer's disease).

Thus, the present invention provides a compound of formula (I) or a pharmaceutically acceptable salt thereof as hereinbefore defined for use in therapy, in particular for the treatment of conditions whose development or symptoms are linked to orexin receptor activity.

The present invention also provides the use of a compound of formula (I) or a pharmaceutically acceptable salt thereof as hereinbefore defined for the preparation of a medicament for the treatment of conditions whose development or symptoms are linked to orexin receptor activity.

In the context of the present specification, the term "therapy" also includes "prophylaxis" unless there are specific indications to the contrary. The terms "therapeutic" and "therapeutically" should be construed accordingly.

Prophylaxis is expected to be particularly relevant to the treatment of persons who have suffered a previous episode of, or are otherwise considered to be at increased risk of, the disorder or condition in question. Persons at risk of developing a particular disorder or condition generally include those having a family history of the disorder or condition, or those who have been identified by genetic testing or screening to be particularly susceptible to developing the disorder or condition or those in the prodromal phase of a disorder.

In particular, the compounds of the invention (including pharmaceutically acceptable salts) may be used in the treatment of the positive symptoms of schizophrenia, schizophreniform disorder or schizoaffective disorder (e.g. voices or hallucinations), cognitive disorders (such as dementia and impaired learning), anxiety disorders (such as post-traumatic stress disorder or panic disorders), or addiction.

The invention also provides a method of treating at least one symptom or condition associated with schizophrenia and other psychotic disorders (e.g., psychotic disorder, psychosis or schizoaffective disorder); dementia and other cognitive disorders; anxiety disorders (e.g., generalized anxiety disorder, post-traumatic stress disorder, panic disorders, acute stress disorder, social anxiety disorder, phobias including agoraphobia, obsessive compulsive disorder, trichlofillomania or body dismorphic disorder); mood disorders (e.g., depressive disorders, major depressive disorders, bipolar disorders including bipolar I and II, bipolar mania, bipolar depression); addiction including substance dependence (e.g. cocaine, opiates, cannabis or prescription drug dependence), alcohol dependence, nicotine dependence or gambling disorder; eating disorders (e.g. binge eating, bulimia nervosa, anorexia nervosa or obesity); sleep disorders (e.g. rapid eye movement sleep disorder); disorders usually first diagnosed in infancy, childhood, or adolescence (e.g., attention-deficit disorder, autistic spectrum disorders, Rett syndrome, Fragile X syndrome, Asperger syndrome and disruptive behaviour disorders); restless leg syndrome; pain (e.g. neuropathic pain including chemotherapy induced pain or migraine); and neurodegenerative disorders (e.g. Parkinson's or Alzheimer's disease) which comprises administering to a patient in need thereof a therapeutically effective amount of a compound of formula (I) or a pharmaceutically acceptable salt thereof as hereinbefore defined.

Such symptoms and conditions include, but are not limited to, anxiety, agitation, hostility, panic, an eating disorder, an affective symptom, a mood symptom, a negative and positive psychotic symptom commonly associated with psychosis and neurodegenerative disorder.

For the above-mentioned therapeutic uses the dosage administered will, of course, vary with the compound employed, the mode of administration, the treatment desired and the disorder indicated. For example, the daily dosage of the compound of the invention, if inhaled, may be in the range from 0.05 micrograms per kilogram body weight (μg/kg) to 100 micrograms per kilogram body weight (μg/kg). Alternatively, if the compound is administered orally, then the daily dosage of the compound of the invention may be in the range from 0.01 micrograms per kilogram body weight (μg/kg) to 100 milligrams per kilogram body weight (mg/kg).

The compounds of formula (I) and pharmaceutically acceptable salts thereof may be used on their own but will generally be administered in the form of a pharmaceutical composition in which the formula (I) compound/salt (active ingredient) is in association with a pharmaceutically acceptable adjuvant, diluent or carrier.

Therefore the present invention further provides a pharmaceutical composition comprising a compound of formula (I) or a pharmaceutically acceptable salt thereof as hereinbefore defined, in association with a pharmaceutically acceptable adjuvant, diluent or carrier.

The invention still further provides a process for the preparation of a pharmaceutical composition of the invention which comprises mixing a compound of formula (I) or a pharmaceutically acceptable salt thereof as hereinbefore defined with a pharmaceutically acceptable adjuvant, diluent or carrier.

Conventional procedures for the selection and preparation of suitable pharmaceutical formulations are described in, for example, "Pharmaceutics—The Science of Dosage Form Design", M. E. Aulton, Churchill Livingstone, 1988.

Pharmaceutically acceptable adjuvants, diluents or carriers that may be used in the pharmaceutical compositions of the invention are those conventionally employed in the field of pharmaceutical formulation, and include, but are not limited to, sugars, sugar alcohols, starches, ion exchangers, alumina, aluminium stearate, lecithin, serum proteins, such as human serum albumin, buffer substances such as phosphates, glycerine, sorbic acid, potassium sorbate, partial glyceride mixtures of saturated vegetable fatty acids, water, salts or electrolytes, such as protamine sulphate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The pharmaceutical compositions of the present invention may be administered orally, parenterally, by inhalation spray, rectally, nasally, buccally, vaginally or via an implanted reservoir. Oral administration is preferred. The pharmaceutical compositions of the invention may contain any conventional non-toxic pharmaceutically acceptable adjuvants, diluents or carriers. The term parenteral as used herein includes subcutaneous, intracutaneous, intravenous, intramuscular, intra-articular, intrasynovial, intrasternal, intrathecal, intralesional and intracranial injection or infusion techniques.

The pharmaceutical compositions may be in the form of a sterile injectable preparation, for example, as a sterile injectable aqueous or oleaginous suspension. The suspension may be formulated according to techniques known in the art using suitable dispersing or wetting agents (such as, for example, Tween 80) and suspending agents. The sterile injectable preparation may also be a sterile injectable solution or suspension in a non-toxic parenterally acceptable diluent or solvent, for example, as a solution in 1,3-butanediol. Among the acceptable diluents and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically acceptable oils, such as olive oil or castor oil, especially in their polyoxyethylated versions. These oil solutions or suspensions may also contain a long-chain alcohol diluent or dispersant.

The pharmaceutical compositions of this invention may be orally administered in any orally acceptable dosage form including, but not limited to, capsules, tablets, powders, granules, and aqueous suspensions and solutions. These dosage forms are prepared according to techniques well-known in the art of pharmaceutical formulation. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are administered orally, the active ingredient is combined with emulsifying and suspending agents. If desired, certain sweetening and/or flavouring and/or colouring agents may be added.

The pharmaceutical compositions of the invention may also be administered in the form of suppositories for rectal administration. These compositions can be prepared by mixing the active ingredient with a suitable non-irritating excipient which is solid at room temperature but liquid at the rectal temperature and therefore will melt in the rectum to release the active ingredient. Such materials include, but are not limited to, cocoa butter, beeswax and polyethylene glycols.

The pharmaceutical compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilising or dispersing agents known in the art.

Depending on the mode of administration, the pharmaceutical composition will preferably comprise from 0.05 to 99% w (percent by weight), more preferably from 0.05 to 80% w, still more preferably from 0.10 to 70% w, and even more preferably from 0.10 to 50% w, of active ingredient, all percentages by weight being based on total composition.

The compounds of the invention (that is, compounds of formula (I) and pharmaceutically acceptable salts thereof) may also be administered in conjunction with other compounds used for the treatment of the above conditions.

The invention therefore further relates to combination therapies wherein a compound of the invention or a pharmaceutical composition or formulation comprising a compound of the invention is administered with another therapeutic agent or agents for the treatment of one or more of the conditions previously indicated. Such therapeutic agents may be selected from the following:

(i) antidepressants such as, for example, amitriptyline, amoxapine, bupropion, citalopram, clomipramine, desipramine, doxepin duloxetine, elzasonan, escitalopram, fluvoxamine, fluoxetine, gepirone, imipramine, ipsapirone, maprotiline, nortriptyline, nefazodone, paroxetine, phenelzine, protriptyline, reboxetine, robaizotan, sertraline, sibutramine, tianeptine, thionisoxetine, tranylcypromaine, trazodone, trimipramine, venlafaxine, vortioxetine and equivalents and pharmaceutically active isomer(s) and/or metabolite(s) thereof;

(ii) antipsychotics including, for example, amisulpride, aripiprazole, asenapine, benzisoxidil, bifeprunox, brexpiprazole, carbamazepine, cariprazine, clozapine, chlorpromazine, debenzapine, divalproex, duloxetine, eszopiclone, haloperidol, iloperidone, lamotrigine, loxapine, lurasidone, mesoridazine, olanzapine, paliperidone, perlapine, perphenazine, phenothiazine, phenylbutlypiperidine, pimozide, prochlorperazine, quetiapine, risperidone, sertindole, sulpiride, suproclone, suriclone, thioridazine, trifluoperazine, trimetozine, valproate, valproic acid, zopiclone, zotepine, zicronapine, ziprasidone, and equivalents and pharmaceutically active isomer(s) and/or metabolite(s) thereof;

(iii) anxiolytics including, for example, alnespirone, azapirones, benzodiazepines, barbiturates, and equivalents and pharmaceutically active isomer(s) and/or metabolite(s) thereof. Example anxiolytics include adinazolam, alprazolam, balezepam, bentazepam, bromazepam, brotizolam, buspirone, clonazepam, clorazepate, chlordiazepoxide, cyprazepam, diazepam, diphenhydramine, estazolam, fenobam, flunitrazepam, flurazepam, fosazepam, lorazepam, lormetazepam, meprobamate, midazolam, nitrazepam, oxazepam, prazepam, quazepam, reclazepam, tracazolate, trepipam, temazepam, triazolam, uldazepam, and zolazepam; and equivalents and pharmaceutically active isomer(s) and/or metabolite(s) thereof;

(iv) anticonvulsants including, for example, carbamazepine, valproate, lamotrigine, levetiracetam and gabapentin, and equivalents and pharmaceutically active isomer(s) and/or metabolite(s) thereof;

(v) Alzheimer's therapies including, for example, donepezil, galantamine, memantine, rivastigmine, tacrine, and equivalents and pharmaceutically active isomer(s) and/or metabolite(s) thereof;

(vi) Parkinson's therapies including, for example, L-dopa, ropinirole, pramipexole, monoamine oxidase type B (MAO-B) inhibitors such as deprenyl, selegiline and rasagiline, catechol-O-methyl transferase (COMT) inhibitors such as entacapone or tolcapone, adenosine A-2 inhibitors, dopamine re-uptake inhibitors, NMDA antagonists, Nicotine agonists, and Dopamine agonists and inhibitors of neuronal nitric oxide synthase, and equivalents and pharmaceutically active isomer(s) and/or metabolite(s) thereof;

(vii) migraine therapies including, for example, almotriptan, amantadine, botulinum toxin A, bromocriptine, butalbital, cabergoline, dichloralphenazone, dihydroergotamine, eletriptan, frovatriptan, lisuride, naratriptan, pergolide, pramipexole, rizatriptan, ropinirole, sumatriptan, topiramate, zolmitriptan, and zomitriptan, and equivalents and pharmaceutically active isomer(s) and/or metabolite(s) thereof;

(viii) stroke therapies including, for example, abciximab, activase, citicoline, desmoteplase, and equivalents and pharmaceutically active isomer(s) and/or metabolite(s) thereof;

(ix) urinary incontinence therapies including, for example, darafenacin, duloxetine, falvoxate, mirabegron, oxybutynin, propiverine, robalzotan, solifenacin, and tolterodine, and equivalents and pharmaceutically active isomer(s) and/or metabolite(s) thereof;

(x) neuropathic pain therapies including, for example, capsaicin, gabapentin, lidoderm, and pregabalin, and equivalents and pharmaceutically active isomer(s) and/or metabolite(s) thereof;

(xi) nociceptive pain therapies such as, for example, celecoxib, etoricoxib, lumiracoxib, rofecoxib, valdecoxib, diclofenac, loxoprofen, naproxen, and paracetamol, and equivalents and pharmaceutically active isomer(s) and/or metabolite(s) thereof;

(xii) insomnia therapies including, for example, allobarbital, alonimid, amobarbital, benzoctamine, butabarbital, capuride, chloral, cloperidone, clorethate, dexclamol, ethchlorvynol, eszopiclone, etomidate, glutethimide, halazepam, hydroxyzine, lorediplon, mecloqualone, melatonin, mephobarbital, methaqualone, midaflur, nisobamate, pentobarbital, phenobarbital, propofol, ralmeteon, roletamide, suvorexant, triclofos, secobarbital, zaleplon, and zolpidem, zopiclone and equivalents and pharmaceutically active isomer(s) and/ or metabolite(s) thereof;

(xiii) mood stabilizers including, for example, carbamazepine, divalproex, gabapentin, lamotrigine, lithium, olanzapine, quetiapine, valproate, valproic acid, and verapamil, and equivalents and pharmaceutically active isomer(s) and/ or metabolite(s) thereof;

(xiv) 5HT1B ligands such as, for example, compounds disclosed in WO 99/05134 and WO 02/08212;

(xv) mGluR2 agonists;

(xvi) alpha 7 nicotinic agonists such as, for example, compounds disclosed in WO 96/006098, WO 97/030998, WO 99/003859, WO 00/042044, WO 01/029034, WO 01/60821, WO 01/36417, WO 02/096912, WO 03/087102, WO 03/087103, WO 03/087104, WO 2004/016617, WO 2004/016616, and WO 2004/019947;

(xvii) chemokine receptor CCR1 inhibitors; and (xviii) delta opioid agonists such as, for example, compounds disclosed in WO 97/23466 and WO 02/094794.

Such combination products employ the compounds of this invention within the dosage range described herein and the other pharmaceutically active agent within approved dosage ranges and/or the dosage such as described in the publication reference.

In a further aspect the present invention provides a combination (for example for the treatment of schizophrenia, cognitive disorders or pain) of a compound of formula (I) or a pharmaceutically acceptable salt thereof as hereinbefore defined and one or more agents selected from carbamazepine, olanzapine, quetiapine, verapamil, lamotrigine, oxcarbazepine, risperidone, aripiprazole, ziprasidone and lithium.

The invention also provides a pharmaceutical product comprising, in combination, a preparation of a first active ingredient which is a compound of formula (I) or a pharmaceutically acceptable salt thereof as hereinbefore defined, and a preparation of a second active ingredient which is carbamazepine, olanzapine, quetiapine, verapamil, lamotrigine, oxcarbazepine, risperidone, aripiprazole, ziprasidone or lithium, for simultaneous, sequential or separate use in therapy.

In another aspect, the invention provides a kit comprising a preparation of a first active ingredient which is a compound of formula (I) or a pharmaceutically acceptable salt thereof as hereinbefore defined, and a preparation of a second active ingredient which is carbamazepine, olanzapine, quetiapine, verapamil, lamotrigine, oxcarbazepine, risperidone, aripiprazole, ziprasidone or lithium, and instructions for the simultaneous, sequential or separate administration of the preparations to a patient in need thereof.

The present invention will now be further explained by reference to the following illustrative examples. In the illustrative examples, the compounds synthesised are both named and illustrated structurally. Whilst every effort has been made to ensure that the chemical names and the chemical structures are consistent, if any inconsistencies occur the illustrated chemical structure should be taken to be correct, unless the illustrated chemical structure is chemically impossible.

The methods used for synthesis of the compounds of the invention are illustrated by the general schemes below and the preparative examples that follow. The starting materials and reagents used in preparing these compounds are available from commercial suppliers. These general schemes are merely illustrative of methods by which the compounds of this invention can be synthesised, and various modifications to these schemes can be made and will be suggested to one skilled in the art having referred to this disclosure.

Nuclear magnetic resonance (NMR) spectra were recorded at 400 MHz; the chemical shifts ($\delta$) are reported in parts per million. Spectra were recorded using a Bruker 400 Avance instrument fitted with a 5 mm BBFO probe or DUL probe. Instrument control was by Bruker TopSpin 2.1 software, unless stated otherwise.

Purity was assessed using UPLC with UV (photodiode array) detection over a wide range of wavelengths, normally 220-450 nm, using a Waters Acquity UPLC system equipped with Acquity UPLC BEH or HSS C18 columns (2.1 mm id×50 mm long) operated at 50 or 60° C. Mobile phases typically consisted of acetonitrile or methanol mixed with water containing either 0.05% formic acid or 0.025% ammonia.

Mass spectra were recorded with a Waters SQD single quadrupole mass spectrometer using atmospheric pressure ionisation, unless stated otherwise.

Compounds were purified using normal phase chromatography on silica or alumina, or by reverse phase chromatographic methods, using Biotage or Isolute KPNH Cartridge, SCX cartridge and SCX-2 solid phase extraction cartridges.

Preparative High Performance Liquid Chromatography (HPLC) was performed using an Agilent Technologies 1100 Series system or Waters autopurification system typically using Waters 19 mm id×100 mm or 19 mm id×250 mm C18 columns such as XBridge or SunFire 5 µm materials at 20 mL/min. Mobile phases typically consisted of acetonitrile or methanol mixed with water containing either 0.1% formic acid or 0.1% ammonia, unless stated otherwise.

Preparative Supercritical Fluid Chromatography (SFC) was performed using the following: Waters prep30/MS system typically using Daicel 10 mm id×250 mm long columns at 30 ml/min, 40° C. and 100 bar.

In the following descriptions "room temperature" denotes a temperature in the range from 20° C. to 25° C.

The abbreviations used in the specific examples have the following meanings:

aq.=aqueous
Aza-HOBt (HOAt)=(7-aza-1-hydroxybenzotriazole)
BINAP=(2,2'-bis(Diphenylphosphino)-1,1'-binaphthyl)
Boc=Butyloxycarbonyl
n-BuLi=n-Butyllithium
CDI=Carbonyldiimidazole
DAST=Diethylaminosulfur trifluoride
DIAD=Diisopropyl azodicarboxylate
DMF=N,N-Dimethylformamide
DMSO=Dimethylsulfoxide
DIPEA=N,N-Diisopropylethylamine
EDC=1-Ethyl-3-(3-dimethylaminopropyl)carbodiimide
mCPBA=meta-Chlorobenzoic acid
min=minute(s)
MTBE=Methyl tert-butyl ether
NMP=N-Methyl-2-pyrrolidone
Pd$_2$(dba)$_3$=Tris(dibenzylideneacetone)dipalladium(0)
PMB=4-Methoxybenzyl ether
PTSA=para-Toluene sulfonic acid
TBAF=Tetra-n-butylammonium fluoride
TBTU=O-(Benzotriazol-1-yl)-N,N,N',N'-tetramethyluronium tetrafluoroborate
TFA=Trifluoroacetic acid
THF=Tetrahydrofuran

1. INTERMEDIATES

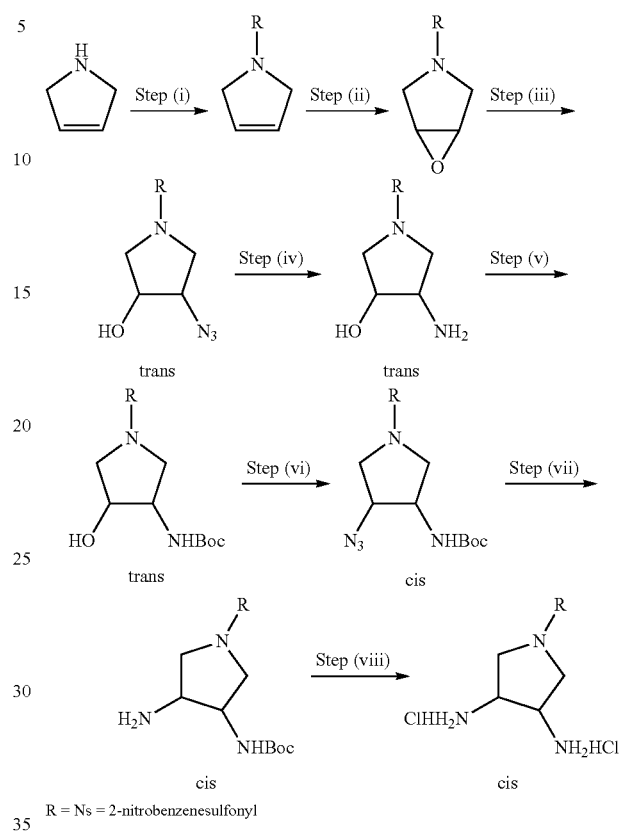

R = Ns = 2-nitrobenzenesulfonyl

Intermediate 1: cis-1-[(2-Nitrobenzene)sulfonyl]pyrrolidine-3,4-diamine

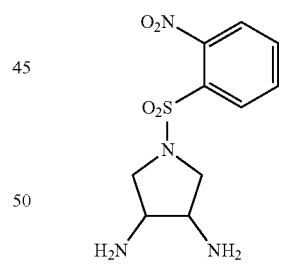

Step (i) 1-[(2-Nitrobenzene)sulfonyl]-2,5-dihydro-1H-pyrrole

To a mixture of 2,5-dihydro-1H-pyrrole (500 mg, 7.69 mmol) and pyridine (3 ml) in dichloromethane (40 ml) was added 2-nitrobenzenesulfonyl chloride (1.7 g, 7.69 mmol) in dichloromethane (10 ml) drop-wise at 0° C. The mixture was stirred whilst allowing to warm to room temperature over 2 hours, washed with dilute hydrochloric acid (1 M), brine, dried (sodium sulphate), and concentrated in vacuo to afford the title compound which was used without further purification.

Step (ii): 3-[(2-Nitrobenzene)sulfonyl]-6-oxa-3-azabicyclo[3.1.0]hexane

To a solution of 1-[(2-nitrobenzene)sulfonyl]-2,5-dihydro-1H-pyrrole (1.7 g, 6.8 mmol) in dichloromethane (50 ml), mCPBA (1.4 g, 8.1 mmol) was added portion-wise at 0° C. and then the reaction was stirred at room temperature for 24 hours. The mixture was then washed with aqueous sodium bicarbonate solution and brine, dried (sodium sulphate) and concentrated in vacuo. The crude product was purified via column chromatography (silica, ethyl acetate/petrol=3:1) to afford the title compound.

$^1$H NMR (CDCl$_3$): δ ppm 3.52 (d, 2H), 3.73 (s, 2H), 3.96 (d, 2H), 7.67-7.73 (m, 3H), 7.99 (d, 1H)

Step (iii) trans-4-Azido-1-[(2-nitrobenzene)sulfonyl]pyrrolidin-3-ol

To a mixture of 3-[(2-nitrobenzene)sulfonyl]-6-oxa-3-azabicyclo[3.1.0]hexane (500 mg, 1.88 mmol), ethanol (20 ml), water (4 ml) and ammonium chloride (303 mg, 5.64 mmol) was added sodium azide (367 mg, 5.64 mmol) and the mixture was heated to reflux for 24 hours. Upon cooling water was added and the organics were extracted into ether washed with brine, dried (sodium sulphate) and concentrated in vacuo to afford the title compound which was used without further purification.

$^1$H NMR (CDCl$_3$): δ ppm 3.53-3.60 (m, 2H), 3.73 (d, 1H), 3.84 (d, 1H), 4.05-4.07 (m, 1H), 4.31-4.33 (m, 1H), 7.67-7.76 (m, 3H), 8.05-8.07 (m, 1H)

Step (iv): trans-4-Amino-1-[(2-nitrobenzene)sulfonyl]pyrrolidin-3-ol

To a mixture of trans-4-azido-1-[(2-nitrobenzene)sulfonyl]pyrrolidin-3-ol (1.7 g, 5.45 mmol) in THF (100 ml) and water (20 ml) was added triphenylphosphine (2.14 g, 8.17 mmol) and the mixture was heated to reflux for 16 hours. Upon cooling it was acidified with hydrochloric acid (2 N) and extracted with ethyl acetate (50 ml). The aqueous phase was basified to pH~9-10 with aqueous sodium hydroxide solution (2 M), extracted with dichloromethane (containing 10% methanol), washed with brine, dried (sodium sulphate) and concentrated in vacuo to afford the title compound which was used without further purification.

1H NMR (CDCl$_3$): δ ppm 3.25-3.30 (m, 1H), 3.39-3.43 (m, 2H), 3.75-3.81 (m, 2H), 4.04-4.06 (m, 1H), 4.31-4.33 (m, 1H), 7.64-7.73 (m, 3H), 8.05-8.07 (m, 1H)

Step (v): trans-tert-Butyl N-{4-hydroxy-1-[(2-nitrobenzene)sulfonyl]pyrrolidin-3-yl}-carbamate To a solution of trans-4-amino-1-[(2-nitrobenzene) sulfonyl]pyrrolidin-3-ol (1.1 g, 3.83 mmol) in THF (50 ml) was added triethylamine (1.6 ml, 11.5 mmol) followed by Boc anhydride (1.25 g, 5.7 mmol) and the mixture was stirred at room temperature for 24 hours. Ethyl acetate (10 ml) was added and the resulting mixture was washed with dilute hydrochloric acid (1 M) and brine and then dried (sodium sulphate) and concentrated in vacuo to afford the title compound which was used without further purification.

$^1$H NMR (CDCl$_3$): δ ppm 1.43 (s, 9H), 3.22 (br, 1H), 3.36-3.40 (m, 2H), 3.74-3.83 (m, 2H), 3.95-3.97 (m, 1H), 4.29-4.32 (m, 1H), 4.83 (br, 1H), 7.63-7.74 (m, 3H), 8.03-8.05 (m, 1H)

MS ES$^+$: (M-99) 288

Step (vi): cis-tert-Butyl N-{4-azido-1-[(2-nitrobenzene)sulfonyl]pyrrolidin-3-yl}carbamate To a solution of triphenylphosphine (672 mg, 2.56 mmol) in THF (50 ml) cooled to −78° C., was added DIAD (0.5 ml, 2.56 mmol) followed by triethylamine in toluene (1 ml, 2.5 M) and the mixture was stirred at −78° C. for 4 hours. A solution of trans-tert-butyl N-{4-hydroxy-1-[(2-nitrobenzene)sulfonyl]pyrrolidin-3-yl}carbamate (248 mg, 0.64 mmol, 1 equiv.) in THF (2 ml) was added and the whole mixture was stirred for 3 hours before being allowed to warm to room temperature overnight. The reaction was quenched with methanol, concentrated in vacuo and purified by column chromatography (silica, dichloromethane-methanol, 30:1) to afford the title compound.

$^1$H NMR (CDCl$_3$): δ ppm 1.45 (s, 9H), 3.74-3.76 (m, 2H), 4.28 (s, 1H), 4.37-4.40 (m, 1H), 4.93-5.03 (m, 2H), 6.49 (br s, 1H), 7.67-7.77 (m, 3H), 8.03-8.05 (m, 1H)

Step (vii): cis-tert-Butyl N-{4-amino-1-[(2-nitrobenzene)sulfonyl]pyrrolidin-3-yl}carbamate To a mixture of cis-tert-butyl N-{4-azido-1-[(2-nitrobenzene)sulfonyl]pyrrolidin-3-yl}carbamate (2.2 g, 5.34 mmol) in THF (100 ml) and water (20 ml) was added triphenylphosphine (2.1 g, 8.01 mmol) and the mixture was heated to reflux for 24 hours. Upon cooling the mixture was acidified with dilute hydrochloric acid (2 M), extracted into ethyl acetate and the aqueous phase was basified with dilute sodium hydroxide (2 M) to pH~9-10. The resulting mixture was extracted with dichloromethane (containing 10% methanol) and concentrated in vacuo to afford the title compound which was used to the next step without further purification.

Step (viii): cis-1-[(2-Nitrobenzene)sulfonyl]pyrrolidine-3,4-diamine dihydrochloride To a solution of cis-tert-butyl N-{4-amino-1-[(2-nitrobenzene)-sulfonyl]pyrrolidin-3-yl}carbamate (2.0 g, 5.2 mmol) in ethyl acetate (5 ml) was added a solution of hydrogen chloride in ethyl acetate (excess, 4 M) and the mixture was stirred at room temperature for 24 hours before being concentrated in vacuo. The residue was taken up in ethyl acetate, filtered and the solid was dried to afford the title compound which was used without further purification.

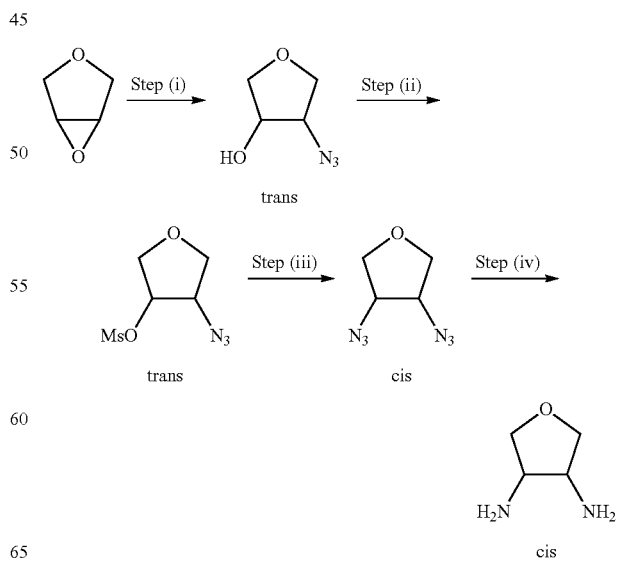

Intermediate 2: cis-Oxolane-3,4-diamine

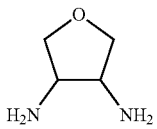

Step (i): trans-4-Azidooxolan-3-ol

A mixture of 3,6-dioxabicyclo[3.1.0]hexane (5.0 g, 58 mmol), ethanol (540 ml), water (108 ml), sodium azide (11.3 g, 174 mmol) and ammonium chloride (9.3 g, 174 mmol) was heated to reflux for 24 hours. The reaction was allowed to cool to room temperature and partially concentrated in vacuo before water (50 ml) was added and the residue extracted with ethyl acetate. The combined organics were washed with brine and dried (sodium sulphate) and the solvent was removed in vacuo to afford the title compound which was used without further purification.

$^1$H NMR (CDCl$_3$): δ ppm 3.20-3.40 (br s, 1H), 3.70 (d, J=10.0 Hz, 1H), 3.78 (d, J=10.0 Hz, 1H), 3.91-3.95 (m, 1H), 3.95-3.99 (m, 1H), 4.03-4.94 (m, 1H), 4.29 (s, 1H)

Step (ii): trans-4-Azidooxolan-3-yl methanesulfonate

A solution of methanesulfonyl chloride (4.9 ml, 63.1 mmol) in dichloromethane (20 ml) was added to a mixture of trans-4-azidooxolan-3-ol (6.8 g, 52.6 mmol), dichloromethane (250 ml) and dry pyridine (5.9 ml, 73.6 mmol) at 0° C. under nitrogen. The solution was stirred for 24 hours at room temperature and then an aqueous sodium bicarbonate solution (5%, 50 ml) was added. The aqueous phase was extracted with dichloromethane and the combined organics were washed with brine and dried (sodium sulphate). The solvent was removed in vacuo to afford the title compound which was used without further purification.

$^1$H NMR (CDCl$_3$): δ ppm 3.67 (s, 3H), 3.83-3.90 (m, 1H), 3.96-3.99 (m, 1H), 4.09 (d, J=11.2 Hz, 1H), 4.10 (d, J=10.0 Hz, 1H), 4.29-4.30 (m, 1H), 5.05-5.06 (m, 1H)

Step (iii): cis-3,4-Diazidooxolane

A mixture of trans-4-azidooxolan-3-yl methanesulfonate (9.3 g, 45 mmol), sodium azide (5.9 g, 90 mmol), DMF (414 ml), pyridine (13 ml) and water (85 ml) was heated to reflux for 24 hours. Upon cooling, the reaction was quenched by the addition of cold water (800 ml) and extracted with diethyl ether. The combined organics were washed with brine and dried (sodium sulphate) and the solvent was removed in vacuo. The crude product was purified via column chromatography (silica, petrol-dichloromethane, 1:1) to afford the title compound.

Step (iv): cis-Oxolane-3,4-diamine dihydrochloride

A mixture of cis-3,4-diazidooxolane (1.8 g, 11.6 mmol), methanol (100 ml), 20% palladium hydroxide on carbon (600 mg) and hydrochloric acid (2 M, 10 ml) was stirred at 60 psi hydrogen for 16 hours. Removal of the methanol from the filtrate and lyophilization of the aqueous residue gave a solid which was then triturated with ethanol to afford the title compound which was used without further purification.

$^1$H NMR (D$_2$O): δ ppm 4.06 (10.8 Hz, 2H), 4.18 (10.8 Hz, 2H), 4.32-4.36 (m, 2H)

Intermediate 3: 5-Methyl-2-(2H-1,2,3-triazol-2-yl)benzoic acid

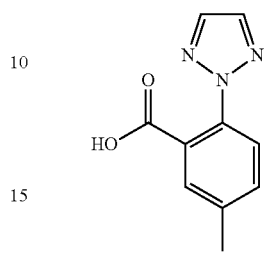

To the solution of 1,2,3-triazole (1.99 g, 28.93 mmol) in DMF (7.0 ml) at 0-10° C. was added cesium carbonate (4.7 g, 14.45 mmol), N,N-dimethylethylenediamine (0.127 g, 1.45 mmol), copper(I) iodide (0.068 g, 0.36 mmol) and 2-iodo-5-methylbenzoic acid (3.79 g, 14.46 mmol). The reaction was subjected to microwave irradiation at 125° C. for 15 minutes, and then poured into water (20 ml) and extracted with ethyl acetate. The combined organics were washed with brine, dried (sodium sulphate) and concentrated in vacuo. The crude product was purified by column chromatography (0-3% methanol in dichloromethane) to afford the title compound.

$^1$H NMR (DMSO-d$_6$) δ ppm 2.42 (s, 3H), 7.49-7.52 (m, 1H), 7.58-7.64 (m, 2H), 8.05 (s, 2H), 13.01 (s, 1H)

MS ES$^+$: 204

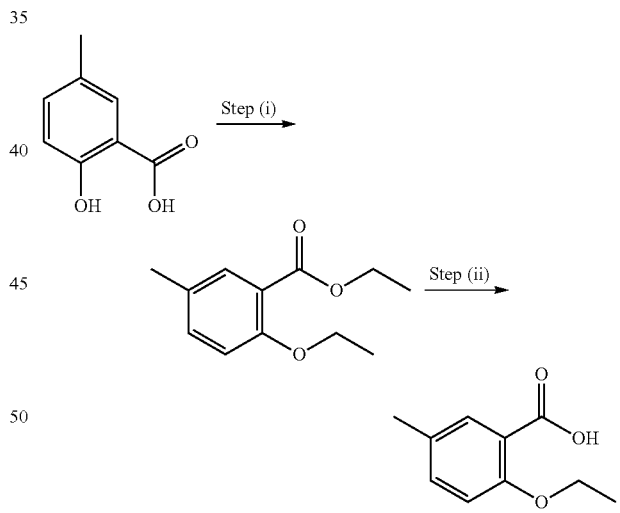

Intermediate 4: 2-Ethoxy-5-methylbenzoic acid

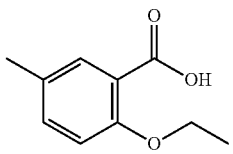

Step (i): Ethyl 2-ethoxy-5-methylbenzoate

To the solution of 2-hydroxy-5-methylbenzoic acid (0.5 g, 3.28 mmol) in acetone (3.0 ml) was added ethyl sulphate (1.51 g, 9.86 mmol) and potassium carbonate (1.13 g, 8.22 mmol) and the resulting mixture was stirred at room temperature for 15 hours. The reaction mixture was quenched with water (10 ml) and extracted into ethyl acetate and the combined organics were washed with brine and dried (sodium sulphate). The mixture was concentrated in vacuo and the crude product was purified via column chromatography (silica, 0-30% ethyl acetate in n-hexane) to afford the title compound.
MS ES$^+$: 209

Step (ii): 2-Ethoxy-5-methylbenzoic acid

To a solution of ethyl 2-ethoxy-5-methylbenzoate (0.5 g, 2.403 mmol) in methanol (1 ml) was added aqueous sodium hydroxide solution (0.192 g, 4.807 mmol) and the resulting mixture was heated to 80° C. for 1 hour. Upon cooling, the reaction was extracted with ethyl acetate which was discarded and then the acidity of the aqueous phase was adjusted to pH~2-3 and product was extracted into ethyl acetate. The combined organics were washed with water and brine then dried (sodium sulphate) and concentrated in vacuo to crude obtain the title compound which was used without further purification.
$^1$H NMR (DMSO-d$_6$) δ ppm 1.29-1.34 (m, 3H), 2.25 (s, 3H), 4.01-4.07 (m, 2H), 6.69-7.00 (d, 1H), 7.26-7.28 (m, 1H), 7.41-7.42 (d, 1H), 12.42 (s, 1H)
MS ES$^+$: 181

Intermediate 5: (1S,2R)-1-N-(1,3-Benzoxazol-2-yl)cyclopentane-1,2-diamine hydrochloride

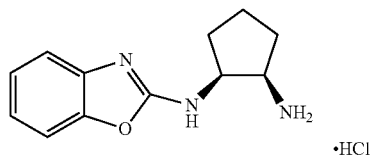 [SMILES: N[C@@H]1CCC[C@@H]1Nc1nc2ccccc2o1 ; Cl]

·HCl

To a solution of tert-butyl ((1R,2S)-2-aminocyclopentyl)carbamate (500 mg, 2.497 mmol) in dry acetonitrile (8.3 ml) was added DIPEA (1.3 ml, 7.49 mmol) and 2-chloro-1,3-benzooxazole (422 mg, 2.75 mmol). The reaction was subjected to microwave irradiation at 100° C. for 2 hours before being concentrated in vacuo to give a brown oil. This was purified by column chromatography (silica, 0-100% ethyl acetate in petrol). The intermediate was then dissolved in 1,4-dioxane (3 ml) and added to a solution of hydrogen chloride in 1,4-dioxane (4 M, 3 ml) and stirred at room temperature for 2 hours. The mixture was concentrated in vacuo and then azeotropically distilled with toluene to afford the title compound.
MS ES$^+$: 218

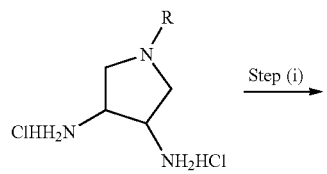

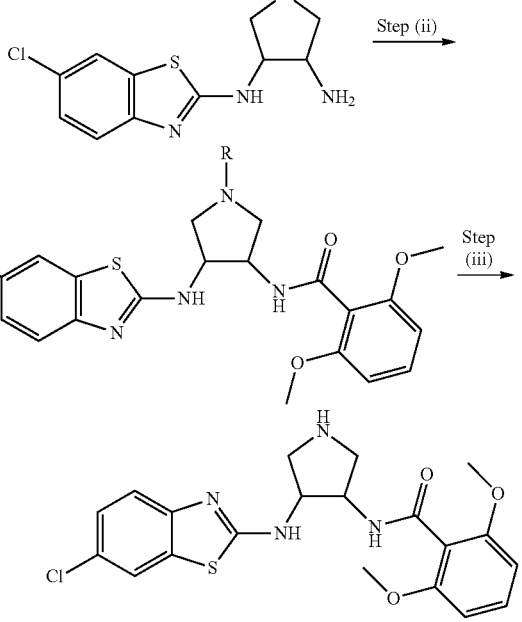

R = Ns = 2-nitrophenylsulfonyl

Intermediate 6: cis-N-{4-[(6-chloro-1,3-benzothiazol-2-yl)amino]pyrrolidin-3-yl}-2,6-dimethoxybenzamide

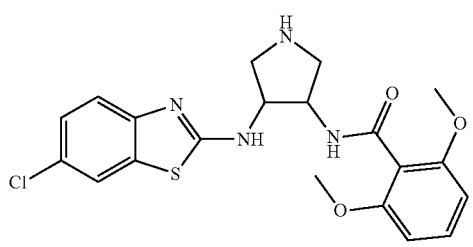

cis

Step (i): cis-3-N-(6-Chloro-1,3-benzothiazol-2-yl)-1-[(2-nitrobenzene)sulfonyl]-pyrrolidine-3,4-diamine A mixture of cis-1-[(2-nitrobenzene)sulfonyl]pyrrolidine-3,4-diamine dihydrochloride (Intermediate 1: 100 mg, 0.28 mmol), water (2 ml) and sodium bicarbonate (94 mg, 1.12 mmol) was stirred for 20 minutes and then 2,6-dichloro-1,3-benzothiazole (114 mg, 0.56 mmol) was added followed by iso-propanol (15 ml). The mixture was subjected to microwave irradiation at 130° C. for 3 hours, allowed to cool and then concentrated in vacuo. Ethyl acetate was added and the whole was washed with dilute hydrochloric acid (1 M) and brine, dried (sodium sulphate), concentrated in vacuo and purified by preparative TLC to afford the title compound.

Step (ii): cis-N-{4-[(6-Chloro-1,3-benzothiazol-2-yl) amino]-1-[(2-nitrobenzene)-sulfonyl]pyrrolidin-3-yl}-2,6-dimethoxybenzamide To a solution of cis-3-N-(6-chloro-1,3-benzothiazol-2-yl)-1-[(2-nitrobenzene)sulfonyl]-pyrrolidine-3,4-diamine (130 mg, 0.29 mmol) in dichloromethane (10 ml) was added triethylamine (0.12 ml, 0.86 mmol) and the mixture was cooled to 0° C. 2,6-Dimethoxybenzoic acid chloride (70 mg, 0.35 mmol) in dichloromethane (2 ml) was added drop-wise and the reaction was allowed to stir for 30 minutes, concentrated in vacuo and purified by preparative TLC to afford the title compound which was used to the next step without further purification.

Step (iii): cis-N-{4-[(6-Chloro-1,3-benzothiazol-2-yl)amino]pyrrolidin-3-yl}-2,6-dimethoxybenzamide To a solution of N-[cis-4-[(6-chloro-1,3-benzothiazol-2-yl)amino]-1-[(2-nitrobenzene)-sulfonyl]pyrrolidin-3-yl]-2,6-dimethoxybenzamide (400 mg, crude) in acetonitrile (20 ml) was added potassium carbonate (268 mg) followed by benzenethiol (71 mg) and the mixture was stirred at room temperature for 24 hours. The reaction was concentrated in vacuo then purified via column chromatography (silica, dichloromethane/methanol=20:1 to 10:1) to afford the title compound.

Intermediate 7: cis-3-N-(6-Chloro-1,3-benzothiazol-2-yl)oxolane-3,4-diamine

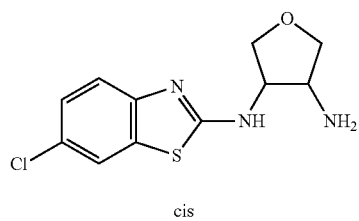 [SMILES: NC1COCC1Nc1nc2ccc(Cl)cc2s1]

cis

A mixture of cis-oxolane-3,4-diamine (Intermediate 2, 900 mg, 5.13 mmol), 2,6-dichlorobenzothiazole (2.6 g, 12.8 mmol), sodium bicarbonate (1.7 g, 20 mmol), iso-propanol (36 ml) and water (4.8 ml) was heated to reflux for 18 hours. The mixture was partially concentrated in vacuo, triturated with ethyl acetate and dried (sodium sulphate). After filtration of the desiccant the solution was concentrated in vacuo and the crude residue was purified by flash chromatography (silica, dichloromethane/methanol=100:0 to 94:06) to afford the title compound.

$^1$H NMR (CDCl$_3$): δ ppm 3.59-3.42 (m, 1H), 3.71-3.78 (m, 2H), 4.05-4.10 (m, 1H), 4.23-4.30 (m, 1H), 4.31-4.35 (m, 1H), 6.43 (s, 1H), 7.23-7.30 (m, 1H), 7.42 (d, J=8.4 Hz, 1H), 7.53 (d, J=2.0 Hz, 1H)

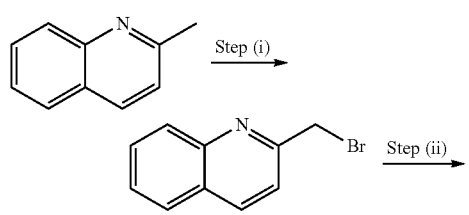

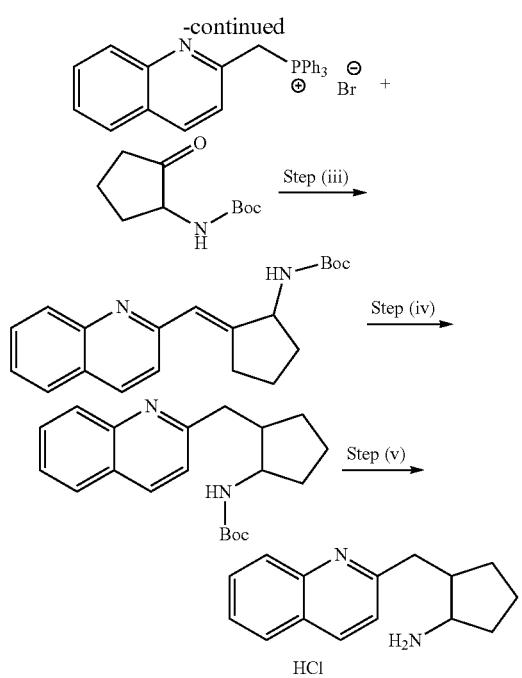

Intermediate 8: 2-(Quinolin-2-ylmethyl)cyclopentan-1-amine hydrochloride

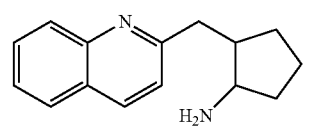

Step (i): 2-(Bromomethyl)quinoline

To a solution of 2-methylquinoline (40 g, 279 mmol) in carbon tetrachloride (700 ml) was added benzoyl peroxide (1.69 g, 6.993 mmol) and N-bromosuccinamide (59.74 g, 335 mmol) and the resulting mixture was heated to reflux overnight. On cooling to room temperature, the reaction mixture was filtered through a "Celite" bed and washed with dichloromethane. The mother liquor was evaporated in vacuo and the crude compound was purified by column chromatography (silica, 0-15% ethyl acetate in n-hexane) to afford the title compound.

$^1$H NMR (CDCl$_3$) δ ppm 4.74 (s, 2H), 7.58-7.61 (m, 2H), 7.74-7.78 (m, 1H), 7.83-7.85 (m, 1H), 8.08-8.11 (m, 1H), 8.19-8.21 (m, 1H)

Step (ii): Triphenyl(quinolin-2-ylmethyl)phosphonium bromide

To the solution of 2-(bromomethyl)quinoline (25 g, 112 mmol) in toluene (500 ml) was added triphenylphosphine (35 g, 135 mmol) and the resulting mixture was heated to reflux for 16 hours. Upon cooling, the toluene was evaporated in vacuo and the crude compound was purified by triturating with diethyl ether to afford the title compound.

<sup>1</sup>H NMR (DMSO-d<sub>6</sub>) δ ppm 5.74-5.78 (m, 2H), 7.50-7.58 (m, 1H), 7.60-7.69 (m, 2H), 7.70-7.74 (m, 7H), 7.82-7.95 (m, 10H), 8.34-8.36 (m, 1H)

Step (iii): tert-Butyl N-[2-(E)-2-(quinolin-2-ylmethylidene)cyclopentyl]carbamate To the suspension of triphenyl(quinolin-2-ylmethyl)phosphonium bromide (40 g, 82.47 mmol) in THF (400 ml) was added n-butyl lithium (23%, 45.56 ml, 164.9 mmol) at 0° C. and the resulting mixture was stirred at room temperature for 2 hours. A solution of tert-butyl 2-oxocyclopentylcarbamate (16.41 g, 82.47 mmol) in THF (50 ml) was added and the resulting mixture was stirred at room temperature for 14 hours before being quenched with saturated aqueous ammonium chloride solution (50 ml). The resulting mixture was then poured into water before the product was extracted into ethyl acetate. The combined organics were washed with brine, dried (sodium sulphate) and concentrated in vacuo. The crude product was purified by column chromatography (silica, 0-15% ethyl acetate in n-hexane) afford the title compound.
MS ES<sup>+</sup>: 324

Step (iv): tert-Butyl N-[2-(quinolin-2-ylmethyl)cyclopentyl]carbamate

To a solution of tert-butyl N-[2-(E)-2-(quinolin-2-ylmethylidene)cyclopentyl]carbamate (15 g, 46.296 mmol) in methanol (60 ml) was added palladium on carbon (2 g) and the resulting mixture was stirred under hydrogen gas for 2 hours. The reaction was filtered through diatomaceous earth (commercially sold under the trade mark "Celite") and washed with methanol and the mother liquors were evaporated in vacuo. The crude product was purified by column chromatography (silica, 0-20% ethyl acetate in n-hexane) to afford the title compound.
MS ES<sup>+</sup>: 327

Step (v): 2-(Quinolin-2-ylmethyl)cyclopentan-1-amine hydrochloride

To a solution of tert-butyl N-[2-(quinolin-2-ylmethyl)cyclopentyl]carbamate (14 g, 4.28 mmol) in 1,4-dioxane (5 ml) was added hydrogen chloride in 1,4-dioxane (12%, 20 ml) at 0° C. and the resulting mixture was stirred at room temperature for 1 hour. The reaction was concentrated in vacuo and the crude compound was purified via column chromatography (silica, 0-2% methanol in dichloromethane) to afford the cis- and trans-isomers of the title compound.
Isomer 1 Racemic
1H NMR (DMSO-d<sub>6</sub>) δ ppm 1.50-1.70 (m, 2H), 1.75-1.86 (m, 2H), 1.94-2.02 (m, 1H), 2.61-2.68 (m, 1H), 3.17-3.25 (m, 2H), 3.48-3.57 (t, 1H), 3.63-3.65 (t, 1H), 7.83-7.87 (t, 1H), 7.96 (s, 1H), 8.04-8.06 (m, 1H), 8.25-8.27 (t, 1H), 8.37 (s, 4H), 8.85-9.01 (br s, 1H)
MS ES<sup>+</sup>: 228
Isomer 2 Racemic
<sup>1</sup>H NMR (DMSO-d<sub>6</sub>) δ ppm 1.39-1.50 (m, 1H), 1.60-1.72 (m, 3H), 1.72-1.83 (m, 1H), 2.02-2.15 (m, 1H), 3.14-3.25 (m, 1H), 3.32-3.44 (m, 1H), 3.60-3.90 (m, 1H), 7.81-8.01 (m, 2H), 8.02-8.12 (m, 1H), 8.23-8.49 (m, 5H), 8.85-9.05 (br s, 1H)
MS ES<sup>+</sup>: 228

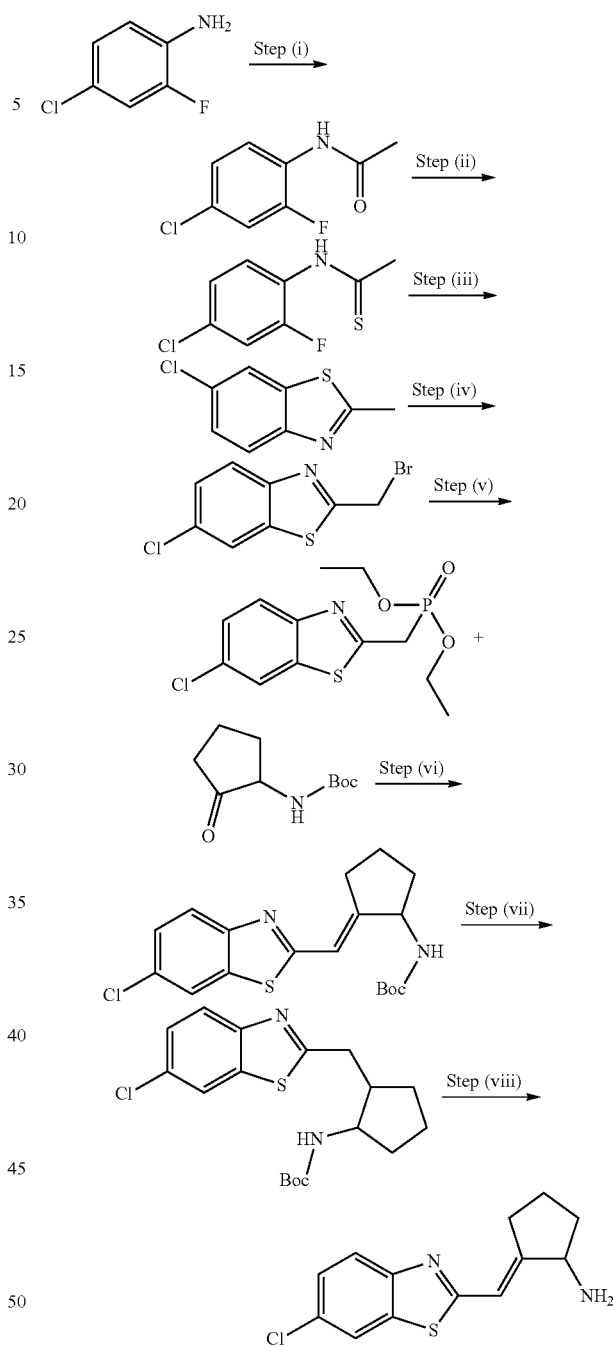

Intermediate 9: 2-[(6-Chloro-1,3-benzothiazol-2-yl)methyl]cyclopentan-1-amine

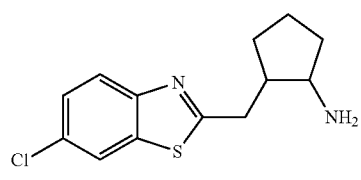 [SMILES: NC1CCCC1Cc1nc2ccc(Cl)cc2s1]

Step (i): N-(4-Chloro-2-fluorophenyl)acetamide

To the solution of 4-chloro-2-fluoroaniline (25.0 g, 172.41 mmol) in dichloromethane (500 ml) was added triethylamine (34.82 g, 344.82 mmol) and acetyl chloride (14.79 g, 189.65 mmol) and the resulting reaction mixture was stirred at room temperature for 16 hours. The reaction mass was quenched with water and the aqueous layer was extracted into dichloromethane. The organic layer was dried (sodium sulphate) and evaporated in vacuo to afford the crude product which was triturated from diethyl ether and used without further purification.

$^1$H NMR (DMSO-$d_6$) δ ppm 2.09 (s, 3H) 7.35-7.37 (m, 1H), 7.47-7.50 (m, 1H), 7.92-7.96 (m, 1H), 9.84 (br. s, 1H)
MS ES$^+$: 188

Step (ii): N-(4-Chloro-2-fluorophenyl)ethanethioamide

To a suspension of phosphorus pentasulfide (25.52 g, 115.5 mmol) in anhydrous benzene (400 ml) was added N-(4-chloro-2-fluorophenyl) acetamide (24.0 g, 128.34 mol) and the bright yellow suspension was heated to reflux for 3 hours. The solution was cooled to 0° C. and filtered and the precipitate was washed with diethyl ether and discarded. The combined organics were extracted with dilute aqueous sodium hydroxide solution (10%). After cooling the aqueous layer to 0° C., it was carefully acidified with concentrated hydrochloric acid (to pH 2-3). The precipitated product was collected by filtration and washed with water to obtain the title compound.

$^1$H NMR (DMSO-$d_6$) δ ppm 2.57 (s, 3H) 7.35-7.37 (m, 1H) 7.55-7.60 (m, 2H), 11.46 (s, 1H)

Step (iii): 6-Chloro-2-methyl-1,3-benzothiazole

To a suspension of sodium hydride (2.88 g, 120.21 mmol) in anhydrous toluene (500 ml) was added N-(4-chloro-2-fluorophenyl)ethane thioamide (20.0 g, 109.28 mmol) in one portion at 0° C. The resulting solution was allowed to warm to room temperature over 1 hour and then heated to reflux. After 30 min, DMF (60 ml) was carefully added and the reaction was stirred for an additional 2 hours. The mixture was then cooled to 0° C. and added to ice-water before being extracted with ethyl acetate. The combined organics were washed with brine and dried (magnesium sulphate) filtered and concentrated in vacuo to afford the title compound.

$^1$H NMR (DMSO-$d_6$) δ ppm 2.79 (s, 3H), 7.49-7.51 (d, 1H) 7.88-7.91 (d, 1H), 8.17 (s, 1H)

Step (iv): 2-(Bromomethyl)-6-chloro-1,3-benzothiazole

To the solution of 6-chloro-2-methyl-1,3-benzothiazole (15 g, 81.96 mmol) in carbon tetrachloride (500 ml) was added benzoyl peroxide (0.92 g, 0.364 mmol) and N-bromosuccinimide (18.52 g, 10.40 mmol) and the resulting mixture was stirred at reflux for 14 hours. Upon cooling the mixture was filtered through a "Celite" bed, washed with dichloromethane and the solvent was evaporated in vacuo to obtain crude product. The crude compound was purified by column chromatography (silica, 0-5% ethyl acetate in n-hexane) to afford the title compound.

$^1$H NMR (DMSO-$d_6$) δ ppm 5.14 (s, 2H), 7.58-7.61 (d, 1H), 8.01-8.03 (d, 1H), 8.3 (s, 1H)

Step (v): Diethyl [(6-chloro-1,3-benzothiazol-2-yl)methyl]phosphonate

To the solution of 2-(bromomethyl)-6-chlorobenzo-1,3-thiazole (5.0 g, 19.04 mmol) in toluene (250 ml) was added triethylphosphite (6.32 g, 38.08 mmol) and the resulting reaction mixture was refluxed for 12 hours. On cooling, the toluene was evaporated in vacuo to obtain the crude product which was used without purification (4.6 g, 14.42 mmol, 76% yield).
MS ES$^+$: 319

Step (vi): tert-Butyl N-[2-(E)-2-[(6-chloro-1,3-benzothiazol-2-yl)methylidene]cyclopentyl]-carbamate To the suspension of diethyl [(6-chloro-1,3-benzothiazol-2-yl)methyl]phosphonate (4.6 g, 14.42 mmol) in THF (300 ml) was added n-butyl lithium (23%, 1.84 g, 8.0 ml, 28.84 mmol) at 0° C. and then the mixture was stirred at room temperature for 2 hours. A solution of tert-butyl 2-oxocyclopentylcarbamate (5.76 g, 28.84 mmol) in THF (25 ml) was then added and resulting mixture was stirred at room temperature for 16 hours. The reaction was quenched with saturated aqueous ammonium chloride solution and then poured into water and the product was extracted into ethyl acetate. The combined organics were washed with brine, dried (sodium sulphate) and concentrated in vacuo. The crude product was purified by column chromatography (silica, 0-15% ethyl acetate in n-hexane) to afford the title compound.
MS ES$^+$: 364

Step (vii): tert-Butyl N-{2-[(6-chloro-1,3-benzothiazol-2-yl)methyl]cyclopentyl}carbamate To the solution of tert-butyl N-[2-(E)-2-[(6-chloro-1,3-benzothiazol-2-yl)methylidene]-cyclopentyl]-carbamate (0.9 g, 2.472 mmol) in methanol (15 ml) was added platinum oxide (150 mg) and then the mixture was stirred under an atmosphere of hydrogen for 2 hours. The reaction mass was then filtered through a "Celite" bed and washed with methanol and the mother liquors were evaporated in vacuo. The crude product was purified by column chromatography (silica, 0-20% ethyl acetate in n-hexane) to the title compound.
MS ES$^+$: 366

Step (viii): 2-[(6-Chloro-1,3-benzothiazol-2-yl)methyl]cyclopentan-1-amine tert-Butyl N-{2-[(6-chloro-1,3-benzothiazol-2-yl)methyl]cyclopentyl}carbamate (0.8 g, 1.91 mmol) was dissolved in 1,4-dioxane (1 ml) and then hydrogen chloride in 1,4-dioxane (12%, 7 ml) was added drop-wise at 0° C. and the resulting solution was stirred at room temperature for 1 hour before the reaction mixture was concentrated in vacuo and following basification, the crude product was purified by column chromatography (silica, eluted in 0-2% methanol) to yield the cis- and trans-isomers of the title compound.

Isomer 1, Racemic $^1$H NMR (400 MHz DMSO-$d_6$) δ ppm 1.61-1.69 (m, 2H), 1.70-1.76 (m, 4H), 1.99-2.03 (m, 1H), 3.11-3.14 (m, 1H), 3.35-3.41 (m, 1H), 3.70-3.71 (m, 1H), 7.53-7.56 (m, 1H), 7.97-7.99 (d, 1H), 8.06 (m, 2H), 8.25 (s, 1H)

Isomer 2, Racemic $^1$H NMR (400 MHz DMSO-d$_6$) δ ppm 1.55-1.60 (m, 2H), 1.63-1.68 (m, 4H), 1.71-1.80 (m, 1H), 3.08-3.14 (m, 1H), 3.35-3.40 (m, 1H), 3.71 (m, 1H), 7.53-7.55 (d, 1H), 7.94-8.01 (m, 3H), 8.26 (s, 1H)

Intermediate 10: N-[(1S,2R)-2-Aminocyclopentyl]-2,6-dimethoxybenzamide hydrochloride

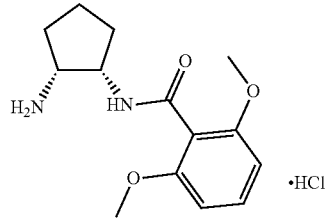 [SMILES: COc1cccc(OC)c1C(=O)N[C@H]1CCC[C@H]1N ; Cl]

To a solution of tert-butyl ((1R,2S)-2-aminocyclopentyl)carbamate (500 mg, 2.497 mmol) in dry dichloromethane (8.3 ml) was added DIPEA (1.3 ml, 7.49 mmol) and 2,6-dimethoxybenzoyl chloride (751 mg, 3.74 mmol). The reaction was stirred at room temperature under an atmosphere of nitrogen for 17 hours before being partitioned between dichloromethane and water and passed through a phase separator. The organic portion was concentrated in vacuo to give a yellow solid which was purified by column chromatography (silica, 50-100% ethyl acetate in petrol). The intermediate was dissolved in 1,4-dioxane (2 ml) and hydrochloric acid in 1,4-dioxane (4 M, 2 ml). The reaction was stirred at room temperature for 2 hours and then concentrated in vacuo, with the subsequent addition of portions of toluene and removal by azeotropic distillation to the title compound.

MS ES$^+$: 265

Intermediate 11: N-[(1S,2S)-2-Aminocyclopentyl]-2,6-dimethoxybenzamide hydrochloride

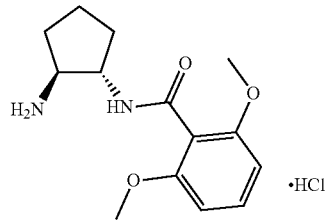 [SMILES: COc1cccc(OC)c1C(=O)N[C@H]1CCC[C@@H]1N ; Cl]

Prepared according to the procedure for N-[(1S,2R)-2-aminocyclopentyl]-2,6-dimethoxybenzamide hydrochloride (Intermediate 10) from tert-butyl ((1S,2S)-2-aminocyclopentyl)carbamate (1.0 g, 4.99 mmol) and dimethoxybenzoyl chloride (1.503 g, 7.99 mmol) except that after the reaction was complete it was portioned between dichloromethane and saturated sodium bicarbonate and passed through a phase separator and the intermediate Boc-derivative was purified by column chromatography (silica, 0-100% ethyl acetate in petrol) to give a white solid. After deprotection with hydrogen chloride solution azeotropic distillation from toluene afforded the title compound.

MS ES$^+$: 265

Intermediate 12: N-[(1S,2S)-2-Aminocyclopentyl]-5-methyl-2-(2H-1,2,3-triazol-2-yl)benzamide hydrochloride

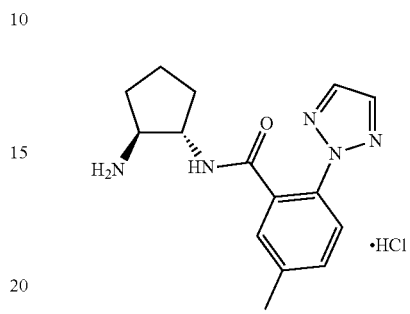

To a solution of 5-methyl-2-(2H-1,2,3-triazol-2-yl)benzoic acid (Intermediate 3, 254 mg, 1.248 mmol) in dry dichloromethane (4.16 ml) was added EDC (359 mg, 1.872 mmol), 3H-[1,2,3]triazolo[4,5-b]pyridin-3-ol (255 mg, 1.872 mmol), triethylamine (6.9 ml, 4.99 mmol) and tert-butyl ((1S,2S)-2-aminocyclopentyl)carbamate (250 mg, 1.248 mmol). The yellow solution was stirred at room temperature under an atmosphere of nitrogen for 72 hours and then partitioned between dichloromethane and water and passed through a phase separator. The organics were concentrated in vacuo to give a yellow oil which was then purified via column chromatography (silica, 0-100% ethyl acetate in petrol) to afford a pale white solid. This Boc-protected intermediate was dissolved in hydrogen chloride in 1,4-dioxane (4 M, 3 ml) and stirred at room temperature for 17 hours. The resulting mixture was concentrated in vacuo, azeotropically distilled with toluene to afford the title compound.

MS ES$^+$: 285

Intermediate 13: 2,6-Dimethoxy-N-[(1S,2S)-2-(methylamino)cyclopentyl]benzamide

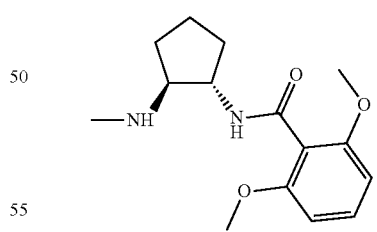

To a solution of tert-butyl ((1S,2S)-2-aminocyclopentyl)carbamate (1 g, 4.99 mmol) in dry dichloromethane (16.64 ml) was added DIPEA (2.62 ml, 14.98 mmol) and 2,6-dimethoxybenzoyl chloride (1.503 g, 7.49 mmol). The reaction was stirred at room temperature for 3 hours and the resulting mixture was partitioned between dichloromethane and a saturated aqueous solution of sodium bicarbonate before being passed through a phase separator and concentrated in vacuo. The crude material was then purified by column chromatography (silica, 0-100% ethyl acetate in petrol then 0-20% methanol in ethyl acetate). A part of this (300 mg, 0.823 mmol) was taken up in dry THF (2744 µl) and a solution of lithium aluminium hydride in THF (1235 µl, 1.235 mmol) was added drop-wise and the mixture was stirred at 60° C. under nitrogen for 1 hour. The reaction was quenched by the addition of sodium sulfate decahydrate and stirred. This mixture was then filtered through a "Celite" bed, washing with ethyl acetate and the organics were concentrated in vacuo. To this was then added hydrogen chloride in dioxane (4 M) and the reaction concentrated in vacuo once more. The resulting solid was then triturated with diethyl ether and filtered but solid was hydroscopic so it was re-dissolved in methanol and the organics concentrated. This was then purified by SCX chromatography, eluting with ammonia in methanol (2 M) and concentrated to give the title compound.

MS ES+: 279

Intermediate 14: N-[(1R,2R)-2-Aminocyclopentyl]-2,6-dimethoxybenzamide hydrochloride

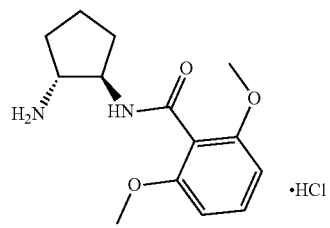 [SMILES: COc1cccc(OC)c1C(=O)N[C@@H]1CCC[C@H]1N ; Cl]

Prepared according to the procedure for N-[(1S,2R)-2-aminocyclopentyl]-2,6-dimethoxybenzamide hydrochloride (Intermediate 10) from tert-butyl ((1R,2R)-2-aminocyclopentyl)carbamate (1.0 g, 4.99 mmol) and 2,6-dimethoxybenzoyl chloride (1.50 g, 7.49 mmol) to afford the title compound.

Intermediate 15: N-[(1S,2R)-2-Aminocyclopentyl]-2,6-diethoxybenzamide hydrochloride

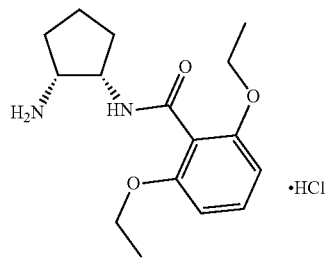 [SMILES: CCOc1cccc(OCC)c1C(=O)N[C@H]1CCC[C@H]1N ; Cl]

Prepared according to the procedure for N-[(1S,2S)-2-aminocyclopentyl]-5-methyl-2-(2H-1,2,3-triazol-2-yl)benzamide hydrochloride (Intermediate 12) from 2,6-diethoxybenzoic acid (1.57 g, 7.49 mmol) and tert-butyl ((1R,2S)-2-aminocyclopentyl)carbamate (1.0 g, 4.99 mmol).

MS ES+: 293

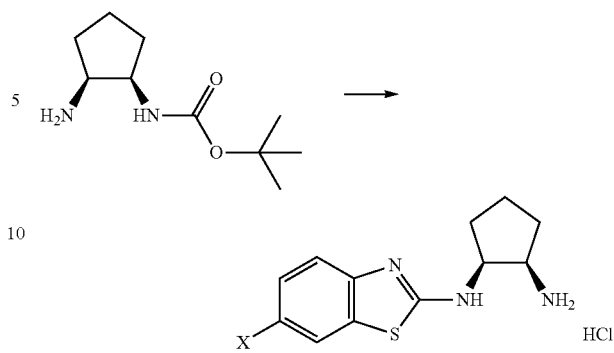

Intermediate 16a: (1S,2S)-1-N-(6-Fluoro-1,3-benzothiazol-2-yl)cyclopentane-1,2-diamine hydrochloride

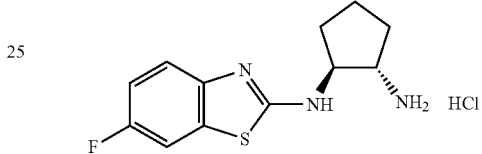

tert-Butyl ((1S,2S)-2-aminocyclopentyl)carbamate (1 g, 4.99 mmol) and 2-chloro-6-fluoro-1,3-benzothiazole (1.030 g, 5.49 mmol) were combined in a microwave vial and dissolved in dry DMSO (15 ml). DIPEA (2.62 ml, 14.98 mmol) was added before the vial was flushed with nitrogen and sealed. The reaction was heated with microwave irradiation to 140° C. for 1.5 hours and upon cooling was dissolved in ethyl acetate and washed with hydrochloric acid (0.5 M), water and brine. The combined organics were filtered through a hydrophobic frit and solvent evaporated in vacuo. The crude compound was purified by chromatography (silica, 0-50% ethyl acetate/petrol) to afford the Boc-protected intermediate which was dissolved in dioxane (5 ml) and hydrogen chloride in dioxane (4 M, 4 ml, 16.00 mmol) was added. The mixture was stirred at room temperature for 2 hours and the solvent was evaporated in vacuo. The resulting off-white solid was dried under vacuum to afford the title compound which was used without further purification.

MS ES+: 252

Intermediate 16b: (1S,2R)-1-N-(6-Chloro-1,3-benzothiazol-2-yl)cyclopentane-1,2-diamine hydrochloride

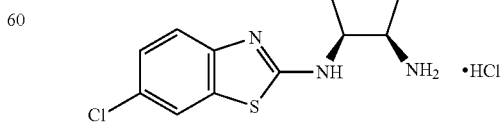

Prepared as described for (1S,2S)-1-N-(6-fluoro-1,3-benzothiazol-2-yl)cyclopentane-1,2-diamine hydrochloride (Intermediate 16a) from tert-butyl ((1R,2S)-2-aminocyclopentyl)carbamate (200 mg, 0.999 mmol) and 2-chloro-6-fluoro-1,3-benzothiazole (224 mg, 1.098 mmol) to afford the title compound.

MS ES+: 268

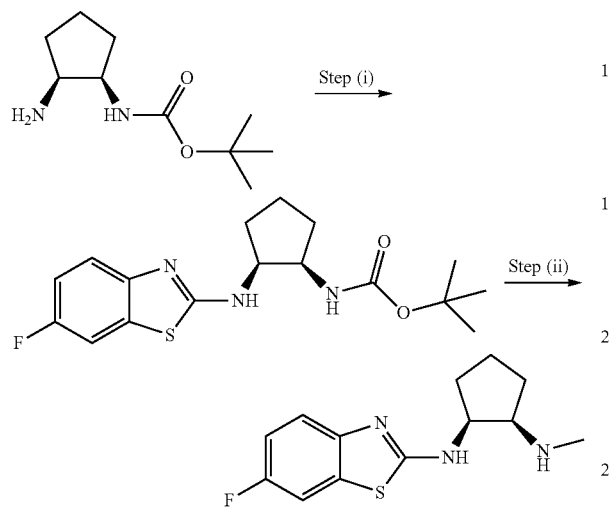

Intermediate 17: (1S,2S)-1-N-(6-Fluoro-1,3-benzothiazol-2-yl)-2-N-methylcyclopentane-1,2-diamine

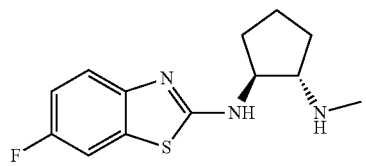 [SMILES: CN[C@H]1CCC[C@@H]1Nc1nc2ccc(F)cc2s1]

Step (i): tert-Butyl N-[(1S,2S)-2-[(6-fluoro-1,3-benzothiazol-2-yl)amino]cyclopentyl]-carbamate tert-Butyl N-[(1S,2S)-2-aminocyclopentyl]carbamate (1 g, 4.99 mmol) and 2-chloro-6-fluoro-1,3-benzothiazole (1.030 g, 5.49 mmol) were combined in a microwave vial and dissolved in dry DMSO (16 ml). DIPEA (2.62 ml, 14.98 mmol) was added then the vial flushed with nitrogen and sealed. The reaction was heated with microwave irradiation to 140° C. for 1.5 hours. Upon cooling, the mixture was dissolved in ethyl acetate and washed with water and brine. The organics were filtered through a hydrophobic frit and solvent evaporated in vacuo to afford the crude product which was purified by column chromatography (silica, 0-50% ethyl acetate/ether) to afford the title compound.

MS ES+: 352

Step (ii): (1S,2S)-1-N-(6-Fluoro-1,3-benzothiazol-2-yl)-2-N-methylcyclopentane-1,2-diamine tert-butyl N-[(1S,2S)-2-[(6-fluoro-1,3-benzothiazol-2-yl)amino]cyclopentyl]-carbamate (150 mg, 0.427 mmol) was dissolved in dry THF (1.42 ml). To this was then added a solution of lithium aluminium hydride in tetrahydrofuran (1M, 0.64 ml, 0.640 mmol) dropwise and the mixture was then heated to 60° C. under nitrogen. Upon cooling, the mixture was quenched by the addition of sodium sulfate decahydrate and filtered. The organics were concentrated in vacuo to give an oil, which was purified by column chromatography (basic silica, 0-100% ethyl acetate/petrol then 0-20% methanol/ethyl acetate) to afford the title compound.

MS ES+: 265

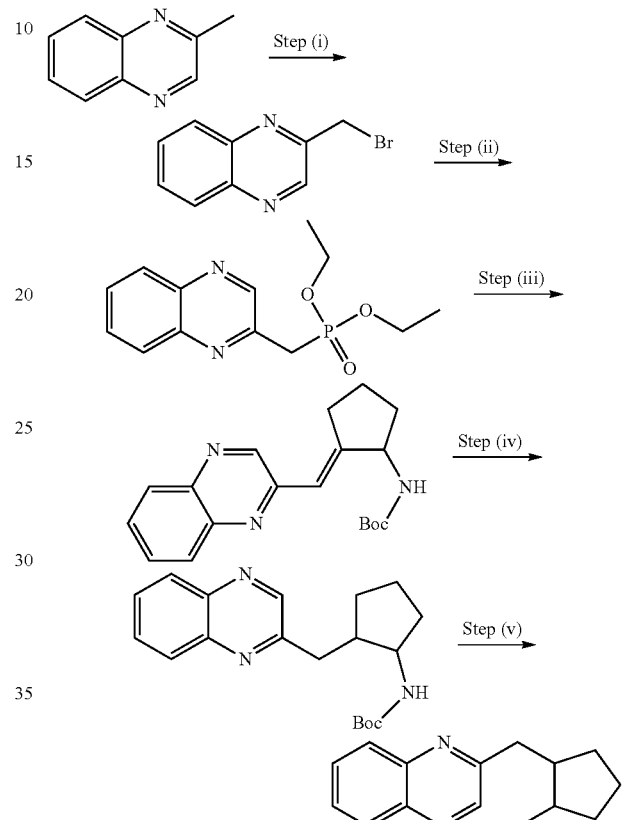

Intermediate 18a and b: cis- and trans-2-(Quinoxalin-2-ylmethyl)cyclopentan-1-amine

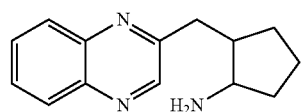

Step (i): 2-(Bromomethyl)quinoxaline

To the solution of 2-methylquinoxaline (10 g, 69.44 mmol) in carbon tetrachloride (500 ml) was added benzoyl peroxide (0.504 g, 2.08 mmol) and N-bromosuccinamide (14.83 g, 83.33 mmol) and the resulting mixture was heated to reflux overnight with stirring. Upon completion the reaction was cooled to room temperature and filtered through a bed of diatomaceous earth ("Celite" bed) washed with dichloromethane (100 ml) and the mother liquor was evaporated in vacuo. The crude product was purified by column chromatography (silica, 0-15% ethyl acetate/n-hexane) to afford the title compound.

$^1$H NMR (DMSO-d$_6$) δ ppm 4.93 (s, 2H), 7.89-7.95 (m, 2H), 8.07-8.13 (m, 2H), 9.08 (s, 1H)

Step (ii): Diethyl (quinoxalin-2-ylmethyl)phosphonate

To a solution of 2-(bromomethyl)quinoxaline (5.0 g, 22.421 mmol) in toluene (150 ml) was added triethylphosphite (11.16 g, 67.24 mmol) and the resulting reaction mixture was heated to reflux overnight with stirring. Upon completion the solvent was evaporated in vacuo to obtain crude product which was used in the next step without further purification.

$^1$H NMR (DMSO-d$_6$) δ ppm 1.20-1.27 (m, 6H), 3.75-3.80 (m, 2H), 3.96-4.09 (m, 4H), 7.82-7.89 (m, 2H), 8.04-8.11 (m, 2H), 8.91 (s, 1H)

Step (iii): tert-Butyl N-[(2E)-2-(quinoxalin-2-ylmethylidene)cyclopentyl]carbamate To a suspension of diethyl (quinoxalin-2-ylmethyl)phosphonate (5.0 g, 17.85 mmol) in THF (200 ml) was added potassium tert-butoxide (4.21 g, 35.71 mmol) at 0° C. The reaction was stirred at room temperature for 30 minutes followed by the addition of a solution of tert-butyl 2-oxo-cyclopentylcarbamate (4.26 g, 21.428 mmol) in THF (20 ml). The resulting mixture was stirred at room temperature for 1 hour and then heated to reflux for 24 hours. Upon cooling, the mixture was quenched with water and extracted with ethyl acetate. The combined organic layers were washed with brine, dried (sodium sulphate) and concentrated in vacuo. The crude product was purified by column chromatography (silica, 0-15% ethyl acetate/n-hexane) to afford the title compound.

MS ES$^+$: 326

Step (iv): tert-Butyl N-[2-(quinoxalin-2-ylmethyl)cyclopentyl]carbamate

To a solution of tert-butyl N-[(2E)-2-(quinoxalin-2-ylmethylidene)cyclopentyl]carbamate (4.5 g, 13.84 mmol) in methanol (60 ml) was added palladium on carbon (1.0 g) and aqueous sodium hydroxide solution (1 M) and the resulting mixture was stirred under hydrogen gas for 2 hours at atmospheric pressure. The reaction was then filtered through a pad of diatomaceous earth ("Celite" bed) and washed with methanol. The mother liquors were evaporated in vacuo and the crude product was purified by column chromatography (silica, 0-20% ethyl acetate/n-hexane) to afford the title compound.

MS ES$^+$: 328

Step (v): 2-(Quinoxalin-2-ylmethyl)cyclopentan-1-amine tert-Butyl N-[2-(quinoxalin-2-ylmethyl)cyclopentyl]carbamate (4.2 g, 12.844 mmol) was dissolved in dioxane (5 ml) and a solution of hydrogen chloride in dioxane (12%, 20 ml) was added drop-wise at 0° C. The resulting mixture was stirred at room temperature for 1 hour and then concentrated in vacuo and following basification, the crude product was purified by column chromatography (silica, 0-2% methanol/dichloromethane) to afford the cis- and trans-isomers of the title compound.

Intermediate 18a: Isomer 1, racemic $^1$H NMR (DMSO-d$_6$) δ ppm 1.49-1.57 (m, 4H), 1.70-1.77 (m, 2H), 1.80-2.10 (br. s, 2H), 2.24-2.26 (m, 2H), 2.90-2.96 (m, 1H), 3.12-3.18 (m, 1H), 7.77-7.84 (m, 2H), 8.01-8.07 (m, 2H), 8.91 (s, 1H)

Intermediate 18b: Isomer 2, racemic $^1$H NMR (DMSO-d$_6$) δ ppm 1.22-1.33 (m, 4H), 1.53-1.58 (m, 2H), 1.65-1.68 (m, 1H), 1.86-1.89 (m, 1H), 2.01-2.02 (m, 1H), 2.78-2.86 (m, 1H), 2.88-2.92 (m, 1H), 3.26-3.31 (m, 1H), 7.77-7.85 (m, 2H), 8.02-8.08 (m, 2H), 8.90 (s, 1H)

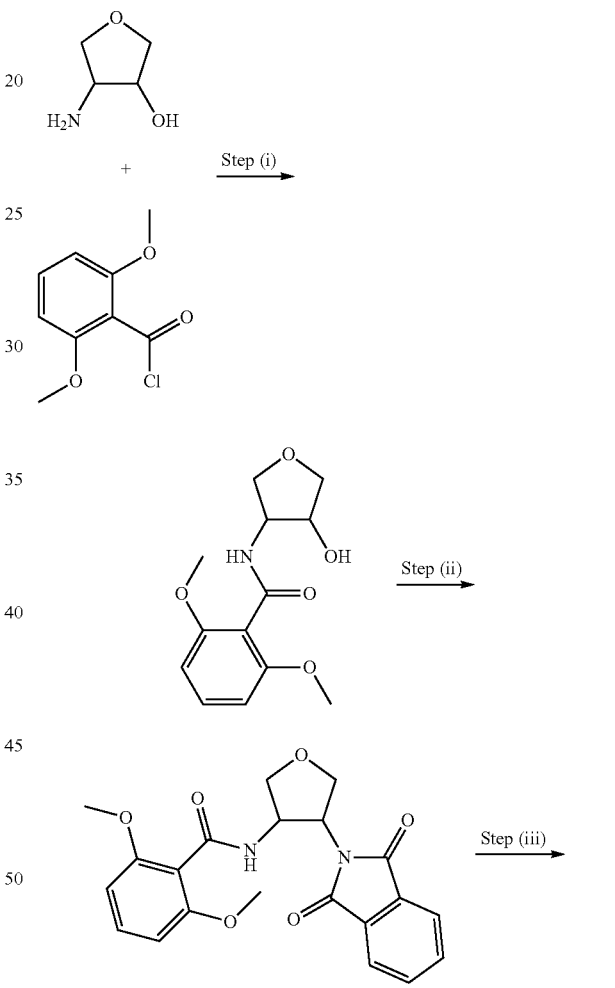

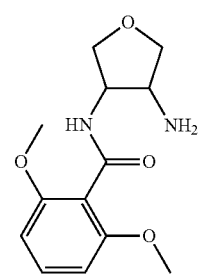

Intermediate 19: trans-N-(4-Aminooxolan-3-yl)-2,6-dimethoxybenzamide

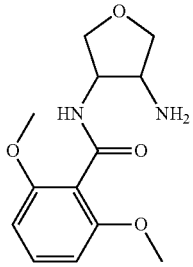 [SMILES: COc1cccc(OC)c1C(=O)NC1COCC1N]

Step (i): cis-N-(4-Hydroxyoxolan-3-yl)-2,6-dimethoxybenzamide

To a suspension of cis-4-aminotetrahydrofuran-3-ol hydrochloride (500 mg, 3.58 mmol) in a mixture of DIPEA (1.877 ml, 10.75 mmol) and dichloromethane (10 ml) was added 2,6-dimethoxybenzoyl chloride (755 mg, 3.76 mmol) slowly. The reaction mixture was stirred at room temperature for 2 hours then washed with water and filtered through a hydrophobic frit. The solvent was evaporated in vacuo and the resulting residue purified by column chromatography (silica, 0-5% ethyl acetate/methanol) to afford the title compound.

MS ES$^+$: 266

Step (ii): trans-N-[4-(1,3-Dioxo-2,3-dihydro-1H-isoindol-2-yl)oxolan-3-yl]-2,6-dimethoxybenzamide cis-N-(4-Hydroxyoxolan-3-yl)-2,6-dimethoxybenzamide (100 mg, 0.374 mmol), isoindoline-1,3-dione (60.6 mg, 0.412 mmol) and triphenylphosphine (128 mg, 0.486 mmol) were suspended in dichloromethane (1.5 ml) and the mixture placed under nitrogen. DIAD (0.095 ml, 0.486 mmol) was added slowly and the reaction was stirred at room temperature for 18 hours. Additional triphenylphosphine (128 mg, 0.486 mmol), isoindoline-1,3-dione (60.6 mg, 0.412 mmol) and DIAD (0.095 ml, 0.486 mmol) were added and the reaction was stirred for a further 24 hours before being diluted with dichloromethane and washed with water. The mixture was filtered through a hydrophobic frit and concentrated in vacuo before the crude product was partially purified by column chromatography (silica, 20-100% ethyl acetate/petrol). The residue was suspended in ether and filtered to afford the title compound contaminated with some triphenylphosphine oxide.

MS ES$^+$: 397

Step (iii): trans-N-(4-Aminooxolan-3-yl)-2,6-dimethoxybenzamide trans-N-[4-(1,3-Dioxo-2,3-dihydro-1H-isoindol-2-yl)oxolan-3-yl]-2,6-dimethoxybenzamide (1.139 g, 0.977 mmol) was dissolved in ethanol (5 ml) in a microwave vial. Hydrazine hydrate (0.74 ml, 9.77 mmol) was added and the vial sealed and heated to 50° C. for 18 hours. The resulting mixture was concentrated in vacuo and the residue suspended in mixture of methanol and dichloromethane and filtered to remove solid (phthalimide bi-product). Purification of the evaporated liquors by SCX chromatography afforded the title compound.

MS ES$^+$: 267

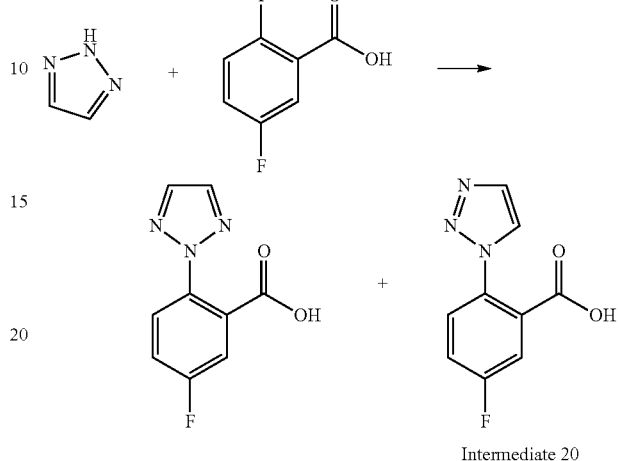

Intermediate 20

Intermediate 20: 5-Fluoro-2-(1H-1,2,3-triazol-1-yl)benzoic acid

To the solution of 1,2,3-triazole (4.0 g, 57.97 mmol) in DMF (14.0 ml) was added cesium carbonate (18.84 g, 57.97 mmol), N,N-dimethylethylenediamine (0.510 g, 5.797 mmol), copper(I) iodide (0.276 g, 1.449 mmol) and 2-iodo-5-fluorobenzoic acid (7.71 g, 28.98 mmol) at 0-10° C. The resulting reaction mixture was then heated with microwave irradiation at 125° C. for 15 hours with stirring. The reaction mass was poured into water and the product was extracted into ethyl acetate. The combined organic layers were washed with brine, dried (sodium sulphate) and concentrated in vacuo. The crude mixture was separated by column chromatography (silica, 0-3% methanol in dichloromethane) to obtain homogeneous 5-fluoro-2-(2H-1,2,3-triazol-2-yl)benzoic acid (also commercially available) and crude 5-fluoro-2-(1H-1,2,3-triazol-1-yl)benzoic acid.

The crude compound obtained above was purified again by column chromatography (silica, 0-3% methanol in dichloromethane) and further purified by preparative HPLC [Shimadzu CBM-20A.UFLC using a Waters 19 mm id×250 mm long C18 column X Bridge 5 µm materials at 12 ml/min. Mobile phase: acetonitrile/water (with 25 mM ammonium acetate)] to obtain the title compound.

$^1$H NMR (DMSO-d$_6$): δ ppm 7.41-7.45 (m, 1H), 7.50-7.52 (m, 1H), 7.57-7.60 (m, 1H), 7.83-7.84 (d, 1H), 8.42 (s, 1H)

MS ES$^+$: 208

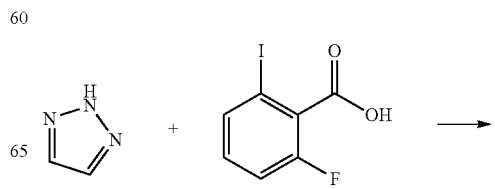

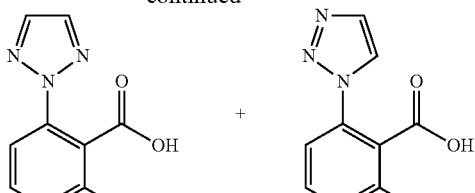

Intermediate 21

Intermediate 21:
2-Fluoro-6-(2H-1,2,3-triazol-2-yl)benzoic acid

To a solution of 2H-1,2,3-triazole (5.0 g, 72.46 mmol) in DMF (20 ml) was added cesium carbonate (23.55 g, 72.46 mmol), N,N-dimethylethylenediamine (1.02 g, 7.24 mmol), copper(I) iodide (0.34 g, 1.811 mmol) and 2-fluoro-6-iodobenzoic acid (9.63 g, 36.23 mmol) at 0-10° C. The reaction was stirred at 125° C. for 15 min in the microwave and then poured into water (100 ml) and extracted with ethyl acetate (100 ml×3). The aqueous layer was acidified with dilute HCl to pH 2 and extracted with ethyl acetate (100 ml×3). The combined organic layer was washed with brine, dried over sodium sulphate and concentrated in vacuo. This was then purified by column chromatography (0-3% methanol/dichloromethane) to afford the title compound.

$^1$H NMR (400 MHz DMSO-d$_6$): δ ppm 7.43-7.47 (m, 1H), 7.66-7.72 (m, 1H), 7.78-7.80 (m, 1H), 8.13 (s, 2H), 13.71 (s, 1H)

MS ES$^+$: 208

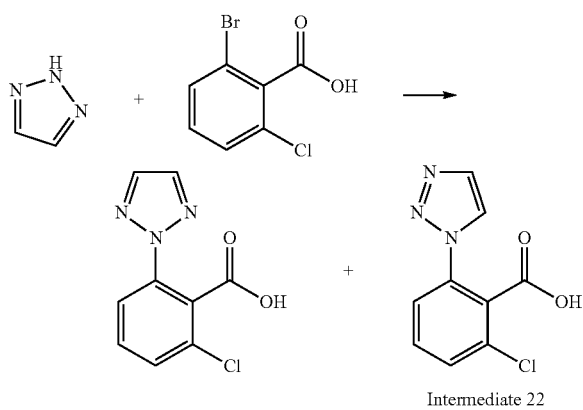

Intermediate 22

Intermediate 22:
2-Chloro-6-(2H-1,2,3-triazol-2-yl)benzoic acid

To the solution of 2H-1,2,3-triazole (4.0 g, 57.97 mmol) in DMF (14 ml) was added cesium carbonate (18.84 g, 57.97 mmol), N,N-dimethylethylenediamine (0.510 g, 5.797 mmol), copper(I) iodide (0.276 g, 1.449 mmol) and 2-bromo-6-chlorobenzoic acid (6.78 g, 28.98 mmol) at 0-10° C. The reaction was stirred at 125° C. for 15 min in the microwave and then was poured into water (100 ml) and extracted with ethyl acetate (100 ml×3). The aqueous layer was acidified with dilute HCl to pH 2 and extracted with ethyl acetate (100×3) ml. The combined organic layer was washed with brine, dried over sodium sulphate and concen- trated in vacuo. This was then purified by column chroma- tography (0-3% methanol/dichloromethane) to afford the title compound.

$^1$H NMR (400 MHz DMSO-d$_6$): δ ppm 7.62-7.67 (m, 2H), 7.92-7.94 (m, 1H), 8.17 (s, 2H), 13.73 (s, 1H)

MS ES$^+$: 224, 226

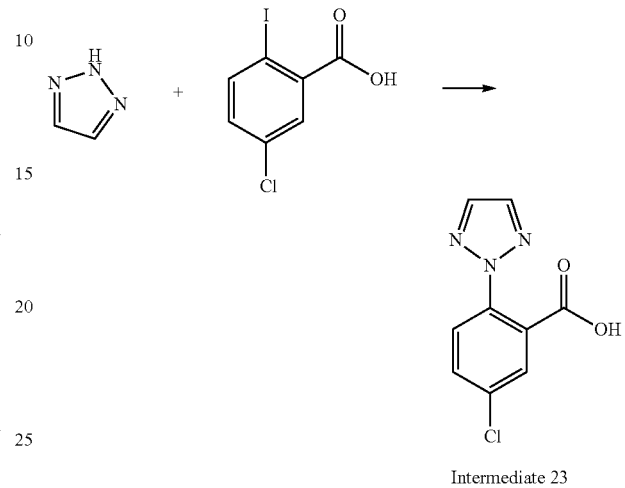

Intermediate 23

Intermediate 23:
5-Chloro-2-(1H-pyrazol-1-yl)benzoic acid

To the solution of 1H-pyrazole (1.5 g, 22.05 mmol) in DMF (7.0 ml) was added cesium carbonate (7.16 g, 22.05 mmol), trans-N,N'-cyclohexyl-1,2-diamine (0.31 g, 2.20 mmol), copper(I) iodide (0.104 g, 0.55 mmol) and 5-chloro-2-iodobenzoic acid (3.11 g, 11.02 mmol) at 0-10° C. The reaction was stirred at 125° C. for 15 min in microwave and then poured into water (100 ml) and extracted with ethyl acetate (100 ml×3). The aqueous layer was acidified with dilute HCl to pH 2 and extracted with ethyl acetate (100 ml×3). The combined organic layer was washed with brine, dried over sodium sulphate and concentrated in vacuo. This was then purified by column chromatography (0-3% methanol/dichloromethane) to afford the title compound.

$^1$H NMR (400 MHz DMSO-d$_6$): δ ppm 6.50-6.60 (m, 1H), 7.62-7.74 (m, 3H), 8.12-8.17 (m, 1H), 13.23 (s, 1H)

MS ES$^+$: 223, 225

Intermediate 24: N-[(1S,2R)-2-Aminocyclopentyl]-2-(2H-1,2,3-triazol-2-yl)benzamide hydrochloride

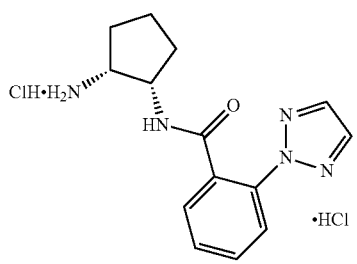

To a solution of tert-butyl N-[(1R,2S)-2-aminocyclopen- tyl]carbamate (CAS number 721395-15-9; 250 mg, 1.248 mmol) in dry DCM (4 ml) was added 2-(2H-1,2,3-triazol-2-yl)benzoic acid (CAS number 1001401-62-2; 283 mg, 1.498 mmol), aza-HOBt (289 mg, 1.872 mmol), triethylamine (0.522 ml, 3.74 mmol) and EDC (359 mg, 1.872 mmol). The reaction was stirred at room temperature for 18 hours then diluted with DCM (20 ml) and washed with HCl (aq, 1M, 20 ml), water (10 ml), saturated sodium bicarbonate solution (20 ml) and brine (10 ml). The organics were filtered through a hydrophobic frit and concentrated in vacuo to afford a residue which was purified by column chromatography (silica, 10-100% ethyl acetate/petrol) to afford a solid. This Boc-protected intermediate was dissolved in hydrogen chloride in 1,4-dioxane (4 M, 10 ml) and stirred at room temperature for 2 hours. The resulting mixture was concentrated in vacuo then azeotropically distilled with toluene to afford the title compound.

$^1$H NMR (400 MHz, DMSO-$d_6$): δ ppm 1.48-1.69 (m, 1H), 1.61-1.84 (m, 3H), 1.85-1.97 (m, 1H), 1.96-2.13 (m, 1H), 3.52-3.67 (m, 1H), 4.19-4.37 (m, 1H), 7.50-7.62 (m, 1H), 7.61-7.71 (m, 1H), 7.70-7.78 (m, 1H), 7.81-7.85 (m, 1H), 7.93 (br. s., 3H), 8.08 (s, 2H), 8.32-8.48 (m, 1H)

MS ES$^+$: 272

Intermediate 25: N-[(1S,2S)-2-Aminocyclopentyl]-2-(2H-1,2,3-triazol-2-yl)benzamide hydrochloride

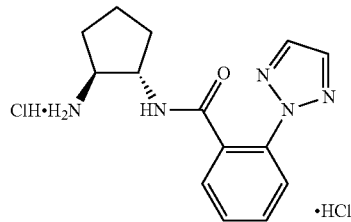

To a solution of tert-butyl N-[(1S,2S)-2-aminocyclopentyl]carbamate (CAS number 586961-34-4; 5 g, 24.97 mmol) in dry DMF (83 ml) was added 2-(2H-1,2,3-triazol-2-yl) benzoic acid (CAS number 1001401-62-2; 4.72 g, 24.97 mmol), HATU (14.24 g, 37.4 mmol) and triethylamine (10.44 ml, 74.9 mmol). The reaction was stirred at room temperature for 17 hours then was diluted with ethyl acetate and washed with saturated sodium bicarbonate solution and brine. The organics were dried over magnesium sulfate, filtered and concentrated in vacuo to afford a residue which was purified by column chromatography (silica, 0-100% ethyl acetate/petrol) to afford a solid. This Boc-protected intermediate was dissolved in hydrogen chloride in 1,4-dioxane (4 M, 20 ml) and stirred at room temperature for 60 hours. The solid was collected by filtration to afford the title compound.

$^1$H NMR (400 MHz DMSO-$d_6$): δ ppm 1.47-1.83 (m, 4H), 1.92-2.14 (m, 2H), 3.32-3.49 (m, 1H), 4.04-4.17 (m, 1H), 7.48-7.59 (m, 1H), 7.60-7.70 (m, 2H), 7.77-7.87 (m, 1H), 8.08 (s, 2H), 8.33 (br. s., 3H), 8.59-8.69 (m, 1H)

MS ES$^+$: 272

Intermediate 26: N-[(1S,2S)-2-Aminocyclopentyl]-2-(3-methyl-1,2,4-oxadiazol-5-yl)benzamide hydrochloride

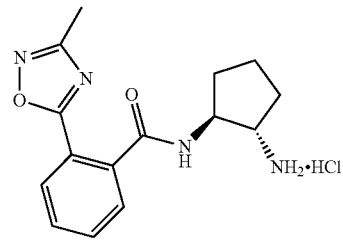

Prepared as described for N-[(1S,2S)-2-aminocyclopentyl]-2-(2H-1,2,3-triazol-2-yl)benzamide hydrochloride (Intermediate 25) from tert-butyl N-[(1S,2S)-2-aminocyclopentyl]carbamate (CAS number 586961-34-4; 750 mg, 3.74 mmol) and 2-(3-methyl-1,2,4-oxadiazol-5-yl)benzoic acid (CAS number 475105-77-2; 841 mg, 4.12 mmol) to afford the title compound.

$^1$H NMR (300 MHz, DMSO-$d_6$): δ ppm 1.54-1.88 (m, 4H), 1.92-2.13 (m, 2H), 2.42 (s, 3H), 3.41-3.54 (m, 1H), 4.08-4.25 (m, 1H), 7.63-7.79 (m, 3H), 7.94-8.04 (m, 1H), 8.15 (br. s., 3H), 8.70-8.86 (m, 1H)

MS ES$^+$: 287

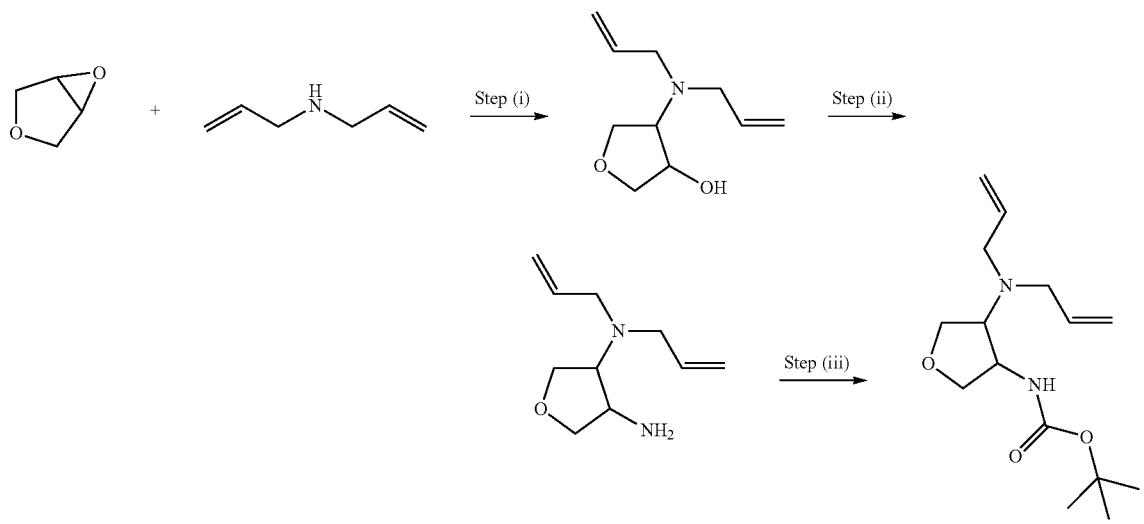

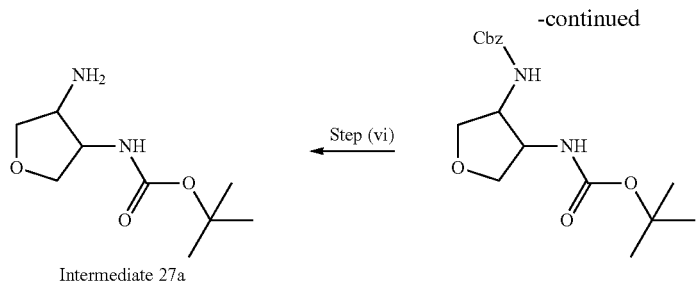

Intermediate 27a

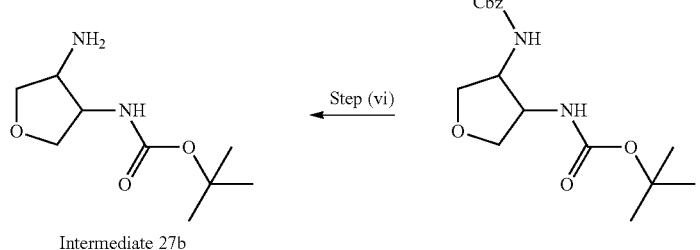

Intermediate 27b

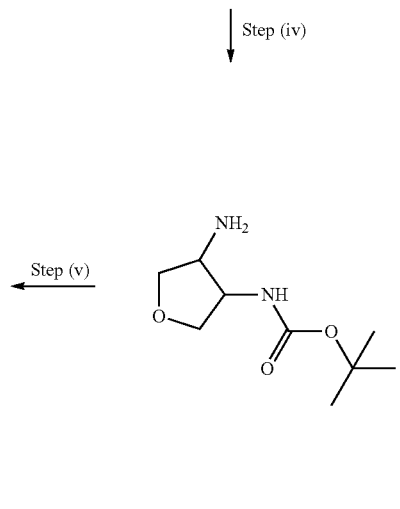

Intermediates 27a and 27b: trans-tert-Butyl N-(4-aminooxolan-3-yl)carbamate

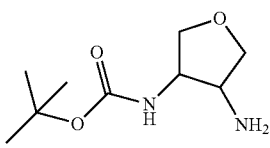

Step (i): trans-4-[Bis(prop-2-en-1-yl)amino]oxolan-3-ol

To the solution of 3,6-dioxabicyclo [3.1.0]hexane (CAS Number 285-69-8; 20.0 g, 232.5 mmol) in methanol (60 ml) was added di-allyl amine (CAS Number; 124-02-7; 67.7 g, 697.5 mmol). The reaction mixture was stirred at 72° C. for 48 hours and then concentrated in vacuo to afford the title compound.

¹H NMR (400 MHz, DMSO-d): δ ppm 2.00-2.20 (m, 1H), 3.05-3.17 (m, 5H), 3.41-3.44 (m, 1H), 3.49-3.54 (m, 1H), 3.80-3.87 (m, 2H), 4.10-4.19 (m, 1H), 5.02-5.05 (m, 1H), 5.09-5.19 (m, 3H), 5.78-5.85 (m, 2H)

MS ES⁺: 184

Step (ii): trans-3-N,3-N-Bis(prop-2-en-1-yl)oxolane-3,4-diamine

To a solution of trans-4-[bis(prop-2-en-1-yl)amino]oxolan-3-ol (40.0 g, 217.3 mmol) and triethylamine (43.8 g, 436.66 mmol) in MTBE (670 ml) at 0° C. was added mesyl chloride (29.7 g, 260.52 mmol) over 30 minutes. The solution was stirred for 30 minutes at 0° C. and then further triethylamine (43.8 g, 436.66 mmol) was added. The reaction mixture was then stirred for 30 minutes and to this was then added aq. ammonium hydroxide (28%, 600 ml). The reaction mixture was allowed to warm to room temperature and stirred for 24 hours and then partitioned between MTBE and water. The combined organics were dried over sodium sulphate and concentrated in vacuo to afford the title compound.

¹H NMR (400 MHz, DMSO-d): δ ppm 1.68 (br. s 2H), 2.44-2.51 (m, 1H), 2.93-3.22 (m, 5H), 3.52-3.57 (m, 1H), 3.73-3.87 (m, 3H), 5.09-5.26 (m, 4H), 5.76-5.87 (m, 2H)

MS ES⁺: 183

Step (iii): trans-tert-Butyl N-{4-[bis(prop-2-en-1-yl)amino]oxolan-3-yl}carbamate To a solution of trans-3-N,3-N-bis(prop-2-en-1-yl)oxolane-3,4-diamine (38.0 g, 208.79 mmol) in THF (380.0 ml) at −5° C. was added sodium carbonate (1M, 33.18 g, 313.05 mmol) and Boc-anhydride (68.2 g, 313.05 mmol). The reaction mixture was warmed to room temperature and stirred for 24 hours. The organics were extracted with ethyl acetate (11×2), dried over sodium sulphate and concentrated in vacuo to afford the title compound.

¹H NMR (400 MHz, DMSO-d): δ ppm 1.38 (s, 9H), 2.94-2.98 (m, 1H), 3.01-3.17 (m, 2H), 3.23-3.31 (m, 1H), 3.30-3.36 (m, 1H), 3.54-3.58 (m, 1H), 3.74-3.79 (m, 2H), 3.88-3.92 (m, 1H), 3.98-4.01 (m, 1H), 5.08-5.27 (m, 4H), 5.74-5.86 (m, 2H), 7.16-7.18 (m, 1H)

MS ES⁺: 283

Step (iv): trans-tert-Butyl N-(4-aminooxolan-3-yl)carbamate

To a solution of trans-tert-butyl N-{4-[bis(prop-2-en-1-yl)amino]oxolan-3-yl}carbamate (35.0 g, 123.67 mmol) in dichloromethane (700 ml) was added N,N-dimethylbarbituric acid (52.6 g, 216.14 mmol) and tetrakis(triphenylphosphine)palladium(0) (3.28 g, 2.83 mmol). The reaction mixture was stirred at 45° C. for 24 hours. The reaction was concentrated in vacuo and then purified by column chromatography (silica, 0-5% methanol/dichloromethane) to afford the title compound.

¹H NMR (400 MHz, DMSO-d): δ ppm 1.38 (s, 9H), 1.90 (br. s, 2H), 3.19-3.23 (m, 1H), 3.26-3.29 (m, 1H), 3.39-3.42 (m, 1H), 3.53-3.56 (m, 1H), 3.79-3.83 (m, 1H), 3.85-3.92 (m, 1H), 7.04-7.05 (m, 1H)

MS ES⁺: 203

Step (v): trans-Benzyl N-(4-{[(tert-butoxy)carbonyl]amino}oxolan-3-yl)carbamate To a solution of trans-tert-butyl N-(4-aminooxolan-3-yl)carbamate (10.0 g, 49.5 mmol) in dichloromethane (150 ml) at 0° C. was added benzyl chloroformate (10.0 g, 59.4 mmol). The reaction was stirred at room temperature for 24 hours and then partitioned between water and dichloromethane (100 ml). The organics were dried over sodium sulphate, concentrated in vacuo and purified by column chromatography (silica, 0-5% methanol/dichloromethane) to afford the title compound. The two trans-enantiomers were then purified by chiral HPLC (Chiralpak ADH (250×20 mm) 5 m, heptane (85%): IPA (11%): EtOH (4%): TFA (0.1%))
Enantiomer-1:
$^1$H NMR (400 MHz, DMSO-d): δ ppm 1.40 (s, 9H), 3.41-3.47 (m, 2H), 3.85-3.94 (m, 4H), 5.02 (s, 2H), 7.18-7.25 (m, 1H), 7.31-7.39 (m, 5H), 7.61-7.63 (m, 1H)
MS ES$^+$: 337
Enantiomer-2:
$^1$H NMR (400 MHz, DMSO-d): δ ppm 1.40 (s, 9H), 3.43-3.47 (m, 2H), 3.85-3.94 (m, 4H), 5.02 (m, 2H), 7.19-7.23 (m, 1H), 7.31-7.38 (m, 5H), 7.61-7.63 (m, 1H)
MS ES$^+$: 337

Step (vi): trans-tert-Butyl N-(4-aminooxolan-3-yl)carbamate

Intermediate 27a

To the solution of trans-benzyl N-(4-{[(tert-butoxy)carbonyl]amino}oxolan-3-yl)carbamate, Enantiomer 1 (1.5 g, 4.46 mmol) in ethanol (15 ml) was added palladium on carbon (0.3 g, 50% wet). The reaction mixture was stirred at room temperature under a balloon of hydrogen for 1 hour. The reaction was filtered through a "Celite" (trade mark) bed, concentrated in vacuo and purified by column chromatography (silica, 0-5% methanol/dichloromethane) to afford the title compound.
$^1$H NMR (400 MHz, DMSO-d): δ ppm 1.38 (s, 9H), 1.77-1.82 (m, 2H), 3.18-3.22 (m, 1H), 3.25-3.28 (m, 1H), 3.39-3.42 (m, 1H), 3.53-3.57 (m, 1H), 3.79-3.83 (m, 1H), 3.88-3.91 (m, 1H), 7.04-7.05 (m, 1H)
MS ES$^+$: 203

Intermediate 27b

To the solution of trans-benzyl N-(4-{[(tert-butoxy)carbonyl]amino}oxolan-3-yl)carbamate, Enantiomer 2 (1.5 g, 4.46 mmol) in ethanol (15 ml) was added palladium on carbon (0.3 g, 50% wet). The reaction mixture was stirred at room temperature under a balloon of hydrogen for 1 hour. The reaction was filtered through a "Celite" (trade mark) bed, concentrated in vacuo and purified by column chromatography (silica, 0-5% methanol/dichloromethane) to afford the title compound.
$^1$H NMR (400 MHz, DMSO-d): δ ppm 1.38 (s, 9H), 1.77-1.82 (m, 2H), 3.19-3.22 (m, 1H), 3.25-3.28 (m, 1H), 3.39-3.42 (m, 1H), 3.51-3.55 (m, 1H), 3.79-3.83 (m, 1H), 3.88-3.92 (m, 1H), 7.03-7.05 (m, 1H)
MS ES$^+$: 203

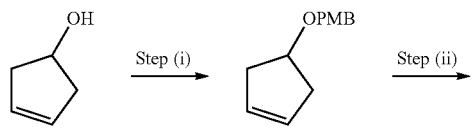

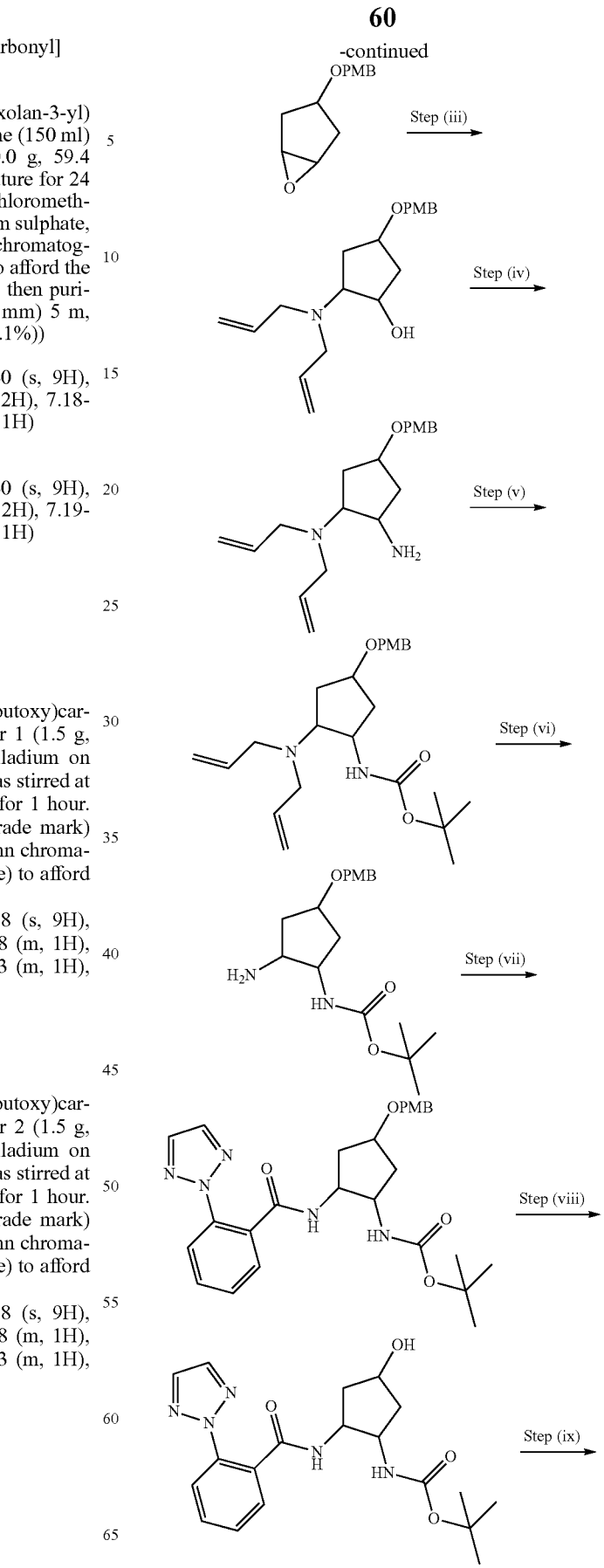

-continued

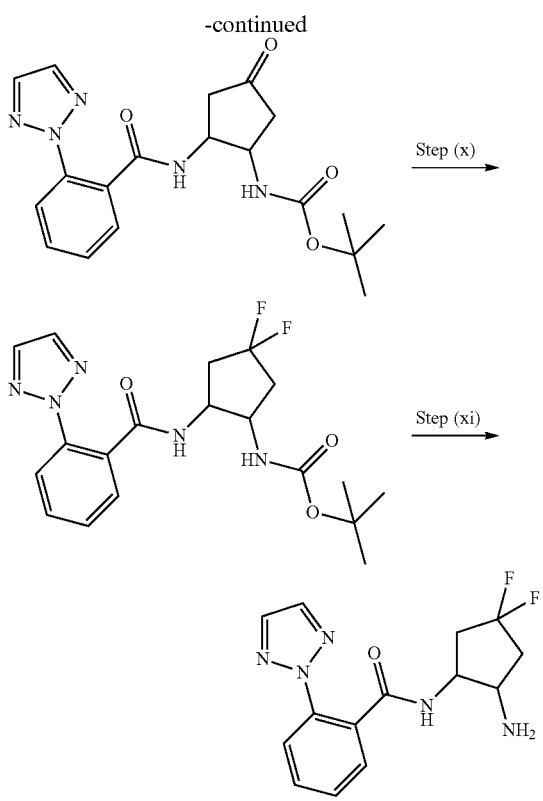

Intermediate 28: N-(2-Amino-4,4-difluorocyclopentyl)-2-(2H-1,2,3-triazol-2-yl)benzamide hydrochloride

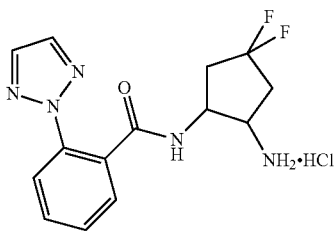

Step (i): 1-[(cyclopent-3-en-1-yloxy)methyl]-4-methoxybenzene

To a solution of cyclopent-3-en-1-ol (CAS number 14320-38-8; 15 g, 178 mmol) in dry THF (357 ml) at 0° C. under nitrogen was added sodium hydride (60%, 9.27 g, 232 mmol). After fizzing had ceased, to this was then added dropwise 1-(chloromethyl)-4-methoxybenzene (CAS number 824-94-2; 31.4 ml, 232 mmol). The reaction was then allowed to warm to room temperature for 17 hours. The reaction mixture was quenched by the addition of methanol and then concentrated in vacuo. The organics were partitioned between ethyl acetate and water. The organics were dried over magnesium sulfate, concentrated in vacuo and purified by column chromatography (silica, 0-50% dichloromethane/petrol) to afford the title compound.

$^1$H NMR (400 MHz, DCM-d$_2$) δ ppm 2.33-2.47 (m, 2H), 2.49-2.66 (m, 2H), 3.79 (s, 3H), 4.20-4.32 (m, 1H), 4.40 (s, 2H), 5.62-5.75 (m, 2H), 6.86 (d, J=8.59 Hz, 2H), 7.24 (d, J=8.59 Hz, 2H)

Step (ii): 3-[(4-methoxyphenyl)methoxy]-6-oxabicyclo[3.1.0]hexane

To a solution of 1-[(cyclopent-3-en-1-yloxy)methyl]-4-methoxybenzene (9.64 g, 47.2 mmol) in dry DCM (52 ml) at 0° C. under an atmosphere of nitrogen was added 3-chlorobenzene-1-carboperoxoic acid (CAS number 937-14-4; 16.29 g, 94 mmol) in one portion. The reaction was allowed to warm to room temperature and stirred for 17 hours. The reaction was filtered and the filtrate was washed with a saturated solution of sodium thiosulfate and then with a saturated solution of sodium bicarbonate. The organics were then dried over magnesium sulfate, concentrated in vacuo and purified by column chromatography (silica, 0-50% ethyl acetate/petrol) to afford the title compound.

$^1$H NMR (400 MHz, DCM-d$_2$) δ ppm 1.86-2.17 (m, 4H), 3.39-3.50 (m, 2H), 3.78 (s, 3H), 3.99-4.14 (m, 1H), 4.32 (s, 2H), 6.85 (d, J=8.60 Hz, 2H), 7.22 (d, J=8.59 Hz, 2H)

Step (iii): 2-[bis(prop-2-en-1-yl)amino]-4-[(4-methoxyphenyl)methoxy]cyclopentan-1-ol To a solution of 3-[(4-methoxyphenyl)methoxy]-6-oxabicyclo[3.1.0]hexane (10.21 g, 46.4 mmol) in ethanol (66 ml) was added bis(prop-2-en-1-yl)amine (CAS number 124-02-7; 13.51 g, 139 mmol). The reaction was heated in a sealed vial at 105° C. for 72 hours. The reaction mixture was concentrated in vacuo and then purified by column chromatography (silica, 0-50% ethyl acetate/petrol then 0-30% (0.1% ammonia/methanol)/ethyl acetate) to afford the title compound.

$^1$H NMR (400 MHz, DMSO-d$_6$) δ ppm 1.33-1.54 (m, 1H), 1.56-1.73 (m, 1H), 1.73-1.88 (m, 1H), 2.06-2.25 (m, 1H), 2.78-2.95 (m, 1H), 2.99-3.23 (m, 4H), 3.74 (s, 3H), 3.78-3.94 (m, 1H), 3.95-4.09 (m, 1H), 4.27-4.36 (m, 2H), 4.57-4.67 (m, 1H), 5.02-5.25 (m, 4H), 5.71-5.90 (m, 2H), 6.89 (d, J=8.59 Hz, 2H), 7.22 (d, J=8.60 Hz, 2H)

MS ES$^+$: 318

Step (iv): 4-[(4-methoxyphenyl)methoxy]-1-N,1-N-bis(prop-2-en-1-yl)cyclopentane-1,2-diamine To a solution of 2-[bis(prop-2-en-1-yl)amino]-4-[(4-methoxyphenyl)methoxy]cyclopentan-1-ol (8.75 g, 27.6 mmol) in dry MTBE (92 ml) at 0° C. under nitrogen was added triethylamine (7.68 ml, 55.1 mmol) and methanesulfonyl chloride (2.58 ml, 33.1 mmol). The reaction was stirred at 0° C. for 30 minutes. To this was then added further triethylamine (7.68 ml, 55.1 mmol) and the reaction was stirred at 0° C. for 30 minutes followed by the addition of ammonium hydroxide (25% aq, 82 ml, 590 mmol). The reaction was then allowed to warm to room temperature for 17 hours. The reaction mixture was partitioned between MTBE and water. The aqueous layer was re-extracted with MTBE. The combined organics were dried over magnesium sulfate and concentrated in vacuo to afford the title compound.

$^1$H NMR (400 MHz, DMSO-d$_6$) δ ppm 1.28-2.21 (m, 4H), 2.72-3.29 (m, 6H), 3.66-3.78 (m, 3H), 3.81-3.99 (m, 1H), 4.25-4.43 (m, 2H), 5.00-5.32 (m, 4H), 5.65-5.93 (m, 2H), 6.82-6.98 (m, 2H), 7.14-7.29 (m, 2H)

MS ES$^+$: 317

Step (v): tert-butyl N-{2-[bis(prop-2-en-1-yl) amino]-4-[(4-methoxyphenyl)methoxy] cyclopentyl}carbamate To a solution of 4-[(4-methoxyphenyl)methoxy]-1-N,1-N-bis(prop-2-en-1-yl)cyclopentane-1,2-diamine (9.79 g, 30.9 mmol) in THF (56 ml) at 0° C. under nitrogen was added saturated sodium carbonate solution (46.4 ml, 46.4 mmol) and di-tert-butyl dicarbonate (CAS number 24424-99-5; 10.77 ml, 46.4 mmol). The reaction was allowed to warm to room temperature for 72 hours. The reaction mixture was partitioned between ethyl acetate and water. The organics were washed with water and brine, dried over magnesium sulfate, concentrated in vacuo and purified by reverse phase chromatography (silica, eluted with 5-95% water containing 0.05% ammonia in acetonitrile) to afford the title compound.

$^1$H NMR (400 MHz, DMSO-$d_6$) δ ppm 1.38 (s, 9H), 1.47-1.59 (m, 1H), 1.61-1.79 (m, 1H), 1.79-1.93 (m, 1H), 1.93-2.21 (m, 1H), 2.91-3.07 (m, 3H), 3.07-3.24 (m, 2H), 3.74 (s, 3H), 3.79-3.98 (m, 2H), 4.24-4.41 (m, 2H), 4.93-5.26 (m, 4H), 5.66-5.89 (m, 2H), 6.89 (d, J=8.34 Hz, 2H), 7.22 (d, J=8.34 Hz, 2H)

MS ES$^+$: 417

Step (vi): tert-butyl N-{2-amino-4-[(4-methoxyphenyl)methoxy]cyclopentyl}carbamate To a solution of tert-butyl N-{2-[bis(prop-2-en-1-yl) amino]-4-[(4-methoxyphenyl)methoxy] cyclopentyl}carbamate (1.77 g, 4.25 mmol) in dry dichloromethane (21 ml) was added 1,3-dimethyl-1,3-diazinane-2,4,6-trione (CAS number 769-42-6; 1.161 g, 7.44 mmol) and tetrakis(triphenylphosphane) palladium (0.113 g, 0.098 mmol). The reaction was stirred at 45° C. under an atmosphere of nitrogen for 3 hours. The reaction mixture was concentrated in vacuo and purified by SCX to afford the title compound.

$^1$H NMR (400 MHz, DMSO-$d_6$) δ ppm 1.28-1.42 (m, 10H), 1.44-1.61 (m, 1H), 1.81-2.07 (m, 1H), 2.12-2.37 (m, 1H), 2.72-3.09 (m, 1H), 3.18-3.52 (m, 1H), 3.73 (s, 3H), 3.81-3.95 (m, 1H), 4.22-4.38 (m, 2H), 6.89 (d, J=8.34 Hz, 2H), 7.22 (d, J=8.30 Hz, 2H)

MS ES$^+$: 337

Step (vii): tert-butyl N-{4-[(4-methoxyphenyl) methoxy]-2-[2-(2H-1,2,3-triazol-2-yl)benzamido] cyclopentyl}carbamate To a solution of tert-butyl N-{2-amino-4-[(4-methoxyphenyl)methoxy]cyclopentyl}carbamate (1.71 g, 5.08 mmol) in dry DMF (17 ml) was added 2-(2H-1,2,3-triazol-2-yl)benzoic acid (CAS number 1001401-62-2; 1.058 g, 5.59 mmol), HATU (2.90 g, 7.62 mmol) and triethylamine (2.125 ml, 15.25 mmol). The reaction was stirred at room temperature for 72 hours. The reaction was partitioned between ethyl acetate and water, washed with brine, dried over magnesium sulfate, concentrated in vacuo and purified by column chromatography (silica, 0-100% ethyl acetate/petrol) to afford the title compound.

$^1$H NMR (400 MHz, DMSO-$d_6$) δ ppm 1.37 (s, 9H), 1.46-1.59 (m, 1H), 1.58-1.77 (m, 1H), 1.86-1.97 (m, 1H), 2.18-2.37 (m, 1H), 3.67-3.79 (m, 4H), 3.83-4.01 (m, 2H), 4.32 (s, 2H), 6.85-6.95 (m, 2H), 7.17-7.31 (m, 2H), 7.44-7.54 (m, 2H), 7.55-7.66 (m, 1H), 7.76 (s, 1H), 7.96-8.05 (m, 2H)

MS ES$^+$: 508

Step (viii): tert-butyl N-{4-hydroxy-2-[2-(2H-1,2,3-triazol-2-yl)benzamido]cyclopentyl}carbamate To a solution of tert-butyl N-{4-[(4-methoxyphenyl) methoxy]-2-[2-(2H-1,2,3-triazol-2-yl)benzamido] cyclopentyl}carbamate (1.85 g, 3.64 mmol) in DCM (36 ml) and water (0.364 ml) at 0° C. under an atmosphere of nitrogen was added 4,5-dichloro-3,6-dioxocyclohexa-1,4-diene-1,2-dicarbonitrile (CAS number 84-58-2; 1.655 g, 7.29 mmol). The reaction was then stirred at 0° C. for 1 hour and then was partitioned between saturated solution of sodium bicarbonate and DCM, filtered through a hydrophobic frit and concentrated in vacuo. The resulting residue was purified by column chromatography (silica, 0-100% ethyl acetate/petrol then 0-30% methanol/ethyl acetate) to afford the title compound.

$^1$H NMR (400 MHz, DMSO-$d_6$) δ ppm 1.25-1.48 (m, 10H), 1.55-1.86 (m, 2H), 2.11-2.27 (m, 1H), 3.92 (m, 1H), 3.99-4.11 (m, 1H), 4.57-4.71 (m, 1H), 6.64-6.86 (m, 1H), 7.41-7.56 (m, 2H), 7.57-7.66 (m, 1H), 7.71-7.83 (m, 1H), 7.95-8.06 (m, 2H), 8.19-8.36 (m, 1H)

MS ES$^+$: 388

Step (ix): tert-butyl N-{4-oxo-2-[2-(2H-1,2,3-triazol-2-yl)benzamido]cyclopentyl}carbamate To a solution of tert-butyl N-{4-hydroxy-2-[2-(2H-1,2,3-triazol-2-yl)benzamido]cyclopentyl}carbamate (910 mg, 2.349 mmol) in dry DCM (12 ml) at 0° C. under an atmosphere of nitrogen was added Dess-Martin periodinane (3.4 g, 7.99 mmol). The reaction was allowed to warm to room temperature for 2 hours and then was concentrated in vacuo. This was then purified by column chromatography (silica, 0-100% ethyl acetate/petrol) to afford the title compound.

MS ES$^+$: 386

$^1$H NMR (400 MHz, DMSO-$d_6$) δ ppm 1.28-1.47 (m, 10H), 1.56-1.87 (m, 2H), 2.07-2.27 (m, 1H), 3.82-4.00 (m, 1H), 4.00-4.12 (m, 1H), 6.58-6.79 (m, 1H), 7.41-7.54 (m, 2H), 7.55-7.71 (m, 1H), 7.73-7.85 (m, 1H), 7.93-8.06 (m, 2H), 8.17-8.40 (m, 1H)

Step (x): tert-butyl N-{4,4-difluoro-2-[2-(2H-1,2,3-triazol-2-yl)benzamido]cyclopentyl}carbamate To a solution of tert-butyl N-{4-oxo-2-[2-(2H-1,2,3-triazol-2-yl)benzamido]cyclopentyl}carbamate (950 mg, 2.465 mmol) in dry DCM (12.3 ml) at 0° C. under an atmosphere of nitrogen was added dropwise diethylaminosulfur trifluoride (CAS number 38078-09-0; 1.628 ml, 12.32 mmol) as a solution in dry DCM (12.3 ml). The reaction was then allowed to warm to room temperature for 2 hours. The reaction was cooled to 0° C. and then to this was added further diethylaminosulfur trifluoride (CAS number 38078-09-0; 1.628 ml, 12.32 mmol). The reaction was then allowed to warm to room temperature and stirred for 17 hours (overnight). The reaction was then cooled to 0° C. and then basified by the cautious addition of sodium carbonate (2M, aq). The organics were extracted with DCM, filtered through a hydrophobic frit and the solvent evaporated in vacuo. This was then purified by column chromatography (silica, 0-100% ethyl acetate/petrol) to afford the title compound.

¹H NMR (400 MHz, DMSO-d₆) δ ppm 1.37 (s, 9H), 1.88-2.17 (m, 2H), 2.36-2.48 (m, 2H), 3.93-4.09 (m, 1H), 4.14-4.30 (m, 1H), 6.97-7.15 (m, 1H), 7.45-7.56 (m, 2H), 7.57-7.70 (m, 1H), 7.75-7.86 (m, 1H), 8.03 (s, 2H), 8.46-8.60 (m, 1H)
MS ES⁺: 408

Step (xi): N-(2-amino-4,4-difluorocyclopentyl)-2-(2H-1,2,3-triazol-2-yl)benzamide hydrochloride To a solution of tert-butyl N-{4,4-difluoro-2-[2-(2H-1,2,3-triazol-2-yl)benzamido]cyclopentyl}carbamate (640 mg, 1.571 mmol) in dry dioxane (5 ml) was added HCl in dioxane (4M, 3.9 ml, 15.71 mmol). The reaction was stirred at room temperature for 6 hours. The reaction mixture was concentrated in vacuo and azeotroped with toluene to afford the title compound.

¹H NMR (400 MHz, DMSO-d₆) δ ppm 2.01-2.42 (m, 2H), 2.55-2.78 (m, 2H), 3.30-3.54 (m, 1H), 3.60-3.75 (m, 1H), 7.50-7.61 (m, 1H), 7.62-7.77 (m, 2H), 7.80-7.91 (m, 1H), 8.08 (s, 2H), 8.51 (br. s, 3H), 8.72-8.88 (m, 1H)
MS ES⁺: 308

Intermediate 29: N-(2-Amino-2-methylcyclopentyl)-2-(2H-1,2,3-triazol-2-yl)benzamide hydrochloride Step (i): tert-butyl N-{1-methyl-2-[2-(2H-1,2,3-triazol-2-yl)benzamido]cyclopentyl}carbamate To a solution of tert-butyl N-(2-amino-1-methylcyclopentyl)carbamate (Intermediate 30; 500 mg, 2.333 mmol) in dry DMF (8 ml) was added 2-(2H-1,2,3-triazol-2-yl)benzoic acid (CAS number 1001401-62-2; 485 mg, 2.57 mmol), HATU (1331 mg, 3.50 mmol) and triethylamine (976 μl, 7.00 mmol). The reaction was stirred at room temperature under nitrogen for 17 hours. The reaction was partitioned between ethyl acetate and saturated solution of sodium bicarbonate, washing with brine and dried over magnesium sulfate, filtered and concentrated in vacuo. The crude oil was purified by column chromatography (silica, 0-100% ethyl acetate/petrol) and then by column chromatography (basic silica, 0-100% ethyl acetate/petrol) to afford the title compound.

¹H NMR (400 MHz, DMSO-d₆) δ ppm 1.11-1.23 (m, 3H), 1.37 (s, 9H), 1.51-1.69 (m, 3H), 1.75-1.91 (m, 2H), 2.00-2.06 (m, 1H), 4.13-4.31 (m, 1H), 6.56 (br. s., 1H), 7.50-7.60 (m, 2H), 7.60-7.69 (m, 1H), 7.77-7.86 (m, 1H), 8.00 (s, 2H), 8.48-8.67 (m, 1H)

Step (ii): N-(2-amino-2-methylcyclopentyl)-2-(2H-1,2,3-triazol-2-yl)benzamide hydrochloride tert-butyl N-{1-methyl-2-[2-(2H-1,2,3-triazol-2-yl)benzamido]cyclopentyl}carbamate was dissolved in methanol (5 ml) and to this was then added HCl in dioxane (4M, 583 μl, 2.333 mmol). The reaction was stirred at room temperature for 17 hours. The reaction was concentrated in vacuo, azeotroping with toluene to afford the title compound.

¹H NMR (400 MHz, DMSO-d₆) δ ppm 1.15-1.34 (m, 3H), 1.54-1.79 (m, 4H), 1.86-2.05 (m, 2H), 4.13-4.29 (m, 1H), 7.51-7.72 (m, 3H), 7.76-7.90 (m, 1H), 8.06 (s, 5H), 8.61-8.75 (m, 1H)
MS ES⁺: 286

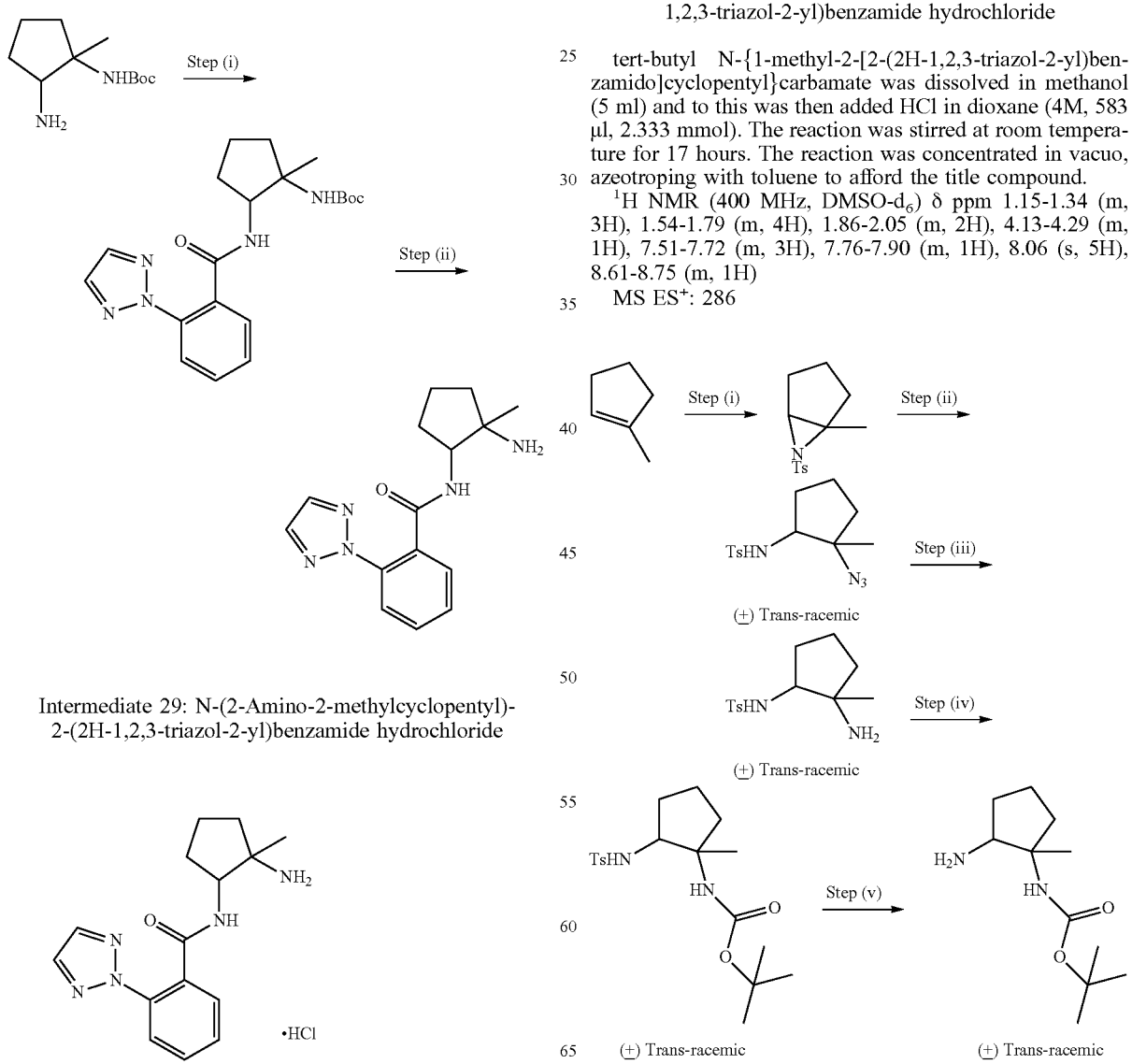

Intermediate 30: tert-Butyl N-(2-amino-1-methylcyclopentyl)carbamate

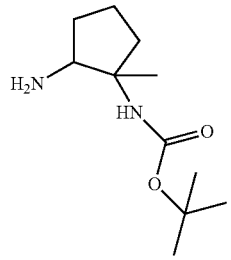

(±) Trans-racemic

Step (i): 1-methyl-6-(4-methylbenzenesulfonyl)-6-azabicyclo[3.1.0]hexane

To a solution of 1-methylcyclopent-1-ene (CAS number 693-89-0; 50.0 g, 609.75 mmol) and sodium chloro(4-methylbenzenesulfonyl)azanide (CAS number 127-65-1; 192 g, 680.85 mmol) in THF (2500 ml) was added trimethylphenylammonium tribromide (13.3 g, 61.57 mmol). The reaction was stirred vigorously at 25° C. for 12 hours. The reaction mixture was poured into water (1500 ml) and the organics were extracted with ethyl acetate (1000 ml×3). The combined organics were washed with water (500 ml), brine (500 ml), dried over sodium sulphate and concentrated in vacuo. This was then purified by column chromatography (silica, 0-2.5% ethyl acetate/n-hexane) to afford the title compound.

$^1$H NMR (400 MHz, DMSO-$d_6$) δ ppm 1.15-1.25 (m, 1H), 1.46-1.70 (m, 4H), 1.75 (s, 3H) 1.88-1.93 (m, 1H), 2.50 (s, 3H), 3.34-3.35 (m, 1H), 7.40-7.42 (m, 2H), 7.74-7.76 (m, 2H)

MS ES$^+$: 251

Step (ii): N-(2-azido-2-methylcyclopentyl)-4-methylbenzene-1-sulfonamide

To a solution of 1-methyl-6-(4-methylbenzenesulfonyl)-6-azabicyclo[3.1.0]hexane (55 g, 219.12 mmol) in IPA (1000 ml) and water (1000 ml) was added sodium azide (57.0 g, 876.92 mmol). The reaction mixture was stirred at room temperature for 17 hours. The reaction was cooled to room temperature and water (1000 ml) was added. The aqueous layer was extracted with diethyl ether (500 ml×3). The combined organics were washed with brine (250 ml), dried over sodium sulfate, concentrated in vacuo to afford the title compound.

$^1$H NMR (400 MHz, DMSO-$d_6$) δ ppm 1.20-1.30 (m, 4H), 1.45-1.63 (m, 5H), 2.38 (s, 3H) 3.33-3.39 (m, 1H), 7.38-7.40 (m, 2H), 7.69-7.77 (m, 3H)

MS ES$^+$: 294

Step (iii): N-(2-amino-2-methylcyclopentyl)-4-methylbenzene-1-sulfonamide

To a solution of N-(2-azido-2-methylcyclopentyl)-4-methylbenzene-1-sulfonamide (52.0 g, 176.87 mmol) in methanol (1100 ml) was added 10% palladium on carbon (10.0 g). The reaction mixture was stirred at room temperature under hydrogen atmosphere for 12 hours. The reaction mixture was filtered through a "celite" bed and the filtrate was concentrated in vacuo to afford the title compound.

$^1$H NMR (400 MHz, DMSO-$d_6$) δ ppm 0.93 (s, 3H), 1.20-1.22 (m, 1H), 1.36-1.52 (m, 5H) 2.38 (s, 3H) 2.94-2.98 (m, 1H) 4.11 (br. s, 1H), 7.37-7.39 (m, 2H), 7.69-7.71 (m, 2H)

MS ES$^+$: 268

Step (iv): tert-butyl N-[1-methyl-2-(4-methylbenzenesulfonamido)-cyclopentyl]carbamate To a solution of N-(2-amino-2-methylcyclopentyl)-4-methylbenzene-1-sulfonamide (48.0 g, 179.10 mmol) in DCM (1400 ml) was added triethylamine (27.13 g, 268.65 mmol) and di-tert-butyl dicarbonate (CAS number 24424-99-5; 46.85 g, 214.92 mmol). The reaction mixture was stirred at room temperature for 15 hours. The reaction mixture was concentrated in vacuo and the resulting residue was partitioned between ethyl acetate (1000 ml) and water (800 ml). The organics were dried over sodium sulphate and concentrated in vacuo. The solid was then triturated with hexane (300 ml) to afford the title compound.

$^1$H NMR (400 MHz, DMSO-$d_6$) δ ppm 1.16 (s, 3H), 1.18-1.57 (m, 14H), 1.92 (m, 1H) 2.67 (s, 3H) 3.53 (m, 1H) 6.24 (br. s, 1H), 7.27-7.39 (m, 2H), 7.60-7.69 (m, 3H)

MS ES$^+$: 368

Step (v): tert-butyl N-(2-amino-1-methylcyclopentyl)carbamate

A mixture of lithium granules (7.17 g, 1195 mmol) and naphthalene (57.39 g, 448.36 mmol) in dry dimethoxyethane (1900 ml) was stirred at room temperature for 2 hours. The deep blue solution was then cooled to 0° C. and a solution of tert-butyl N-[1-methyl-2-(4-methylbenzenesulfonamido) cyclopentyl]carbamate (55.0 g, 149.45 mmol) in dry dimethoxyethane (300 ml) was added drop wise over 30 minutes. The mixture was stirred at 0° C. for 3 hours. The undissolved lithium was removed by filtration and 1M HCl solution (aq., 720 ml) was added to the filtrate. The organic layer was washed with further 1M HCl solution (aq., 600 ml×2). The combined aqueous layers were washed with diethyl ether (600×2), and then basified with 2M NaOH solution to give pH 12-14. The aqueous layer was then extracted with ethyl acetate (600 ml×5). The combined organics were dried over sodium sulfate and then concentrated in vacuo. This was then purified by column chromatography (silica, 0-4% methanol/DCM) to afford the title compound.

$^1$H NMR (400 MHz, DMSO-$d_6$) δ ppm 1.10 (s, 3H), 1.14-1.27 (m, 2H), 1.40 (s, 9H) 1.44-1.55 (m, 2H) 1.76-1.86 (m, 2H) 2.72 (br. s, 2H), 3.09 (m, 1H) 6.61 (br. s, 1H)

MS ES$^+$: 214

2. EXAMPLES

Example 1

2,6-Dimethoxy-N-[(1S,2R)-2-[(quinoxalin-2-yl)amino]cyclopentyl]-benzamide

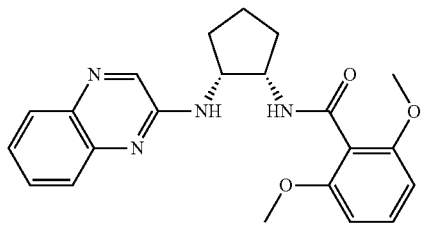 [SMILES: COc1cccc(OC)c1C(=O)N[C@H]1CCC[C@H]1Nc1cnc2ccccc2n1]

A microwave vial was charged with N-((1S,2R)-2-aminocyclopentyl)-2,6-dimethoxybenzamide hydrochloride (Intermediate 10; 100 mg, 0.332 mmol), 2-chloro-quinoxazoline (60 mg, 0.366 mmol), DIPEA (0.17 ml, 0.997 mmol) and dry acetonitrile (1 ml). The reaction was subjected to microwave irradiation at 160° C. for 2.5 hours and on cooling was then concentrated in vacuo. The crude product was then loaded directly onto silica and purified by column chromatography (0-100% ethyl acetate/petrol then 0-20% methanol/ethyl acetate) to give desired product, this was further purified by reverse phase preparative HPLC (eluted with acetonitrile/water with 0.1% ammonia) to afford the title compound.

$^1$H NMR (DMSO-$d_6$) δ ppm 1.52-1.90 (m, 4H), 2.02 (d, J=9.09 Hz, 2H), 3.59 (s, 6H), 4.42-4.59 (m, 2H), 6.63 (d, J=8.34 Hz, 2H), 6.83 (d, J=7.58 Hz, 1H), 7.25-7.38 (m, 2H), 7.50-7.62 (m, 2H), 7.74-7.84 (m, 2H), 8.23 (s, 1H)

MS ES$^+$: 393

Example 2

2,6-Dimethoxy-N-((1S,2S)-2-(quinoxalin-2-ylamino) cyclopentyl)benzamide

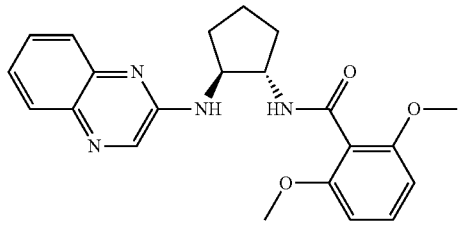 [SMILES: COc1cccc(OC)c1C(=O)N[C@H]1CCC[C@@H]1Nc1cnc2ccccc2n1]

To a solution of N-((1S,2S)-2-aminocyclopentyl)-2,6-dimethoxybenzamide hydrochloride (Intermediate 11; 0.07 g, 0.233 mmol) in toluene (1.5 ml), was added BINAP (0.014 g, 0.022 mmol), cesium carbonate (0.303 g, 0.933 mmol) and 2-chloroquinoxaline (0.042 g, 0.256 mmol). The reaction mixture was degassed with nitrogen for 5 minutes before Pd$_2$(dba)$_3$ (0.010 g, 0.01 mmol) was added at room temperature and the whole mixture was stirred at 100° C. for 15 hours. Upon cooling the reaction was poured into water and extracted with ethyl acetate and the combined organic layers were dried (sodium sulphate) and concentrated in vacuo. The crude product was purified by flash column chromatography (silica, 0-50% ethyl acetate/hexane) to afford the title compound.

$^1$H NMR (DMSO-$d_6$) δ ppm 1.52-1.57 (m, 2H), 1.73 (m, 2H), 2.09-2.11 (m, 2H), 3.53 (s, 6H), 4.16-4.20 (m, 1H), 4.29-4.32 (m, 1H), 6.56-6.58 (d, 2H, J=8 Hz), 7.21-7.25 (t, 1H), 7.28-7.32 (t, 1H), 7.40-7.42 (d, 1H, J=8 Hz), 7.47-7.51 (t, 1H), 7.70-7.76 (m, 2H), 8.23-8.25 (d, 1H, J=8 Hz), 8.34 (s, 1H)

MS ES$^+$: 393

Example 3

N-[(1S,2S)-2-[(6-Fluoro-1,3-benzothiazol-2-yl)amino]cyclopentyl]-2,6-dimethoxybenzamide

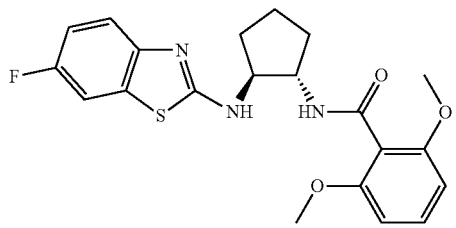 [SMILES: COc1cccc(OC)c1C(=O)N[C@H]1CCC[C@@H]1Nc1nc2ccc(F)cc2s1]

A microwave vial was charged N-((1S,2S)-2-aminocyclopentyl)-2,6-dimethoxybenzamide hydrochloride (Intermediate 11; 80 mg, 0.266 mmol), DIPEA (0.26 ml, 0.266 mmol) and 2-chloro-6-fluoro-1,3-benzothiazole (50 mg, 0.266 mmol) and the resulting mixture was heated with microwave irradiation at 250° C. for 20 minutes. The reaction was purified by reverse phase preparative HPLC eluted with acetonitrile/water (with 0.1% ammonia) to afford the title compound.

$^1$H NMR (DMSO-$d_6$) δ ppm 1.48-1.77 (m, 4H), 2.02-2.14 (m, 2H), 3.62 (s, 6H), 4.09-4.27 (m, 2H), 6.51-6.65 (m, 2H), 7.03-7.05 (m, 1H), 7.18-7.38 (m, 2H), 7.59 (m, 1H) and 8.12-8.15 (m, 2H)

MS ES$^+$: 416

Example 4

N-[(1S,2S)-2-[(1,3-Benzothiazol-2-yl)amino]cyclopentyl]-2,6-dimethoxybenzamide

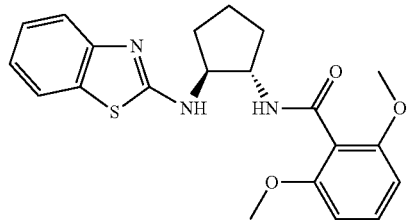

A solution of 2-chloro-1,3-benzothiazole (0.248 mg, 1.463 mmol), N-((1S,2S)-2-aminocyclopentyl)-2,6-dimethoxybenzamide hydrochloride (Intermediate 11, 400 mg, 1.330 mmol) and DIPEA (0.70 ml, 3.99 mmol) in DMSO (4.8 ml) was subjected to microwave irradiation at 140° C. for 30 minutes. The resulting mixture was then partitioned between ethyl acetate and water, washed with brine, dried (magnesium sulphate), filtered and concentrated in vacuo. The remaining brown oil was dissolved in dichloromethane (5 ml) and then purified by column chromatography (silica, 0-100% ethyl acetate/petrol). The product was triturated from di-isopropyl ether to afford the homogeneous title compound.

$^1$H NMR (DMSO-$d_6$) δ ppm 1.48-1.81 (m, 4H), 1.96-2.14 (m, 2H), 3.32 (s, 6H), 4.15-4.20 (m, 2H), 6.56-6.70 (m, 2H), 7.00 (t, 1H), 7.17-7.38 (m, 3H), 7.63-7.73 (m, 1H), 8.06-8.21 (m, 1H)

MS ES$^+$: 398

Example 5

N-[(1S,2R)-2-[(1,3-Benzothiazol-2-yl)amino]cyclopentyl]-2,6-dimethoxybenzamide

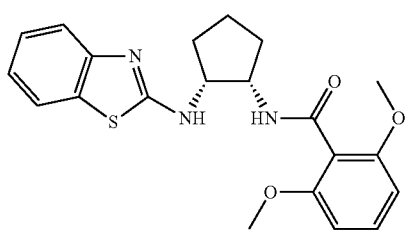 [SMILES: COc1cccc(OC)c1C(=O)N[C@H]1CCC[C@H]1Nc1nc2ccccc2s1]

Prepared as described for 2,6-dimethoxy-N-[(1S,2R)-2-[(quinoxalin-2-yl)amino]cyclopentyl]-benzamide (Example 1) from N-((1S,2R)-2-aminocyclopentyl)-2,6-dimethoxybenzamide hydrochloride (Intermediate 10; 1.0 g, 0.332 mmol) and 2-chloro-1,3-benzothiazole (620 mg, 3.66 mmol). The product was purified by column chromatography (silica, 0-100% ethyl acetate/petrol then 0-20% methanol/ethyl acetate) to afford the title compound.

$^1$H NMR (DMSO-$d_6$) δ ppm 1.42-1.81 (m, 4H), 2.07-2.10 (m, 2H), 3.32 (s, 6H), 4.05-4.26 (m, 2H), 6.51-6.72 (m, 2H), 6.87-7.11 (m, 1H), 7.12-7.38 (m, 3H), 7.60-7.74 (m, 1H), 8.05-8.21 (m, 2H)

MS ES$^+$: 398

Example 6

N-[(1S,2S)-2-[(5-Chloro-1,3-benzothiazol-2-yl)amino]cyclopentyl]-2,6-dimethoxybenzamide

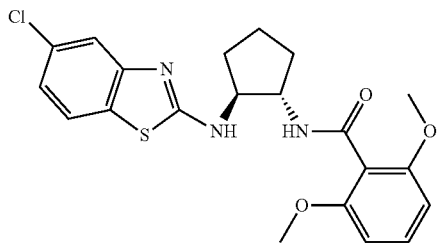 [SMILES: COc1cccc(OC)c1C(=O)N[C@H]1CCC[C@@H]1Nc1nc2cc(Cl)ccc2s1]

A microwave vial was charged with N-((1S,2S)-2-aminocyclopentyl)-2,6-dimethoxybenzamide hydrochloride (Intermediate 11, 80 mg, 0.266 mmol), DIPEA (0.14 ml, 0.798 mmol) and 2,5-dichloro-1,3-benzothiazole (65 mg, 0.319 mmol) in dry NMP (0.9 ml) and the resulting mixture was subjected to microwave irradiation at 250° C. for 20 minutes. On cooling, the reaction mixture was evaporated in vacuo and the crude material was purified by reverse phase preparative HPLC (eluted with acetonitrile/water containing 0.1% ammonia) to afford the title compound.

$^1$H NMR (DMSO-$d_6$) δ ppm 1.43-1.76 (m, 4H), 1.98-2.16 (m, 2H), 3.32 (s, 6H), 4.06-4.23 (m, 2H), 6.54-6.70 (m, 1H), 7.03 (d, J=8.34 Hz, 1H), 7.23-7.44 (m, 2H), 7.68 (d, J=8.34 Hz, 1H), 8.16 (d, J=7.33 Hz, 1H), 8.35 (d, J=7.07 Hz, 1H)

MS ES$^+$: 432

Example 7

N-[(1S,2R)-2-[(1,3-Benzoxazol-2-yl)amino]cyclopentyl]-2,6-dimethoxybenzamide

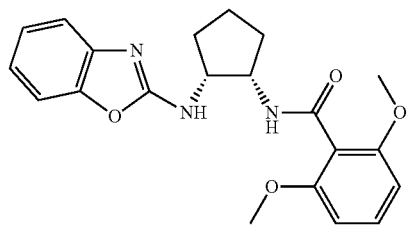 [SMILES: COc1cccc(OC)c1C(=O)N[C@H]1CCC[C@H]1Nc1nc2ccccc2o1]

Prepared as described for 2,6-dimethoxy-N-[(1S,2R)-2-[(quinoxalin-2-yl)amino]cyclopentyl]-benzamide (Example 1) from N-((1S,2R)-2-aminocyclopentyl)-2,6-dimethoxybenzamide hydrochloride (Intermediate 10; 1.0 g, 0.332 mmol) and 2-chloro-1,3-benzoxazole (1.1 g, 0.366 mmol) under microwave irradiation at 140° C. for 30 minutes. The crude product was purified by column chromatography (silica, 0-100% ethyl acetate in petrol then 0-20% methanol in ethyl acetate) to afford the title compound.

$^1$H NMR (DMSO-$d_6$) δ ppm 1.49-1.80 (m, 1H), 1.90-2.11 (m, 3H), 2.47-2.57 (m, 2H), 3.67 (s, 6H), 4.19-4.22 (m, 1H), 4.40-4.54 (m, 1H), 6.60-6.72 (m, 2H), 6.86 (d, J=7.83 Hz, 1H), 6.95-7.02 (m, 1H), 7.04-7.21 (m, 1H), 7.23-7.40 (m, 2H), 7.91 (d, J=8.08 Hz, 1H)

MS ES$^+$: 382

Example 8

N-[(1S,2S)-2-[(6-Fluoro-1,3-benzothiazol-2-yl)(methyl)amino]cyclopentyl]-2,6-dimethoxybenzamide

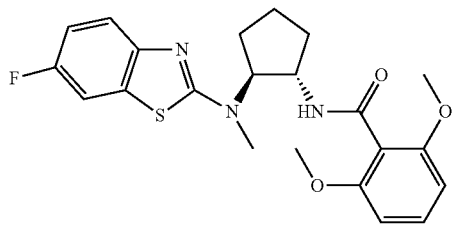 [SMILES: COc1cccc(OC)c1C(=O)N[C@H]1CCC[C@@H]1N(C)c1nc2ccc(F)cc2s1]

Prepared as described for N-[(1S,2S)-2-[(1,3-benzothiazol-2-yl)amino]cyclopentyl]-2,6-dimethoxybenzamide (Example 4) from 2,6-dimethoxy-N-((1S,2S)-2-(methylamino)-cyclopentyl)benzamide (Intermediate 13; 180 mg, 0.67 mmol) and 2-chloro-6-fluoro-1,3-benzothiazole (127 mg, 0.679 mmol). The reaction was subjected to microwave irradiation at 140° C. for 2 hours and the crude product was purified by column chromatography (silica, 0-100% ethyl acetate/petrol then 0-20% methanol in ethyl acetate). The product was further purified by reverse phase preparative HPLC (eluted with acetonitrile/water containing 0.1% ammonia) to afford the title compound.

¹H NMR (DMSO-d₆) δ ppm 1.50-1.81 (m, 4H), 1.86-2.01 (m, 2H), 3.11 (s, 3H), 3.41-3.55 (m, 6H), 4.24-4.35 (m, 1H), 4.51-4.55 (m, 1H), 6.49-6.58 (m, 3H), 7.08-7.10 (m, 1H), 7.19-7.25 (m, 1H), 7.39-7.44 (m, 1H), 7.67-7.70 (m, 1H), 8.10 (d, 1H)

MS ES⁺: 430

Example 9

N-[(1S,2S)-2-[(1,3-Benzoxazol-2-yl)amino]cyclopentyl]-2,6-dimethoxy-benzamide

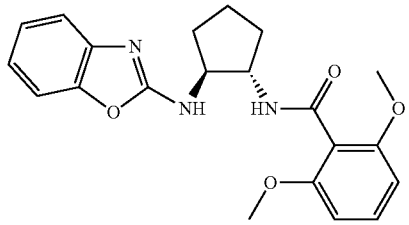 [SMILES: COc1cccc(OC)c1C(=O)N[C@H]1CCC[C@@H]1Nc1nc2ccccc2o1]

Prepared as described for 2,6-dimethoxy-N-[(1S,2R)-2-[(quinoxalin-2-yl)amino]cyclopentyl]-benzamide (Example 1) from N-((1S,2S)-2-aminocyclopentyl)-2,6-dimethoxybenzamide hydrochloride (Intermediate 11; 200 mg, 0.665 mmol) and 2-chloro-1,3-benzoxazole (112 mg, 0.731 mmol). The crude product was purified by column chromatography (silica, 0-100% ethyl acetate/petrol then 0-20% methanol in ethyl acetate) to afford the title compound.

¹H NMR (DMSO-d₆) δ ppm 1.44-1.75 (m, 4H), 1.98-2.13 (m, 2H), 3.55-3.70 (s, 6H), 4.04-4.10 (m, 1H), 4.23-4.30 (m, 1H), 6.60 (d, J=8.34 Hz, 2H), 6.92-7.01 (m, 1H), 7.04-7.12 (m, 1H), 7.17-7.28 (m, 2H), 7.28-7.36 (m, 1H), 7.94 (d, J=7.58 Hz, 1H), 8.11 (d, J=7.83 Hz, 1H)

MS ES⁺: 382

Example 10

N-[(1S,2S)-2-[(6-Chloro-1,3-benzothiazol-2-yl)amino]cyclopentyl]-2,6-dimethoxybenzamide

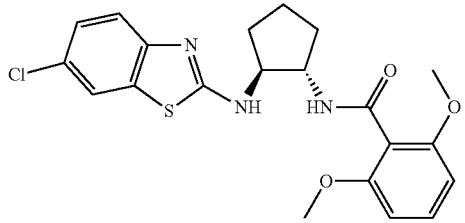 [SMILES: COc1cccc(OC)c1C(=O)N[C@H]1CCC[C@@H]1Nc1nc2ccc(Cl)cc2s1]

Prepared as described for 2,6-dimethoxy-N-[(1S,2R)-2-[(quinoxalin-2-yl)amino]cyclopentyl]-benzamide (Example 1) from N-((1S,2S)-2-aminocyclopentyl)-2,6-dimethoxybenzamide hydrochloride (Intermediate 11; 200 mg, 0.665 mmol) and 2,6-dichloro-1,3-benzothiazole (112 mg, 0.731 mmol). The crude product was purified by column chromatography (silica, 0-100% ethyl acetate/petrol then 0-20% methanol/ethyl acetate) to afford the title compound.

¹H NMR (DMSO-d₆) δ ppm 1.46-1.61 (m, 2H), 1.66-1.73 (m, 2H), 1.97-2.14 (m, 2H), 3.52-3.65 (m, 6H), 4.06-4.25 (m, 2H), 6.61 (d, J=8.34 Hz, 2H), 7.14-7.31 (m, 3H), 7.78 (s, 1H), 8.14 (d, J=7.07 Hz, 1H), 8.25 (d, J=7.07 Hz, 1H)

MS ES⁺: 432

Example 11

N-[(1R,2R)-2-[(1,3-Benzothiazol-2-yl)amino]cyclopentyl]-2,6-dimethoxybenzamide

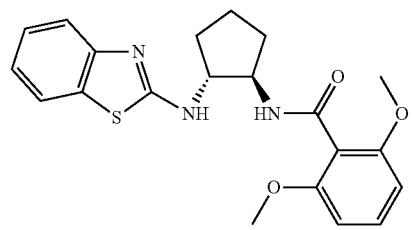 [SMILES: COc1cccc(OC)c1C(=O)N[C@@H]1CCC[C@H]1Nc1nc2ccccc2s1]

Prepared as described for 2,6-dimethoxy-N-[(1S,2R)-2-[(quinoxalin-2-yl)amino]cyclopentyl]-benzamide (Example 1) from N-((1R,2R)-2-aminocyclopentyl)-2,6-dimethoxybenzamide hydrochloride (Intermediate 14, 110 mg, 0.366 mmol) and 2-chloro-1,3-benzothiazole (62 mg, 0.402 mmol). The resulting mixture was subjected to microwave irradiation at 140° C. for 1 hour. On cooling, the reaction was concentrated in vacuo and then dissolved in DMSO (1 ml) and this mixture was purified by reverse phase preparative HPLC (eluted with acetonitrile/water containing 0.1% ammonia) to afford the title compound.

¹H NMR (DMSO-d₆) δ ppm 1.40-1.77 (m, 4H), 2.01-2.16 (m, 2H), 3.31 (s, 6H), 4.15-4.20 (m, 2H), 6.61 (d, J=8.34 Hz, 2H), 7.00 (t, J=7.45 Hz, 1H), 7.15-7.32 (m, 3H), 7.62-7.70 (m, 1H), 8.03-8.21 (m, 2H)

MS ES⁺: 398

Example 12

N-[(1R,2R)-2-[(1,3-Benzoxazol-2-yl)amino]cyclopentyl]-2,6-dimethoxy-benzamide

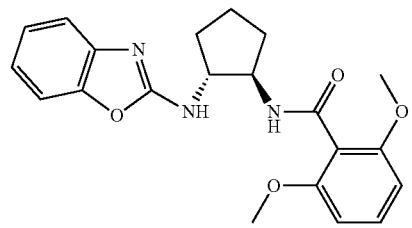 [SMILES: COc1cccc(OC)c1C(=O)N[C@@H]1CCC[C@H]1Nc1nc2ccccc2o1]

Prepared as described for 2,6-dimethoxy-N-[(1S,2R)-2-[(quinoxalin-2-yl)amino]cyclopentyl]-benzamide (Example 1) from N-((1R,2R)-2-aminocyclopentyl)-2,6-dimethoxybenzamide hydrochloride (Intermediate 14; 110 mg, 0.366 mmol) and 2-chloro-1,3-benzoxazole (68.1 mg, 0.402 mmol). The crude product was then purified by column chromatography (silica, 0-100% ethyl acetate in petrol then 0-20% methanol/ethyl acetate) to afford the title compound.

$^1$H NMR (DMSO-d$_6$) δ ppm 1.50-1.75 (m, 4H), 1.94-2.13 (m, 2H), 3.57 (s, 6H), 4.01-4.08 (m, 1H), 4.23-4.29 (m, 1H), 6.45-6.67 (m, 2H), 6.91-6.98 (m, 1H), 7.10 (t, J=7.58 Hz, 1H), 7.16-7.27 (m, 2H), 7.33 (d, J=7.83 Hz, 1H), 7.94 (d, J=7.83 Hz, 1H), 8.11 (d, J=7.83 Hz, 1H)

MS ES$^+$: 382

Example 13

N-[(1R,2S)-2-[(6-Chloro-1,3-benzothiazol-2-yl)amino]cyclopentyl]-2,6-dimethoxybenzamide

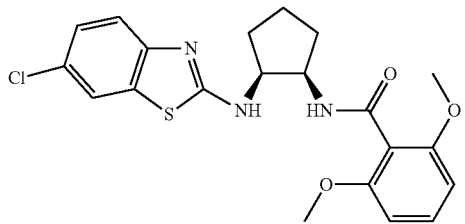 [SMILES: COc1cccc(OC)c1C(=O)N[C@@H]1CCC[C@@H]1Nc1nc2ccc(Cl)cc2s1]

To a solution of (1S,2R)-1-N-(6-chloro-1,3-benzothiazol-2-yl)cyclopentane-1,2-diamine hydrochloride (Intermediate 16b, 304 mg, 0.999 mmol) in dry dichloromethane (3.3 ml) was added DIPEA (5.2 ml, 3.00 mmol) and 2,6-dimethoxybenzoyl chloride (221 mg, 1.099 mmol). The reaction was stirred at room temperature for 17 hours and then partitioned between water and dichloromethane and passed through a phase separator. The combined organics were concentrated in vacuo and the resulting cream solid was crystalised from methanol to afford the title compound.

$^1$H NMR (DMSO-d$_6$) δ ppm 1.48-1.84 (m, 4H), 1.90-2.12 (m, 2H), 3.65 (s, 6H), 4.17-4.27 (m, 1H), 4.43-4.50 (m, 1H), 6.66 (d, J=8.34 Hz, 2H), 7.20-7.44 (m, 4H), 7.72-7.85 (m, 2H)

MS ES$^+$: 432

Example 14

N-[(1R,2R)-2-[(6-Chloro-1,3-benzothiazol-2-yl)amino]cyclopentyl]-2,6-dimethoxybenzamide

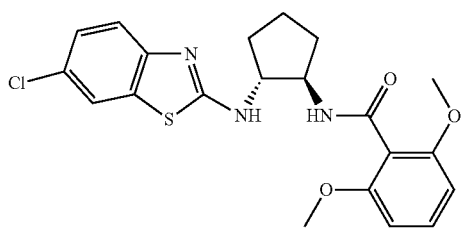 [SMILES: COc1cccc(OC)c1C(=O)N[C@@H]1CCC[C@H]1Nc1nc2ccc(Cl)cc2s1]

Prepared as described for 2,6-dimethoxy-N-[(1S,2R)-2-[(quinoxalin-2-yl)amino]cyclopentyl]-benzamide (Example 1) from N-((1R,2R)-2-aminocyclopentyl)-2,6-dimethoxybenzamide (Intermediate 14, 110 mg, 0.366 mmol) and 2,6-dichloro-1,3-benzothiazole (82 mg, 0.402 mmol) subjecting to microwave irradiation at 140° C. for 1 hour. The crude product was then purified by column chromatography (silica, 0-100% ethyl acetate/petrol then 0-20% methanol in ethyl acetate) to afford the title compound.

$^1$H NMR (DMSO-d$_6$) δ ppm 1.48-1.75 (m, 4H), 1.97-2.16 (m, 2H), 3.61 (s, 6H), 4.08-4.23 (m, 2H), 6.61 (d, J=8.34 Hz, 2H), 7.18-7.31 (m, 3H), 7.79 (d, J=2.02 Hz, 1H), 8.14 (d, J=7.07 Hz, 1H) and 8.25 (d, J=7.07 Hz, 1H)

MS ES$^+$: 432

Example 15

N-[(1S,2R)-2-[(6-Chloro-1,3-benzothiazol-2-yl)amino]cyclopentyl]-2,6-dimethoxybenzamide

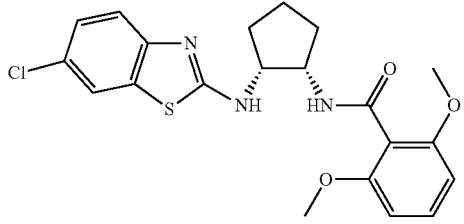 [SMILES: COc1cccc(OC)c1C(=O)N[C@H]1CCC[C@H]1Nc1nc2ccc(Cl)cc2s1]

Prepared as described for 2,6-dimethoxy-N-[(1S,2R)-2-[(quinoxalin-2-yl)amino]cyclopentyl]-benzamide (Example 1) from N-((1S,2R)-2-aminocyclopentyl)-2,6-dimethoxybenzamide, hydrochloride (Intermediate 10, 100 mg, 0.332 mmol) and 2,6-dichloro-1,3-benzothiazole (75 mg, 0.366 mmol) under microwave irradiation at 160° C. for 1.5 hours. The crude mixture was then loaded directly onto silica and purified by column chromatography (0-100% ethyl acetate/petrol then 0-20% methanol/ethyl acetate) to afford the title compound.

$^1$H NMR (DMSO-d$_6$) δ ppm 1.53-1.82 (m, 4H), 1.92-2.09 (m, 2H), 3.31 (s, 6H), 4.14-4.28 (m, 1H), 4.43-4.50 (m, 1H), 6.66 (d, J=8.34 Hz, 2H), 7.08-7.46 (m, 4H), 7.72-7.86 (m, 2H)

MS ES$^+$: 432

Example 16

N-[(1S,2S)-2-[(6-Fluoro-1,3-benzothiazol-2-yl)amino]cyclopentyl]-5-methyl-2-(2H-1,2,3-triazol-2-yl)benzamide

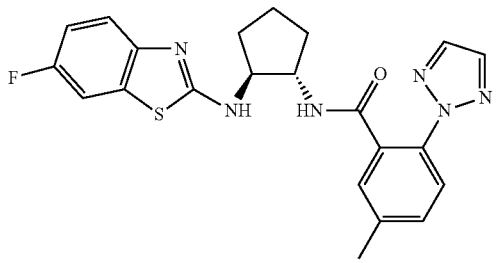 [SMILES: Cc1ccc(-n2nccn2)c(C(=O)N[C@H]2CCC[C@@H]2Nc2nc3ccc(F)cc3s2)c1]

To the solution of N-((1S,2S)-2-aminocyclopentyl)-5-methyl-2-(2H-1,2,3-triazol-2-yl)benzamide hydrochloride (Intermediate 12, 0.05 g, 0.155 mmol) in DMF (0.7 ml), was added potassium carbonate (0.086 g, 0.623 mmol) and 2-chloro-6-fluoro-1,3-benzothiazole (0.029 g, 0.623 mmol) at 90° C. for 12 hours. On cooling, the reaction mixture was quenched with water and extracted with ethyl acetate, the combined organics were washed with brine and dried (sodium sulphate) and evaporated in vacuo. The crude product was purified by column chromatography (silica, 0-70% ethyl acetate/n-hexane to afford the title compound.

$^1$H NMR (DMSO-$d_6$) δ ppm 1.48-1.51 (m, 2H), 1.53-1.70 (m, 2H), 1.93-2.08 (m, 2H), 2.32-2.33 (s, 3H), 4.05-4.15 (m, 2H), 7.03-7.08 (m, 1H), 7.19 (s, 1H), 7.32-7.39 (m, 2H), 7.59-7.63 (m, 2H), 7.95-7.96 (d, 2H), 8.10-8.12 (d, 1H), 8.44-8.46 (d, 1H)

ES MS$^+$: 437

Example 17

N-[(1R,2S)-2-[(1,3-Benzoxazol-2-yl)amino]cyclopentyl]-2,6-diethoxy-benzamide

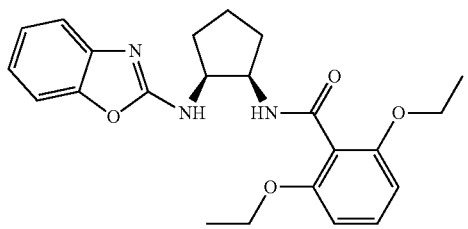 [SMILES: CCOc1cccc(OCC)c1C(=O)N[C@@H]1CCC[C@@H]1Nc1nc2ccccc2o1]

2,6-Diethoxybenzoic acid (124 mg, 0.591 mmol) was added to a solution of DIPEA (2.7 ml, 1.576 mmol), aza-HOBt (80 mg, 0.591 mmol), (1S,2R)-1-N-(1,3-benzooxazol-2-yl)cyclopentane-1,2-diamine hydrochloride (Intermediate 5, 100 mg, 0.394 mmol), EDC (113 mg, 0.591 mmol) and dichloromethane (1.3 ml) under nitrogen. The reaction was stirred at room temperature for 22 hours and then diluted with water, before being passed through a phase separator and concentrated in vacuo to afford a pale brown oil. The resulting brown oil was dissolved in dichloromethane (5 ml) then purified via column chromatography (silica, 0-100% ethyl acetate/petrol, then 0-20% methanol/ethyl acetate) to afford the title compound.

$^1$H NMR (DMSO-$d_6$) δ ppm 1.14 (t, J=6.95 Hz, 6H), 1.53-1.83 (m, 4H), 1.90-2.11 (m, 2H), 3.89-4.03 (m, 4H), 4.12-4.26 (m, 1H), 4.45 (br. s., 1H), 6.63 (d, J=8.34 Hz, 2H), 6.93-7.03 (m, 2H), 7.12 (t, J=7.58 Hz, 1H), 7.18-7.35 (m, 3H), 7.79 (d, J=8.08 Hz, 1H)

MS ES$^+$: 409

Example 18

N-[(1S,2R)-2-[(1,3-Benzoxazol-2-yl)amino]cyclopentyl]-2,6-diethoxy-benzamide

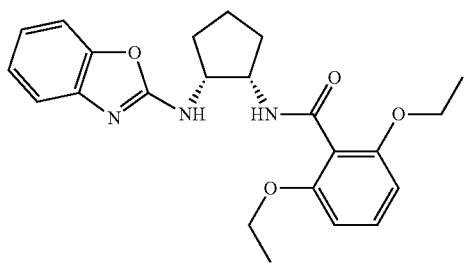 [SMILES: CCOc1cccc(OCC)c1C(=O)N[C@H]1CCC[C@H]1Nc1nc2ccccc2o1]

Prepared as described for 2,6-dimethoxy-N-[(1S,2R)-2-[(quinoxalin-2-yl)amino]cyclopentyl]-benzamide (Example 1) from N-((1S,2R)-2-aminocyclopentyl)-2,6-diethoxybenzamide hydrochloride (Intermediate 15; 0.771 g, 2.35 mmol) and 2-chlorobenzoxazole (0.273 ml, 2.35 mmol). The product was purified by chromatography (KP—NH cartridge, ethyl acetate petrol 0-45%) to afford the title compound.

$^1$H NMR (DMSO-$d_6$) δ ppm 1.14 (t, J=6.95 Hz, 6H), 1.52-1.80 (m, 4H), 1.87-2.11 (m, 2H), 3.96-3.99 (m, 4H), 4.17-4.20 (m, 1H), 4.40-4.51 (m, 1H), 6.63 (d, J=8.34 Hz, 2H), 6.91-7.03 (m, 2H), 7.09-7.17 (m, 1H), 7.21-7.42 (m, 3H), 7.79 (d, J=8.08 Hz, 1H)

MS ES$^+$: 410

Example 19

N-[(1S,2S)-2-[(1,3-Benzothiazol-2-yl)amino]cyclopentyl]-5-methyl-2-(2H-1,2,3-triazol-2-yl)benzamide

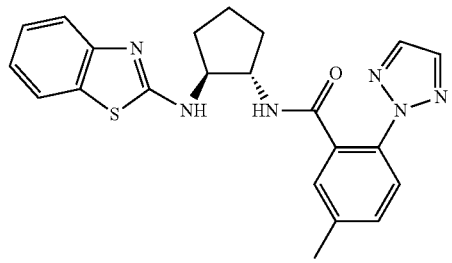 [SMILES: Cc1ccc(-n2nccn2)c(C(=O)N[C@H]2CCC[C@@H]2Nc2nc3ccccc3s2)c1]

Prepared as described for 2,6-dimethoxy-N-[(1S,2R)-2-[(quinoxalin-2-yl)amino]cyclopentyl]-benzamide (Example 1) from 2-chloro-1,3-benzothiazole (58 mg, 0.342 mmol) and N-[(1S,2S)-2-aminocyclopentyl]-5-methyl-2-(2H-1,2,3-triazol-2-yl)benzamide hydrochloride (Intermediate 12; 100 mg; 0.311 mmol) under microwave irradiation for 2 hours at 140° C. The crude product was purified by reverse phase chromatography (silica, eluted with 5-95% water containing 0.05% ammonia in acetonitrile) to afford the crude product which had co-eluted with DIPEA. Therefore this mixture was re-purified by reverse phase chromatography (0.05% formic acid in acetonitrile) to afford the title compound.

$^1$H NMR (CDCl$_3$) δ ppm 1.39-1.68 (m, 4H), 1.79-1.93 (m, 2H), 2.17-2.29 (m, 1H), 2.27-2.40 (m, 3H), 2.39-2.54 (m, 1H), 3.96-4.06 (m, 1H), 4.18-4.35 (m, 1H), 5.98 (d, J=4.55 Hz, 1H), 6.69 (d, J=6.32 Hz, 1H), 7.10-7.15 (m, 1H), 7.29-7.38 (m, 1H), 7.46 (d, J=8.08 Hz, 1H), 7.58 (d, J=7.83 Hz, 1H), 7.61-7.75 (m, 3H)

MS ES$^+$: 419

Example 20

5-Methyl-N-[(1S,2S)-2-[(quinolin-2-yl)amino]cyclopentyl]-2-(2H-1,2,3-triazol-2-yl)benzamide

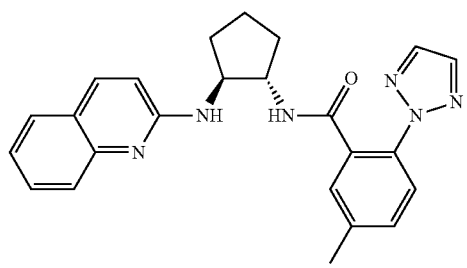 [SMILES: Cc1ccc(-n2nccn2)c(C(=O)N[C@H]2CCC[C@@H]2Nc2ccc3ccccc3n2)c1]

Prepared as described for 2,6-dimethoxy-N-[(1S,2R)-2-[(quinoxalin-2-yl)amino]cyclopentyl]-benzamide (Example 1) from 2-chloroquinoline (55.9 mg; 0.342 mmol) and N-((1S,2S)-2-aminocyclopentyl)-5-methyl-2-(2H-1,2,3-triazol-2-yl)benzamide hydrochloride (Intermediate 12; 100 mg; 0.311 mmol) under microwave irradiation for 2 hours at 140° C. The crude product was purified by reverse phase chromatography (silica, eluted with 5-95% water containing 0.05% ammonia/acetonitrile) and then by reverse phase chromatography (0.05% formic acid/acetonitrile) to afford the title compound.

$^1$H NMR (CDCl$_3$) δ ppm 1.53-1.69 (m, 4H), 1.77-1.93 (m, 2H), 2.05-2.15 (m, 3H), 2.22-2.35 (m, 1H), 2.41-2.58 (m, 1H), 3.93-4.05 (m, 1H), 4.28-4.40 (m, 1H), 6.55-6.68 (m, 1H), 7.17-7.35 (m, 3H), 7.34-7.47 (m, 1H), 7.49-7.66 (m, 4H), 7.79 (d, J=8.84 Hz, 1H), 8.22 (br. s., 1H)

MS ES$^+$: 413

Example 21

5-Methyl-N-((1S,2S)-2-(quinoxalin-2-ylamino)cyclopentyl)-2-(2H-1,2,3-triazol-2-yl) benzamide

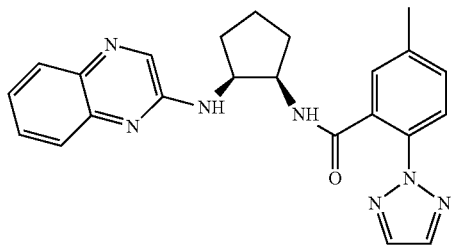 [SMILES: Cc1ccc(-n2nccn2)c(C(=O)N[C@@H]2CCC[C@@H]2Nc2cnc3ccccc3n2)c1]

Prepared as described for 2,6-dimethoxy-N-((1S,2S)-2-(quinoxalin-2-ylamino) cyclopentyl) benzamide (Example 2) from N-((1S,2S)-2-aminocyclopentyl)-5-methyl-2-(2H-1,2,3-triazol-2-yl)benzamide hydrochloride (Intermediate 12; 0.10 g; 0.311 mmol) and 2-chloroquinoxaline (56 mg; 0.342 mmol). The crude compound was purified via reverse phase preparative HPLC (acetonitrile/water containing 0.1% ammonia) to afford the title compound.

$^1$H NMR (DMSO-d$_6$) δ ppm 1.16-1.24 (m, 2H), 1.50-1.58 (m, 2H), 1.60-1.73 (m, 2H), 2.25 (s, 3H), 4.09-4.13 (m, 1H), 4.30-4.34 (m, 1H), 7.15 (s, 1H), 7.25-7.37 (m, 2H), 7.51-7.53 (m, 2H), 7.59-7.61 (m, 1H), 7.68-7.70 (m, 1H), 7.74-7.76 (m, 1H), 7.91 (s, 2H), 8.30 (s, 1H), 8.46-8.48 (m, 1H)

MS ES$^+$: 413

Example 22

Benzyl cis-3-[(6-chloro-1,3-benzothiazol-2-yl)amino]-4-[(2,6-dimethoxybenzene)amido]pyrrolidine-1-carboxylate

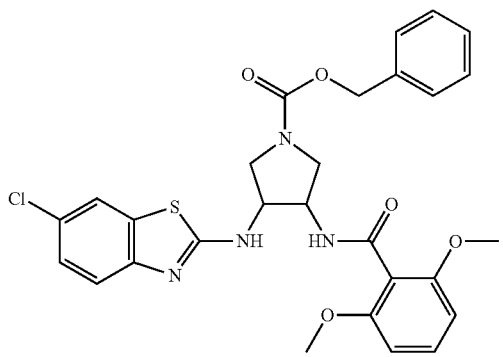 [SMILES: COc1cccc(OC)c1C(=O)NC1CN(C(=O)OCc2ccccc2)CC1Nc1nc2ccc(Cl)cc2s1]

To a solution of benzyl cis-3-amino-4-[(6-chloro-1,3-benzothiazol-2-yl)amino]pyrrolidine-1-carboxylate (which may be prepared from Intermediate 1 by treatment with 2,6-dichloro-1,3-benzothiazole followed by deprotection, typically done with samarium iodide or tributyltin hydride and then with benzyl chloroformate; 50 mg, 0.12 mmol) in dichloromethane (5 ml) was added triethylamine (62 mg, 0.60 mmol). The mixture was cooled to 0° C. and a solution of 2,6-dimethoxybenzoyl chloride (36 mg, 0.18 mmol) in dichloromethane (2 ml) was added drop-wise and the whole mixture was stirred for 30 minutes, concentrated in vacuo and purified by preparative TLC to afford the title compound.

$^1$H NMR (300 MHz, CDCl$_3$) δ ppm 3.17-3.29 (m, 1H), 3.50-3.67 (m, 1H), 3.76-3.85 (m, 7H), 4.16-4.23 (m, 1H), 4.65-4.70 (m, 1H), 4.98-5.04 (m, 1H), 5.12 (s, 2H), 6.03-6.21 (m, 2H), 6.59 (d, J=8.7 Hz, 2H), 7.22-7.25 (m, 1H), 7.26-7.44 (m, 7H), 7.52 (d, J=2.1 Hz, 1H)

MS ES$^+$: 567

Example 23

Ethyl cis-3-[(6-Chloro-1,3-benzothiazol-2-yl)amino]-4-[(2,6-dimethoxy-benzene)amido]pyrrolidine-1-carboxylate

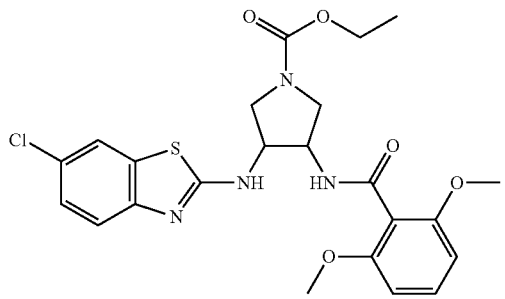 [SMILES: CCOC(=O)N1CC(NC(=O)c2c(OC)cccc2OC)C(Nc2nc3ccc(Cl)cc3s2)C1]

Prepared as described for benzyl cis-3-[(6-chloro-1,3-benzothiazol-2-yl)amino]-4-[(2,6-dimethoxybenzene)amido]pyrrolidine-1-carboxylate (Example 22) from N-{cis-4-[(6-chloro-1,3-benzothiazol-2-yl)amino]pyrrolidin-3-yl}-2,6-dimethoxybenzamide (Intermediate 6; 80 mg; 0.235 mmol) and ethyl chloroformate (0.1 ml). The crude compound was purified by preparative TLC to afford the title compound.

$^1$H NMR (CDCl$_3$): δ ppm 1.22-1.25 (m, 3H), 3.12-3.22 (m, 1H), 3.45-3.57 (m, 1H), 3.69-3.76 (m, 1H), 3.81 (s, 6H), 4.04-4.13 (m, 3H), 4.64-4.69 (m, 1H), 4.95-4.98 (m, 1H), 6.00-6.23 (m, 2H), 6.54 (d, J=8.4 Hz, 2H), 7.18-7.21 (m, 1H), 7.26 (t, J=8.4 Hz, 1H), 7.35-7.40 (m, 1H), 7.47 (s, 1H)

MS ES$^+$: 505

Example 24

N-{cis-4-[(6-Chloro-1,3-benzothiazol-2-yl)amino]oxolan-3-yl}-2,6-dimethoxybenzamide

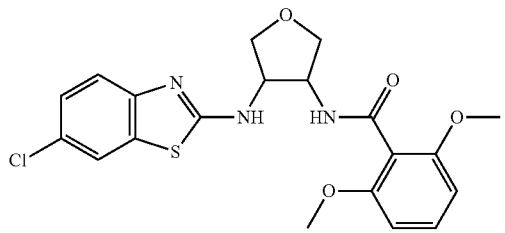 [SMILES: COc1cccc(OC)c1C(=O)NC1COCC1Nc1nc2ccc(Cl)cc2s1]

To a mixture of cis-3-N-(6-chloro-1,3-benzothiazol-2-yl)oxolane-3,4-diamine dihydrochloride (Intermediate 7, 110 mg, 0.409 mmol), triethylamine (140 ml, 1.5 mmol) and dichloromethane (5 ml) at 0° C. was added a solution 2,6-dimethoxybenzoyl chloride (86 mg, 0.430 mmol) in dichloromethane (2 ml). The mixture was agitated for 15 minutes at room temperature before a saturated solution of sodium bicarbonate (5 ml) was added and the resulting mixture was treated with dichloromethane. The aqueous layer was extracted with dichloromethane and the combined organics were dried (sodium sulphate), concentrated in vacuo and the crude residue was purified by triturating from diethyl ether then ethanol to afford the title compound.

$^1$H NMR (DMSO-$d_6$): δ ppm 3.61 (s, 6H), 3.62-2.69 (m, 2H), 4.01-4.07 (m, 2H), 4.57-4.60 (m, 1H), 4.70-4.74 (m, 1H), 6.64 (d, J=8.4 Hz, 2H), 7.27 (d, J=8.8, Hz, 1H), 7.28 (t, J=8.4 Hz, 1H), 7.41 (d, J=8.8 Hz, 1H), 7.58 (d, J=7.6, Hz, 1H), 7.85 (d, J=1.6 Hz, 1H), 7.97 (d, J=7.6 Hz, 1H)

MS ES$^+$: 433

Example 25

N-[(1S,2R,4R)-2-[(6-Chloro-1,3-benzothiazol-2-yl)amino]-4-hydroxycyclopentyl]-2,6-dimethoxybenzamide

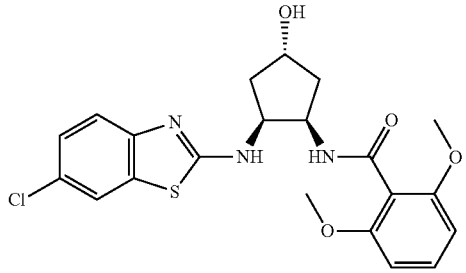 [SMILES: COc1cccc(OC)c1C(=O)N[C@@H]1C[C@@H](O)C[C@@H]1Nc1nc2ccc(Cl)cc2s1]

To a mixture of (1R,3S,4R)-3-amino-4-[(6-chloro-1,3-benzothiazol-2-yl)amino]cyclo-pentan-1-ol (prepared according to methods described in References 1, 2 and 3 below; 170 mg, 0.6 mmol), triethylamine (209 ml, 1.5 mmol) and dichloromethane (10 ml) at −78° C. was added 2,6-dimethoxybenzoyl chloride (0.12 g, 0.6 mmol) in dichloromethane (2 ml). The resulting mixture was agitated for 1 hour whilst being allowed to warm from −78° C. to 0° C. giving a white precipitate. A saturated solution of sodium bicarbonate (10 ml) was added and the resulting mass was diluted with a mixture of dichloromethane and methanol (9:1, 40 ml). Upon thorough shaking the aqueous solution was further extracted with a mixture of dichloromethane and methanol (4:1, 3×10 ml). The combined organics were dried (sodium sulphate), concentrated in vacuo and the residue (254 mg, 95%) was purified by triturating from ethanol to afford the title compound.

$^1$H NMR (Methanol-$d_4$): δ ppm 1.70-1.80 (m, 2H), 2.37-2.50 (m, 2H), 3.72 (s, 6H), 4.32-4.35 (m, 1H), 4.40-4.45 (m, 1H), 4.67-4.70 (m, 1H), 6.64 (d, J=8.4 Hz, 2H), 7.23 (d, J=8.4 Hz, 1H), 7.30 (t, J=8.4 Hz, 1H), 7.37 (d, J=8.4 Hz, 1H), 7.63 (s, 1H)

MS ES$^+$: 448

REFERENCES

1. Guan, Y.; Grenn, M. A.; Bergstrom, D. E., Stereocontrolled Synthesis of (1R,3R,4S)- and (1S,3R,4S)-3,4-diaminocyclopentanols, *Synlett* 1999, 4, 426-428;

2. Hess, H. M.; Brown, H. C., Synthesis of 3-cyclopenten-1-one and 3-cyclopenten-1-ol, *J. Org Chem.*, 1967, 32, 4138-4139;

3. Brookes, P.; Milne, D. J.; Murphy, P. J.; Spolaore, B., Epoxide rearrangements using dilithiated amino alcohols as chiral bases, *Tetrahedron* 2002, 58, 4675-4680.

Example 26

N-[(1S,2R)-2-[(6-Chloro-1,3-benzothiazol-2-yl)amino]-4-fluorocyclo-pentyl]-2,6-dimethoxybenzamide

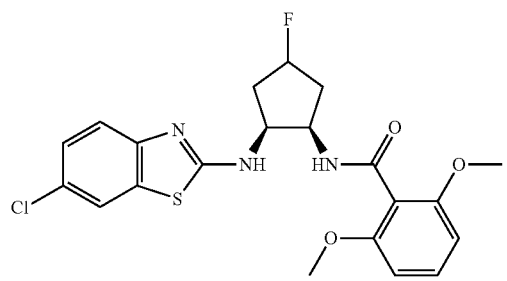 [SMILES: COc1cccc(OC)c1C(=O)N[C@@H]1CC(F)C[C@@H]1Nc1nc2ccc(Cl)cc2s1]

To a solution of N-[(1S,2R,4R)-2-[(6-chloro-1,3-benzothiazol-2-yl)amino]-4-hydroxycyclopentyl]-2,6-dimethoxybenzamide (Example 25, 70 mg, 0.15 mmol) in dichloromethane (1 ml) at 0° C. was added DAST (100 ml, 1.0 mmol). The reaction mixture was stirred for 15 minutes then a saturated aqueous solution of sodium bicarbonate (2 ml) was added. The aqueous phase was extracted with dichloromethane. The organic layer was washed with brine and dried (sodium sulphate) and the solvent was removed in vacuo. The crude product was washed with diethyl ether and purified via preparative TLC (dichloromethane/methanol=98:2) then washed with diethyl ether to afford the title compound.

$^1$H NMR (CDCl$_3$): δ ppm 2.15-2.62 (m, 4H), 3.80 (s, 6H), 4.65-4.70 (m, 2H), 5.15-5.28 (m, 1H), 6.10 (d, J=7.2 Hz, 1H), 6.27 (s, 1H), 6.56 (d, J=8.4 Hz, 2H), 7.22 (d, J=8.4 Hz, 1H), 7.26 (t, J=8.4 Hz, 1H), 7.39 (d, J=8.4 Hz, 1H), 7.50 (d, J=2.0 Hz, 1H)

MS ES$^+$: 450

Example 27

5-Methyl-N-[2-(quinolin-2-ylmethyl)cyclopentyl]-2-(2H-1,2,3-triazol-2-yl)benzamide

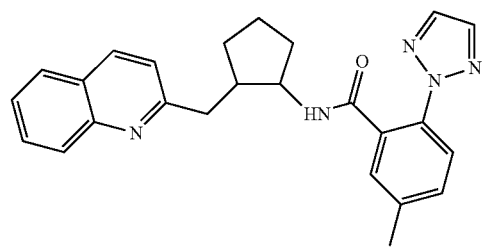 [SMILES: Cc1ccc(-n2nccn2)c(C(=O)NC2CCCC2Cc2ccc3ccccc3n2)c1]

To a mixture of 2-(quinolin-2-ylmethyl)cyclopentanamine hydrochloride (Intermediate 8, isomer 1; 75 mg, 0.285 mmol), EDC (82 mg, 0.428 mmol), HOAt (58.3 mg, 0.428 mmol) and DIPEA (150 μl, 0.856 mmol) in DCM (951 μl) was added 5-methyl-2-(2H-1,2,3-triazol-2-yl)benzoic acid (Intermediate 3; 87 mg, 0.428 mmol) under nitrogen and the reaction was stirred at room temperature for 24 hours. The mixture was then diluted with water and passed through a phase separator. The organic layer was concentrated in vacuo and the crude product was purified by reverse phase preparative HPLC (eluted with acetonitrile/water (containing 0.1% formic acid) to afford the title compound $^1$H NMR (DMSO-d$_6$) δ ppm 1.39-1.75 (m, 5H), 1.82-1.91 (m, 1H), 2.42 (s, 3H), 2.53-2.61 (m, 1H), 2.80 (d, J=13.77 Hz, 1H), 3.16 (d, J=13.77 1H), 4.24-4.34 (m, 1H), 7.33 (s, 1H), 7.42 (d, 2H), 7.54 (t, J=7.45 Hz, 1H), 7.65-7.76 (m, 1H), 7.87-8.00 (m, 4H), 8.25-8.39 (m, 2H)

MS ES$^+$: 412

Example 28

2-Ethoxy-5-methyl-N-[2-(quinolin-2-ylmethyl)cyclopentyl]-benzamide

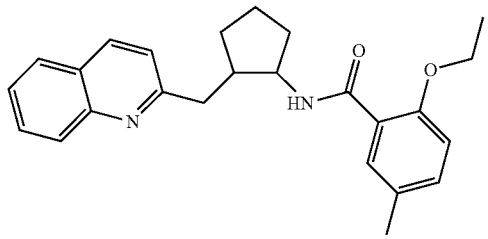 [SMILES: CCOc1ccc(C)cc1C(=O)NC1CCCC1Cc1ccc2ccccc2n1]

Prepared as described for 5-methyl-N-[2-(quinolin-2-ylmethyl)cyclopentyl]-2-(2H-1,2,3-triazol-2-yl)benzamide (Example 27) from 2-(quinolin-2-ylmethyl)cyclopentanamine hydrochloride (Intermediate 8, isomer 1; 75 mg; 0.285 mmol) and 2-ethoxy-5-methylbenzoic acid (Intermediate 4; 77 mg; 0.428 mmol). The crude product was purified by reverse phase preparative HPLC (eluted with acetonitrile/water containing 0.1% ammonia) to afford the title compound.

$^1$H NMR (DCM-d$_2$) δ ppm 1.53-1.93 (m, 9H), 2.00-2.17 (m, 1H), 2.31-2.41 (s, 3H), 2.66-2.80 (m, 1H), 2.88 (d, J=11.37 Hz, 1H), 3.25 (d, J=13.14, 1 H), 4.11-4.35 (m, 2H), 4.64 (d, J=12.44 Hz, 1H), 6.92 (d, J=8.34 Hz, 1H), 7.22-7.41 (m, 2H), 7.48-7.56 (m, 1H), 7.70 (t, J=7.58 Hz, 1H), 7.81 (d, J=8.08 Hz, 1H), 7.91-8.24 (m, 3H)

MS ES$^+$: 389

Example 29

2,6-Dimethoxy-N-[2-(quinolin-2-ylmethyl)cyclopentyl]benzamide

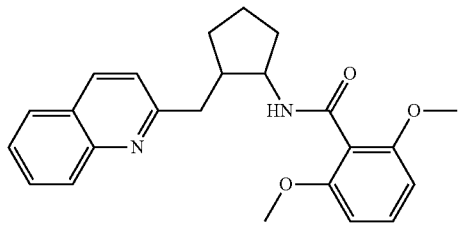 [SMILES: COc1cccc(OC)c1C(=O)NC1CCCC1Cc1ccc2ccccc2n1]

To a mixture of 2-(quinolin-2-ylmethyl)cyclopentanamine hydrochloride (Intermediate 8, isomer 1; 75 mg, 0.285 mmol) and DIPEA (150 μl, 0.856 mmol) in DCM (951 μl) was added 2,6-dimethoxybenzoyl chloride (86 mg, 0.428 mmol) under nitrogen. The reaction was stirred at room temperature for 24 hours and then diluted with water and passed through a phase separator. The organic layer was concentrated in vacuo and the crude mixture was purified by reverse phase preparative HPLC (eluted with acetonitrile/water containing 0.1% formic acid) to afford the title compound.

$^1$H NMR (DCM-d$_2$) δ ppm 1.37-1.54 (m, 1H), 1.57-1.92 (m, 4H), 2.11 (d, J=5.56 Hz, 1H), 2.68 (d, J=7.33 Hz, 1H), 3.02-3.08 (m, 1H), 3.32-3.40 (m, 1H), 3.81 (s, 6H), 4.48-4.68 (m, 1H), 6.62 (d, J=8.34 Hz, 2H), 6.91 (d, J=8.08 Hz, 1H), 7.34 (t, J=8.46 Hz, 1H), 7.44 (d, J=8.34 Hz, 1H), 7.48-7.60 (m, 1H), 7.66 (t, J=7.33 Hz, 1H), 7.73-7.93 (m, 2H), 8.08-8.24 (m, 1H)

MS ES$^+$: 391

Example 30

2,6-Diethoxy-N-(2-(quinolin-2-ylmethyl)cyclopentyl)benzamide

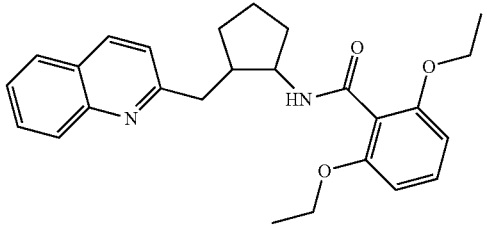 [SMILES: CCOc1cccc(OCC)c1C(=O)NC1CCCC1Cc1ccc2ccccc2n1]

To the solution of 2,6-diethoxybenzoic acid (66 mg, 0.314 mmol) in dichloromethane (5 ml) was added a catalytic amount of DMF, followed by oxalyl chloride (39 mg, 0.314 mmol) at 0° C. and then the reaction mixture was stirred at ambient temperature for 30 min. Independently, to a solution of 2-(quinolin-2-ylmethyl)cyclopentanamine hydrochloride (Intermediate 8, isomer 2; 75 mg, 0.286 mmol) in dichloromethane (10 ml) was added triethylamine (144 mg, 1.431 mmol) at ambient temperature, followed by addition of synthesized acid chloride at 0° C. over 10 minutes and then reaction mixture was stirred at room temperature for 2 hours before being poured into water and the product was extracted with dichloromethane. The combined organic layers were washed with brine, dried (sodium sulphate) and concentrated in vacuo. The crude product was purified via column chromatography (silica, 0-40% ethyl acetate/n-hexane) to afford the title compound.

$^1$H NMR (DMSO-d$_6$) δ ppm 1.20-1.29 (m, 6H), 1.29-1.31 (m, 1H), 1.47-1.65 (m, 4H), 1.92-1.96 (m, 1H), 2.29-2.33 (m, 1H), 2.71-2.77 (m, 1H), 3.30-3.35 (m, 1H), 3.97-4.03 (m, 5H), 6.62-6.64 (d, 2H), 7.21-7.25 (t, 1H), 7.43-7.45 (d, 1H), 7.52-7.56 (t, 1H), 7.69-7.72 (t, 1H), 7.90-7.93 (m, 2H), 8.10-8.12 (d, 1H), 8.25-8.27 (d, 1H)

MS ES$^+$: 419

Example 31

2-Ethoxy-5-methyl-N-(2-(quinolin-2-ylmethyl)cyclopentyl)-benzamide

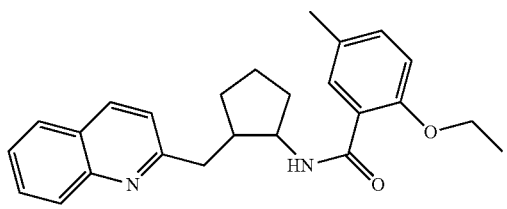 [SMILES: CCOc1ccc(C)cc1C(=O)NC1CCCC1Cc1ccc2ccccc2n1]

To a solution of 2-(quinolin-2-ylmethyl)cyclopentan-1-amine hydrochloride (Intermediate 8, isomer 2; 0.075 g, 0.287 mmol) in DMF (3 ml) was added DIPEA (0.148 g, 1.149 mmol), TBTU (0.11 g, 0.344 mmol) and 2-ethoxy-5-methylbenzoic acid (0.052 g, 0.287 mmol) and the reaction was stirred at room temperature for 1 hour. It was then poured into water and extracted with ethyl acetate and the combined organic extracts were washed with water and brine then dried (sodium sulphate) and concentrated in vacuo. The crude product was purified by column chromatography (silica, 0-60% ethyl acetate/n-hexane) to afford the title compound.

$^1$H NMR (DMSO-$d_6$) δ ppm 1.34-1.45 (m, 5H), 1.50-1.60 (m, 2H), 1.62-1.77 (m, 3H), 2.24-2.30 (m, 1H), 2.32-2.38 (m, 1H), 2.82-2.87 (m, 1H), 3.17-3.21 (m, 1H), 3.98-4.11 (m, 3H), 6.93-6.95 (d, 1H), 7.20-7.22 (d, 1H), 7.41-7.45 (t, 2H), 7.50-7.54 (t, 1H), 7.68-7.72 (t, 1H), 7.87-7.92 (m, 2H), 8.10-8.11 (d, 1H), 8.20-8.22 (d, 1H)

MS ES$^+$: 389

Example 32

N-{2-[(6-Chloro-1,3-benzothiazol-2-yl)methyl]cyclopentyl}-2,6-dimethoxybenzamide

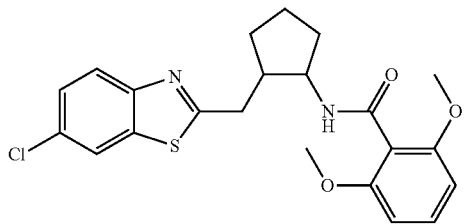 [SMILES: COc1cccc(OC)c1C(=O)NC1CCCC1Cc1nc2ccc(Cl)cc2s1]

Prepared as described for 2,6-diethoxy-N-(2-(quinolin-2-ylmethyl)cyclopentyl)benzamide (Example 30; 40 mg, 0.15 mmol) from 2,6-dimethoxybenzoic acid (30 mg; 165 mmol) and 2-[(6-chloro-1,3-benzothiazol-2-yl)methyl]cyclopentane-1-amine (Intermediate 9, isomer 1; 40 mg; 0.15 mmol). The crude product was purified by column chromatography (silica, 0-70% ethyl acetate/n-hexane) to yield the title compound.

$^1$H NMR (DMSO-$d_6$) δ ppm 1.36-1.78 (m, 5H), 1.89-2.08 (m, 1H), 2.94-3.03 (m, 1H), 3.34-3.40 (m, 1H), 3.73-3.75 (d, 1H), 3.81 (s, 6H), 4.37-4.44 (m, 1H), 6.66-6.69 (m, 2H), 7.27-7.32 (t, 1H), 7.51-7.53 (t, 1H), 7.93-7.95 (d, 1H), 8.14-8.16 (d, 1H), 8.22-8.23 (d, 1H)

ES MS$^+$: 431

Example 33

N-{2-[(6-Chloro-1,3-benzothiazol-2-yl)methyl]cyclopentyl}-5-methyl-2-(2H-1,2,3-triazol-2-yl)benzamide

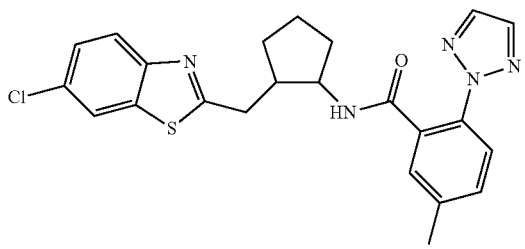 [SMILES: Cc1ccc(-n2nccn2)c(C(=O)NC2CCCC2Cc2nc3ccc(Cl)cc3s2)c1]

To the solution of 5-methyl-2-(2H-1,2,3-triazol-2-yl)benzoic acid (Intermediate 3, 0.038 g, 0.188 mmol) in DMF (2.0 ml) was added 2-[(6-chloro-1,3-benzothiazol-2-yl)methyl]cyclopentan-1-amine (Intermediate 9, isomer 1; 0.05 g, 0.188 mmol), DIPEA (0.072 g, 0.563 mmol) and TBTU (0.072 g, 0.225 mmol) at room temperature. The reaction was stirred for 2 hours before being poured into water and extracted with ethyl acetate. The combined organics were washed with brine, dried (sodium sulphate) and concentrated in vacuo. The crude product was purified by column chromatography (silica, eluted in 0-70% ethyl acetate in n-hexane) to afford the title compound.

$^1$H NMR (DMSO-$d_6$) δ ppm 1.46-1.48 (m, 3H), 1.53-1.57 (m, 1H), 1.61-1.67 (m, 2H), 1.69-1.72 (m, 1H), 2.33 (s, 3H), 2.97-3.03 (m, 1H), 3.31-3.35 (m, 1H), 4.31-4.34 (m, 1H), 7.31 (s, 1H), 7.41-7.43 (d, 1H), 7.51-7.54 (d, 1H), 7.67-7.66 (d, 1H), 7.93-7.95 (d, 1H), 7.98 (s, 1H), 8.23 (s, 1H), 8.35-8.37 (d, 2H)

MS ES$^+$: 452

Example 34

N-[(1S,2S)-2-[(6-Fluoro-1,3-benzothiazol-2-yl)amino]cyclopentyl]-2,6-dimethoxy-N-methylbenzamide

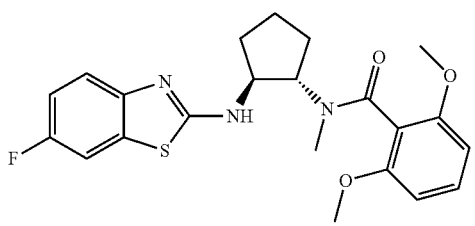 [SMILES: COc1cccc(OC)c1C(=O)N(C)[C@H]1CCC[C@@H]1Nc1nc2ccc(F)cc2s1]

(1S,2S)-1-N-(6-Fluoro-1,3-benzothiazol-2-yl)-2-N-methylcyclopentane-1,2-diamine (Intermediate 17, 60 mg, 0.226 mmol) was dissolved in dry dichloromethane (7.5 ml) and to this was added triethylamine (47 ml, 0.339 mmol) and 2,6-dimethoxybenzoyl chloride (68 mg, 0.339 mmol). The reaction was stirred at room temperature under nitrogen for 2 hours and then partitioned between dichloromethane and saturated aqueous sodium bicarbonate, passing through a phase separator. The organics were concentrated in vacuo to afford an oil which was then purified by column chromatography (silica, 0-100% ethyl acetate/petrol then 0-20% methanol/ethyl acetate to afford the title compound.

$^1$H NMR (DMSO-$d_6$) δ ppm 1.41-2.17 (m, 6H), 2.67 (s, 1H), 2.95 (s, 2H), 3.29 (s, 1H), 3.46-3.57 (m, 2H), 3.69-3.85 (m, 3.5H), 4.26-4.51 (m, 1H), 4.85-4.99 (m, 0.5H), 6.48-6.75 (m, 2H), 6.94-7.11 (m, 1H), 7.17-7.36 (m, 2H), 7.53-7.70 (m, 1.5H), 8.09 (d, J=8.84 Hz, 0.5H)

MS ES$^+$: 430

Example 35

N-[(1S,2S)-2-[(6-Fluoro-1,3-benzothiazol-2-yl)amino]cyclopentyl]-2-(1H-pyrazol-1-yl)benzamide

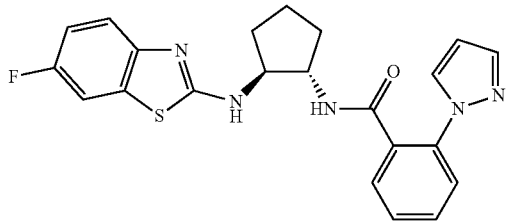 [SMILES: O=C(N[C@H]1CCC[C@@H]1Nc1nc2ccc(F)cc2s1)c1ccccc1-n1cccn1]

To 2-(1H-pyrazol-1-yl)benzoic acid (CAS number 55317-53-8, 0.033 g, 0.347 mmol) was added to (1S,2S)-1-N-(6-fluoro-1,3-benzothiazol-2-yl)cyclopentane-1,2-diamine hydrochloride (Intermediate 16a, 50 mg, 0.174 mmol), triethylamine (0.07 ml, 0.521 mmol) and dry dichloromethane (0.5 ml). 2,4,6-Tripropyl-1,3,5,2,4,6-trioxatriphosphinane 2,4,6-trioxide (0.2 ml, 0.347 mmol) was added and the reaction was stirred at room temperature for 24 hours. Additional 2-(1H-pyrazol-1-yl)benzoic acid (0.033 g, 0.347 mmol), triethylamine (0.07 ml, 0.521 mmol) and 2,4,6-tripropyl-1,3,5,2,4,6-trioxatriphosphinane 2,4,6-trioxide (0.2 ml, 0.347 mmol) was added and the mixture was stirred for a further 24 hours. The reaction was washed with water and filtered through a phase separator. The organic phase was concentrated in vacuo and the crude product was purified by reverse phase preparative HPLC (acetonitrile/water with 0.1% ammonia) to afford the title compound.

$^1$H NMR (Methanol-$d_4$) δ ppm 1.47-1.68 (m, 2H), 1.72-1.90 (m, 2H), 2.09-2.30 (m, 2H), 4.01-4.25 (m, 2H), 6.34 (t, 1H), 7.02-7.04 (m, 1H), 7.27-7.67 (m, 7H), 7.76-7.87 (m, 1H)

MS ES$^+$: 422

Example 36

5-Fluoro-N-[(1S,2S)-2-[(6-fluoro-1,3-benzothiazol-2-yl)amino]cyclopentyl]-2-(2H-1,2,3-triazol-2-yl)benzamide

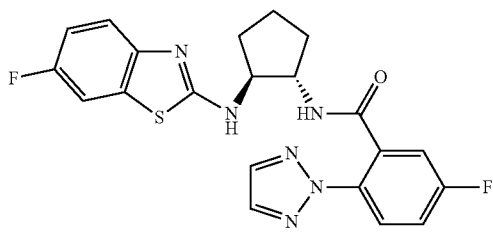 [SMILES: O=C(N[C@H]1CCC[C@@H]1Nc1nc2ccc(F)cc2s1)c1cc(F)ccc1-n1nccn1]

Prepared as described for N-[(1S,2S)-2-[(6-fluoro-1,3-benzothiazol-2-yl)amino]cyclopentyl]-2-(1H-pyrazol-1-yl)benzamide (Example 35) from 5-fluoro-2-(2H-1,2,3-triazol-2-yl)benzoic acid (CAS number 1152964-04-09; 36 mg; 0.173 mmol) and (1S,2S)-1-N-(6-fluoro-1,3-benzothiazol-2-yl)cyclopentane-1,2-diamine hydrochloride (Intermediate 16a; 50 mg; 0.174 mmol).

$^1$H NMR (Methanol-$d_4$) δ ppm 1.51-1.70 (m, 2H), 1.74-1.91 (m, 2H), 2.10-2.36 (m, 2H), 4.10-4.25 (m, 2H), 7.01-7.04 (m, 1H), 7.22-7.28 (m, 1H), 7.28-7.48 (m, 3H), 7.78 (s, 2H), 7.87 (m, 1H)

MS ES$^+$: 441

Example 37

2-Chloro-N-[(1S,2S)-2-[(6-fluoro-1,3-benzothiazol-2-yl)amino]cyclopentyl]benzamide

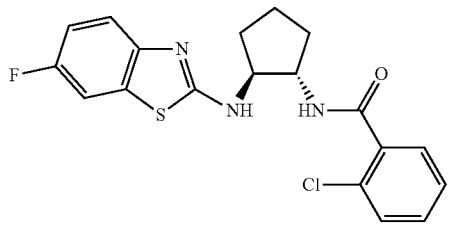 [SMILES: O=C(N[C@H]1CCC[C@@H]1Nc1nc2ccc(F)cc2s1)c1ccccc1Cl]

Prepared as described for N-[(1S,2S)-2-[(6-fluoro-1,3-benzothiazol-2-yl)amino]cyclopentyl]-2-(1H-pyrazol-1-yl)benzamide (Example 35) from 2-chlorobenzoic acid (75 mg; 0.48 mmol) and (1S,2S)-1-N-(6-fluoro-1,3-benzothiazol-2-yl)cyclopentane-1,2-diamine hydrochloride (Intermediate 16a; 50 mg; 0.199 mmol).

$^1$H NMR (Methanol-$d_4$) δ ppm 1.62-1.79 (m, 2H), 1.80-1.96 (m, 2H), 2.22-2.32 (m, 2H), 4.20-4.38 (m, 2H), 6.98-7.03 (m, 1H), 7.22-7.46 (m, 6H)

MS ES$^+$: 390

Example 38

N-[(1S,2S)-2-[(6-Fluoro-1,3-benzothiazol-2-yl)amino]cyclopentyl]-5-methyl-2-(1H-1,2,3-triazol-1-yl)benzamide

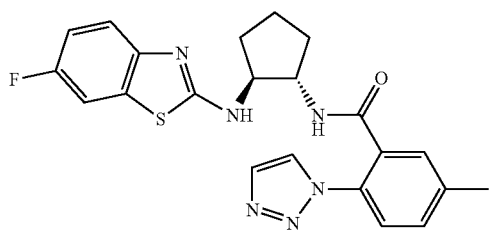 [SMILES: Cc1ccc(-n2ccnn2)c(C(=O)N[C@H]2CCC[C@@H]2Nc2nc3ccc(F)cc3s2)c1]

Prepared as described for N-[(1S,2S)-2-[(6-fluoro-1,3-benzothiazol-2-yl)amino]cyclopentyl]-2-(1H-pyrazol-1-yl)benzamide (Example 35) from 5-methyl-2-(1H-1,2,3-triazol-1-yl)benzoic acid (CAS number 1149352-55-5; 35 mg; 0.172 mmol) and (1S,2S)-1-N-(6-fluoro-1,3-benzothiazol-2-yl)cyclopentane-1,2-diamine hydrochloride (Intermediate 16a; 50 mg; 0.174 mmol) to afford the title compound.

¹H NMR (Methanol-d₄) δ ppm 1.46-1.70 (m, 2H), 1.72-1.87 (m, 2H), 2.02-2.26 (m, 2H), 2.32 (s, 3H), 4.05-4.25 (m, 2H), 7.00-7.05 (m, 1H), 7.24 (s, 1H), 7.32-7.35 (m, 1H), 7.38-7.51 (m, 3H), 7.74 (s, br, 1H), 8.11 (s, br, 1H)
MS ES⁺: 437

Example 39

N-[(1S,2S)-2-[(6-Fluoro-1,3-benzothiazol-2-yl)amino]cyclopentyl]-2-(3-methyl-1,2,4-oxadiazol-5-yl)benzamide

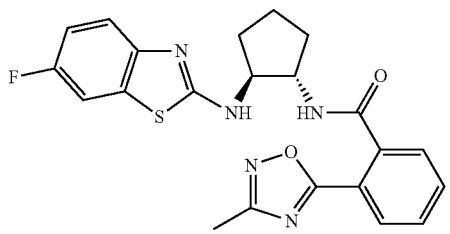 [SMILES: Cc1noc(-c2ccccc2C(=O)N[C@H]2CCC[C@@H]2Nc2nc3ccc(F)cc3s2)n1]

Prepared as described for N-[(1S,2S)-2-[(6-fluoro-1,3-benzothiazol-2-yl)amino]cyclopentyl]-2-(1H-pyrazol-1-yl)benzamide (Example 35) from 2-(3-methyl-1,2,4-oxadiazol-5-yl)benzoic acid (CAS number 475105-77-2; 35 mg; 0.71 mmol) and (1S,2S)-1-N-(6-fluoro-1,3-benzothiazol-2-yl)cyclopentane-1,2-diamine hydrochloride (Intermediate 16a; 50 mg; 0.174 mmol).
¹H NMR (Methanol-d₄) δ ppm 1.56-1.93 (m, 4H), 2.13-2.43 (m, 5H), 4.16-4.31 (m, 2H), 6.90-7.05 (m, 1H), 7.25-7.30 (m, 1H), 7.38-7.40 (m, 1H), 7.50-7.54 (m, 1H), 7.58-7.73 (m, 2H), 7.99-8.04 (m, 1H)
MS ES⁺: 438

Example 40

N-[(1S,2S)-2-[(6-Fluoro-1,3-benzothiazol-2-yl)amino]cyclopentyl]-2-(pyrimidin-2-yl)benzamide

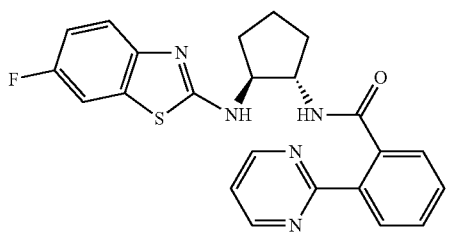 [SMILES: O=C(N[C@H]1CCC[C@@H]1Nc1nc2ccc(F)cc2s1)c1ccccc1-c1ncccn1]

Prepared as described for N-[(1S,2S)-2-[(6-fluoro-1,3-benzothiazol-2-yl)amino]cyclopentyl]-2-(1H-pyrazol-1-yl)benzamide (Example 35) from 2-(pyrimidin-2-yl)benzoic acid (CAS number 400892-62-8; 35 mg; 0.175 mmol) and (1S,2S)-1-N-(6-fluoro-1,3-benzothiazol-2-yl)cyclopentane-1,2-diamine hydrochloride (Intermediate 16a; 50 mg; 0.174 mmol).
¹H NMR (Methanol-d₄) δ ppm 1.51-1.75 (m, 2H), 1.76-1.92 (m, 2H), 2.25-2.30 (m, 2H), 4.18-4.20 (m, 2H), 7.02-7.05 (m, 1H), 7.20 (t, 1H), 7.29-7.31 (m, 1H), 7.37-7.64 (m, 4H), 8.06 (d, 1H), 8.70 (d, 2H)
MS ES⁺: 434

Example 41

N-[(1S,2S)-2-[(6-Fluoro-1,3-benzothiazol-2-yl)amino]cyclopentyl]-2,5-dimethoxybenzamide

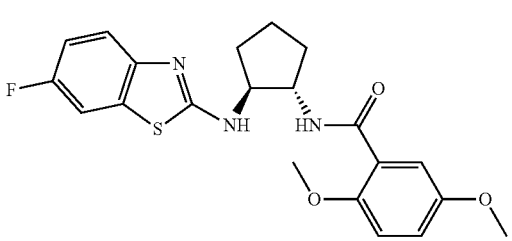 [SMILES: COc1ccc(OC)c(C(=O)N[C@H]2CCC[C@@H]2Nc2nc3ccc(F)cc3s2)c1]

Prepared as described for N-[(1S,2S)-2-[(6-fluoro-1,3-benzothiazol-2-yl)amino]cyclopentyl]-2-(1H-pyrazol-1-yl)benzamide (Example 35) from 2,5-dimethoxybenzoic acid (87 mg; 0.48 mmol) and (1S,2S)-1-N-(6-fluoro-1,3-benzothiazol-2-yl)cyclopentane-1,2-diamine hydrochloride (Intermediate 16a; 50 mg; 0.174 mmol).
MS ES⁺: 416

Example 42

5-Fluoro-N-[(1S,2S)-2-[(6-fluoro-1,3-benzothiazol-2-yl)amino]cyclopentyl]-2-(pyrimidin-2-yl)benzamide

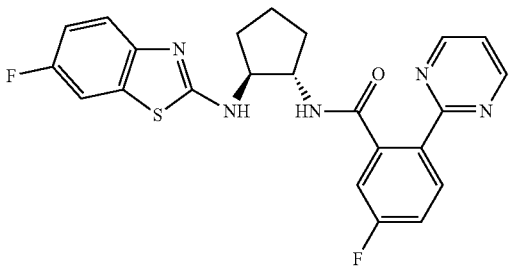 [SMILES: O=C(N[C@H]1CCC[C@@H]1Nc1nc2ccc(F)cc2s1)c1cc(F)ccc1-c1ncccn1]

Prepared as described for N-[(1S,2S)-2-[(6-fluoro-1,3-benzothiazol-2-yl)amino]cyclopentyl]-2-(1H-pyrazol-1-yl)benzamide (Example 35) from 5-fluoro-2-(pyrimidin-2-yl)benzoic acid (CAS number 1293284-57-7; 45 mg; 0.208 mmol) and (1S,2S)-1-N-(6-fluoro-1,3-benzothiazol-2-yl)cyclopentane-1,2-diamine hydrochloride (Intermediate 16a; 50 mg; 0.174 mmol).
¹H NMR (Methanol-d₄) δ ppm 1.56-1.74 (m, 2H), 1.79-1.87 (m, 2H), 2.25 (m, 2H), 4.11-4.29 (m, 2H), 7.01-7.05 (m, 1H), 7.12-7.23 (m, 2H), 7.24-7.43 (m, 3H), 8.15-8.20 (m, 1H), 8.69 (d, 2H)
MS ES⁺: 452

Example 43

N-[(1S,2S)-2-[(6-Fluoro-1,3-benzothiazol-2-yl)amino]cyclopentyl]-2-(1H-imidazol-1-yl)benzamide

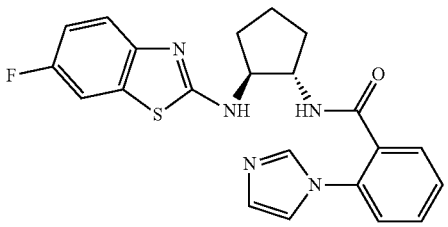 [SMILES: O=C(N[C@H]1CCC[C@@H]1Nc1nc2ccc(F)cc2s1)c1ccccc1-n1ccnc1]

Prepared as described for N-[(1S,2S)-2-[(6-fluoro-1,3-benzothiazol-2-yl)amino]cyclopentyl]-2-(1H-pyrazol-1-yl)benzamide (Example 35) from 2-(1H-imidazol-1-yl)benzoic acid (CAS number 159589-67-0; 33 mg; 0.175 mmol) and (1S,2S)-1-N-(6-fluoro-1,3-benzothiazol-2-yl)cyclopentane-1,2-diamine hydrochloride (Intermediate 16a; 50 mg; 0.174 mmol).

MS ES+: 422.

Example 44

N-[(1S,2S)-2-[(6-Fluoro-1,3-benzothiazol-2-yl)amino]cyclopentyl]-2-(1H-1,2,4-triazol-1-yl)benzamide

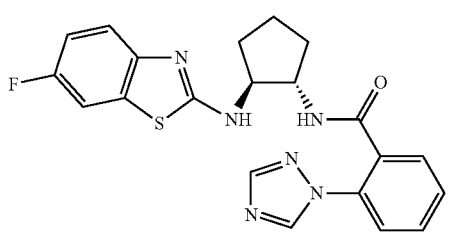 [SMILES: O=C(N[C@H]1CCC[C@@H]1Nc1nc2ccc(F)cc2s1)c1ccccc1-n1cncn1]

Prepared as described for N-[(1S,2S)-2-[(6-fluoro-1,3-benzothiazol-2-yl)amino]cyclopentyl]-2-(1H-pyrazol-1-yl)benzamide (Example 35) from 2-(1H-1,2,4-triazol-1-yl)benzoic acid (CAS number 138479-54-6; 33 mg; 0.174 mmol) and (1S,2S)-1-N-(6-fluoro-1,3-benzothiazol-2-yl)cyclopentane-1,2-diamine hydrochloride (Intermediate 16a; 50 mg; 0.174 mmol).

$^1$H NMR (Methanol-$d_4$) δ ppm 1.48-1.70 (m, 2H), 1.81-1.90 (m, 2H), 2.08-2.30 (m, 2H), 4.09-4.19 (m, 2H), 7.01-7.09 (m, 1H), 7.27-7.43 (m, 2H), 7.51-7.72 (m, 4H), 8.03 (s, 1H), 8.67 (s, 1H)

MS ES+: 423

Example 45

5-Fluoro-N-[(1S,2S)-2-[(6-fluoro-1,3-benzothiazol-2-yl)amino]cyclopentyl]-2-(1H-1,2,3-triazol-1-yl)benzamide

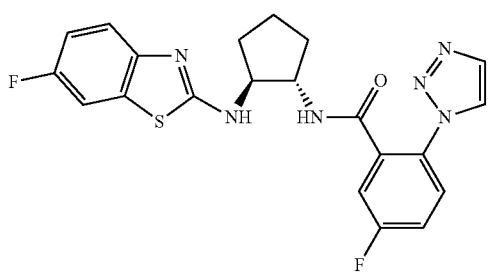 [SMILES: O=C(N[C@H]1CCC[C@@H]1Nc1nc2ccc(F)cc2s1)c1cc(F)ccc1-n1ccnn1]

Prepared as described for N-[(1S,2S)-2-[(6-fluoro-1,3-benzothiazol-2-yl)amino]cyclopentyl]-2-(1H-pyrazol-1-yl)benzamide (Example 35) from 5-fluoro-2-(1H-1,2,3-triazol-1-yl)benzoic acid (Intermediate 20; 43 mg; 0.208 mmol) and (1S,2S)-1-N-(6-fluoro-1,3-benzothiazol-2-yl)cyclopentane-1,2-diamine hydrochloride (Intermediate 16a; 50 mg; 0.174 mmol).

$^1$H NMR (Methanol-$d_4$) δ ppm 1.44-1.69 (m, 2H), 1.80-1.85 (m, 2H), 2.05-2.28 (m, 2H), 4.05-4.24 (m, 2H), 7.02-7.09 (m, 1H), 7.25-7.45 (m, 4H), 7.65-7.69 (m, 1H), 7.75-7.79 (m, 1H), 8.14 (d, 1H)

MS ES+: 441

Example 46

2-Fluoro-N-[(1S,2S)-2-[(6-fluoro-1,3-benzothiazol-2-yl)amino]cyclopentyl]-6-methoxybenzamide

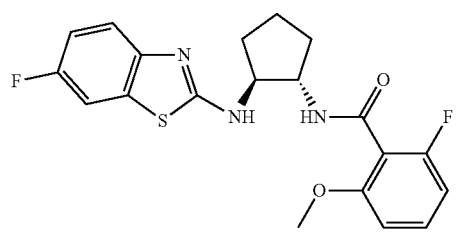 [SMILES: COc1cccc(F)c1C(=O)N[C@H]1CCC[C@@H]1Nc1nc2ccc(F)cc2s1]

Prepared as described for N-[(1S,2S)-2-[(6-fluoro-1,3-benzothiazol-2-yl)amino]cyclopentyl]-2-(1H-pyrazol-1-yl)benzamide (Example 35) from 2-fluoro-6-methoxybenzoic acid (81 mg; 0.476 mmol) and (1S,2S)-1-N-(6-fluoro-1,3-benzothiazol-2-yl)cyclopentane-1,2-diamine hydrochloride (Intermediate 16a; 50 mg; 0.174 mmol).

$^1$H NMR (Methanol-$d_4$) δ ppm 1.53-1.75 (m, 2H), 1.87-1.90 (m, 2H), 2.27-2.30 (m, 2H), 3.62 (s, 3H), 4.14-4.36 (m, 2H), 6.60-6.87 (m, 2H), 6.91-7.00 (m, 1H), 7.20-7.52 (m, 3H)

MS ES+: 404

Example 47

2,6-Difluoro-N-[(1S,2S)-2-[(6-fluoro-1,3-benzothiazol-2-yl)amino]-cyclopentyl]benzamide

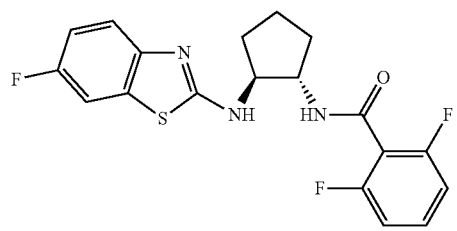 [SMILES: O=C(N[C@H]1CCC[C@@H]1Nc1nc2ccc(F)cc2s1)c1c(F)cccc1F]

Prepared as described for N-[(1S,2S)-2-[(6-fluoro-1,3-benzothiazol-2-yl)amino]cyclopentyl]-2-(1H-pyrazol-1-yl)benzamide (Example 35) using 2,6-difluorobenzoic acid (75 mg; 0.474 mmol) and (1S,2S)-1-N-(6-fluoro-1,3-benzothiazol-2-yl)cyclopentane-1,2-diamine hydrochloride (Intermediate 16a; 50 mg; 0.174 mmol).

$^1$H NMR (Methanol-$d_4$) δ ppm 1.61-1.74 (m, 2H), 1.87-1.90 (m, 2H), 2.23-2.40 (m, 2H), 4.10-4.42 (m, 2H), 6.87-7.06 (m, 3H), 7.23-7.51 (m, 3H)

MS ES+: 392

Example 48

2-Fluoro-N-[(1S,2S)-2-[(6-fluoro-1,3-benzothiazol-2-yl)amino]cyclopentyl]-benzamide

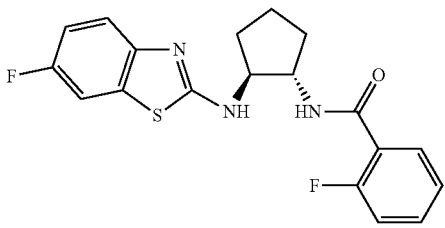 [SMILES: O=C(N[C@H]1CCC[C@@H]1Nc1nc2ccc(F)cc2s1)c1ccccc1F]

Prepared as described for N-[(1S,2S)-2-[(6-fluoro-1,3-benzothiazol-2-yl)amino]cyclopentyl]-2-(1H-pyrazol-1-yl)benzamide (Example 35) from 2-fluorobenzoic acid (67 mg; 0.497 mmol) and (1S,2S)-1-N-(6-fluoro-1,3-benzothiazol-2-yl)cyclopentane-1,2-diamine hydrochloride (Intermediate 16a; 50 mg; 0.174 mmol).

$^1$H NMR (Methanol-$d_4$) δ ppm 1.61-1.78 (m, 2H), 1.80-1.98 (m, 2H), 2.20-2.41, (m, 2H), 4.21-4.38 (m, 2H), 6.97-7.02 (m, 1H), 7.09-7.25 (m, 2H), 7.27-7.42 (m, 2H), 7.43-7.53 (m, 1H), 7.57-7.61 (m, 1H)

MS ES$^+$: 374

Example 49

2-Ethoxy-N-[(1S,2S)-2-[(6-fluoro-1,3-benzothiazol-2-yl)amino]cyclopentyl]-benzamide

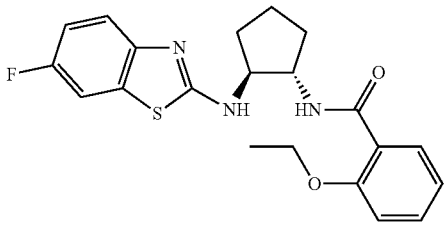 [SMILES: CCOc1ccccc1C(=O)N[C@H]1CCC[C@@H]1Nc1nc2ccc(F)cc2s1]

Prepared as described for N-[(1S,2S)-2-[(6-fluoro-1,3-benzothiazol-2-yl)amino]cyclopentyl]-2-(1H-pyrazol-1-yl)benzamide (Example 35) from 2-ethoxybenzoic acid (79 mg; 0.475 mmol) and (1S,2S)-1-N-(6-fluoro-1,3-benzothiazol-2-yl)cyclopentane-1,2-diamine hydrochloride (Intermediate 16a; 50 mg; 0.174 mmol).

$^1$H NMR (Methanol-$d_4$) δ ppm 1.38 (t, 3H), 1.61-1.75 (m, 2H), 1.89-1.90 (m, 2H), 2.28-2.42 (m, 2H), 4.06-4.35 (m, 4H), 6.93-7.11 (m, 3H), 7.29-7.49 (m, 3H), 7.82-7.90 (m, 1H)

MS ES$^+$: 400

Example 50

N-[(1S,2S)-2-[(6-Fluoro-1,3-benzothiazol-2-yl)amino]cyclopentyl]-2-methoxybenzamide

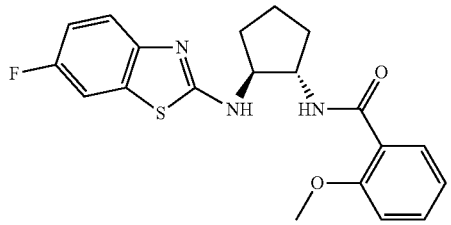 [SMILES: COc1ccccc1C(=O)N[C@H]1CCC[C@@H]1Nc1nc2ccc(F)cc2s1]

Prepared as described for N-[(1S,2S)-2-[(6-Fluoro-1,3-benzothiazol-2-yl)amino]cyclopentyl]-2-(1H-pyrazol-1-yl)benzamide (Example 35) from 2-methoxybenzoic acid (79 mg; 0.476 mmol) and (1S,2S)-1-N-(6-fluoro-1,3-benzothiazol-2-yl)cyclopentane-1,2-diamine hydrochloride (Intermediate 16a; 50 mg; 0.174 mmol).

$^1$H NMR (Methanol-$d_4$) δ ppm 1.60-1.78 (m, 2H), 1.80-1.96 (m, 2H), 2.25-2.35 (m, 2H), 3.82 (s, 3H), 4.21-4.36 (m, 2H), 6.94-7.11 (m, 3H), 7.28-7.40 (m, 2H), 7.41-7.50 (m, 1H), 7.73-7.77 (m, 1H)

MS ES$^+$: 386

Example 51

N-[(1S,2S)-2-[(6-Fluoro-1,3-benzothiazol-2-yl)amino]cyclopentyl]-2-methylbenzamide

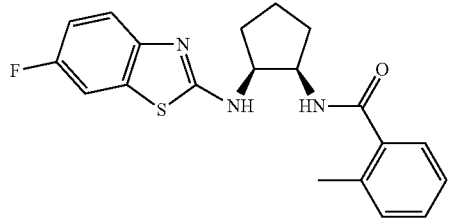 [SMILES: Cc1ccccc1C(=O)N[C@@H]1CCC[C@@H]1Nc1nc2ccc(F)cc2s1]

Prepared as described for N-[(1S,2S)-2-[(6-fluoro-1,3-benzothiazol-2-yl)amino]cyclopentyl]-2-(1H-pyrazol-1-yl)benzamide (Example 35) from 2-methylbenzoic acid (65 mg; 0.478 mmol) and (1S,2S)-1-N-(6-fluoro-1,3-benzothiazol-2-yl)cyclopentane-1,2-diamine hydrochloride (Intermediate 16a; 50 mg; 0.174 mmol).

MS ES$^+$: 370

Example 52

2,6-Dichloro-N-[(1S,2S)-2-[(6-fluoro-1,3-benzothiazol-2-yl)amino]-cyclopentyl]benzamide

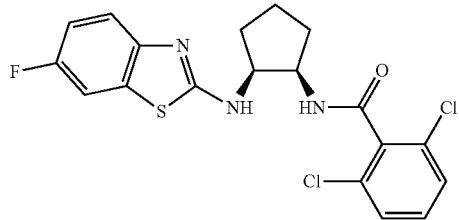 [SMILES: O=C(N[C@@H]1CCC[C@@H]1Nc1nc2ccc(F)cc2s1)c1c(Cl)cccc1Cl]

Prepared as described for N-[(1S,2S)-2-[(6-fluoro-1,3-benzothiazol-2-yl)amino]cyclopentyl]-2-(1H-pyrazol-1-yl)benzamide (Example 35) from 2,6-dichlorobenzoic acid (273 mg; 1.23 mmol) and (1S,2S)-1-N-(6-fluoro-1,3-benzothiazol-2-yl)cyclopentane-1,2-diamine hydrochloride (Intermediate 16a; 75 mg; 0.261 mmol).

$^1$H NMR (DMSO-d$_6$) δ ppm 1.45-1.83 (m, 4H), 2.08-2.10 (m, 2H), 4.11-4.34 (m, 2H), 7.03-7.06 (m, 1H), 7.26-7.51 (m, 4H), 7.59-7.61 (m, 1H), 8.14-8.16 (m, 1H), 8.79 (d, 1H)

MS ES$^+$: 424

Example 53

5-Fluoro-N-[(1S,2S)-2-[(6-fluoro-1,3-benzothiazol-2-yl)amino]cyclopentyl]-2-methoxybenzamide Prepared as described for N-[(1S,2S)-2-[(6-fluoro-1,3-benzothiazol-2-yl)amino]cyclopentyl]-2-(1H-pyrazol-1-yl)benzamide (Example 35) from 5-fluoro-2-methoxybenzoic acid (81 mg, 0.476 mmol) and (1S,2S)-1-N-(6-fluoro-1,3-benzothiazol-2-yl)cyclopentane-1,2-diamine hydrochloride (Intermediate 16a; 50 mg, 0.199 mmol).

$^1$H NMR (Methanol-d$_4$) δ ppm 1.58-1.78 (m, 2H), 1.81-1.94 (m, 2H), 2.25-2.38 (m, 2H), 3.82 (s, 3H), 4.20-4.40 (m, 2H), 7.00-7.05 (m, 1H), 7.08-7.10 (m, 1H), 7.19-7.22 (m, 1H), 7.28-7.39 (m, 2H), 7.47-7.50 (m, 1H)

MS ES$^+$: 404

Example 54

3-Fluoro-N-[(1S,2S)-2-[(6-fluoro-1,3-benzothiazol-2-yl)amino]cyclopentyl]-2-methoxybenzamide Prepared as described for N-[(1S,2S)-2-[(6-fluoro-1,3-benzothiazol-2-yl)amino]cyclopentyl]-2-(1H-pyrazol-1-yl)benzamide (Example 35) from 3-fluoro-2-methoxybenzoic acid (81 mg, 0.476 mmol) and (1S,2S)-1-N-(6-fluoro-1,3-benzothiazol-2-yl)cyclopentane-1,2-diamine hydrochloride (Intermediate 16a; 50 mg, 0.199 mmol).

$^1$H NMR (Methanol-d$_4$) δ ppm 1.61-1.77 (m, 2H), 1.85-1.93 (m, 2H), 2.23-2.39 (m, 2H), 3.86 (s, 3H), 4.21-4.37 (m, 2H), 6.97-7.02 (m, 1H), 7.06-7.11 (m, 1H), 7.23-7.28 (m, 1H), 7.30-7.42 (m, 3H)

MS ES$^+$: 404

Example 55

2-(Difluoromethoxy)-N-[(1S,2S)-2-[(6-fluoro-1,3-benzothiazol-2-yl)amino]-cyclopentyl]benzamide Prepared as described for N-[(1S,2S)-2-[(6-fluoro-1,3-benzothiazol-2-yl)amino]cyclopentyl]-2-(1H-pyrazol-1-yl)benzamide (Example 35) from 2-(difluoromethoxy)benzoic acid (49 mg, 0.266 mmol) and (1S,2S)-1-N-(6-fluoro-1,3-benzothiazol-2-yl)cyclopentane-1,2-diamine hydrochloride (Intermediate 16a; 50 mg, 0.174 mmol).

$^1$H NMR (DMSO-d$_6$) δ ppm 1.49-1.63 (m, 2H), 1.73-1.79 (m, 2H), 1.96-2.24 (m, 2H), 4.11-4.29 (m, 2H), 6.97-7.11 (m, 1H), 7.16-7.36 (m, 3H), 7.40-7.54 (m, 3H), 7.59-7.62 (m, 1H), 8.15 (d, 1H), 8.45 (d, 1H)

MS ES$^+$: 422

Example 56

N-[(1S,2S)-2-[(6-Fluoro-1,3-benzothiazol-2-yl)amino]cyclopentyl]-3-methoxybenzamide Prepared as described for N-[(1S,2S)-2-[(6-fluoro-1,3-benzothiazol-2-yl)amino]cyclopentyl]-2-(1H-pyrazol-1-yl)benzamide (Example 35) from 3-methoxybenzoic acid (73 mg, 0.48 mmol) and (1S,2S)-1-N-(6-fluoro-1,3-benzothiazol-2-yl)cyclopentane-1,2-diamine hydrochloride (Intermediate 16a; 50 mg, 0.199 mmol).

$^1$H NMR (Methanol-d$_4$) δ ppm 1.61-1.78 (m, 2H), 1.81-1.97 (m, 2H), 2.21-2.38 (m, 2H), 3.79 (s, 3H), 4.21-4.27 (m, 1H), 4.31-4.37 (m, 1H), 6.93-7.12 (m, 2H), 7.25-7.42 (m, 5H)

MS ES$^+$: 386

Example 57

N-[(1S,2S)-2-[(6-Fluoro-1,3-benzothiazol-2-yl)amino]cyclopentyl]-3-methylbenzamide

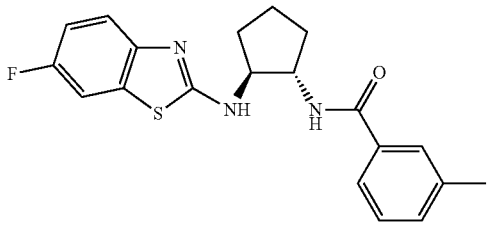 [SMILES: Cc1cccc(C(=O)N[C@H]2CCC[C@@H]2Nc2nc3ccc(F)cc3s2)c1]

Prepared as described for N-[(1S,2S)-2-[(6-fluoro-1,3-benzothiazol-2-yl)amino]cyclopentyl]-2-(1H-pyrazol-1-yl)benzamide (Example 35) from 3-methylbenzoic acid (65 mg, 0.133 mmol) and (1S,2S)-1-N-(6-fluoro-1,3-benzothiazol-2-yl)cyclopentane-1,2-diamine hydrochloride (Intermediate 16a; 50 mg, 0.199 mmol) to afford the title compound.

$^1$H NMR (Methanol-$d_4$) δ ppm 1.61-1.76 (m, 2H), 1.82-1.99 (m, 2H), 2.22-2.39 (m, 5H), 4.21-4.27 (m, 1H), 4.32-4.38 (m, 1H), 6.98-7.03 (m, 1H), 7.22-7.42 (m, 4H), 7.48-7.60 (m, 2H)

MS ES$^+$: 370

Example 58

2-Cyclopropyl-N-[(1S,2S)-2-[(6-fluoro-1,3-benzothiazol-2-yl)amino]-cyclopentyl]benzamide

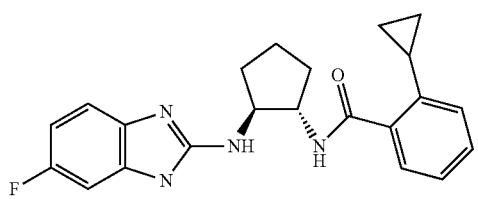 [SMILES: O=C(N[C@H]1CCC[C@@H]1Nc1nc2ccc(F)cc2[nH]1)c1ccccc1C1CC1]

To a solution of DIPEA (0.303 ml, 1.737 mmol) in dichloromethane (0.500 ml) was added (1S,2S)-1-N-(6-fluoro-1,3-benzothiazol-2-yl)cyclopentane-1,2-diamine hydrochloride (Intermediate 16a, 50 mg, 0.174 mmol). A solution of 2-cyclopropylbenzoyl chloride (250 mg, 0.692 mmol) in dichloromethane (0.500 ml) was then added cautiously and the reaction stirred at room temperature for 18 hours. The mixture was diluted with dichloromethane and washed with saturated sodium bicarbonate solution. Filtration through a hydrophobic frit and concentration in vacuo afforded a residue which was purified by reverse phase preparative HPLC (acetonitrile/water with 0.1% ammonia) and then by flash chromatography (silica, 0-50% ethyl acetate/petrol).

$^1$H NMR (DMSO-$d_6$) δ ppm 0.47-0.79 (m, 5H), 1.50-1.79 (m, 4H), 1.98-2.20 (m, 2H), 4.25-4.30 (m, 2H), 6.84 (d, 1H), 7.00-7.34 (m, 5H), 7.58-7.60 (m, 1H), 8.16 (d, 1H), 8.41 (d, 1H)

MS ES$^+$: 396

Example 59

N-[(1S,2S)-2-[(6-Fluoro-1,3-benzothiazol-2-yl)amino]cyclopentyl]-2-(2H-1,2,3-triazol-2-yl)benzamide

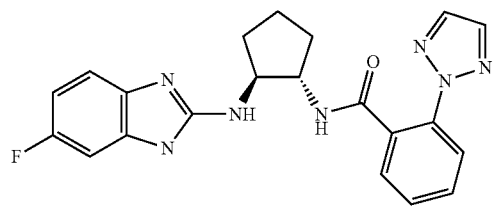 [SMILES: O=C(N[C@H]1CCC[C@@H]1Nc1nc2ccc(F)cc2[nH]1)c1ccccc1-n1nccn1]

Prepared as described for N-[(1S,2S)-2-[(6-fluoro-1,3-benzothiazol-2-yl)amino]cyclopentyl]-2-(1H-pyrazol-1-yl)benzamide (Example 35) from 2-(2H-1,2,3-triazol-2-yl)benzoic acid (83 mg, 0.438 mmol) and (1S,2S)-1-N-(6-fluoro-1,3-benzothiazol-2-yl)cyclopentane-1,2-diamine hydrochloride (Intermediate 16a; 100 mg, 0.398 mmol).

$^1$H NMR (Methanol-$d_4$) δ ppm 1.57-1.71 (m, 2H), 1.77-1.88 (m, 2H), 2.15-2.37 (m, 2H), 4.08-4.31 (m, 2H), 7.01-7.10 (m, 1H), 7.32 (m, 1H), 7.37-7.50 (m, 3H), 7.56-7.67 (m, 1H), 7.78 (s, 2H), 7.86 (d, 1H)

MS ES$^+$: 423

Example 60

5-Methyl-N-[(1S,2S)-2-[(quinazolin-2-yl)amino]cyclopentyl]-2-(2H-1,2,3-triazol-2-yl)benzamide

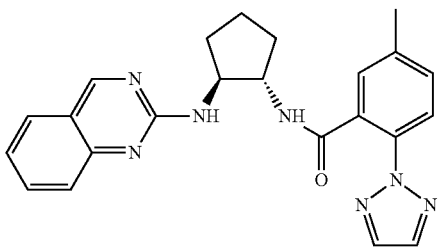 [SMILES: Cc1ccc(-n2nccn2)c(C(=O)N[C@H]2CCC[C@@H]2Nc2ncc3ccccc3n2)c1]

To a solution of N-((1S,2S)-2-aminocyclopentyl)-5-methyl-2-(2H-1,2,3-triazol-2-yl)benzamide hydrochloride (Intermediate 12, 0.1 g, 0.311 mmol) in NMP (1.0 ml) was added DIPEA (0.16 g, 1.24 mmol) and 2-chloroquinazoline (0.061 g, 0.374 mmol) at room temperature. The reaction mixture was stirred at 150° C. for 15 hours after which it was poured into water and extracted with ethyl acetate. The combined organics were dried (sodium sulphate) and evaporated in vacuo to obtain crude product which was purified by reverse phase preparative HPLC (acetonitrile/water with 0.1% ammonia) to afford the homogeneous title compound.

$^1$H NMR (DMSO-$d_6$) δ ppm 1.52-1.59 (m, 2H), 1.64-1.70 (m, 2H), 2.02-2.10 (m, 2H), 2.24 (s, 3H), 4.10-4.14 (m, 1H), 4.25-4.28 (m, 1H), 7.15 (s, 1H), 7.15-7.24 (t, 1H), 7.35-7.37 (m, 1H), 7.41-7.43 (m, 2H), 7.59-7.61 (m, 1H), 7.65-7.69 (m, 1H), 7.83-7.85 (m, 1H), 7.91 (s, 2H), 8.47 (s, br, 1H), 9.11 (s, 1H)

MS ES$^+$: 413

Examples 61 and 62

5-Methyl-N-[2-(quinolin-2-ylmethyl)cyclopentyl]-2-(2H-1,2,3-triazol-2-yl)benzamide

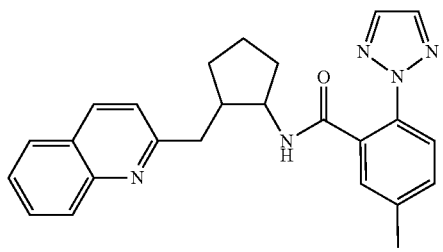 [SMILES: Cc1ccc(-n2nccn2)c(C(=O)NC2CCCC2Cc2ccc3ccccc3n2)c1]

Chiral separation of 5-Methyl-N-[2-(quinolin-2-ylmethyl)cyclopentyl]-2-(2H-1,2,3-triazol-2-yl)benzamide (Example 27).
Method:
ChiralPAK AD-H 250×10 mm, 5 um column.
Running isocratically with 20:80 IPA:$CO_2$.
Compound separated. Absolute conformation not assigned.
Product 1 (Example 61): MS ES$^+$: 412.
Product 2 (Example 62): MS ES$^+$: 412.

Example 61

$^1$H NMR (DMSO-$d_6$) δ ppm 1.39-1.92 (m, 6H), 2.42 (s, 3H), 2.57 (s, br, 1H), 2.74-2.87 (m, 1H), 3.16-3.20 (m, 1H), 4.18-4.33 (m, 1H), 7.33 (s, 1H), 7.43-7.39 (m, 2H), 7.49-7.59 (m, 1H), 7.62-7.75 (m, 2H), 7.87-8.04 (m, 4H), 8.20-8.43 (m, 2H)

Example 62

$^1$H NMR (DMSO-$d_6$) δ ppm 1.40-1.94 (m, 6H), 2.42 (s, 3H), 2.57 (s, br, 1H), 2.80-2.85 (m, 1H), 3.16-3.20 (m, 1H), 4.21-4.34 (m, 1H), 7.33 (s, 1H), 7.43 (d, 2H), 7.49-7.59 (m, 1H), 7.62-7.75 (m, 2H), 7.88-8.02 (m, 4H), 8.22-8.37 (m, 2H)

Example 63

5-Methyl-N-[2-(quinoxalin-2-ylmethyl)cyclopentyl]-2-(2H-1,2,3-triazol-2-yl)benzamide

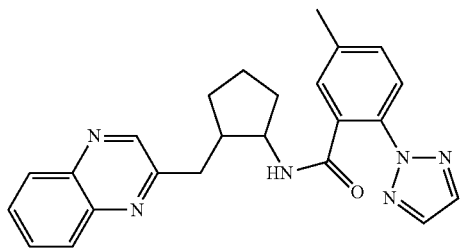 [SMILES: Cc1ccc(-n2nccn2)c(C(=O)NC2CCCC2Cc2cnc3ccccc3n2)c1]

To a solution of 2-(quinoxalin-2-ylmethyl)cyclopentan-1-amine (Intermediate 18a; 0.07 g, 0.308 mmol) in DMF (5 mL) was added 5-methyl-2-(2H-1,2,3-triazol-2-yl)benzoic acid (Intermediate 3; 0.062 g, 0.308 mmol) DIPEA (0.079 g, 0.616 mmol) and TBTU (0.118 g, 0.370 mmol) at room temperature and the reaction was stirred for 1 hour. The reaction was poured into water and extracted into ethyl acetate before being concentrated in vacuo. The crude compound was purified by column chromatography (silica, eluted with 0-2% methanol in dichloromethane) to yield the title compound.

$^1$H NMR (DMSO-$d_6$) δ ppm 1.46-1.50 (m, 2H), 1.51-1.60 (m, 2H), 1.61-1.63 (m, 1H), 1.80-1.89 (m, 1H), 2.41 (s, 3H), 2.58-2.60 (m, 1H), 2.87-2.92 (m, 1H), 3.20-3.25 (m, 1H), 4.28-4.30 (m, 1H), 7.30 (s, 1H), 7.41-7.43 (m, 1H), 7.64-7.66 (m, 1H), 7.79-7.85 (m, 2H), 7.98 (s, 2H), 8.01-8.08 (m, 2H), 8.34-8.36 (m, 1H), 8.85 (s, 1H)
MS ES$^+$: 413

Example 64

5-Methyl-N-[2-(quinoxalin-2-ylmethyl)cyclopentyl]-2-(2H-1,2,3-triazol-2-yl)benzamide

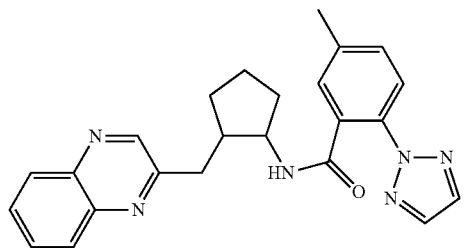 [SMILES: Cc1ccc(-n2nccn2)c(C(=O)NC2CCCC2Cc2cnc3ccccc3n2)c1]

Prepared as described for N-{3-[(6-chlorobenzo 1,3-benzothiazol-2-yl)amino]butan-2-yl}-5-methyl-2-(2H-1,2,3-triazol-2-yl)benzamide (Example 63 from 2-(quinoxalin-2-ylmethyl)cyclopentan-1-amine (Intermediate 18b; 118 mg, 0.370 mmol) and 5-methyl-2-(2H-1,2,3-triazol-2-yl)benzoic acid (Intermediate 3; 62 mg, 0.308 mmol). The crude compound was purified by column chromatography using (silica, 0-2% methanol/dichloromethane) to afford the title compound.

$^1$H NMR (DMSO-$d_6$) δ ppm 1.30-1.35 (m, 1H), 1.41-1.44 (m, 1H), 1.46-1.59 (m, 2H), 1.70-1.73 (m, 1H), 1.91-1.98 (m, 1H), 2.26-2.50 (m, 4H), 2.94-2.97 (m, 1H), 3.24-3.33 (m, 1H), 3.03-3.98 (m, 1H), 6.98 (s, 1H), 7.35-7.38 (m, 1H), 7.61-7.63 (m, 1H), 7.79-7.83 (m, 2H), 7.97 (s, 2H), 8.03-8.09 (m, 2H), 8.26-8.28 (m, 1H), 8.88 (s, 1H)
MS ES$^+$: 413

Example 65 trans-N-{4-[(6-Fluoro-1,3-benzothiazol-2-yl)amino]oxolan-3-yl}-2,6-dimethoxybenzamide

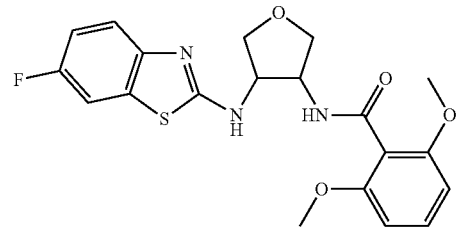 [SMILES: COc1cccc(OC)c1C(=O)NC1COCC1Nc1nc2ccc(F)cc2s1]

trans-N-(4-Aminooxolan-3-yl)-2,6-dimethoxybenzamide (Intermediate 19, 262 mg, 0.984 mmol), 2-chloro-6-fluoro- 1,3-benzothiazole (277 mg, 1.476 mmol) and DIPEA (0.516 ml, 2.95 mmol) were dissolved in dry acetonitrile (1.96 ml) and the reaction was heated with microwave irradiation at 150° C. for 5 hours. Upon cooling, the mixture was diluted with dichloromethane and washed with hydrochloric acid (1M) and water. The aqueous phases were combined, basified with sodium hydroxide and extracted into ethyl acetate and the combined organic phases were dried (magnesium sulfate), filtered and the solvent was evaporated in vacuo. The crude was purified by SCX followed by chromatography (silica, 20%-100% ether/petrol followed by 100% ethyl acetate) and then further purified by reverse phase preparative HPLC (acetonitrile/water containing 0.1% ammonia) to afford the title compound.

$^1$H NMR (Methanol-$d_4$) δ ppm 3.73-3.88 (m, 8H), 4.12-4.29 (m, 2H), 4.44-4.64 (m, 2H), 6.68 (d, 2H), 7.03-7.05 (m, 1H), 7.29-7.48 (m, 3H)

MS ES$^+$: 418

Example 66

N-[(1S,2S)-2-[(6-Fluoro-1,3-benzoxazol-2-yl)amino]cyclopentyl]-2,6-dimethoxybenzamide

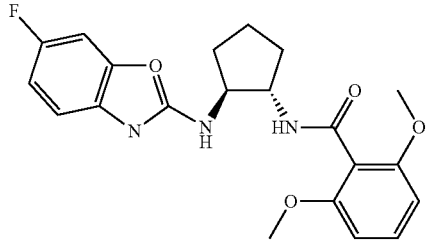

To a solution of N-((1S,2S)-2-aminocyclopentyl)-2,6-dimethoxybenzamide hydrochloride (Intermediate 11, 100 mg, 0.332 mmol) in dry DMSO (1 ml) was added 2-chloro-6-fluoro-1,3-benzoxazole (57 mg, 0.332 mmol) and DIPEA (0.17 ml, 0.997 mmol). The reaction was irradiated under microwave conditions at 150° C. for 8 hours and, upon cooling, was partitioned between ethyl acetate and water. The organic portion was washed with water and brine, dried (magnesium sulfate), filtered and concentrated in vacuo. The crude product was purified by reverse phase preparative HPLC (acetonitrile/water containing 0.1% ammonia) to afford the title compound.

$^1$H NMR (DMSO-$d_6$) δ ppm 1.47-1.75 (m, 4H), 1.95-2.12 (m, 2H), 3.57 (s, 6H), 4.01-4.07 (m, 1H), 4.23-4.30 (m, 1H), 6.57-6.66 (m, 2H), 6.87-7.02 (m, 1H), 7.13-7.26 (m, 2H), 7.33-7.44 (m, 1H), 7.92-8.20 (m, 2H)

MS ES$^+$: 400

Example 67

N-[(1S,2S)-2-[(6-Fluoro-1,3-benzothiazol-2-yl)amino]cyclopentyl]-2-methoxy-5-methylbenzamide

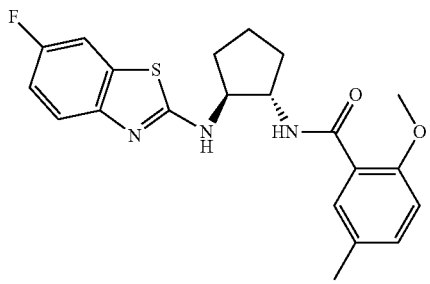 [SMILES: COc1ccc(C)cc1C(=O)N[C@H]1CCC[C@@H]1Nc1nc2ccc(F)cc2s1]

Prepared as described for N-[(1S,2S)-2-[(6-Fluoro-1,3-benzothiazol-2-yl)amino]cyclopentyl]-2-(1H-pyrazol-1-yl)benzamide (Example 35) from 2-methoxy-5-methylbenzoic acid (CAS number 25045-36-7; 79 mg; 0.476 mmol) and (1S,2S)-1-N-(6-fluoro-1,3-benzothiazol-2-yl)cyclopentane-1,2-diamine hydrochloride (Intermediate 16a; 50 mg; 0.174 mmol).

$^1$H NMR (400 MHz, MeOD-$d_4$): δ ppm 1.60-1.74 (m, 2H), 1.83-1.90 (m, 2H), 2.22 (s, 3H), 2.24-2.33 (m, 2H), 3.77 (s, 3H), 4.18-4.34 (m, 2H), 6.90-7.02 (m, 2H), 7.20-7.26 (m, 1H), 7.28-7.38 (m, 2H), 7.48-7.52 (m, 1H)

MS ES$^+$: 400

Example 68

N-[(1S,2S)-2-[(6-Fluoro-1,3-benzothiazol-2-yl)amino]cyclopentyl]-2,6-dimethylbenzamide

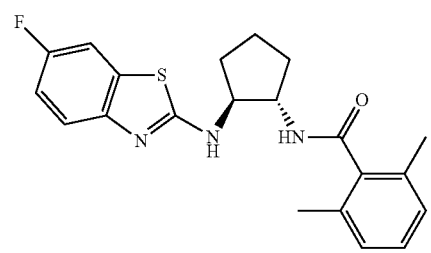 [SMILES: Cc1cccc(C)c1C(=O)N[C@H]1CCC[C@@H]1Nc1nc2ccc(F)cc2s1]

Prepared as described for 2-cyclopropyl-N-[(1S,2S)-2-[(6-fluoro-1,3-benzothiazol-2-yl)amino]cyclopentyl]benzamide (Example 58) from 2,6-dimethylbenzoyl chloride (CAS number 21900-37-8; 220 mg, 1.303 mmol) and (1S,2S)-1-N-(6-fluoro-1,3-benzothiazol-2-yl)cyclopentane-1,2-diamine hydrochloride (Intermediate 16a; 75 mg, 0.261 mmol). The crude compound was purified by reverse phase preparative HPLC (acetonitrile/water with 0.1% ammonia) to afford the title compound.

$^1$H NMR (400 MHz, CD$_2$Cl$_2$-$d_2$): δ ppm 1.54-1.72 (m, 2H), 1.79-1.93 (m, 2H), 2.05-2.22 (m, 6H), 2.24-2.46 (m, 2H), 4.05-4.16 (m, 1H), 4.22-4.36 (m, 1H), 6.04-6.27 (m, 1H), 6.70-6.79 (m, 1H), 6.90-7.00 (m, 3H), 7.09-7.21 (m, 2H), 7.24-7.31 (m, 1H)

MS ES$^+$: 384

Example 69

2-Fluoro-N-[(1S,2S)-2-[(6-fluoro-1,3-benzothiazol-2-yl)amino]cyclopentyl]-6-(2H-1,2,3-triazol-2-yl)benzamide

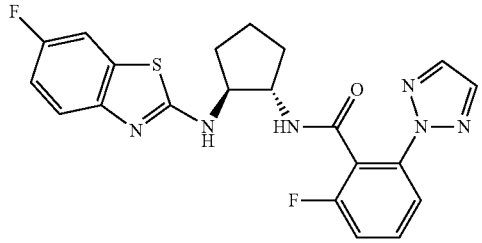 [SMILES: O=C(N[C@H]1CCC[C@@H]1Nc1nc2ccc(F)cc2s1)c1c(F)cccc1-n1nccn1]

To a solution of (1S,2S)-1-N-(6-fluoro-1,3-benzothiazol-2-yl)cyclopentane-1,2-diamine hydrochloride (Intermediate 16a, 50 mg, 0.174 mmol) in dry DCM (2 ml) was added 2-fluoro-6-(2H-1,2,3-triazol-2-yl)benzoic acid (Intermediate 21, 54.0 mg, 0.261 mmol), triethylamine (0.073 ml, 0.521 mmol) and HATU (99 mg, 0.261 mmol). The reaction was stirred at room temperature for 18 hours then diluted with DCM, washed with water, filtered through a hydrophobic frit and concentrated in vacuo. The crude product was purified by reverse phase preparative HPLC (acetonitrile/water with 0.1% ammonia) to afford the title compound.

$^1$H NMR (400 MHz, MeOD-d$_4$): δ ppm 1.56-1.72 (m, 2H), 1.75-1.89 (m, 2H), 2.16-2.32 (m, 2H), 4.09-4.18 (m, 1H), 4.22-4.31 (m, 1H), 6.93-7.02 (m, 1H), 7.19-7.30 (m, 2H), 7.33-7.40 (m, 1H), 7.53-7.62 (m, 1H), 7.74 (s, 2H), 7.76-7.80 (m, 1H)

MS ES$^+$: 441

Example 70

2-Chloro-6-fluoro-N-[(1S,2S)-2-[(6-fluoro-1,3-benzothiazol-2-yl)amino]cyclopentyl]benzamide

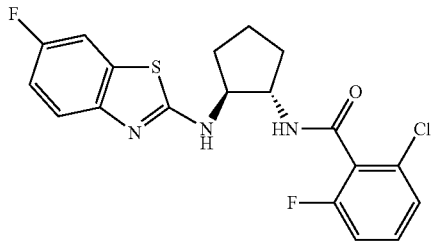 [SMILES: O=C(N[C@H]1CCC[C@@H]1Nc1nc2ccc(F)cc2s1)c1c(F)cccc1Cl]

Prepared as described for 2-cyclopropyl-N-[(1S,2S)-2-[(6-fluoro-1,3-benzothiazol-2-yl)amino]cyclopentyl]benzamide (Example 58) from 2-chloro-6-fluorobenzoyl chloride (CAS number 79455-63-3; 40 mg, 0.208 mmol) and (1S,2S)-1-N-(6-fluoro-1,3-benzothiazol-2-yl)cyclopentane-1,2-diamine (Intermediate 16a; 50 mg, 0.174 mmol). The reaction mixture was diluted with dichloromethane and washed with water. Filtration through a hydrophobic frit and concentration in vacuo afforded a residue which was purified by reverse phase preparative HPLC (acetonitrile/water with 0.1% ammonia) to afford the title compound.

$^1$H NMR (400 MHz, MeOD-d$_4$): δ ppm 1.60-1.76 (m, 2H), 1.82-1.90 (m, 2H), 2.21-2.31 (m, 2H), 4.17-4.27 (m, 1H), 4.29-4.39 (m, 1H), 6.89-7.02 (m, 1H), 7.05-7.13 (m, 1H), 7.19-7.31 (m, 2H), 7.33-7.45 (m, 2H)

MS ES$^+$: 408

Example 71

2-Chloro-N-[(1S,2S)-2-[(6-fluoro-1,3-benzothiazol-2-yl)amino]cyclopentyl]-6-(2H-1,2,3-triazol-2-yl)benzamide

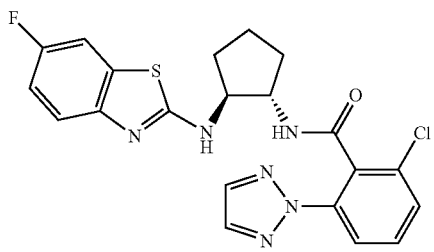 [SMILES: O=C(N[C@H]1CCC[C@@H]1Nc1nc2ccc(F)cc2s1)c1c(Cl)cccc1-n1nccn1]

Prepared as described for 2-fluoro-N-[(1S,2S)-2-[(6-fluoro-1,3-benzothiazol-2-yl)amino]cyclopentyl]-6-(2H-1,2,3-triazol-2-yl)benzamide (Example 69) from 2-chloro-6-(2H-1,2,3-triazol-2-yl)benzoic acid (Intermediate 22, 58 mg, 0.261 mmol) and (1S,2S)-1-N-(6-fluoro-1,3-benzothiazol-2-yl)cyclopentane-1,2-diamine hydrochloride (Intermediate 16a; 50 mg, 0.174 mmol) to afford the title compound.

$^1$H NMR (400 MHz, MeOD-d$_4$): δ ppm 1.45-1.74 (m, 4H), 1.93-2.12 (m, 2H), 4.04-4.24 (m, 2H), 6.96-7.09 (m, 1H), 7.24-7.40 (m, 1H), 7.53-7.62 (m, 3H), 7.75-7.89 (m, 1H), 7.99 (s, 2H), 8.05-8.13 (m, 1H), 8.54-8.66 (m, 1H)

MS ES$^+$: 457

Example 72

N-[(1S,2S)-2-[(6-Fluoro-1,3-benzothiazol-2-yl)amino]cyclopentyl]-2-(5-methyl-1,3,4-oxadiazol-2-yl)benzamide

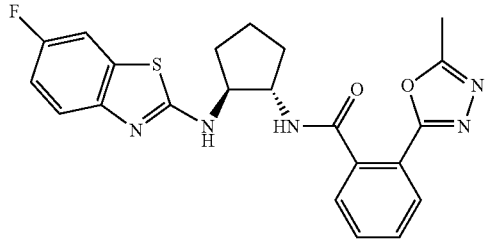 [SMILES: Cc1nnc(-c2ccccc2C(=O)N[C@H]2CCC[C@@H]2Nc2nc3ccc(F)cc3s2)o1]

To a solution of (1S,2S)-1-N-(6-fluoro-1,3-benzothiazol-2-yl)cyclopentane-1,2-diamine hydrochloride (Intermediate 16a, 100 mg, 0.347 mmol) in dry DMF (1 ml) was added 2-(5-methyl-1,3,4-oxadiazol-2-yl)benzoic acid (CAS number 898289-64-0; 85 mg, 0.417 mmol), triethylamine (0.145 ml, 1.042 mmol) and HATU (198 mg, 0.521 mmol). The reaction was stirred at room temperature for 20 hours then diluted with ethyl acetate (25 ml), washed with water (3×20 ml) and brine (20 ml). The organics were filtered through a hydrophobic frit and concentrated in vacuo to afford a residue which was purified by reverse phase preparative HPLC (acetonitrile/water with 0.1% ammonia) to afford the title compound.

$^1$H NMR (400 MHz, DMSO-d$_6$): δ ppm 1.51-1.76 (m, 4H), 2.01-2.15 (m, 2H), 2.53 (s, 3H), 4.10-4.24 (m, 2H), 6.98-7.15 (m, 1H), 7.25-7.39 (m, 1H), 7.46-7.55 (m, 1H), 7.56-7.65 (m, 3H), 7.81-7.89 (m, 1H), 8.11-8.22 (m, 1H), 8.61-8.76 (m, 1H)

MS ES$^+$: 438

Example 73

N-[(1S,2S)-2-[(6-Fluoro-1,3-benzothiazol-2-yl)amino]cyclopentyl]-2-(1H-1,2,3-triazol-1-yl)benzamide

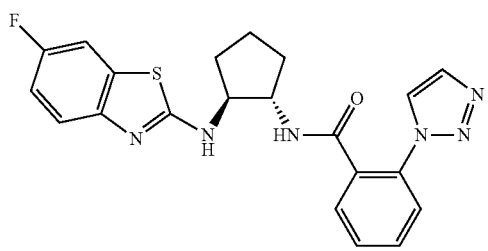 [SMILES: O=C(N[C@H]1CCC[C@@H]1Nc1nc2ccc(F)cc2s1)c1ccccc1-n1ccnn1]

Prepared as described for N-[(1S,2S)-2-[(6-fluoro-1,3-benzothiazol-2-yl)amino]cyclopentyl]-2-(5-methyl-1,3,4-oxadiazol-2-yl)benzamide (Example 72) from 2-(1H-1,2,3-triazol-1-yl)benzoic acid (CAS number 1085458-53-2; 54 mg, 0.287 mmol) and (1S,2S)-1-N-(6-fluoro-1,3-benzothiazol-2-yl)cyclopentane-1,2-diamine hydrochloride (Intermediate 16a; 75 mg, 0.261 mmol) to afford the title compound.

$^1$H NMR (400 MHz, DCM-d$_2$): δ ppm 1.43-1.55 (m, 1H), 1.61-1.76 (m, 1H), 1.77-1.93 (m, 2H), 2.19-2.36 (m, 2H), 3.96-4.13 (m, 2H), 7.00-7.08 (m, 1H), 7.17-7.22 (m, 1H), 7.30-7.37 (m, 2H), 7.50-7.58 (m, 2H), 7.62-7.67 (m, 2H), 7.69-7.74 (m, 1H), 7.86-7.92 (m, 1H)

MS ES$^+$: 423

Example 74

5-Chloro-N-[(1S,2S)-2-[(6-fluoro-1,3-benzothiazol-2-yl)amino]cyclopentyl]-2-(1H-pyrazol-1-yl)benzamide

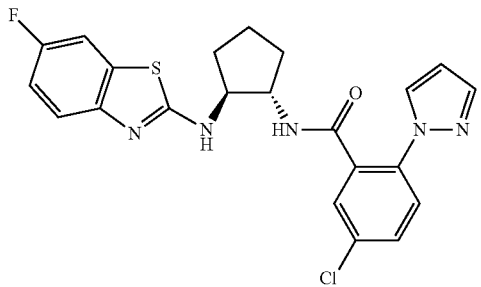 [SMILES: O=C(N[C@H]1CCC[C@@H]1Nc1nc2ccc(F)cc2s1)c1cc(Cl)ccc1-n1cccn1]

Prepared as described for N-[(1R,2S)-2-[(1,3-Benzoxazol-2-yl)amino]cyclopentyl]-2,6-diethoxy-benzamide (Example 17) from 5-chloro-2-(1H-pyrazol-1-yl)benzoic acid (Intermediate 23; 69.6 mg, 0.313 mmol), triethylamine (0.109 ml, 1.576 mmol) and (1S,2S)-1-N-(6-fluoro-1,3-benzothiazol-2-yl)cyclopentane-1,2-diamine hydrochloride (Intermediate 16a; 75 mg, 0.261 mmol) to afford the title compound.

$^1$H NMR (400 MHz, DMSO-d$_6$): δ ppm 1.46-1.60 (m, 2H), 1.62-1.73 (m, 2H), 1.92-2.12 (m, 2H), 4.06-4.20 (m, 2H), 6.31-6.37 (m, 1H), 7.01-7.09 (m, 1H), 7.30-7.37 (m, 1H), 7.40-7.43 (m, 1H), 7.56-7.67 (m, 4H), 7.90-7.96 (m, 1H), 8.08-8.14 (m, 1H), 8.59-8.66 (m, 1H)

MS ES$^+$: 456

Example 75

N-[(1S,2R)-2-[(6-Fluoro-1,3-benzothiazol-2-yl)amino]cyclopentyl]-2-(2H-1,2,3-triazol-2-yl)benzamide

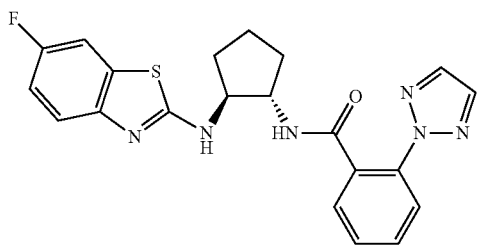 [SMILES: O=C(N[C@H]1CCC[C@@H]1Nc1nc2ccc(F)cc2s1)c1ccccc1-n1nccn1]

To a solution of N-[(1S,2R)-2-aminocyclopentyl]-2-(2H-1,2,3-triazol-2-yl)benzamide hydrochloride (Intermediate 24; 445 mg, 1.446 mmol) in DMSO (5 ml) was added 2-chloro-6-fluoro-1,3-benzothiazole (CAS number 399-74-6; 326 mg, 1.735 mmol) and DIPEA (0.758 ml, 4.34 mmol). The reaction was heated in a microwave at 140° C. for 2 hours and was then diluted with ethyl acetate (50 ml), washed with water (50 ml), saturated sodium bicarbonate solution (2×50 ml) and brine (50 ml). The organics were filtered through a hydrophobic frit and concentrated in vacuo to afford a residue which was purified by column chromatography (silica, 0-25% ethyl acetate/petrol) then by reverse phase preparative HPLC (acetonitrile/water with 0.1% ammonia) to afford the title compound.

$^1$H NMR (400 MHz, DMSO-d$_6$): δ ppm 1.40-1.80 (m, 4H), 1.83-2.08 (m, 2H), 4.13-4.29 (m, 1H), 4.29-4.46 (m, 1H), 6.98-7.20 (m, 1H), 7.30-7.53 (m, 3H), 7.53-7.66 (m, 3H), 7.70-7.82 (m, 1H), 7.96 (s, 2H), 8.00-8.10 (m, 1H)

MS ES$^+$: 423

Example 76

2,6-Difluoro-N-[(1S,2S)-2-[(6-fluoro-1,3-benzothiazol-2-yl)amino]cyclopentyl]-N-methylbenzamide

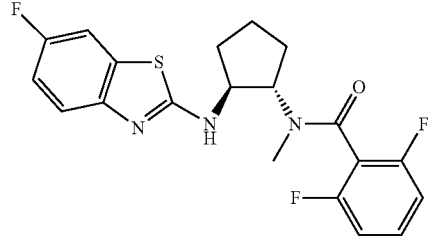 [SMILES: CN(C(=O)c1c(F)cccc1F)[C@H]1CCC[C@@H]1Nc1nc2ccc(F)cc2s1]

To a solution of (1S,2S)-1-N-(6-fluoro-1,3-benzothiazol-2-yl)-2-N-methylcyclopentane-1,2-diamine (Intermediate 17; 50 mg, 0.166 mmol) in DCM (2 ml) was added 2,6-difluorobenzoic acid (CAS number 385-00-2; 31.4 mg, 0.199 mmol), triethylamine (0.069 ml, 0.497 mmol) and HATU (94 mg, 0.249 mmol). The reaction mixture was stirred at room temperature for 18 hours then diluted with DCM, washed with water, filtered through a hydrophobic frit and concentrated in vacuo to afford a residue which was purified by reverse phase preparative HPLC (acetonitrile/water with 0.1% ammonia) to afford the title compound.

$^1$H NMR (400 MHz, DMSO-d$_6$): δ ppm 1.51-2.20 (m, 6H), 2.76-3.10 (m, 3H), 3.91-4.93 (m, 2H), 6.79-7.66 (m, 6H), 7.82-8.17 (m, 1H)

MS ES$^+$: 406

Example 77

N-[(1S,2S)-2-[(6-Fluoro-1,3-benzothiazol-2-yl)amino]cyclopentyl]-2-methoxy-N-methylbenzamide

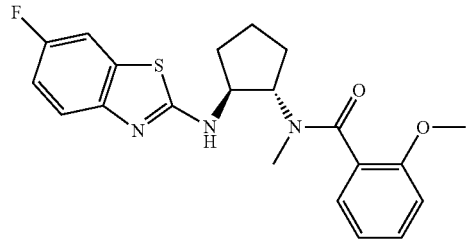 [SMILES: COc1ccccc1C(=O)N(C)[C@H]1CCC[C@@H]1Nc1nc2ccc(F)cc2s1]

Prepared as described for 2,6-difluoro-N-[(1S,2S)-2-[(6-fluoro-1,3-benzothiazol-2-yl)amino]cyclopentyl]-N-methylbenzamide (Example 76) from (1S,2S)-1-N-(6-fluoro-1,3-benzothiazol-2-yl)-2-N-methylcyclopentane-1,2-diamine (Intermediate 17; 50 mg, 0.188 mmol) and 2-methoxybenzoic acid (CAS number 579-75-9; 34 mg, 0.226 mmol) to afford the title compound.

¹H NMR (400 MHz, DMSO-d₆): δ ppm 1.43-2.16 (m, 6H), 2.62-3.05 (m, 3H), 3.45-3.84 (m, 3H), 4.17-5.03 (m, 2H), 6.47-8.21 (m, 8H)

MS ES⁺: 400

Example 78

2-Chloro-N-[(1S,2S)-2-[(6-fluoro-1,3-benzothiazol-2-yl)amino]cyclopentyl]-N-methylbenzamide

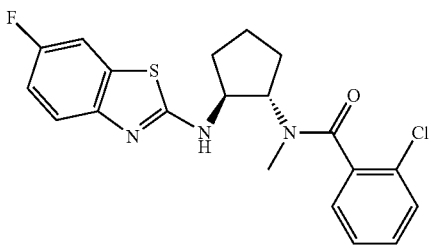 [SMILES: CN(C(=O)c1ccccc1Cl)[C@H]1CCC[C@@H]1Nc1nc2ccc(F)cc2s1]

Prepared as described for 2,6-difluoro-N-[(1S,2S)-2-[(6-fluoro-1,3-benzothiazol-2-yl)amino]cyclopentyl]-N-methylbenzamide (Example 76) from (1S,2S)-1-N-(6-fluoro-1,3-benzothiazol-2-yl)-2-N-methylcyclopentane-1,2-diamine (Intermediate 17; 50 mg, 0.188 mmol) and 2-chlorobenzoic acid (CAS number 118-91-2; 35 mg, 0.226 mmol). This was further purified by column chromatography (silica, 0-100% ethyl acetate/petrol) to afford the title compound.

¹H NMR (400 MHz, DMSO-d₆): δ ppm 1.47-2.20 (m, 6H), 2.64-3.10 (m, 3H), 3.57-5.06 (m, 2H), 6.60-8.31 (m, 8H)

MS ES⁺: 404

Example 79

N-[(1S,2S)-2-[(6-Fluoro-1,3-benzothiazol-2-yl)amino]cyclopentyl]-N-methyl-2-(1H-pyrazol-1-yl)benzamide

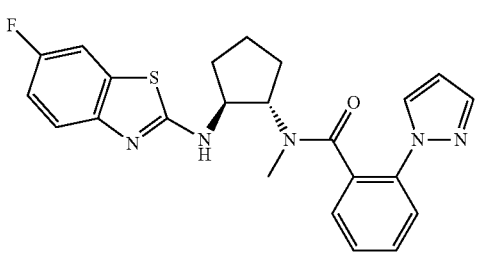 [SMILES: CN(C(=O)c1ccccc1-n1cccn1)[C@H]1CCC[C@@H]1Nc1nc2ccc(F)cc2s1]

Prepared as described for 2,6-difluoro-N-[(1S,2S)-2-[(6-fluoro-1,3-benzothiazol-2-yl)amino]cyclopentyl]-N-methylbenzamide (Example 76) from (1S,2S)-1-N-(6-fluoro-1,3-benzothiazol-2-yl)-2-N-methylcyclopentane-1,2-diamine (Intermediate 17; 50 mg, 0.188 mmol) and 2-(1H-pyrazol-1-yl)benzoic acid (CAS number 55317-53-8; 43 mg, 0.226 mmol) to afford the title compound.

¹H NMR (400 MHz, DMSO-d₆): δ ppm 0.89-2.27 (m, 6H), 2.56-3.03 (m, 3H), 3.57-4.85 (m, 2H), 5.97-8.26 (m, 11H)

MS ES⁺: 436

Example 80

N-[(1S,2S)-2-[(6-Fluoro-1,3-benzothiazol-2-yl)amino]cyclopentyl]-N-methyl-2-(2H-1,2,3-triazol-2-yl)benzamide

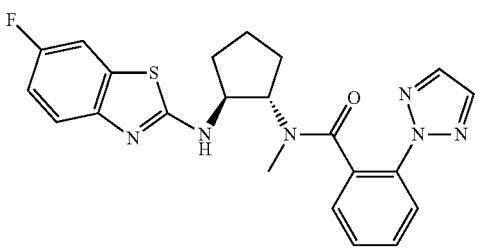 [SMILES: CN(C(=O)c1ccccc1-n1nccn1)[C@H]1CCC[C@@H]1Nc1nc2ccc(F)cc2s1]

Prepared as described for 2,6-difluoro-N-[(1S,2S)-2-[(6-fluoro-1,3-benzothiazol-2-yl)amino]cyclopentyl]-N-methylbenzamide (Example 76) from (1S,2S)-1-N-(6-fluoro-1,3-benzothiazol-2-yl)-2-N-methylcyclopentane-1,2-diamine (Intermediate 17; 50 mg, 0.188 mmol) and 2-(2H-1,2,3-triazol-2-yl)benzoic acid (CAS number 1001401-62-2; 43 mg, 0.226 mmol) to afford the title compound.

¹H NMR (400 MHz, DMSO-d₆): δ ppm 1.00-2.22 (m, 6H), 2.58-3.04 (m, 3H), 3.66-4.88 (m, 2H), 6.77-8.28 (m, 10H)

MS ES⁺: 437

Example 81

5-Fluoro-N-[(1S,2S)-2-[(6-fluoro-1,3-benzothiazol-2-yl)amino]cyclopentyl]-N-methyl-2-(2H-1,2,3-triazol-2-yl)benzamide

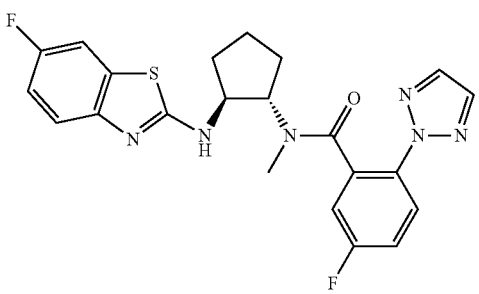 [SMILES: CN(C(=O)c1cc(F)ccc1-n1nccn1)[C@H]1CCC[C@@H]1Nc1nc2ccc(F)cc2s1]

Prepared as described for 2,6-difluoro-N-[(1S,2S)-2-[(6-fluoro-1,3-benzothiazol-2-yl)amino]cyclopentyl]-N-methylbenzamide (Example 76) from (1S,2S)-1-N-(6-fluoro-1,3-benzothiazol-2-yl)-2-N-methylcyclopentane-1,2-diamine (Intermediate 17; 50 mg, 0.188 mmol) and 5-fluoro-2-(2H-1,2,3-triazol-2-yl)benzoic acid (CAS number 1152964-04-09; 47 mg, 0.226 mmol) to afford the title compound.

¹H NMR (400 MHz, DMSO-d₆): δ ppm 0.95-2.20 (m, 6H), 2.61-3.03 (m, 3H), 3.61-4.86 (m, 2H), 6.46-8.29 (m, 9H)

MS ES⁺: 455

Example 82

N-[(1S,2S)-2-[(6-Fluoro-1,3-benzothiazol-2-yl)amino]cyclopentyl]-N-methyl-2-(pyrimidin-2-yl)benzamide

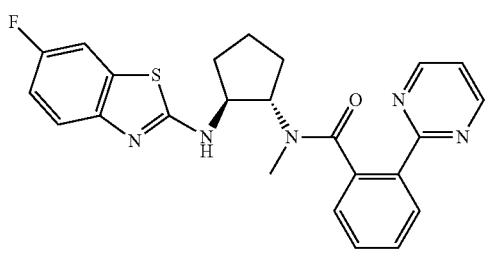 [SMILES: CN(C(=O)c1ccccc1-c1ncccn1)[C@H]1CCC[C@@H]1Nc1nc2ccc(F)cc2s1]

Prepared as described for 2,6-difluoro-N-[(1S,2S)-2-[(6-fluoro-1,3-benzothiazol-2-yl)amino]cyclopentyl]-N-methylbenzamide (Example 76) from (1S,2S)-1-N-(6-fluoro-1,3-benzothiazol-2-yl)-2-N-methylcyclopentane-1,2-diamine (Intermediate 17; 50 mg, 0.188 mmol) and 2-(pyrimidin-2-yl)benzoic acid (CAS number 400892-62-8; 45 mg, 0.226 mmol). This was further purified by column chromatography (silica, 0-100% ethyl acetate/petrol) to afford the title compound.

$^1$H NMR (400 MHz, DMSO-$d_6$): δ ppm 1.06-2.25 (m, 6H), 2.59-3.05 (m, 3H), 3.72-4.91 (m, 2H), 6.65-8.94 (m, 11H)

MS ES$^+$: 448

Example 83

N-[(1S,2S)-2-[(6-Fluoro-1,3-benzothiazol-2-yl)amino]cyclopentyl]-N-methyl-2-(3-methyl-1,2,4-oxadiazol-5-yl)benzamide

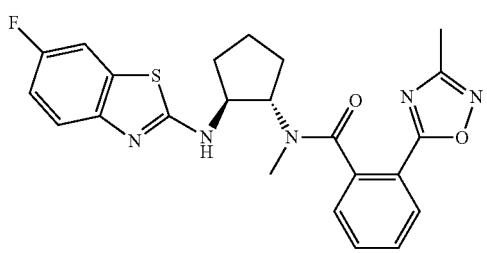 [SMILES: Cc1noc(-c2ccccc2C(=O)N(C)[C@H]2CCC[C@@H]2Nc2nc3ccc(F)cc3s2)n1]

Prepared as described for 2,6-difluoro-N-[(1S,2S)-2-[(6-fluoro-1,3-benzothiazol-2-yl)amino]cyclopentyl]-N-methylbenzamide (Example 76) from (1S,2S)-1-N-(6-fluoro-1,3-benzothiazol-2-yl)-2-N-methylcyclopentane-1,2-diamine (Intermediate 17; 50 mg, 0.188 mmol) and 2-(3-methyl-1,2,4-oxadiazol-5-yl)benzoic acid (CAS number 475105-77-2; 46 mg, 0.226 mmol) to afford the title compound.

$^1$H NMR (400 MHz, DMSO-$d_6$): δ ppm 1.12-2.46 (m, 9H), 2.61-3.14 (m, 3H), 3.55-4.97 (m, 2H), 6.73-8.43 (m, 8H)

MS ES$^+$: 452

Example 84

N-[(1S,2S)-2-[(5-Fluoro-1,3-benzothiazol-2-yl)amino]cyclopentyl]-2,6-dimethoxybenzamide

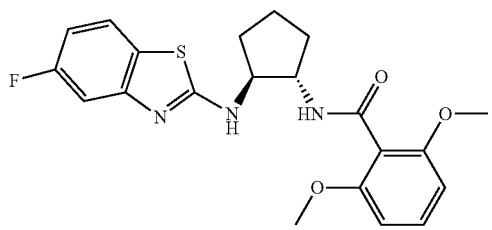 [SMILES: COc1cccc(OC)c1C(=O)N[C@H]1CCC[C@@H]1Nc1nc2cc(F)ccc2o1]

To a solution of N-[(1S,2S)-2-aminocyclopentyl]-2,6-dimethoxybenzamide hydrochloride (Intermediate 11; 200 mg, 0.665 mmol) in dry DMSO (2 ml) was added 2-chloro-5-fluoro-1,3-benzothiazole (CAS number 154327-27-2; 137 mg, 0.731 mmol) and DIPEA (0.348 ml, 1.995 mmol). The reaction was heated in the microwave at 120° C. for 2 hours and then purified by reverse phase preparative HPLC (acetonitrile/water with 0.1% ammonia) to afford the title compound.

$^1$H NMR (300 MHz, DMSO-$d_6$): δ ppm 1.43-1.63 (m, 2H), 1.62-1.82 (m, 2H), 1.93-2.22 (m, 2H), 3.32 (s, 6H), 4.03-4.25 (m, 2H), 6.56-6.66 (m, 2H), 6.76-6.92 (m, 1H), 7.04-7.18 (m, 1H), 7.18-7.32 (m, 1H), 7.59-7.72 (m, 1H), 8.07-8.21 (m, 1H), 8.23-8.38 (m, 1H)

MS ES$^+$: 416

Example 85

N-[(1S,2S)-2-[(5-Fluoro-1,3-benzoxazol-2-yl)amino]cyclopentyl]-2,6-dimethoxybenzamide

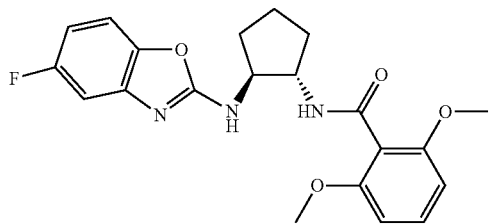

Prepared as described for N-[(1S,2S)-2-[(5-fluoro-1,3-benzothiazol-2-yl)amino]cyclopentyl]-2,6-dimethoxybenzamide (Example 84) from N-[(1S,2S)-2-aminocyclopentyl]-2,6-dimethoxybenzamide hydrochloride (Intermediate 11; 200 mg, 0.665 mmol) and 2-chloro-5-fluoro-1,3-benzoxazole (CAS Number 135533-78-7; 125 mg, 0.731 mmol) to afford the title compound.

$^1$H NMR (300 MHz, DMSO-$d_6$): δ ppm 1.46-1.78 (m, 4H), 1.94-2.12 (m, 2H), 3.57 (s, 6H), 3.95-4.14 (m, 1H), 4.16-4.31 (m, 1H), 6.55-6.65 (m, 2H), 6.70-6.81 (m, 1H), 6.99-7.09 (m, 1H), 7.20-7.28 (m, 1H), 7.28-7.39 (m, 1H), 8.03-8.24 (m, 2H)

MS ES$^+$: 400

Example 86

N-[(1S,2S)-2-[(1,3-Benzoxazol-2-yl)amino]cyclopentyl]-2-(2H-1,2,3-triazol-2-yl)benzamide

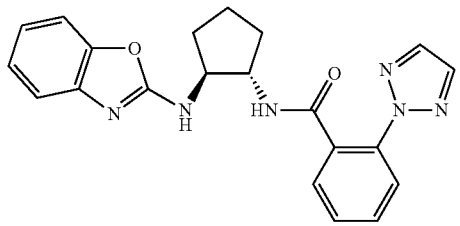 [SMILES: O=C(N[C@H]1CCC[C@@H]1Nc1nc2ccccc2o1)c1ccccc1-n1nccn1]

To a solution of N-[(1S,2S)-2-aminocyclopentyl]-2-(2H-1,2,3-triazol-2-yl)benzamide hydrochloride (Intermediate 25; 100 mg, 0.325 mmol) in dry DMSO (1 ml) was added DIPEA (170 μl, 0.975 mmol) and 2-chloro-1,3-benzoxazole (CAS Number: 615-18-9; 55 mg, 0.357 mmol). The reaction was sealed and heated in a sand bath at 140° C. for 17 hours and purified by reverse phase preparative HPLC (acetonitrile/water with 0.1% ammonia) to afford the title compound.

$^1$H NMR (400 MHz, DMSO-d$_6$): δ ppm 1.50-1.75 (m, 4H) 1.93-2.13 (m, 2H) 3.98-4.10 (m, 1H) 4.12-4.26 (m, 1H) 6.93-7.03 (m, 1H) 7.08-7.15 (m, 1H) 7.19-7.28 (m, 1H) 7.30-7.38 (m, 1H) 7.45-7.52 (m, 2H) 7.55-7.63 (m, 1H) 7.71-7.79 (m, 1H) 7.90-7.99 (m, 3H) 8.43-8.51 (m, 1H)

MS ES$^+$: 389

Example 87

N-[(1S,2S)-2-[(6-Fluoro-1,3-benzoxazol-2-yl)amino]cyclopentyl]-2-(2H-1,2,3-triazol-2-yl)benzamide

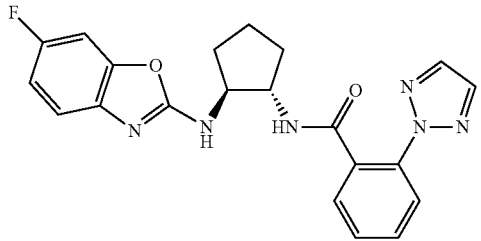 [SMILES: O=C(N[C@H]1CCC[C@@H]1Nc1nc2ccc(F)cc2o1)c1ccccc1-n1nccn1]

Prepared as described for N-[(1S,2S)-2-[(1,3-benzoxazol-2-yl)amino]cyclopentyl]-2-(2H-1,2,3-triazol-2-yl)benzamide (Example 86) from N-[(1S,2S)-2-aminocyclopentyl]-2-(2H-1,2,3-triazol-2-yl)benzamide hydrochloride (Intermediate 25; 100 mg, 0.325 mmol) and 2-chloro-6-fluoro-1,3-benzoxazole (CAS Number 153403-53-3; 61 mg, 0.357 mmol) to afford the title compound.

$^1$H NMR (400 MHz, DMSO-d$_6$): δ ppm 1.49-1.77 (m, 4H), 1.92-2.11 (m, 2H), 3.96-4.07 (m, 1H), 4.13-4.24 (m, 1H), 6.91-7.02 (m, 1H), 7.17-7.24 (m, 1H), 7.32-7.39 (m, 1H), 7.43-7.51 (m, 2H), 7.55-7.63 (m, 1H), 7.72-7.80 (m, 1H), 7.93 (s, 2H), 7.96-8.04 (m, 1H), 8.41-8.50 (m, 1H)

MS ES$^+$: 407

Example 88

N-[(1S,2S)-2-[(5-Fluoro-1,3-benzoxazol-2-yl)amino]cyclopentyl]-2-(2H-1,2,3-triazol-2-yl)benzamide

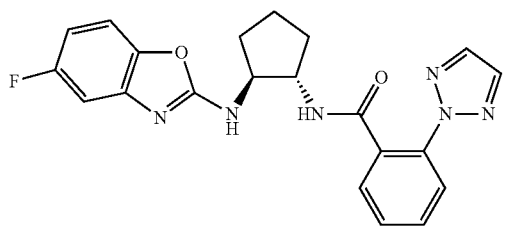 [SMILES: O=C(N[C@H]1CCC[C@@H]1Nc1nc2cc(F)ccc2o1)c1ccccc1-n1nccn1]

Prepared as described for N-[(1S,2S)-2-[(1,3-benzoxazol-2-yl)amino]cyclopentyl]-2-(2H-1,2,3-triazol-2-yl)benzamide (Example 86) from N-[(1S,2S)-2-aminocyclopentyl]-2-(2H-1,2,3-triazol-2-yl)benzamide hydrochloride (Intermediate 25; 100 mg, 0.325 mmol) and 2-chloro-5-fluoro-1,3-benzoxazole (CAS Number 135533-78-7; 61 mg, 0.357 mmol) to afford the title compound.

$^1$H NMR (400 MHz, DMSO-d$_6$): δ ppm 1.48-1.75 (m, 4H), 1.92-2.10 (m, 2H), 3.98-4.10 (m, 1H), 4.13-4.25 (m, 1H), 6.72-6.81 (m, 1H), 7.03-7.09 (m, 1H), 7.29-7.36 (m, 1H), 7.44-7.49 (m, 2H), 7.55-7.63 (m, 1H), 7.71-7.79 (m, 1H), 7.93 (s, 2H), 8.10-8.19 (m, 1H), 8.43-8.50 (m, 1H)

MS ES$^+$: 407

Example 89

N-[(1S,2S)-2-[(5-Chloro-1,3-benzothiazol-2-yl)amino]cyclopentyl]-2-(2H-1,2,3-triazol-2-yl)benzamide

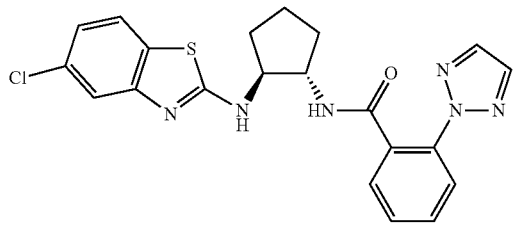 [SMILES: O=C(N[C@H]1CCC[C@@H]1Nc1nc2cc(Cl)ccc2s1)c1ccccc1-n1nccn1]

Prepared as described for N-[(1S,2S)-2-[(1,3-benzoxazol-2-yl)amino]cyclopentyl]-2-(2H-1,2,3-triazol-2-yl)benzamide (Example 86) from N-[(1S,2S)-2-aminocyclopentyl]-2-(2H-1,2,3-triazol-2-yl)benzamide hydrochloride (Intermediate 25; 100 mg, 0.325 mmol) and 2,5-dichloro-1,3-benzothiazole (CAS Number 2941-48-2; 83 mg, 0.405 mmol) to afford the title compound.

$^1$H NMR (400 MHz, DMSO-d$_6$): δ ppm 1.46-1.61 (m, 2H), 1.61-1.73 (m, 2H), 1.95-2.12 (m, 2H), 4.07-4.18 (m, 2H), 7.01-7.07 (m, 1H), 7.35-7.40 (m, 1H), 7.44-7.50 (m, 2H), 7.57-7.64 (m, 1H), 7.65-7.72 (m, 1H), 7.75-7.80 (m, 1H), 7.97 (s, 2H), 8.30-8.37 (m, 1H), 8.42-8.51 (m, 1H)

MS ES$^+$: 439, 441

Example 90

N-[(1S,2S)-2-[(1,3-Benzothiazol-2-yl)amino]cyclopentyl]-2-(2H-1,2,3-triazol-2-yl)benzamide

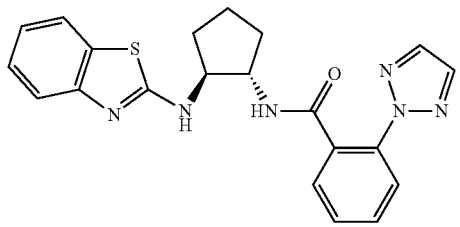

Prepared as described for N-[(1S,2S)-2-[(1,3-benzoxazol-2-yl)amino]cyclopentyl]-2-(2H-1,2,3-triazol-2-yl)benzamide (Example 86) from N-[(1S,2S)-2-aminocyclopentyl]-2-(2H-1,2,3-triazol-2-yl)benzamide hydrochloride (Intermediate 25; 100 mg, 0.325 mmol) and 2-chloro-1,3-benzothiazole (CAS Number 615-20-3; 69 mg, 0.405 mmol) to afford the title compound.

$^1$H NMR (400 MHz, DMSO-$d_6$): δ ppm 1.49-1.61 (m, 2H), 1.63-1.73 (m, 2H), 1.96-2.13 (m, 2H), 4.07-4.19 (m, 2H), 6.98-7.04 (m, 1H), 7.18-7.25 (m, 1H), 7.35-7.39 (m, 1H), 7.43-7.51 (m, 2H), 7.56-7.63 (m, 1H), 7.64-7.69 (m, 1H), 7.74-7.79 (m, 1H), 7.97 (s, 2H), 8.05-8.12 (m, 1H), 8.45-8.51 (m, 1H)

MS ES$^+$: 405

Example 91

N-[(1S,2S)-2-[(6-Chloro-1,3-benzothiazol-2-yl)amino]cyclopentyl]-2-(2H-1,2,3-triazol-2-yl)benzamide

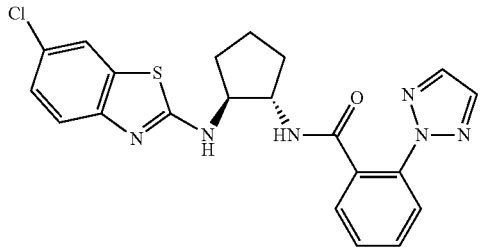 [SMILES: O=C(N[C@H]1CCC[C@@H]1Nc1nc2ccc(Cl)cc2s1)c1ccccc1-n1nccn1]

Prepared as described for N-[(1S,2S)-2-[(1,3-benzoxazol-2-yl)amino]cyclopentyl]-2-(2H-1,2,3-triazol-2-yl)benzamide (Example 86) from N-[(1S,2S)-2-aminocyclopentyl]-2-(2H-1,2,3-triazol-2-yl)benzamide hydrochloride (Intermediate 25; 100 mg, 0.325 mmol) and 2,6-dichloro-1,3-benzothiazole (CAS Number 3622-23-9; 83 mg, 0.405 mmol) to afford the title compound.

$^1$H NMR (400 MHz, DMSO-$d_6$): δ ppm 1.47-1.61 (m, 2H), 1.62-1.73 (m, 2H), 1.95-2.13 (m, 2H), 4.06-4.19 (m, 2H), 7.20-7.26 (m, 1H), 7.31-7.37 (m, 1H), 7.44-7.50 (m, 2H), 7.56-7.63 (m, 1H), 7.73-7.81 (m, 2H), 7.97 (s, 2H), 8.20-8.27 (m, 1H), 8.41-8.50 (m, 1H)

MS ES$^+$: 439, 441

Example 92

N-[(1S,2S)-2-[(5-Fluoro-1,3-benzothiazol-2-yl)amino]cyclopentyl]-2-(2H-1,2,3-triazol-2-yl)benzamide

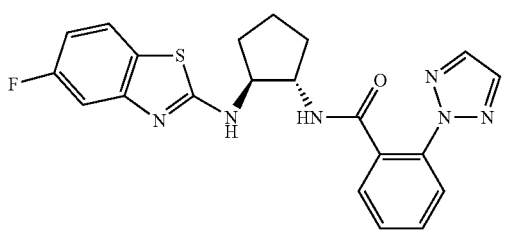

Prepared as described for N-[(3)-2-[(1,3-benzoxazol-2-yl)amino]cyclopentyl]-2-(2H-1,2,3-triazol-2-yl)benzamide (Example 86) from N-[(1S,2S)-2-aminocyclopentyl]-2-(2H-1,2,3-triazol-2-yl)benzamide hydrochloride (Intermediate 25; 100 mg, 0.325 mmol) and 2-chloro-5-fluoro-1,3-benzothiazole (CAS Number 154327-27-2; 76 mg, 0.405 mmol) to afford the title compound.

$^1$H NMR (400 MHz, DMSO-$d_6$): δ ppm 1.48-1.61 (m, 2H), 1.62-1.74 (m, 2H), 1.95-2.14 (m, 2H), 4.07-4.19 (m, 2H), 6.81-6.90 (m, 1H), 7.13-7.20 (m, 1H), 7.44-7.51 (m, 2H), 7.56-7.70 (m, 2H), 7.74-7.80 (m, 1H), 7.97 (s, 2H), 8.24-8.32 (m, 1H), 8.42-8.52 (m, 1H)

MS ES$^+$: 423

Example 93

N-[(1S,2S)-2-[(4,6-Difluoro-1,3-benzothiazol-2-yl)amino]cyclopentyl]-2-(2H-1,2,3-triazol-2-yl)benzamide

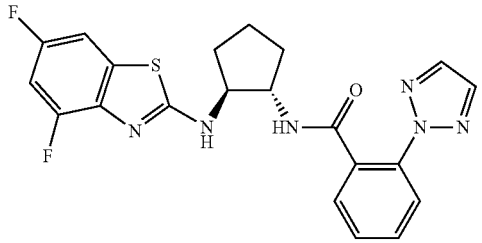 [SMILES: O=C(N[C@H]1CCC[C@@H]1Nc1nc2c(F)cc(F)cc2s1)c1ccccc1-n1nccn1]

Prepared as described for N-[(1S,2S)-2-[(1,3-benzoxazol-2-yl)amino]cyclopentyl]-2-(2H-1,2,3-triazol-2-yl)benzamide (Example 86) from N-[(1S,2S)-2-aminocyclopentyl]-2-(2H-1,2,3-triazol-2-yl)benzamide hydrochloride (Intermediate 25; 100 mg, 0.325 mmol) and 2-chloro-4,6-difluoro-1,3-benzothiazole (CAS number 52681-57-5; 83 mg, 0.405 mmol) to afford the title compound.

$^1$H NMR (400 MHz, DMSO-$d_6$): δ ppm 1.48-1.62 (m, 2H), 1.63-1.74 (m, 2H), 1.95-2.13 (m, 2H), 4.08-4.21 (m, 2H), 7.09-7.18 (m, 1H), 7.42-7.54 (m, 3H), 7.56-7.63 (m, 1H), 7.73-7.80 (m, 1H), 7.97 (s, 2H), 8.29-8.36 (m, 1H), 8.43-8.50 (m, 1H)

MS ES+: 441

Example 94

N-[(1S,2S)-2-[(4-Fluoro-1,3-benzothiazol-2-yl)amino]cyclopentyl]-2-(2H-1,2,3-triazol-2-yl)benzamide

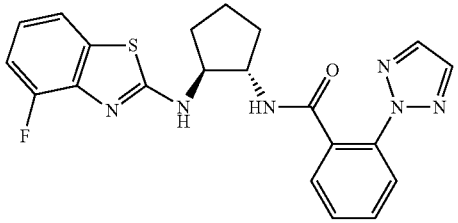 [SMILES: O=C(N[C@H]1CCC[C@@H]1Nc1nc2c(F)cccc2s1)c1ccccc1-n1nccn1]

Prepared as described for N-[(1S,2S)-2-[(1,3-benzoxazol-2-yl)amino]cyclopentyl]-2-(2H-1,2,3-triazol-2-yl)benzamide (Example 86) from N-[(1S,2S)-2-aminocyclopentyl]-2-(2H-1,2,3-triazol-2-yl)benzamide hydrochloride (Intermediate 25; 100 mg, 0.325 mmol) and 2-chloro-4-fluoro-1,3-benzothiazole (CAS Number 182344-56-5; 76 mg, 0.405 mmol) to afford the title compound.

$^1$H NMR (400 MHz, DMSO-d$_6$): δ ppm 1.49-1.62 (m, 2H), 1.64-1.74 (m, 2H), 1.95-2.14 (m, 2H), 4.09-4.23 (m, 2H), 6.97-7.04 (m, 1H), 7.05-7.13 (m, 1H), 7.42-7.54 (m, 3H), 7.56-7.63 (m, 1H), 7.74-7.80 (m, 1H), 7.97 (s, 2H), 8.29-8.36 (m, 1H), 8.44-8.52 (m, 1H)

MS ES+: 423

Example 95

N-[(1S,2S)-2-({[1,3]Thiazolo[5,4-b]pyridin-2-yl}amino)cyclopentyl]-2-(2H-1,2,3-triazol-2-yl)benzamide

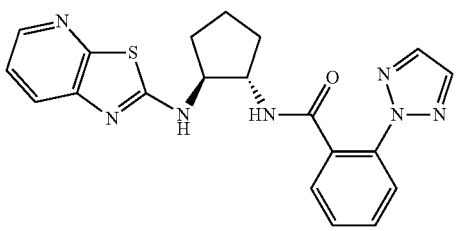 [SMILES: O=C(N[C@H]1CCC[C@@H]1Nc1nc2cccnc2s1)c1ccccc1-n1nccn1]

Prepared as described for N-[(1S,2S)-2-[(1,3-benzoxazol-2-yl)amino]cyclopentyl]-2-(2H-1,2,3-triazol-2-yl)benzamide (Example 86) from N-[(1S,2S)-2-aminocyclopentyl]-2-(2H-1,2,3-triazol-2-yl)benzamide hydrochloride (Intermediate 25; 100 mg, 0.325 mmol) and 2-chloro-[1,3]thiazolo[5,4-b]pyridine (CAS Number 91524-96-8; 61 mg, 0.357 mmol) to afford the title compound.

$^1$H NMR (400 MHz, DMSO-d$_6$): δ ppm 1.50-1.62 (m, 2H), 1.63-1.73 (m, 2H), 1.96-2.14 (m, 2H), 4.09-4.24 (m, 2H), 7.22-7.28 (m, 1H), 7.44-7.50 (m, 2H), 7.55-7.68 (m, 2H), 7.74-7.80 (m, 1H), 7.97 (s, 2H), 8.07-8.12 (m, 1H), 8.39-8.51 (m, 2H)

MS ES+: 406

Example 96

N-[(1S,2S)-2-({7-Chloro-[1,3]thiazolo[5,4-c]pyridin-2-yl}amino)cyclopentyl]-2-(2H-1,2,3-triazol-2-yl)benzamide

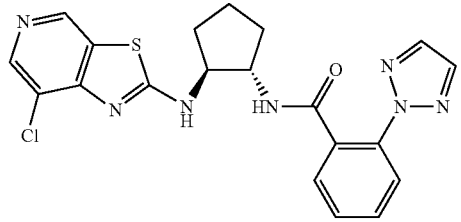 [SMILES: O=C(N[C@H]1CCC[C@@H]1Nc1nc2c(Cl)cncc2s1)c1ccccc1-n1nccn1]

Prepared as described for N-[(1S,2S)-2-[(1,3-benzoxazol-2-yl)amino]cyclopentyl]-2-(2H-1,2,3-triazol-2-yl)benzamide (Example 86) from N-[(1S,2S)-2-aminocyclopentyl]-2-(2H-1,2,3-triazol-2-yl)benzamide hydrochloride (Intermediate 25; 100 mg, 0.325 mmol) and 2,7-dichloro-[1,3]thiazolo[5,4-c]pyridine (CAS number 884860-61-1; 73 mg, 0.357 mmol). This was then further purified by column chromatography (silica, 0-100% ethyl acetate/petrol then 0-20% methanol/ethyl acetate) to afford the title compound.

$^1$H NMR (400 MHz, DMSO-d$_6$): δ ppm 1.52-1.65 (m, 2H), 1.65-1.76 (m, 2H), 1.97-2.16 (m, 2H), 4.09-4.24 (m, 2H), 7.44-7.51 (m, 2H), 7.56-7.64 (m, 1H), 7.75-7.79 (m, 1H), 7.97 (s, 2H), 8.34-8.38 (m, 1H), 8.46-8.52 (m, 1H), 8.71-8.76 (m, 1H), 9.07-9.23 (m, 1H)

MS ES+: 440, 442

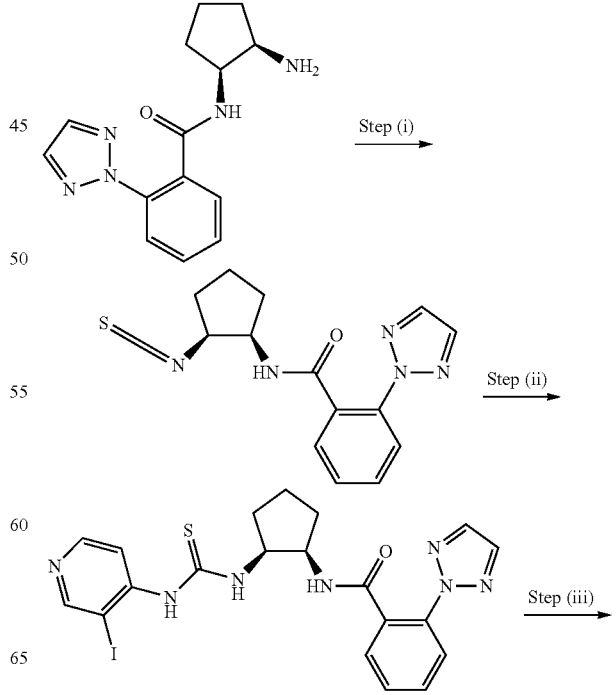

-continued

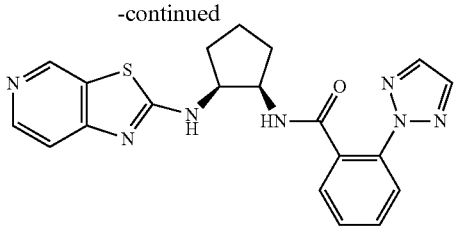

Example 97

N-[(1S,2S)-2-({[1,3]Thiazolo[5,4-c]pyridin-2-yl}amino)cyclopentyl]-2-(2H-1,2,3-triazol-2-yl)benzamide

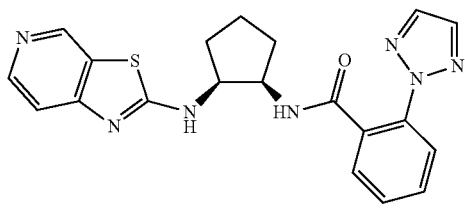 [SMILES: O=C(N[C@@H]1CCC[C@@H]1Nc1nc2ccncc2s1)c1ccccc1-n1nccn1]

Step (i): N-[(1S,2S)-2-Isothiocyanatocyclopentyl]-2-(2H-1,2,3-triazol-2-yl)benzamide To a solution of N-[(1S,2S)-2-aminocyclopentyl]-2-(2H-1,2,3-triazol-2-yl)benzamide hydrochloride (Intermediate 25; 330 mg, 1.072 mmol) in dry DCM (5.3 ml) at 0° C. was added sodium hydroxide (172 mg, 4.29 mmol) and then dropwise phenyl chloromethanethioate (CAS Number: 1005-56-7; 0.148 ml, 1.072 mmol) as a solution in dry DCM (1 ml). Dry THF (1 ml) was subsequently added to aid solubility. The reaction was stirred at 0° C. for 30 minutes and then allowed to warm to room temperature for 17 hours. The reaction mixture was partitioned between water and DCM. The organics were filtered through a hydrophobic frit and concentrated in vacuo to afford a residue which was purified by column chromatography (silica, 0-100% ethyl acetate/petrol) to afford the title compound.

$^1$H NMR (400 MHz, DCM-d$_2$): δ ppm 1.40-1.52 (m, 1H), 1.67-1.91 (m, 3H), 1.92-2.02 (m, 1H), 2.09-2.21 (m, 1H), 3.97-4.03 (m, 1H), 4.22-4.31 (m, 1H), 6.07-6.15 (m, 1H), 7.47-7.52 (m, 1H), 7.57-7.62 (m, 2H), 7.77-7.82 (m, 1H), 7.88 (s, 2H)

MS ES$^+$: 314

Step (ii): N-[(1S,2S)-2-{[(3-Iodopyridin-4-yl)carbamothioyl]amino}cyclopentyl]-2-(2H-1,2,3-triazol-2-yl)benzamide To a solution of 3-iodopyridin-4-amine (CAS Number 88511-27-7; 160 mg, 0.728 mmol) in dry DMF (1 ml) was added sodium hydride (29.1 mg, 0.728 mmol). The reaction was stirred at room temperature for 10 minutes. To this was then added N-[(1S,2S)-2-isothiocyanatocyclopentyl]-2-(2H-1,2,3-triazol-2-yl)benzamide (190 mg, 0.606 mmol) as a solution in dry toluene (1 ml) and dry DMF (1 ml). The reaction was then stirred at room temperature for 4 hours and was then partitioned between ethyl acetate and water. The organics were washed with water and brine, dried over magnesium sulphate, filtered and concentrated in vacuo to afford a residue which was purified by column chromatography (silica, 0-100% ethyl acetate/petrol then 0-20% methanol/ethyl acetate) to afford the title compound.

$^1$H NMR (400 MHz, DCM-d$_2$): δ ppm 1.47-1.70 (m, 2H), 1.70-1.92 (m, 2H), 2.10-2.25 (m, 1H), 2.28-2.54 (m, 1H), 4.34-4.45 (m, 1H), 4.45-4.58 (m, 1H), 7.39-7.52 (m, 1H), 7.51-7.65 (m, 2H), 7.77-8.04 (m, 4H), 8.21-8.43 (m, 1H), 8.63-8.87 (m, 1H)

MS ES$^+$: 534

Step (iii): N-[(1S,2S)-2-({[1,3]Thiazolo[5,4-c]pyridin-2-yl}amino)cyclopentyl]-2-(2H-1,2,3-triazol-2-yl)benzamide A microwave vial was charged with N-[(1S,2S)-2-{[(3-iodopyridin-4-yl)carbamothioyl]amino}cyclopentyl]-2-(2H-1,2,3-triazol-2-yl)benzamide (136 mg, 0.255 mmol), copper (I) iodide (4.86 mg, 0.025 mmol), 1,10-phenanthroline (9.19 mg, 0.051 mmol) cesium carbonate (166 mg, 0.510 mmol) in dry toluene (0.85 ml) and THF (1.7 ml). The reaction mixture was purged with nitrogen and heated in the microwave at 130° C. for 10 minutes and then partitioned between ethyl acetate and water. The organics were washed with water and brine, dried over magnesium sulphate, filtered and concentrated concentrated in vacuo to afford a residue which was purified by reverse phase preparative HPLC (acetonitrile/water with 0.1% ammonia) to afford the title compound.

$^1$H NMR (400 MHz, DCM-d$_2$): δ ppm 1.48-1.73 (m, 2H), 1.79-1.93 (m, 2H), 2.15-2.28 (m, 1H), 2.40-2.53 (m, 1H), 3.94-4.06 (m, 1H), 4.24-4.36 (m, 1H), 6.59-6.73 (m, 1H), 7.01-7.16 (m, 1H), 7.25-7.39 (m, 1H), 7.42-7.50 (m, 1H), 7.52-7.64 (m, 2H), 7.70 (s, 2H), 7.77-7.84 (m, 1H), 8.33-8.49 (m, 1H), 8.69-8.88 (m, 1H)

MS ES$^+$: 406

Example 98

2,6-Dimethoxy-N-[2-(quinolin-2-ylmethyl)cyclopentyl]benzamide

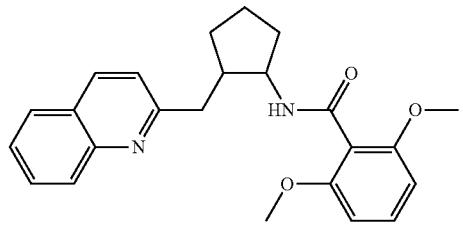 [SMILES: COc1cccc(OC)c1C(=O)NC1CCCC1Cc1ccc2ccccc2n1]

To a solution of 2,6-dimethoxybenzoic acid (CAS number 1466-76-8; 0.036 g, 0.331 mmol) in DCM (5 ml) was added a catalytic amount of DMF, followed by oxalyl chloride (0.050 g, 0.398 mmol) at 0° C. and then the reaction mixture was stirred at ambient temperature for 30 minutes. Separately, to the solution of 2-(quinolin-2-ylmethyl)cyclopentanamine hydrochloride (Intermediate 8, isomer 2; 0.075 g, 0.398 mmol) in DCM (5 ml) was added triethylamine (0.167 g, 1.659 mmol), followed by the pre-made solution of the acid chloride at 0° C. The reaction mixture was stirred at room temperature for 2 hours and then was poured into water (20 ml) and extracted with DCM (15 ml×3). The organic layer was washed with brine, dried over sodium sulfate and concentrated in vacuo. The resulting residue was purified by column chromatography (silica, 0-40% ethyl acetate/n-hexane) to afford the title compound.

¹H NMR (400 MHz, DMSO-d); δ ppm 1.32-1.34 (m, 1H), 1.48-1.63 (m, 4H), 1.93-1.97 (m, 1H), 2.27-2.31 (m, 1H), 2.69-2.75 (m, 1H), 3.38-3.39 (m, 1H), 3.73 (s, 6H), 3.97-4.01 (m, 1H), 6.66-6.70 (m, 2H), 7.26-7.31 (m, 1H), 7.44-7.46 (m, 1H), 7.52-7.56 (m, 1H), 7.69-7.73 (m, 1H), 7.92-7.94 (m, 2H), 8.11-8.13 (m, 1H), 8.26-8.28 (m, 1H)

MS ES⁺: 391

Example 99

N-[(1S,2S)-2-[(6-Fluoro-1,3-benzoxazol-2-yl)amino]cyclopentyl]-2-(3-methyl-1,2,4-oxadiazol-5-yl)benzamide

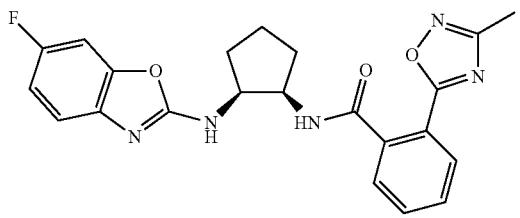 [SMILES: Cc1noc(-c2ccccc2C(=O)N[C@@H]2CCC[C@@H]2Nc2nc3ccc(F)cc3o2)n1]

To a solution of N-[(1S,2S)-2-aminocyclopentyl]-2-(3-methyl-1,2,4-oxadiazol-5-yl)benzamide hydrochloride (Intermediate 26; 100 mg, 0.310 mmol) in dry DMSO (1 ml) was added DIPEA (162 μl, 0.929 mmol) and 2-chloro-6-fluoro-1,3-benzoxazole (CAS Number 153403-53-3; 64 mg, 0.372 mmol). The reaction was subjected to microwave irradiation at 140° C. for 1 hour. The reaction was then purified by reverse phase preparative HPLC (acetonitrile/water with 0.1% ammonia) to afford the title compound.

¹H NMR (400 MHz, DMSO-d₆): δ ppm 1.55-1.78 (m, 4H), 2.00-2.12 (m, 2H), 2.35 (s, 3H), 4.01-4.12 (m, 1H), 4.19-4.29 (m, 1H), 6.91-7.00 (m, 1H), 7.15-7.21 (m, 1H), 7.30-7.36 (m, 1H), 7.50-7.56 (m, 1H), 7.59-7.70 (m, 2H), 7.89-7.95 (m, 1H), 8.02-8.09 (m, 1H), 8.58-8.65 (m, 1H)

MS ES⁺: 422

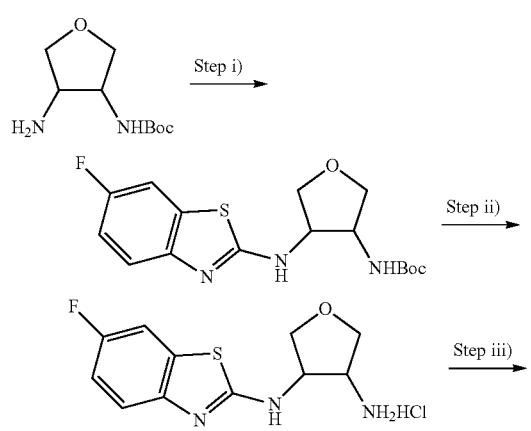

Example 100 trans-N-{4-[(6-Fluoro-1,3-benzothiazol-2-yl)amino]oxolan-3-yl}-2-(2H-1,2,3-triazol-2-yl)benzamide

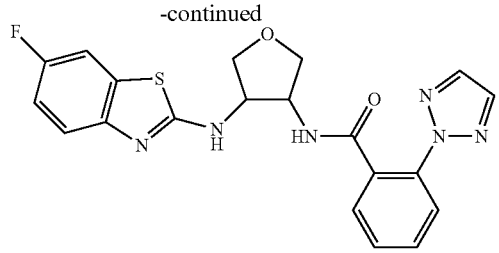

Step i): trans-tert-Butyl N-{4-[(6-fluoro-1,3-benzothiazol-2-yl)amino]oxolan-3-yl}carbamate A solution of trans-tert-butyl N-(4-aminooxolan-3-yl)carbamate (Intermediate 27a, 200 mg, 0.989 mmol), 2-chloro-6-fluoro-1,3-benzothiazole (CAS number 399-74-6; 204 mg, 1.088 mmol) and DIPEA (0.518 ml, 2.97 mmol) in DMSO (20 ml) were subjected to microwave irradiation at 140° C. for 2 hours. The reaction mixture was partitioned between ethyl acetate (25 ml) and water (20 ml). The organics were washed with water (2×20 ml) and brine (20 ml), filtered through a hydrophobic frit and solvent evaporated in vacuo. This was then purified by column chromatography (silica, 0-50% ethyl acetate/petrol) to afford the title compound.

¹H NMR (400 MHz, DCM-d₂): δ ppm 1.47 (s, 9H), 3.65-3.72 (m, 1H), 3.79-3.86 (m, 1H), 4.17-4.35 (m, 4H), 6.99-7.07 (m, 1H), 7.28-7.35 (m, 1H), 7.41-7.48 (m, 1H)

MS ES⁺: 354

Step ii): trans-3-N-(6-Fluoro-1,3-benzothiazol-2-yl)oxolane-3,4-diamine hydrochloride Trans-tert-butyl N-{4-[(6-fluoro-1,3-benzothiazol-2-yl)amino]oxolan-3-yl}carbamate (125 mg, 0.354 mmol) was dissolved in HCl (4M 1,4-dioxane, 2 ml, 8.00 mmol) and stirred at room temperature for 3 hours. The resulting suspension was diluted with ethyl acetate (5 ml) sonicated and the solvent was evaporated under reduced pressure to afford the title compound.

¹H NMR (400 MHz, DMSO-d₆): δ ppm 3.69-3.76 (m, 1H), 3.76-3.86 (m, 2H), 4.02-4.10 (m, 1H), 4.19-4.26 (m, 1H), 4.41-4.48 (m, 1H), 7.10-7.18 (m, 1H), 7.49-7.56 (m, 1H), 7.64-7.72 (m, 1H), 8.53 (br. s., 3H), 8.88 (br. s., 1H)

MS ES⁺: 254

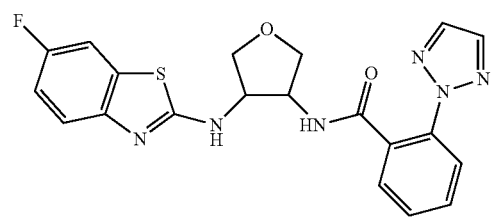 [SMILES: O=C(NC1COCC1Nc1nc2ccc(F)cc2s1)c1ccccc1-n1nccn1]

Step iii) trans-N-{4-[(6-Fluoro-1,3-benzothiazol-2-yl)amino]oxolan-3-yl}-2-(2H-1,2,3-triazol-2-yl)benzamide A solution of trans-3-N-(6-fluoro-1,3-benzothiazol-2-yl)oxolane-3,4-diamine hydrochloride (106 mg, 0.366 mmol), 2-(2H-1,2,3-triazol-2-yl)benzoic acid (CAS number 1001401-62-2; 83 mg, 0.439 mmol), EDC (105 mg, 0.549 mmol), aza-HOBt (85 mg, 0.549 mmol) and triethylamnime (0.153 ml, 1.097 mmol) in DCM (2 ml) was stirred at room temperature for 18 hours. The reaction mixture was diluted with DCM (20 mil) and washed with HCl (aq., 1M, 20 ml) and saturated sodium bicarbonate solution (20 ml). The organics were filtered through a hydrophobic frit and solvent evaporated in vacuo. This was then purified by reverse phase preparative HPLC (acetonitrile/water with 0.1% ammonia) to afford the title compound.

¹H NMR (400 MHz, CD$_2$Cl$_2$-d$_2$): δ ppm 3.58-3.95 (m, 2H), 4.13-4.32 (m, 2H), 4.32-4.51 (m, 2H), 6.77 (br. s., 1H), 6.96-7.11 (m, 1H), 7.25-7.41 (m, 2H), 7.43-7.53 (m, 1H), 7.56-7.65 (m, 2H), 7.76 (s, 2H), 7.81-7.87 (m, 1H)

MS ES⁺: 425

Example 101 trans-N-{4-[(6-Fluoro-1,3-benzothiazol-2-yl)amino]oxolan-3-yl}-2-(2H-1,2,3-triazol-2-yl)benzamide

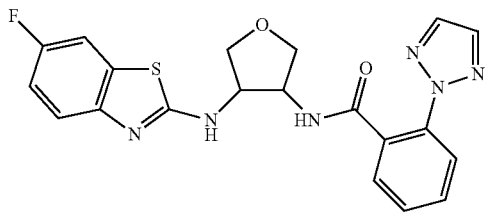 [SMILES: O=C(NC1COCC1Nc1nc2ccc(F)cc2s1)c1ccccc1-n1nccn1]

Prepared as described for trans-N-{4-[(6-fluoro-1,3-benzothiazol-2-yl)amino]oxolan-3-yl}-2-(2H-1,2,3-triazol-2-yl)benzamide (Example 100) from trans-tert-butyl N-(4-aminooxolan-3-yl)carbamate (Intermediate 27b, 200 mg, 0.989 mmol) and 2-chloro-6-fluoro-1,3-benzothiazole (CAS number 399-74-6; 204 mg, 1.088 mmol) to afford the title compound.

¹H NMR (400 MHz, CD$_2$Cl$_2$-d$_2$): δ ppm 3.60-3.91 (m, 2H), 4.18-4.31 (m, 2H), 4.32-4.48 (m, 2H), 6.77 (br. s., 1H), 6.98-7.08 (m, 1H), 7.25-7.41 (m, 2H), 7.43-7.53 (m, 1H), 7.54-7.66 (m, 2H), 7.75 (s, 2H), 7.78-7.86 (m, 1H)

MS ES⁺: 425

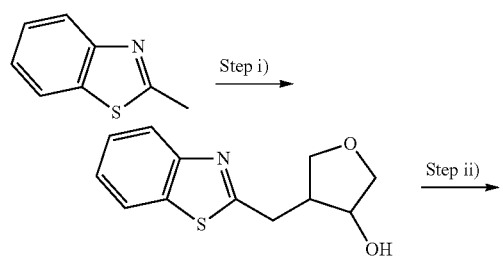

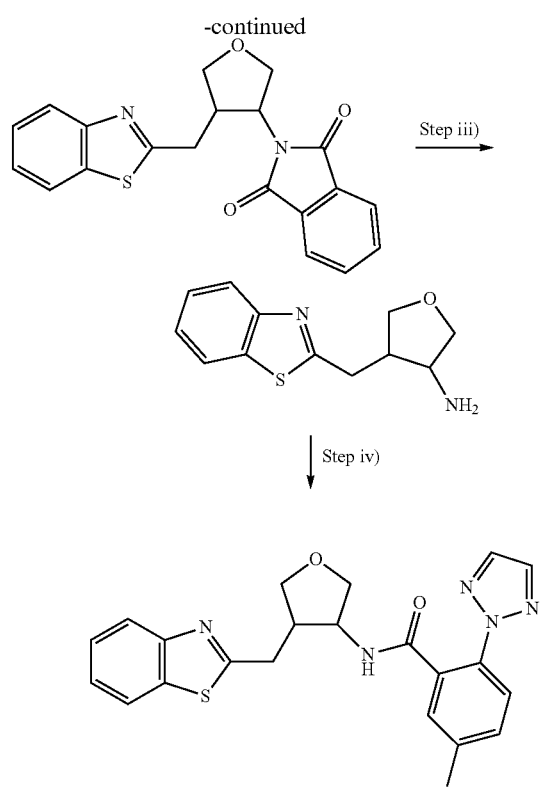

Example 102 cis-N-[4-(1,3-Benzothiazol-2-ylmethyl)oxolan-3-yl]-5-methyl-2-(2H-1,2,3-triazol-2-yl)benzamide

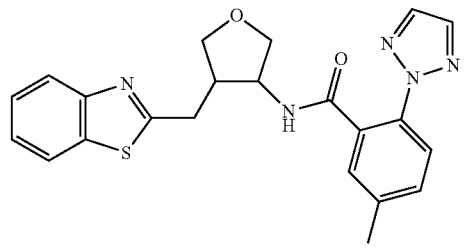 [SMILES: Cc1ccc(-n2nccn2)c(C(=O)NC2COCC2Cc2nc3ccccc3s2)c1]

Step i):
trans-4-(1,3-Benzothiazol-2-ylmethyl)oxolan-3-ol

To a stirred solution of 2-methyl-1,3-benzothiazole (CAS number 120-75-2; 7.0 g, 46.979 mmol) in dry THF (150 ml) at −78° C. was added n-BuLi (2.5 M in hexane; 37.6 ml, 93.959 mmol) dropwise. The reaction was stirred at −78° C. for 2 hours. To this was then added dropwise over 30 minutes 3,6-dioxabicyclo[3.1.0]hexane (CAS number 285-69-8; 6.1 g, 70.469 mmol) as a solution in dry THF (100 ml) and boron trifluoride diethyl etherate (8.9 ml, 70.469 mmol). The reaction mixture was allowed to warm to room temperature and stirred for 30 mins and then quenched with saturated (aq.) ammonium chloride (200 ml) and extracted with diethyl ether (250 ml×3). The organics were washed with water (250 ml), brine (250 ml), dried over sodium sulphate and concentrated in vacuo. The resulting residue was purified by column chromatography (silica, 0-5% ethyl acetate/n-hexane) to afford the title compound.

$^1$H NMR (400 MHz, DMSO-d): δ ppm 3.04-3.18 (m, 2H), 3.48-3.54 (m, 2H), 3.86-3.96 (m, 2H), 4.09-4.15 (m, 1H), 5.11-5.12 (m, 1H), 7.40-7.49 (m, 1H), 7.48-7.51 (m, 1H), 7.94-7.96 (m, 1H), 8.06-8.08 (m, 1H)

MS ES$^+$: 236

Step ii): cis-2-[4-(1,3-Benzothiazol-2-ylmethyl)oxolan-3-yl]-2,3-dihydro-1H-isoindole-1,3-dione To a solution of trans-4-(1,3-benzothiazol-2-ylmethyl)oxolan-3-ol (1.5 g, 6.382 mmol) and phthalimide (1.12 g, 7.619 mmol) in THF (50 ml) at 0° C. was added portionwise triphenylphosphine (2.5 g, 9.574 mmol). The reaction was stirred at 0° C. for 30 mins. To this was then added dropwise over 30 minutes diethyl azodicaboxylate (1.66 g, 9.574 mmol) and the reaction was sonicated for 45 mins at room temperature. The reaction was poured into ice cold water. The precipitate was removed by filtration and then purified by column chromatography (silica, 0-30% ethyl acetate/n-hexane) to afford the title compound.

$^1$H NMR (400 MHz, DMSO-d): δ ppm 3.05-3.18 (m, 3H), 3.88-3.92 (m, 1H), 4.09-4.18 (m, 3H), 4.91-4.97 (m, 1H), 7.34-7.38 (m, 1H), 7.40-7.44 (m, 1H), 7.81-7.99 (m, 5H), 7.78-7.80 (m, 1H)

MS ES$^+$: 365

Step iii): cis-4-(1,3-Benzothiazol-2-ylmethyl)oxolan-3-amine

To a solution of cis-2-[4-(1,3-benzothiazol-2-ylmethyl)oxolan-3-yl]-2,3-dihydro-1H-isoindole-1,3-dione (0.6 g, 1.648 mmol) in ethanol (10 ml) was added hydrazine hydrate (0.329 g, 6.58 mmol). The reaction was refluxed for 2 hours and then cooled to room temperature. The reaction was diluted with 1N NaOH (3 ml) and water (25 ml) and extracted with DCM (50 ml×3). The organics were washed with water (50 ml), brine (50 ml), dried over sodium sulphate and concentrated in vacuo to afford the title compound.

$^1$H NMR (400 MHz, DMSO-d): δ ppm 2.60-2.67 (m, 1H), 3.08-3.14 (m, 1H), 3.32-3.37 (m, 1H), 3.49-3.51 (m, 1H), 3.52-3.56 (m, 2H), 3.83-3.88 (m, 2H), 7.39-7.41 (m, 1H), 7.43-7.49 (m, 1H), 7.93-7.95 (m, 1H), 8.05-8.07 (m, 1H)

MS ES$^+$: 235

Step iv): cis-N-[4-(1,3-Benzothiazol-2-ylmethyl)oxolan-3-yl]-5-methyl-2-(2H-1,2,3-triazol-2-yl)benzamide To a solution of cis-4-(1,3-benzothiazol-2-ylmethyl)oxolan-3-amine (0.1 g, 0.427 mmol) in DMF (3 ml) was added 5-methyl-2-(2H-1,2,3-triazol-2-yl)benzoic acid (Intermediate 3; 0.086 g, 0.423 mmol), TBTU (0.164 g, 0.510 mmol) and DIPEA (0.082 g, 0.635 mmol). The reaction was stirred at room temperature for 2 hours and then diluted with water (25 ml) and extracted with ethyl acetate (30 ml×3). The organics were washed with water (50 ml), brine (25 ml), dried over sodium sulphate and concentrated in vacuo. The resulting residue was purified by column chromatography (silica, 0-45% ethyl acetate/n-hexane) to afford the title compound $^1$H NMR (400 MHz, DMSO-d): δ ppm 2.43 (s, 3H), 2.92-2.96 (m, 1H), 3.11-3.17 (m, 1H), 3.38-3.43 (m, 1H), 3.59-3.63 (m, 2H), 3.90-3.98 (m, 2H), 4.61-4.64 (m, 1H), 7.33-7.33 (m, 1H), 7.40-7.45 (m, 3H), 7.66-7.68 (m, 1H), 7.94-8.08 (m, 4H), 8.66-8.68 (m, 1H)

MS ES$^+$: 420

Examples 103 and 104

N-{4,4-Difluoro-2-[(6-fluoro-1,3-benzothiazol-2-yl)amino]cyclopentyl}-2-(2H-1,2,3-triazol-2-yl)benzamide

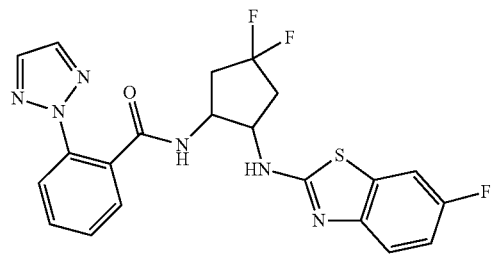 [SMILES: O=C(NC1CC(F)(F)CC1Nc1nc2ccc(F)cc2s1)c1ccccc1-n1nccn1]

To a solution of N-(2-amino-4,4-difluorocyclopentyl)-2-(2H-1,2,3-triazol-2-yl)benzamide hydrochloride (Intermediate 28; 120 mg, 0.349 mmol) in dry DMSO (1.2 ml) was added 2-chloro-6-fluoro-1,3-benzothiazole (CAS number 399-74-6; 72 mg, 0.384 mmol) and DIPEA (183 μl, 1.047 mmol). The reaction was sealed and stirred at 140° C. in a sand bath for 17 hours. The reaction was partitioned between ethyl acetate and water, washing with water, filtered through a hydrophobic frit and concentrated in vacuo. The crude product was then purified by column chromatography (basic silica, 0-100% ethyl acetate/petrol).

The racemic mixture was then purified by SFC to give two enantiomers (Enantiomer 1/Example 103 and Enantiomer 2/Example 104) of the title compound.

Example 103

Enantiomer 1

$^1$H NMR (400 MHz, DCM-d$_2$) δ ppm 2.02-2.28 (m, 2H), 2.72-2.98 (m, 2H), 4.19-4.43 (m, 2H), 6.91-7.14 (m, 1H), 7.20-7.35 (m, 3H), 7.36-7.42 (m, 1H), 7.44-7.51 (m, 1H), 7.52-7.60 (m, 1H), 7.67 (s, 2H), 7.74-7.84 (m, 1H)

MS ES$^+$: 459

Example 104

Enantiomer 2

$^1$H NMR (400 MHz, DCM-d$_2$) δ ppm 2.02-2.28 (m, 2H), 2.72-2.98 (m, 2H), 4.19-4.43 (m, 2H), 6.91-7.14 (m, 1H), 7.20-7.35 (m, 3H), 7.36-7.42 (m, 1H), 7.44-7.51 (m, 1H), 7.52-7.60 (m, 1H), 7.67 (s, 2H), 7.74-7.84 (m, 1H)

MS ES$^+$: 459

Examples 105 and 106

N-{2-[(6-Chloro-1,3-benzothiazol-2-yl)amino]-4,4-difluorocyclopentyl}-2-(2H-1,2,3-triazol-2-yl)benzamide

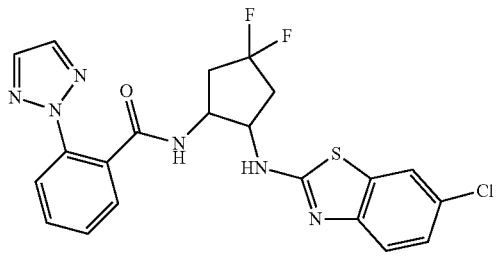 [SMILES: O=C(NC1CC(F)(F)CC1Nc1nc2ccc(Cl)cc2s1)c1ccccc1-n1nccn1]

Prepared as described for N-{4,4-difluoro-2-[(6-fluoro-1,3-benzothiazol-2-yl)amino]cyclopentyl}-2-(2H-1,2,3-triazol-2-yl)benzamide (Examples 103 and 104) from 2,6-dichloro-1,3-benzothiazole (CAS Number 3622-23-9; 78 mg, 0.384 mmol) and (2-amino-4,4-difluorocyclopentyl)-2-(2H-1,2,3-triazol-2-yl)benzamide hydrochloride (Intermediate 28; 120 mg, 0.349 mmol) to afford two enantiomers (Enantiomer 1/Example 105 and Enantiomer 2/Example 106) of the title compound.

Example 105

Enantiomer 1

$^1$H NMR (400 MHz, DMSO-$d_6$) δ ppm 2.01-2.28 (m, 2H), 2.56-2.87 (m, 2H), 4.26-4.53 (m, 2H), 7.20-7.30 (m, 1H), 7.34-7.42 (m, 1H), 7.43-7.49 (m, 2H), 7.55-7.67 (m, 1H), 7.75-7.86 (m, 2H), 7.97 (s, 2H), 8.42-8.52 (m, 1H), 8.68-8.78 (m, 1H)

MS ES$^+$: 475, 477

Example 106

Enantiomer 2

$^1$H NMR (400 MHz, DMSO-$d_6$) δ ppm 2.01-2.27 (m, 2H), 2.54-2.83 (m, 2H), 4.27-4.54 (m, 2H), 7.21-7.30 (m, 1H), 7.34-7.42 (m, 1H), 7.42-7.51 (m, 2H), 7.55-7.66 (m, 1H), 7.75-7.85 (m, 2H), 7.97 (s, 2H), 8.44-8.52 (m, 1H), 8.68-8.78 (m, 1H)

MS ES$^+$: 475, 477

Example 107

N-{2-[(6-Fluoro-1,3-benzothiazol-2-yl)amino]-2-methylcyclopentyl}-2-(2H-1,2,3-triazol-2-yl)benzamide

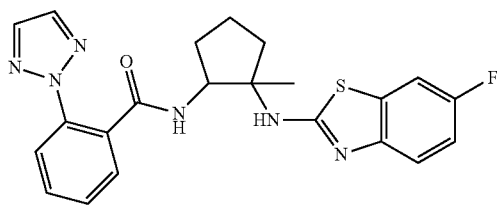 [SMILES: CC1(Nc2nc3ccc(F)cc3s2)CCCC1NC(=O)c1ccccc1-n1nccn1]

To a MW vial were added N-(2-amino-2-methylcyclopentyl)-2-(2H-1,2,3-triazol-2-yl)benzamide hydrochloride (Intermediate 29; 95 mg, 0.295 mmol), 2-chloro-6-fluoro-1,3-benzothiazole (CAS number 399-74-6; 61 mg, 0.325 mmol) and DIPEA (51.6 µl, 0.295 mmol) in DMSO (1 ml). The reaction was sealed and heated in a sand bath at 140° C. for 17 hours. The reaction was partitioned between ethyl acetate and water, washing with water and brine, filtered through a hydrophobic frit and concentrated in vacuo. The resulting oil was then purified by column chromatography (basic silica, 0-100% ethyl acetate/petrol) and then by reverse phase preparative HPLC (eluted with acetonitrile/water with 0.1% ammonia) to afford the title compound.

$^1$H NMR (400 MHz, DMSO-$d_6$) δ ppm 1.35-1.50 (m, 3H), 1.51-1.78 (m, 3H), 1.84-2.08 (m, 2H), 2.23-2.39 (m, 1H), 4.44-4.65 (m, 1H), 6.93-7.13 (m, 1H), 7.29-7.41 (m, 1H), 7.49-7.70 (m, 4H), 7.73-7.86 (m, 2H), 8.01 (s, 2H), 8.46-8.59 (m, 1H)

MS ES$^+$: 437

Example 108

N-{2-[(6-Chloro-1,3-benzothiazol-2-yl)amino]-2-methylcyclopentyl}-2-(2H-1,2,3-triazol-2-yl)benzamide

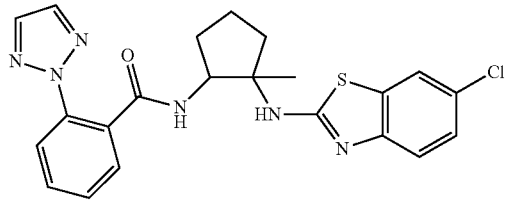 [SMILES: CC1(Nc2nc3ccc(Cl)cc3s2)CCCC1NC(=O)c1ccccc1-n1nccn1]

Prepared as described for N-{2-[(6-fluoro-1,3-benzothiazol-2-yl)amino]-2-methylcyclopentyl}-2-(2H-1,2,3-triazol-2-yl)benzamide (Example 107) from 2,6-dichloro-1,3-benzothiazole (CAS Number 3622-23-9; 66 mg, 0.325 mmol) and (N-(2-amino-2-methylcyclopentyl)-2-(2H-1,2,3-triazol-2-yl)benzamide hydrochloride (Intermediate 29; 95 mg, 0.295 mmol) to afford the title compound.

$^1$H NMR (400 MHz, DMSO-$d_6$) δ ppm 1.41 (s, 3H), 1.52-1.74 (m, 3H), 1.85-2.09 (m, 2H), 2.26-2.40 (m, 1H), 4.47-4.62 (m, 1H), 7.17-7.25 (m, 1H), 7.28-7.38 (m, 1H), 7.51-7.59 (m, 2H), 7.60-7.68 (m, 1H), 7.70-7.84 (m, 2H), 7.88-7.95 (m, 1H), 8.00 (s, 2H), 8.42-8.57 (m, 1H)

MS ES$^+$: 453, 455

3. BIOLOGICAL EFFICACY OF COMPOUNDS OF THE INVENTION

Orexin antagonist activity was determined by measuring changes in intracellular calcium levels using a Ca$^{2+}$ sensitive fluorescent dye. The changes in fluorescent signal were monitored by Fluorescent Imaging Plate Reader (FLIPR™) technology available from Molecular Devices, LLC, U.S.A. Orexin mediated increases in intracellular Ca$^{2+}$ concentration were readily detected upon activation with orexin-A. Twenty-four hours prior to the assay, RBL-2H3 cells stably expressing either human orexin receptor 1 or human orexin receptor 2 were seeded in cell culture medium in black, clear-bottom 384-well plates (commercially available from Corning Inc., U.S.A.) and grown overnight at 37° C., 5% CO$_2$. On the day of the assay, cell culture media was removed and cells were loaded with Calcium 5 Dye (commercially sold by Molecular Devices, LLC, U.S.A.) for 1 hour at 37° C., 5% $CO_2$. Test compounds (at 10 point half log concentration response curves from 10 μM) were added to cells for 15 minutes prior to the addition of orexin-A to all wells, to achieve a final concentration that produces approximately an 80% maximal response. The $IC_{50}$ values were determined from ten point concentration response curves. Curves were generated using the average of two wells for each data point.

Results

| Example Number | Human Orexin1R $IC_{50}$ (nM) | Human Orexin2R $IC_{50}$ (nM) |
|---|---|---|
| 1 | 0.84 | 98 |
| 2 | 36 | 6500 |
| 3 | 4.2 | 7600 |
| 4 | 12 | >10,000 |
| 5 | 12 | 510 |
| 6 | 35 | >10,000 |
| 7 | 26 | 1900 |
| 8 | 35 | 2100 |
| 9 | 99 | >10,000 |
| 10 | 210 | 7200 |
| 11 | 360 | 1800 |
| 12 | 470 | 3500 |
| 13 | 580 | 5300 |
| 14 | 1000 | 680 |
| 15 | 35 | 160 |
| 16 | 13 | 2000 |
| 17 | 130 | 1200 |
| 18 | 25 | 460 |
| 19 | 15 | 7300 |
| 20 | 290 | 4100 |
| 21 | 18 | 5100 |
| 22 | 23 | 8600 |
| 23 | 65 | 620 |
| 24 | 220 | 1400 |
| 25 | 340 | 130 |
| 26 | 64 | >10,000 |
| 27 | 52 | 8500 |
| 28 | 140 | 1900 |
| 29 | 550 | 2900 |
| 30 | 320 | 370 |
| 31 | 92 | 3300 |
| 32 | 900 | 980 |
| 33 | 51 | |
| 34 | 4.7 | 1100 |
| 35 | 6.7 | 4300 |
| 36 | 8.3 | 5400 |
| 37 | 11 | 3500 |
| 38 | 13 | >10,000 |
| 39 | 14 | 3800 |
| 40 | 15 | 3300 |
| 41 | 16 | 2100 |
| 42 | 24 | |
| 43 | 39 | >10,000 |
| 44 | 51 | >10,000 |
| 45 | 80 | |
| 46 | 110 | 6300 |
| 47 | 150 | >10,000 |
| 48 | 160 | 3700 |
| 49 | 190 | 1400 |
| 50 | 190 | 3400 |
| 51 | 250 | 4000 |
| 52 | 270 | |
| 53 | 280 | 3300 |
| 54 | 310 | 3500 |
| 55 | 470 | |
| 56 | 540 | |
| 57 | 780 | |
| 58 | 870 | |
| 59 | 11 | 6700 |
| 60 | 24 | >10,000 |
| 61 | 35 | >10,000 |
| 62 | >10,000 | >10,000 |
| 63 | 48 | 4200 |
| 65 | 29 | >10,000 |
| 66 | 50 | >10,000 |
| 67 | 110 | 6500 |
| 68 | 320 | >10,000 |
| 69 | 15 | 3200 |
| 70 | 38 | >10,000 |
| 71 | 24 | 4200 |
| 72 | 14 | >10,000 |
| 73 | 35 | >10,000 |
| 74 | 38 | 2100 |
| 75 | 5 | 260 |
| 76 | 23 | 2500 |
| 77 | 25 | 1600 |
| 78 | 20 | 2400 |
| 79 | 1 | 1100 |
| 80 | 1 | 650 |
| 81 | 1 | 840 |
| 82 | | |
| 83 | 1 | 1200 |
| 84 | 45 | >10,000 |
| 85 | 23 | >10,000 |
| 86 | 150 | >10,000 |
| 87 | 21 | >10,000 |
| 88 | 21 | 4200 |
| 89 | 27 | 5400 |
| 90 | 16 | >10,000 |
| 91 | 18 | 4700 |
| 92 | 14 | 8600 |
| 93 | 14 | 6200 |
| 94 | 30 | >10,000 |
| 95 | 41 | >10,000 |
| 96 | 480 | >10,000 |
| 97 | 780 | >10,000 |
| 98 | 310 | 2100 |
| 99 | 12 | >10,000 |
| 100 | 22 | >10,000 |
| 101 | 730 | 3800 |
| 102 | 79 | >10,000 |
| 103 | 266 | 627 |
| 104 | 13 | 4500 |
| 105 | 17 | 3544 |
| 106 | 564 | 441 |
| 107 | 7 | 60 |
| 108 | 13 | 186 |

The invention claimed is:

1. A compound of formula

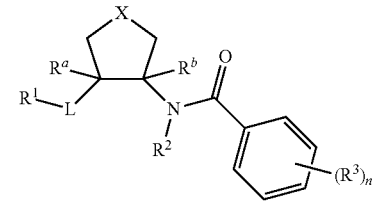

(I)

wherein
$R^1$ represents an 8- to 10-membered fused bicyclic heteroaromatic group optionally substituted by at least one substituent selected from halogen, cyano, hydroxyl, $C_3$-$C_6$ cycloalkyl, $C_1$-$C_3$ alkyl, $C_1$-$C_3$ alkoxy, $C_1$-$C_3$ alkoxycarbonyl, $C_1$-$C_3$ alkoxycarbonylamino, $C_1$-$C_3$ haloalkoxy, —$NR^4R^5$, $C_3$-$C_6$ cycloalkylamino, $C_1$-$C_3$ alkylcarbonyloxy, $C_1$-$C_3$ alkylcarbonylamino, sulphonamido, $C_1$-$C_3$ alkylsulphonyl, $C_1$-$C_3$ alkylsulphonylamino and —C(O)$NR^6R^7$;

L represents $CH_2$, O, NH or $N(CH_3)$;

$R^a$ represents a hydrogen atom or a $C_1$-$C_3$ alkyl or $C_1$-$C_3$ haloalkyl group;

$R^b$ represents a hydrogen atom or a $C_1$-$C_3$ alkyl or $C_1$-$C_3$ haloalkyl group;

X represents $CF_2$, $CHR^8$, O or $NC(O)R^9$;

$R^2$ represents a hydrogen atom or a $C_1$-$C_6$ alkyl group;

n is 0 or an integer 1, 2, 3, 4 or 5;

each $R^3$ independently represents halogen, hydroxyl, cyano, $C_1$-$C_3$ alkyl, $C_1$-$C_3$ haloalkyl, $C_1$-$C_3$ hydroxyalkyl, $C_1$-$C_3$ alkoxy, $C_1$-$C_3$ haloalkoxy, $C_2$-$C_4$ alkenyl, $C_1$-$C_3$ alkylcarbonyloxy, $C_1$-$C_3$ alkoxycarbonyl, —$NR^{10}R^{11}$, —$CONR^{12}R^{13}$, $C_3$-$C_6$ cycloalkyl, $C_3$-$C_6$ cycloalkyloxy, $C_3$-$C_6$ cycloalkylmethyl or a 5- to 6-membered heteroaryl group, the heteroaryl group being optionally substituted by at least one substituent selected from $C_1$-$C_6$ alkyl, $C_1$-$C_6$ alkoxy and $C_1$-$C_6$ haloalkoxy;

$R^4$ and $R^5$ each independently represent a hydrogen atom or a $C_1$-$C_3$ alkyl or $C_3$-$C_6$ cycloalkyl group, or $R^4$ and $R^5$ may together with the nitrogen atom to which they are attached form a 4- to 7-membered saturated heterocyclic ring optionally substituted by at least one substituent selected from halogen and hydroxyl;

$R^6$ and $R^7$ each independently represent a hydrogen atom or a $C_1$-$C_3$ alkyl or $C_3$-$C_6$ cycloalkyl group, or $R^6$ and $R^7$ may together with the nitrogen atom to which they are attached form a 4- to 7-membered saturated heterocyclic ring optionally substituted by at least one substituent selected from halogen and hydroxyl;

$R^8$ represents a hydrogen or halogen atom or a hydroxyl group;

$R^9$ represents a $C_1$-$C_6$ alkyl, $C_1$-$C_6$ alkoxy, benzyloxy, $C_6$-$C_{10}$ aryl, or heteroaryl group;

$R^{10}$ and $R^{11}$ each independently represent a hydrogen atom or a $C_1$-$C_3$ alkyl or $C_3$-$C_6$ cycloalkyl group, or $R^{10}$ and $R^{11}$ may together with the nitrogen atom to which they are attached form a 4- to 7-membered saturated heterocyclic ring optionally substituted by at least one substituent selected from halogen and hydroxyl; and $R^{12}$ and $R^{13}$ each independently represent a hydrogen atom or a $C_1$-$C_3$ alkyl or $C_3$-$C_6$ cycloalkyl group, or $R^{12}$ and $R^{13}$ may together with the nitrogen atom to which they are attached form a 4- to 7-membered saturated heterocyclic ring optionally substituted by at least one substituent selected from halogen and hydroxyl;

or a pharmaceutically acceptable salt thereof.

2. A compound according to claim 1, wherein $R^1$ represents a 9- or 10-membered fused bicyclic heteroaromatic group containing one or two ring heteroatoms independently selected from nitrogen, oxygen and sulphur, the heteroaromatic group being optionally substituted by one or more halogen atoms.

3. A compound according to claim 1, wherein the fused bicyclic heteroaromatic group is selected from quinoxalinyl, benzothiazolyl, benzoxazolyl, quinolinyl and quinazolinyl.

4. A compound according to claim 1, wherein L represents $CH_2$.

5. A compound according to claim 1, wherein L represents NH.

6. A compound according to claim 1, wherein X represents $CHR^8$.

7. A compound according to claim 1, wherein each $R^3$ independently represents fluorine, chlorine, $C_1$-$C_2$ alkyl, $C_1$-$C_2$ alkoxy, $C_1$-$C_2$ haloalkoxy, cyclopropyl or a 5- to 6-membered heteroaryl group, the heteroaryl group being optionally substituted by one or two substituents independently selected from $C_1$-$C_2$ alkyl, $C_1$-$C_2$ alkoxy and $C_1$-$C_2$ haloalkoxy.

8. A compound according to claim 1, wherein, in $R^3$ the heteroaryl group is selected from triazolyl, pyrazolyl, oxadiazolyl, pyrimidinyl and imidazolyl.

9. A compound of formula (I) as defined in claim 1 selected from the group consisting of:

2,6-Dimethoxy-N-[(1S,2R)-2-[(quinoxalin-2-yl)amino] cyclopentyl]-benzamide, 2,6-Dimethoxy-N-((1S,2S)-2-(quinoxalin-2-ylamino) cyclopentyl)benzamide, N-[(1S,2S)-2-[(6-Fluoro-1,3-benzothiazol-2-yl)amino] cyclopentyl]-2,6-dimethoxybenzamide, N-[(1S,2S)-2-[(1,3-Benzothiazol-2-yl)amino]cyclopentyl]-2,6-dimethoxybenzamide, N-[(1S,2R)-2-[(1,3-Benzothiazol-2-yl)amino]cyclopentyl]-2,6-dimethoxybenzamide, N-[(1S,2S)-2-[(5-Chloro-1,3-benzothiazol-2-yl)amino] cyclopentyl]-2,6-dimethoxybenzamide, N-[(1S,2R)-2-[(1,3-Benzoxazol-2-yl)amino]cyclopentyl]-2,6-dimethoxybenzamide, N-[(1S,2S)-2-[(6-Fluoro-1,3-benzothiazol-2-yl)(methyl) amino]cyclopentyl]-2,6-dimethoxybenzamide, N-[(1S,2S)-2-[(1,3-Benzoxazol-2-yl)amino]cyclopentyl]-2,6-dimethoxybenzamide, N-[(1S,2S)-2-[(6-Chloro-1,3-benzothiazol-2-yl)amino] cyclopentyl]-2,6-dimethoxy-benzamide, N-[(1R,2R)-2-[(1,3-Benzothiazol-2-yl)amino]cyclopentyl]-2,6-dimethoxybenzamide, N-[(1R,2R)-2-[(1,3-Benzoxazol-2-yl)amino]cyclopentyl]-2,6-dimethoxy-benzamide, N-[(1R,2S)-2-[(6-Chloro-1,3-benzothiazol-2-yl)amino] cyclopentyl]-2,6-dimethoxybenzamide, N-[(1R,2R)-2-[(6-Chloro-1,3-benzothiazol-2-yl)amino] cyclopentyl]-2,6-dimethoxybenzamide, N-[(1S,2R)-2-[(6-Chloro-1,3-benzothiazol-2-yl)amino] cyclopentyl]-2,6-dimethoxybenzamide, N-[(1 S, 2S)-2-[(6-Fluoro-1,3-benzothiazol-2-yl)amino] cyclopentyl]-5-methyl-2-(2H-1,2,3-triazol-2-yl)benzamide, N-[(1R,2S)-2-[(1,3-Benzoxazol-2-yl)amino]cyclopentyl]-2,6-diethoxy-benzamide, N-[(1S,2R)-2-[(1,3-Benzoxazol-2-yl)amino]cyclopentyl]-2,6-diethoxy-benzamide, N-[(1 S,2S)-2-[(1,3-Benzothiazol-2-yl)amino]cyclopentyl]-5-methyl-2-(2H-1,2,3-triazol-2-yl)benzamide, 5-Methyl-N-[(1S,2S)-2-[(quinolin-2-yl)amino]cyclopentyl]-2-(2H-1,2,3-triazol-2-yl)benzamide, 5-Methyl-N-((1 S, 2S)-2-(quinoxalin-2-ylamino)cyclopentyl)-2-(2H-1,2,3-triazol-2-yl)benzamide, Benzyl cis-3-[(6-chloro-1,3-benzothiazol-2-yl)amino]-4-[(2,6-dimethoxybenzene)amido]pyrrolidine-1-carboxylate, Ethyl cis-3-[(6-Chloro-1,3-benzothiazol-2-yl)amino]-4-[(2,6-dimethoxy-benzene)amido]pyrrolidine-1-carboxylate, N-{cis-4-[(6-Chloro-1,3-benzothiazol-2-yl)amino]oxolan-3-yl}-2,6-dimethoxybenzamide, N-[(1S,2R,4R)-2-[(6-Chloro-1,3-benzothiazol-2-yl) amino]-4-hydroxycyclo-pentyl]-2,6-dimethoxybenzamide, N-[(1S,2R)-2-[(6-Chloro-1,3-benzothiazol-2-yl)amino]-4-fluorocyclo-pentyl]-2,6-dimethoxybenzamide, 5-Methyl-N-[2-(quinolin-2-ylmethyl)cyclopentyl]-2-(2H-1,2,3-triazol-2-yl)benzamide,
2-Ethoxy-5-methyl-N-[2-(quinolin-2-ylmethyl)cyclopentyl]-benzamide,
2,6-Dimethoxy-N-[2-(quinolin-2-ylmethyl)cyclopentyl]benzamide,
2,6-Diethoxy-N-(2-(quinolin-2-ylmethyl)cyclopentyl)benzamide,
N-{2-[(6-Chloro-1,3-benzothiazol-2-yl)methyl]cyclopentyl}-2,6-dimethoxybenzamide,
N-{2-[(6-Chloro-1,3-benzothiazol-2-yl)methyl]cyclopentyl}-5-methyl-2-(2H-1,2,3-triazol-2-yl)benzamide,
N-[(1S,2S)-2-[(6-Fluoro-1,3-benzothiazol-2-yl)amino]cyclopentyl]-2,6-dimethoxy-N-methylbenzamide,
N-[(1S,2S)-2-[(6-Fluoro-1,3-benzothiazol-2-yl)amino]cyclopentyl]-2-(1H-pyrazol-1-yl)benzamide,
5-Fluoro-N-[(1S,2S)-2-[(6-fluoro-1,3-benzothiazol-2-yl)amino]cyclopentyl]-2-(2H-1,2,3-triazol-2-yl)benzamide,
2-Chloro-N-[(1S,2S)-2-[(6-fluoro-1,3-benzothiazol-2-yl)amino]cyclopentyl]benzamide,
N-[(1S,2S)-2-[(6-Fluoro-1,3-benzothiazol-2-yl)amino]cyclopentyl]-5-methyl-2-(1H-1,2,3-triazol-1-yl)benzamide,
N-[(1S,2S)-2-[(6-Fluoro-1,3-benzothiazol-2-yl)amino]cyclopentyl]-2-(3-methyl-1,2,4-oxadiazol-5-yl)benzamide,
N-[(1S,2S)-2-[(6-Fluoro-1,3-benzothiazol-2-yl)amino]cyclopentyl]-2-(pyrimidin-2-yl)benzamide,
N-[(1S,2S)-2-[(6-Fluoro-1,3-benzothiazol-2-yl)amino]cyclopentyl]-2,5-dimethoxybenzamide,
5-Fluoro-N-[(1S,2S)-2-[(6-fluoro-1,3-benzothiazol-2-yl)amino]cyclopentyl]-2-(pyrimidin-2-yl)benzamide,
N-[(1S,2S)-2-[(6-Fluoro-1,3-benzothiazol-2-yl)amino]cyclopentyl]-2-(1H-imidazol-1-yl)benzamide,
N-[(1S,2S)-2-[(6-Fluoro-1,3-benzothiazol-2-yl)amino]cyclopentyl]-2-(1H-1,2,4-triazol-1-yl)benzamide,
5-Fluoro-N-[(1S,2S)-2-[(6-fluoro-1,3-benzothiazol-2-yl)amino]cyclopentyl]-2-(1H-1,2,3-triazol-1-yl)benzamide,
2-Fluoro-N-[(1S,2S)-2-[(6-fluoro-1,3-benzothiazol-2-yl)amino]cyclopentyl]-6-methoxybenzamide,
2,6-Difluoro-N-[(1S,2S)-2-[(6-fluoro-1,3-benzothiazol-2-yl)amino]-cyclopentyl]benzamide,
2-Fluoro-N-[(1S,2S)-2-[(6-fluoro-1,3-benzothiazol-2-yl)amino]cyclopentyl]-benzamide,
2-Ethoxy-N-[(1S,2S)-2-[(6-fluoro-1,3-benzothiazol-2-yl)amino]cyclopentyl]-benzamide,
N-[(1S,2S)-2-[(6-Fluoro-1,3-benzothiazol-2-yl)amino]cyclopentyl]-2-methoxybenzamide,
N-[(1S,2S)-2-[(6-Fluoro-1,3-benzothiazol-2-yl)amino]cyclopentyl]-2-methylbenzamide,
2,6-Dichloro-N-[(1S,2S)-2-[(6-fluoro-1,3-benzothiazol-2-yl)amino]-cyclopentyl]benzamide,
5-Fluoro-N-[(1S,2S)-2-[(6-fluoro-1,3-benzothiazol-2-yl)amino]cyclopentyl]-2-methoxybenzamide,
3-Fluoro-N-[(1S,2S)-2-[(6-fluoro-1,3-benzothiazol-2-yl)amino]cyclopentyl]-2-methoxybenzamide,
2-(Difluoromethoxy)-N-[(1S,2S)-2-[(6-fluoro-1,3-benzothiazol-2-yl)amino]-cyclopentyl]benzamide,
N-[(1S,2S)-2-[(6-Fluoro-1,3-benzothiazol-2-yl)amino]cyclopentyl]-3-methoxybenzamide,
N-[(1S,2S)-2-[(6-Fluoro-1,3-benzothiazol-2-yl)amino]cyclopentyl]-3-methylbenzamide,
2-Cyclopropyl-N-[(1 S, 2S)-2-[(6-fluoro-1,3-benzothiazol-2-yl)amino]-cyclopentyl]benzamide,
N-[(1S,2S)-2-[(6-Fluoro-1,3-benzothiazol-2-yl)amino]cyclopentyl]-2-(2H-1,2,3-triazol-2-yl)benzamide,
5-Methyl-N-[(1S,2S)-2-[(quinazolin-2-yl)amino]cyclopentyl]-2-(2H-1,2,3-triazol-2-yl)benzamide,
5-Methyl-N-[2-(quinoxalin-2-ylmethyl)cyclopentyl]-2-(2H-1,2,3-triazol-2-yl)benzamide, trans-N-{4-[(6-Fluoro-1,3-benzothiazol-2-yl)amino]oxolan-3-yl}-2,6-dimethoxybenzamide,
N-[(1S,2S)-2-[(6-Fluoro-1,3-benzoxazol-2-yl)amino]cyclopentyl]-2,6-dimethoxybenzamide,
N-[(1S,2S)-2-[(6-Fluoro-1,3-benzothiazol-2-yl)amino]cyclopentyl]-2-methoxy-5-methylbenzamide,
N-[(1S,2S)-2-[(6-Fluoro-1,3-benzothiazol-2-yl)amino]cyclopentyl]-2,6-dimethylbenzamide,
2-Fluoro-N-[(1 S, 2S)-2-[(6-fluoro-1,3-benzothiazol-2-yl)amino]cyclopentyl]-6-(2H-1,2,3-triazol-2-yl)benzamide,
2-Chloro-6-fluoro-N-[(1S,2S)-2-[(6-fluoro-1,3-benzothiazol-2-yl)amino]cyclopentyl]benzamide,
2-Chloro-N-[(1 S, 2S)-2-[(6-fluoro-1,3-benzothiazol-2-yl)amino]cyclopentyl]-6-(2H-1,2,3-triazol-2-yl)benzamide,
N-[(1S,2S)-2-[(6-Fluoro-1,3-benzothiazol-2-yl)amino]cyclopentyl]-2-(5-methyl-1,3,4-oxadiazol-2-yl)benzamide,
N-[(1S,2S)-2-[(6-Fluoro-1,3-benzothiazol-2-yl)amino]cyclopentyl]-2-(1H-1,2,3-triazol-1-yl)benzamide,
5-Chloro-N-[(1S,2S)-2-[(6-fluoro-1,3-benzothiazol-2-yl)amino]cyclopentyl]-2-(1H-pyrazol-1-yl)benzamide,
N-[(1S,2R)-2-[(6-Fluoro-1,3-benzothiazol-2-yl)amino]cyclopentyl]-2-(2H-1,2,3-triazol-2-yl)benzamide,
2,6-Difluoro-N-[(1S,2S)-2-[(6-fluoro-1,3-benzothiazol-2-yl)amino]cyclopentyl]-N-methylbenzamide,
N-[(1 S, 2S)-2-[(6-Fluoro-1,3-benzothiazol-2-yl)amino]cyclopentyl]-2-methoxy-N-methylbenzamide,
2-Chloro-N-[(1S,2S)-2-[(6-fluoro-1,3-benzothiazol-2-yl)amino]cyclopentyl]-N-methylbenzamide,
N-[(1S,2S)-2-[(6-Fluoro-1,3-benzothiazol-2-yl)amino]cyclopentyl]-N-methyl-2-(1H-pyrazol-1-yl)benzamide,
N-[(1S,2S)-2-[(6-Fluoro-1,3-benzothiazol-2-yl)amino]cyclopentyl]-N-methyl-2-(2H-1,2,3-triazol-2-yl)benzamide,
5-Fluoro-N-[(1S,2S)-2-[(6-fluoro-1,3-benzothiazol-2-yl)amino]cyclopentyl]-N-methyl-2-(2H-1,2,3-triazol-2-yl)benzamide,
N-[(1S,2S)-2-[(6-Fluoro-1,3-benzothiazol-2-yl)amino]cyclopentyl]-N-methyl-2-(pyrimidin-2-yl)benzamide,
N-[(1S,2S)-2-[(6-Fluoro-1,3-benzothiazol-2-yl)amino]cyclopentyl]-N-methyl-2-(3-methyl-1,2,4-oxadiazol-5-yl)benzamide,
N-[(1S,2S)-2-[(5-Fluoro-1,3-benzothiazol-2-yl)amino]cyclopentyl]-2,6-dimethoxybenzamide,
N-[(1S,2S)-2-[(5-Fluoro-1,3-benzoxazol-2-yl)amino]cyclopentyl]-2,6-dimethoxybenzamide,
N-[(1S,2S)-2-[(1,3-Benzoxazol-2-yl)amino]cyclopentyl]-2-(2H-1,2,3-triazol-2-yl)benzamide,
N-[(1S,2S)-2-[(6-Fluoro-1,3-benzoxazol-2-yl)amino]cyclopentyl]-2-(2H-1,2,3-triazol-2-yl)benzamide,
N-[(1S,2S)-2-[(5-Fluoro-1,3-benzoxazol-2-yl)amino]cyclopentyl]-2-(2H-1,2,3-triazol-2-yl)benzamide,
N-[(1S,2S)-2-[(5-Chloro-1,3-benzothiazol-2-yl)amino]cyclopentyl]-2-(2H-1,2,3-triazol-2-yl)benzamide,
N-[(1S,2S)-2-[(1,3-Benzothiazol-2-yl)amino]cyclopentyl]-2-(2H-1,2,3-triazol-2-yl)benzamide,
N-[(1S,2S)-2-[(6-Chloro-1,3-benzothiazol-2-yl)amino]cyclopentyl]-2-(2H-1,2,3-triazol-2-yl)benzamide, N-[(1S,2S)-2-[(5-Fluoro-1,3-benzothiazol-2-yl)amino]
cyclopentyl]-2-(2H-1,2,3-triazol-2-yl)benzamide, N-[(1S,2S)-2-[(4,6-Difluoro-1,3-benzothiazol-2-yl)
amino]cyclopentyl]-2-(2H-1,2,3-triazol-2-yl)benz-
amide, N-[(1S,2S)-2-[(4-Fluoro-1,3-benzothiazol-2-yl)amino]
cyclopentyl]-2-(2H-1,2,3-triazol-2-yl)benzamide, N-[(1S,2S)-2-({[1,3]Thiazolo[5,4-b]pyridin-2-yl}amino)
cyclopentyl]-2-(2H-1,2,3-triazol-2-yl)benzamide, N-[(1 S, 2S)-2-({7-Chloro-[1,3]thiazolo[5,4-c]pyridin-2-
yl}amino)cyclopentyl]-2-(2H-1,2,3-triazol-2-yl)benz-
amide, N-[(1 S, 2S)-2-({[1,3]Thiazolo[5,4-c]pyridin-2-
yl}amino)cyclopentyl]-2-(2H-1,2,3-triazol-2-yl)benz-
amide, N-[(1S,2S)-2-[(6-Fluoro-1,3-benzoxazol-2-yl)amino]cy-
clopentyl]-2-(3-methyl-1,2,4-oxadiazol-5-yl)benz-
amide, trans-N-{4-[(6-Fluoro-1,3-benzothiazol-2-yl)amino]oxo-
lan-3-yl}-2-(2H-1,2,3-triazol-2-yl)benzamide, cis-N-[4-(1,3-Benzothiazol-2-ylmethyl)oxolan-3-yl]-5-
methyl-2-(2H-1,2,3-triazol-2-yl)benzamide, N-{4,4-Difluoro-2-[(6-fluoro-1,3-benzothiazol-2-yl)
amino]cyclopentyl}-2-(2H-1,2,3-triazol-2-yl)benz-
amide (Enantiomer 1 substantially as described herein
and with reference to Example 103), N-{4,4-Difluoro-2-[(6-fluoro-1,3-benzothiazol-2-yl)
amino]cyclopentyl}-2-(2H-1,2,3-triazol-2-yl)benz-
amide (Enantiomer 2 substantially as described herein
and with reference to Example 104), N-{2-[(6-Chloro-1,3-benzothiazol-2-yl)amino]-4,4-dif-
luorocyclopentyl}-2-(2H-1,2,3-triazol-2-yl)benzamide
(Enantiomer 1 substantially as described herein and
with reference to Example 105), N-{2-[(6-Chloro-1,3-benzothiazol-2-yl)amino]-4,4-dif-
luorocyclopentyl}-2-(2H-1,2,3-triazol-2-yl)benzamide
(Enantiomer 2 substantially as described herein and
with reference to Example 106), N-{2-[(6-Fluoro-1,3-benzothiazol-2-yl)amino]-2-methyl-
cyclopentyl}-2-(2H-1,2,3-triazol-2-yl)benzamide, N-{2-[(6-Chloro-1,3-benzothiazol-2-yl)amino]-2-meth-
ylcyclopentyl}-2-(2H-1,2,3-triazol-2-yl)benzamide and pharmaceutically acceptable salts thereof.

10. A process for the preparation of a compound of formula (I) or a pharmaceutically acceptable salt thereof as defined in claim 1 which comprises (i) reacting a compound of formula

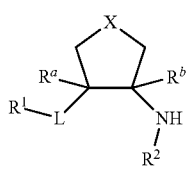

(II)

wherein L, X, $R^a$, $R^b$, $R^1$ and $R^2$ are as defined in formula (I), with a compound of formula

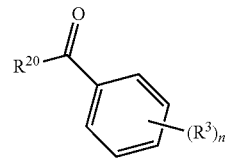

(III)

wherein $R^{20}$ represents a halogen atom or a hydroxyl group and n and $R^3$ are as defined in formula (I), or a salt thereof; or (ii) when L represents NH or N(CH$_3$), reacting a compound of formula

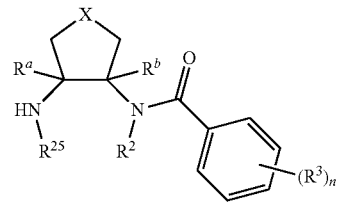

(IV)

wherein $R^2$ represents a hydrogen atom or methyl group and n, X, $R^a$, $R^b$, $R^2$ and $R^3$ are as defined in formula (I), with a compound of formula (V), $R^1$-LG$^1$, wherein LG$^1$ represents a leaving group and $R^1$ is as defined in formula (I);

and optionally thereafter carrying out one or more of the following procedures:
converting a compound of formula (I) into another compound of formula (I)
removing any protecting groups
forming a pharmaceutically acceptable salt.

11. A pharmaceutical composition comprising a compound of formula (I) or a pharmaceutically acceptable salt thereof as claimed in claim 1, in association with a pharmaceutically acceptable adjuvant, diluent or carrier, and optionally one or more other therapeutic agents.

12. A composition according to claim 11, wherein the one or more therapeutic agents are selected from carbamazepine, olanzapine, quetiapine, verapamil, lamotrigine, oxcarbazepine, risperidone, aripiprazole, ziprasidone and lithium.

13. A method of treating schizophrenia, schizophreniform disorder, schizoaffective disorder, cognitive disorders or pain, comprising administering to an individual in need thereof a therapeutically effective amount of a compound of formula (I) or a pharmaceutically acceptable salt thereof as claimed in claim 1.

14. A method treating post-traumatic stress disorder, panic disorders or addiction, comprising administering to an individual in need thereof a therapeutically effective amount of a compound of formula (I) or a pharmaceutically acceptable salt thereof as claimed in claim 1.

15. A kit comprising a preparation of a first active ingredient which is a compound of formula (I) or a pharmaceutically acceptable salt thereof as claimed in claim 1, and a preparation of a second active ingredient which is carbamazepine, olanzapine, quetiapine, verapamil, lamotrigine, oxcarbazepine, risperidone, aripiprazole, ziprasidone or lithium, and instructions for the simultaneous, sequential or separate administration of the preparations to a patient in need thereof.

* * * * *

UNITED STATES PATENT AND TRADEMARK OFFICE
CERTIFICATE OF CORRECTION

PATENT NO. : 9,493,432 B2  
APPLICATION NO. : 15/029356  
DATED : November 15, 2016  
INVENTOR(S) : Fieldhouse et al.

Page 1 of 1

It is certified that error appears in the above-identified patent and that said Letters Patent is hereby corrected as shown below:

On the Title Page

Column 1, under Assignee, Item (73) should read:  
Takeda Pharmaceutical Company Limited, Osaka (JP)

Signed and Sealed this  
Tenth Day of April, 2018

Andrei Iancu  
*Director of the United States Patent and Trademark Office*